(12) United States Patent
Davis

(10) Patent No.: US 7,851,598 B2
(45) Date of Patent: Dec. 14, 2010

(54) RECEPTOR MODULATORS

(75) Inventor: Simon Davis, Oxford (GB)

(73) Assignee: Isis Innovation Limited, Oxford (GB)

( * ) Notice: Subject to any disclaimer, the term of this patent is extended or adjusted under 35 U.S.C. 154(b) by 671 days.

(21) Appl. No.: 10/585,491

(22) PCT Filed: Jan. 10, 2005

(86) PCT No.: PCT/GB2005/000099

§ 371 (c)(1),
(2), (4) Date: Jun. 15, 2007

(87) PCT Pub. No.: WO2005/066867

PCT Pub. Date: Jul. 21, 2005

(65) Prior Publication Data

US 2008/0044837 A1    Feb. 21, 2008

Related U.S. Application Data

(60) Provisional application No. 60/536,354, filed on Jan. 14, 2004.

(30) Foreign Application Priority Data

Jan. 9, 2004  (GB) ................................. 0400440.4

(51) Int. Cl.
*C07K 16/28* (2006.01)
(52) U.S. Cl. .................................... 530/387.1
(58) Field of Classification Search ........................ None
See application file for complete search history.

(56) References Cited

U.S. PATENT DOCUMENTS

| 2002/0160000 | A1* | 10/2002 | Wood et al. | ............... 424/144.1 |
| 2003/0166860 | A1* | 9/2003 | Hunig et al. | ................ 530/350 |
| 2004/0092718 | A1 | 5/2004 | Hunig | |
| 2006/0121021 | A1 | 6/2006 | Hunig | |

FOREIGN PATENT DOCUMENTS

| WO | WO 03/078468 A2 | 9/2003 |
| WO | WO 03/095487 A2 | 11/2003 |
| WO | WO 2004/004768 A1 | 1/2004 |
| WO | WO 2005/066867 A3 | 7/2005 |

OTHER PUBLICATIONS

Watkins et al., J. Virology, 1996, 70: 8431-8437.*
Linsley, P. S. "New Look at an Old Costimulator", *Nature Immunology*, Mar. 2005, pp. 231-232, vol. 6, No. 3.
Lühder, F. et al. "Topological Requirements and Signaling Properties of T Cell-Activating, Anti-CD28 Antibody Superagonists", *J. Exp. Med.*, Apr. 21, 2003, pp. 955-966, vol. 197, No. 8.
Stamper, C. C. et al. "Crystal Structure of the B7-1/CTLA-4 Complex that Inhibits Human Immune Responses", *Nature*, Mar. 29, 2001, pp. 608-611, vol. 410.
Chang, C.Y.Y. et al. "Crystallization and preliminary X-ray analysis of CTLA-4 (CD152) membrane-external domain", *Acta Cryst.*, Section D, 2000, pp. 1468-1469, vol. D56.
Zhang, X. et al. "Crystallization and preliminary X-ray analysis of the complex between human CTLA-4 and B7-2", *Acta Cryst.*, Section D, 2001, pp. 898-899, vol. D57.
Schwartz, J.-C. D. et al. "Structural basis for co-stimulation by the human CTLA-4/B7-2 complex", *Nature*, Mar. 29, 2001, pp. 604-607, vol. 410.
Evans, E. J. "Crystal structure of a soluble CD28-Fab complex", *Nature Immunology*, Mar. 2005, pp. 271-279, vol. 6, No. 3.

* cited by examiner

*Primary Examiner*—Ilia Ouspenski
(74) *Attorney, Agent, or Firm*—Saliwanchik, Lloyd & Saliwanchik

(57) ABSTRACT

Method of identifying a modulator of CD28 comprising comparing a structural model of a candidate modulator with a structural model of CD28 to thereby determine whether the modulator will bind to CD28, wherein the structural model is derived from, or comprises, structural coordinates of a crystal of: (i) CD28, (ii) a fragment of CD28, or (iii) a homologue of (i) or (ii). The crystal of CD28 in a soluble form complexed with the Fab fragment of a mitogenic (superagonistic) antibody has been obtained and used for the determination of the 3D-structure of the receptor. The application also relates to modulators of superagonistic signalling for any receptor of the CD28 family, i.e. to superagonistic antibodies and chimeric proteins thereof, and to the screening of the superagonistic modulators. In the methods of screening, the binding of the candidate modulators to a portion of the receptor proximal to the cell membrane is investigated.

19 Claims, 8 Drawing Sheets

B. Superagonistic antibody signalling *in vivo*

C. Chimeric protein 1 (ligand-based)

chimeric ligand/Fc superagonist:
• binds Fc receptor on cell 1
and receptor 2 on cell 2

Figure 1

D. Chimeric protein 2 (Fv-based)

strong signal

↑

CD45
receptor 2
p56*lck*
cell 2

150-200 Å

CD45 p56*lck*
receptor 1 cell 1

↓ strong signal chimeric Fv superagonist:
• binds receptor 1 on cell 1 and receptor 2 on cell 2

RECEPTOR MODULATORS

CROSS-REFERENCE TO RELATED APPLICATION

This application is the U.S. national stage application of International Patent Application No. PCT/GB2005/000099, filed Jan. 10, 2005, which claims the benefit of U.S. Provisional Patent Application No. 60/536,354, filed Jan. 14, 2004, the disclosures of which are hereby incorporated by reference in their entireties, including all figures, tables and amino acid or nucleic acid sequences.

FIELD OF THE INVENTION

The present invention relates to use of a crystal structure to obtain modulators of a cell surface receptor and to the generation of therapeutic antibodies and chimeric proteins that bind a particular class of signalling receptors.

BACKGROUND OF THE INVENTION

CD28 is present on the surface of T cells and plays an important role in their activation. Signal transduction occurs through CD28 after it is activated (triggered) by binding to its ligand. CD28 activation is dependent on phosphorylation of its cytoplasmic domain. CD28 does not have intrinsic phosphorylation activity but instead is dependent on an extrinsic kinase, e.g. p56lck.

SUMMARY OF THE INVENTION

The invention relates to the obtaining of the structure of CD28. This was done by crystallizing a CD28/Fab fragment complex, subjecting it to X-ray diffraction and deriving the structural coordinates from the diffraction measurements. The Fab fragment is from an antibody that has superagonist activity towards CD28, i.e. is able to cause activation of CD28 without the need for a T cell receptor-derived signal. Conventional antibodies that activate CD28 need an additional signal generated by the T cell receptor. The deduced structure allows modulators of CD28 signalling to be obtained which can in turn be used to modulate the immune system.

Accordingly the invention provides a method of identifying a modulator of CD28 comprising comparing a structural model of a candidate modulator with a structural model of CD28 to thereby determine whether the modulator will bind to CD28, wherein the structural model is derived from, or comprises, structural coordinates of a crystal of: (i) CD28, (ii) a fragment of CD28, or (iii) a homologue of (i) or (ii).

In addition the invention relates to antibodies and chimeric proteins that are capable of being superagonists of particular receptors by preferentially excluding phosphatases (as opposed to kinases) from the vicinity of the said receptor.

Accordingly the invention provides an antibody that causes superagonistic signalling of a cell surface receptor, wherein said antibody binds to the extracellular portion of the receptor at a membrane proximal region and said receptor comprises a cytoplasmic domain which is dependent on an extrinsic protein kinase, wherein said antibody does not bind only the C'-D loop of human CD28.

In addition the invention provides a chimeric protein that causes superagonistic signalling of a cell surface receptor, which chimeric protein comprises (i) sequence representing a fragment of a ligand of the receptor, or a homologue of such a fragment, wherein the fragment or homologue is capable of binding to the extracellular portion of the receptor at a membrane proximal region, and (ii) an Fc region of an antibody, wherein said receptor comprises a cytoplasmic domain which is dependent on an extrinsic protein kinase.

Further the invention provides a chimeric protein that causes superagonistic signalling of a first cell surface receptor, which chimeric protein comprises two Fv regions of an antibody that may be the same or different, wherein at least one of the Fv regions is capable of binding to said first receptor, and the other Fv region binds to a second cell surface receptor expressed on another cell, wherein said first receptor comprises a cytoplasmic domain which is dependent on an extrinsic protein kinase, and the first receptor can be identical to the second receptor.

Figure 1:
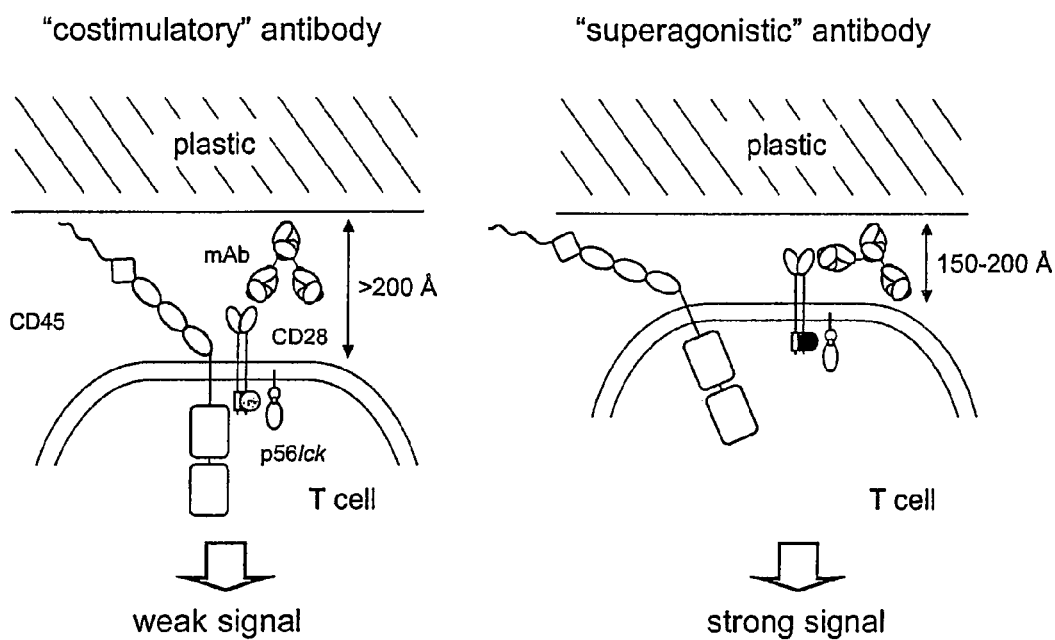
FIG. 1 shows mechanisms of differential triggering of extrinsic kinase-dependent receptors, by superagonistic agents in vitro and in vivo.
Figure 1:
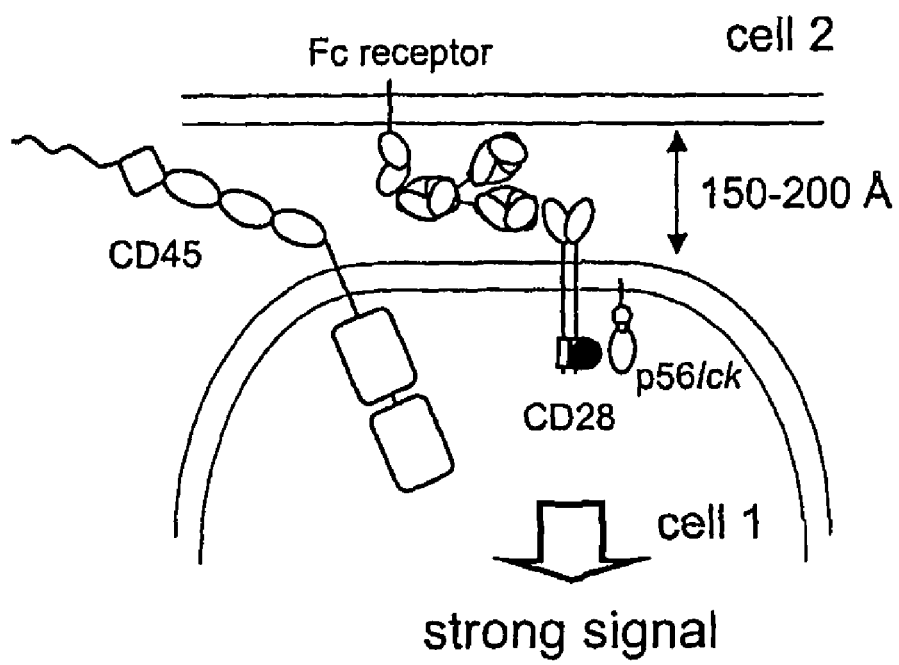
Figure 1:
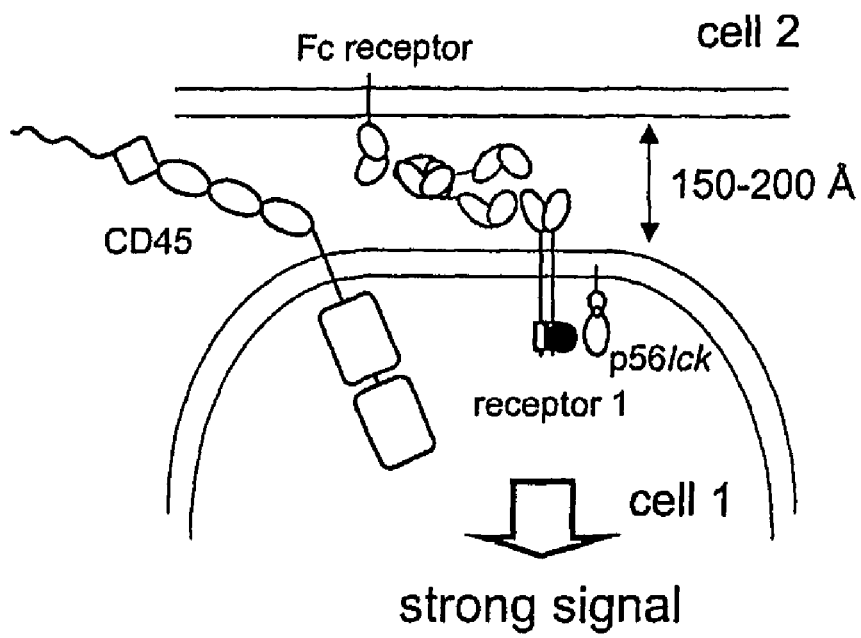
Figure 1:
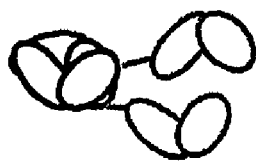

A. In vitro superagonistic signalling, giving the example of CD28 antibodies. The basic signalling principle is as follows. Antibodies raised against CD28 bind distally ("conventional" antibodies, left) or membrane-proximally ("superagonists", right), as indicated by the structure of the CD28-5.11A1 antibody-Fab complex. The antibodies hold the cell surface at certain distances from an immobilising substrate: in this case plastic, and as shown in parts B, C and D of the figure, Fc receptor- or other receptor-bearing cells. For superagonistic antibodies this distance is typically 150-200 Å, whereas for costimulatory antibodies, it is considerably larger.

The induced proximity of the membrane and the immobilising substrate in the region of the immobilised antibody and receptor will lead to the differential steric exclusion, from the immediate vicinity of the receptor, of other molecules whose extracellular domains are comparable in size or larger than CD28-antibody complexes, such as the tyrosine phosphatase, CD45. In contrast, tyrosine kinases, e.g. p56lck, will be unaffected because they are small and/or attached to the inner leaflet of the membrane. The result is that, overall, the phosphorylation of CD28 by the kinases will be favoured over its de-phoshorylation by phosphatases, with the net increase in phosphorylation amounting to receptor triggering. Superagonists are more potent than conventional antibodies because they bind epitopes close to the membrane rather than at the "top" of the molecule, leading to more efficient exclusion of, e.g., CD45, and therefore a larger increase in the net phosphorylation of CD28.

B. In vivo superagonistic signalling, giving the example of CD28 antibodies. The binding of the antibody to the membrane-proximal region of CD28 on a T cell, and to the Fc receptor of, e.g. an antigen presenting cell, forces the membranes of the two cells into close proximity (150-200 Å). This in turn excludes CD45 from the immediate vicinity of CD28 as described in A, leading to signalling by CD28.

C. In vivo superagonistic signalling, giving the example of a chimeric, ligand-based agent. The chimera consists of a receptor-binding region of the ligand of the receptor, fused to the Fc region of an antibody. The binding of the ligand portion of the chimera to the receptor, and of the Fc region of the chimera to the Fc receptor of, e.g. an antigen presenting cell, forces the membranes of the two cells into close proximity (150-200 Å). This in turn excludes CD45 from the immediate vicinity of the receptor as described in A, leading to signalling by the receptor.

D. In vivo superagonistic signalling, giving the example of a chimeric, Fv-based agent. The chimera consists of the receptor-binding Fv region of one antibody, fused to the Fv region of a second antibody reactive with another receptor on a second cell. The binding of the chimera to both receptors forces the membranes of the two cells into close proximity (150-200 Å). This in turn excludes CD45 from the immediate vicinity of the receptor as described in A, leading to signalling by the receptor.

Figure 2:
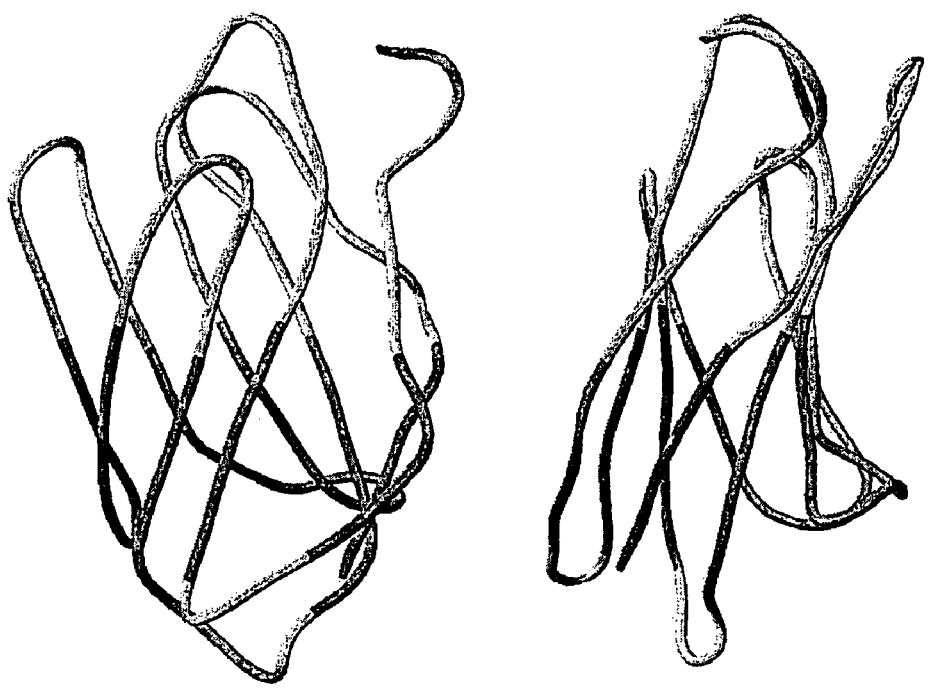
Figure 2:
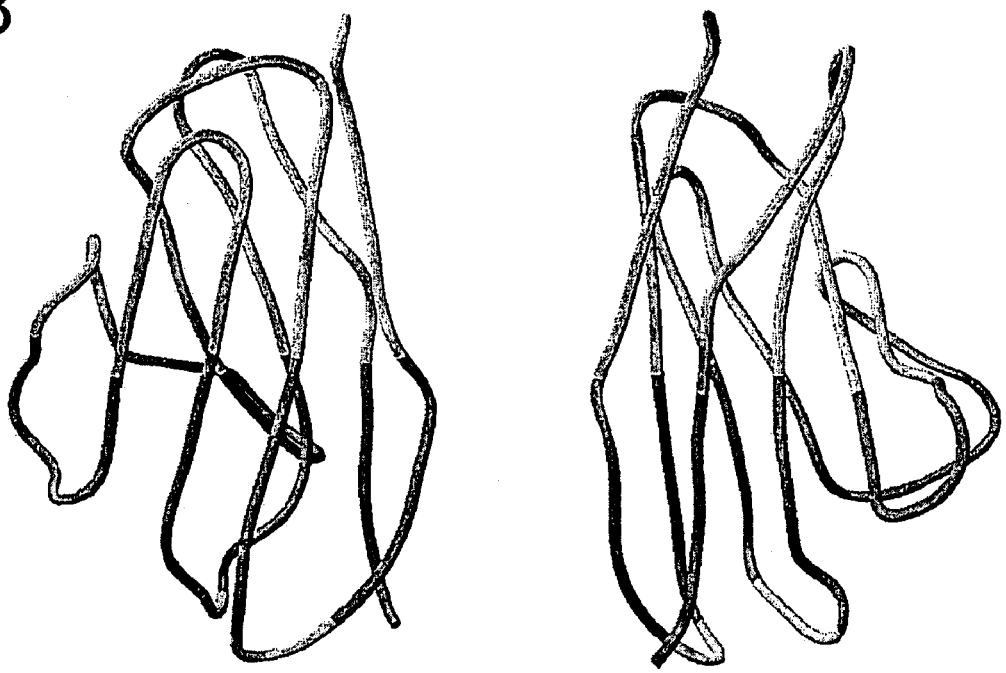
Figure 2:
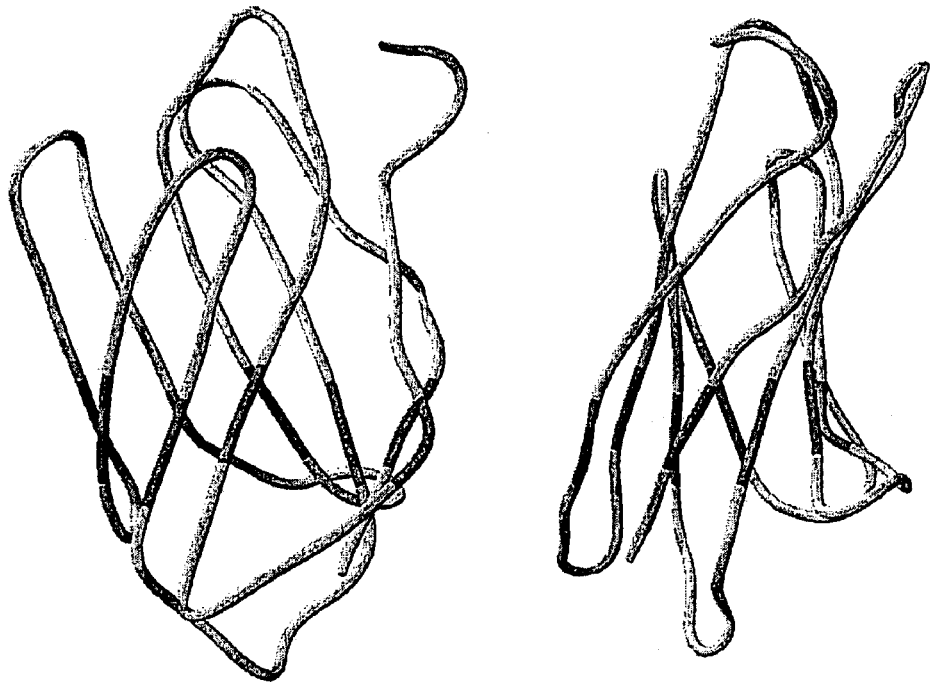
Figure 2:
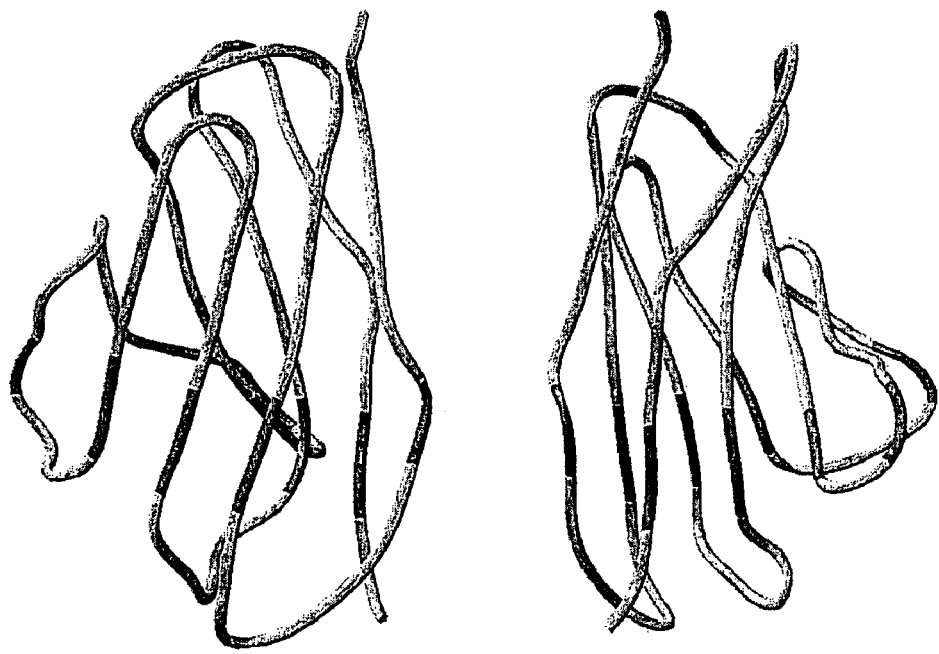

FIG. 2 shows the method for identification of binding sites for superagonist antibodies of receptors raised against example receptors.

DESCRIPTION OF THE SEQUENCES MENTIONED HEREIN

SEQ ID NO:1 shows the amino acid sequence of CD28.
SEQ ID NO:2 shows the sequence of the CD28/Fc fusion protein used to express and dimerise CD28.

DETAILED DESCRIPTION OF THE INVENTION

The CD28 Protein

Many of the different aspects of the invention discussed herein refer to CD28. It is to be understood that references to CD28 herein also include (i) a homologue of CD28, or (ii) a fragment of CD28 or the homologue, or (iii) a fusion protein comprising CD28, (i) or (ii), unless the context requires otherwise. The homologue and/or fragment of CD28 may be of particular lengths, as discussed below, or may have the binding or functional properties of naturally occurring (native) CD28, such as the ability to bind a cell membrane and/or bind to B7-1 or B7-2. The homologue and/or fragment may comprise the extracellular domain of CD28. The homologue and/or fragment may comprise, or essentially consist of, the fragment of CD28 present in the fusion protein of SEQ ID NO:2. The homologue and/or fragment may have the ability to transduce a signal to the cytoplasm of a T cell.

The CD28 may be of any species of animal, such as a mammalian or avian CD28. The CD28 is preferably a human CD28, for example as shown in SEQ ID NO:1. The CD28 protein may be present in particular forms, for example which aid expression and/or crystallization. Thus the CD28 may be fully glycosylated, partially glycosylated or lack glycosylation and/or have a reduced and alkylated stalk region.

The CD28 Crystal

The crystal of CD28 generally comprises CD28 present in a regular repeating array. As mentioned above the term "CD28" includes fragments and/or homologues. Preferred fragments or homologues present in the crystal comprise the extracellular domain of native CD28. In the crystal the CD28 is preferably in the form of a monomer. The crystal may be of CD28 bound to another moiety. Such a moiety may be an antibody specific for CD28, including fragments/derivatives of the antibody (as further discussed below), which bind CD28. In a preferred embodiment the crystal is of CD28 bound to the Fab fragment of an antibody. The crystal may comprise CD28 in a form that aids crystallization, and thus the CD28 may be fully glycosylated, partially glycosylated or lack glycosylation and/or have a reduced and alkylated stalk region. In one embodiment the crystal has the coordinates shown in Table 4.

The crystal is generally obtained by providing a solution that comprises CD28 and optionally a moiety that binds to CD28, such as an antibody fragment, and subjecting the solution to conditions that allow the crystal to form. The CD28 which is to be crystallized is generally obtained by recombinant expression, optionally in the form of a fusion protein. The fusion protein may comprise CD28 and a polypeptide sequence which forms a homodimer. Such a fusion protein aids the formation of a CD28 homodimer. Preferably the fusion protein comprises the sequence of the Fc region of an antibody. The fusion protein may be cleaved before crystallisation to separate CD28 from the other polypeptide sequence, for example by thrombin.

The CD28 may be expressed in any suitable cell that is able to express large amounts of CD28, such as a Chinese hamster ovary (CHO) cell.

The CD28 may be further treated in order to aid crystallization. Binding to an antibody fragment, such as a Fab fragment, may be used to prevent the N-linked glycans present on the fully glycosylated form of CD28 from inhibiting the crystallisation of the protein. In one embodiment the antibody (or fragment thereof) is a superagonistic antibody, which may have any of the properties of the superagonistic antibodies mentioned herein. Thus, in one embodiment the antibody (or fragment thereof) binds to a loop region in the extracellular membrane proximal region of CD28, such as the C'-D loop (said loop being defined for example as defined in US-A1-2003/0166860 as the sequence from amino acid positions 52 to 66 CD28 represented by the sequence GNYSQQLQVYSKTGF).

The treatment may comprise reduction of the interchain disulphide bonds in the stalk-like region of CD28, e.g. using dithioreitol (DTT). The reduced cysteines may then be inactivated, for example by alkylation (typically the alkyl moiety has 2 to 6, preferably 2, carbons). The alkylation may be performed using iodoacetamide.

Crystallisation is typically carried out at 15 to 25° C., such as at 17 to 19° C., preferably 18° C. Magnesium formate and polyethylene glycol (PEG) may be used as precipitating agents. Preferably precipitation is carried out using 0.15 to 0.25 M magnesium formate (such as 0.2 M magnesium formate) and 15 to 25% PEG 3350 (such as 20% PEG 3350).

In the work described in the Examples it was found that in order to crystallise CD28 this protein had to be expressed in the form of a fusion protein with a second protein capable of forming a homodimer (the Fc region of an antibody), the fully glycosylated form of CD28 needed to be complexed with an Fab fragment of an antibody in order that the N-linked glycans did not interfere with crystallisation, and the disulphide bonds in the stalk region of CD28 needed to be reduced and alkylated so that the stalk did not interfere with crystallisation. Thus in a preferred embodiment the method of obtaining a crystal of CD28 (including fragment and/or homologue thereof) comprises
  (a) expressing CD28 in the form of a fusion protein with a second protein that is able to form a homodimer, wherein the presence of the second protein in the fusion protein causes CD28 to dimerise,
  (b) cleaving the second protein from the fusion protein,
  (c) reducing and alkylating the disulphide bond present in the stalk-like region of CD28, and
  (d) crystallising CD28 bound to the Fab fragment of an antibody.

Identifying a Modulator of CD28

The invention provides a method of identifying a modulator using the structural coordinates determined from the above-mentioned crystal of CD28. The structural coordinates used in the method may be in the form of a structural model, such as a three dimensional representation of the structure or a pharmacophore. The coordinates/model typically comprise information relating to the identity of each atom (i.e. whether it is nitrogen, oxygen, hydrogen etc.) and its three dimensional location (normally defined by three spatial coordinates) in the structure. The model may also comprise additional information relevant to obtaining modulators, such as the electronic charge at different locations in the structure or information concerning whether or not the bonds in the structure can be rotated.

The coordinates/model used in the method typically comprise a specific region of the surface of CD28 corresponding to the site where it is desired for the modulator to bind. Such a site typically comprises Glu-32, Arg-34, Tyr-51, Glu-97, Met-99, Tyr-100, Pro-101, Pro-102, Pro-103, Tyr-104 and Leu-105, or a part thereof which comprises one or more of these amino acids. Preferred modulators bind to such a site or part thereof. In one embodiment the modulator is able to inhibit binding of another moiety to this site. Such a moiety may be an antibody which is specific to the site.

In the method the coordinates/model of CD28 are compared to the structural coordinates/model of a candidate modulator to determine whether or not the candidate modulator will bind to CD28. The comparison may be performed by any suitable means, such as the methods described or referenced in Lyne (2002) Drug Discovery Today 7, 1047-1055. Thus one or more of the algorithms described in this document may be used, such as one or more of Dock, FlexX, FlexE, Slide, Fred, Gold, Glide, AutoDock, LigandFit, ICM, QXP, Amber, CHARMM, SCORE, VALIDATE, Chemscore, Ludi, PLP, PMF, Bleep, SmoG, ZAP, VIDA, GRID, MCSS, Superstar and ROCS.

The method typically comprises deducing one or more ways of fitting (docking) a candidate modulator with CD28 followed by an evaluation (scoring) of the fit. The evaluation may comprise deducing the binding energy between CD28 and the modulator. This may be done based on the interatomic distances between the atoms involved in binding or by analysis of the force fields of CD28 and the modulator. In one embodiment the evaluation comprises comparing the similarity between the fit between CD28 and the candidate modulator and the fit between one or more other proteins and their ligands. Thus the evaluation may comprise comparison with a database of structures of proteins fitted/bound to ligands.

A candidate modulator which has been selected computationally as discussed above may be physically tested to determine whether or not it is able to bind or modulate CD28. Any suitable binding or activity assay may be used. The binding assay may measure the extent of direct binding between the candidate modulator and CD28 or instead be in the form of a competition assay. The binding assay may comprise/use of any of the following:

(a) an assay of binding to CD28 (which may be immobilized), for example in which
  (i) the inhibition of B7-1 binding to the CD28 (a soluble form of B7-1 may be used) in the presence of the candidate modulator is measured,
  (ii) inhibition of the binding of an antibody (that binds to the ligand binding face of CD28) to the CD28 in the presence of the candidate modulator is measured,
(b) a scintillation proximity assay (SPA) in which (i) or (ii) above are measured,
(c) an ELISA assay in which (i) or (ii) above are measured.

The activity assay may test the effect of the candidate modulator on the ability of B7-1 or B7-2 to activate CD28. In such an assay, B7-1 or B7-2 may be present on a natural or artificial antigen-presenting cell and CD28 may be present on a T cell. CD28 activity may be detected by measuring the extent of T cell activation, for example by determining the extent of T cell proliferation (e.g. thymidine incorporation) or gene expression in the T cell (e.g. with microarrays).

The candidate modulator may be tested using the assays described in Green N J, Xiang J, Chen J, Chen L, Davies A M, Erbe D, Tam S, Tobin J F. (2003) Structure-activity studies of a series of dipyrazolo[3,4-b:3',4'-d]pyridin-3-ones binding to the immune regulatory protein B7.1. Bioorg Med Chem. 11, 2991-3013 or Erbe D V, Wang S, Xing Y, Tobin J F. (2002) Small molecule ligands define a binding site on the immune regulatory protein B7.1. J Biol Chem. 277, 7363-8.

The Antibody and Chimeric Protein of the Invention

The term "antibody" as used herein is understood to also include fragments and derivatives of the antibody which retain binding ability, unless the context requires otherwise. Such fragments/derivatives include Fv, F(ab') and F(ab')$_2$ fragments, as well as single chain antibodies, camelid antibodies and similarly acting proteins.

The antibody of the invention may be of any species, such as a mammalian or bird antibody, preferably a rodent (such as mouse) or primate (such as human) antibody. The antibody may be a chimeric antibody, a CDR-grafted antibody or a humanised antibody. The antibody may be monoclonal or polyclonal. The antibody is preferably an IgG antibody.

The invention also provides two types of chimeric protein that bind to a receptor. One type of chimeric protein comprises the sequence of a fragment of a ligand of the receptor, or sequence that is homologous to such a fragment. The sequence is capable of binding to an extracellular region of the receptor, as discussed further below. The chimeric protein also comprises the Fc region of an antibody, such as that of any of the types of antibody discussed above. Where the chimeric protein is administered to an individual the Fc region may be of an antibody of the same species as the individual.

The second type of chimeric protein provided by the invention comprises two Fv regions of an antibody. The Fv regions may be the same or different. One of the Fv regions is capable of binding to the extracellular region of the receptor (the "first" receptor). The other Fv region may bind the extracellular region of a "second" apposing receptor, this being the same type of receptor as the first receptor (with the second Fv binding at a location which is the same or different from the first Fv region) or an entirely different cell surface receptor, for example in the case where the first and second receptors are each expressed on the surfaces of two cells capable of interacting/contacting each other. Such cells may be any of the types of cell mentioned herein, including T cells.

In one embodiment the second Fv region of the second type of chimeric protein binds to a protein expressed on the surface of T cells, such as the T cell receptor, CD2, CD4, CD5, CD8, CD52 or CS1. The second Fv region may bind proteins expressed on the surface of other cells, such as CD48, CD58, CD59, B7-1 or B7-2. The term "receptor" when used in the present context refers to a protein expressed on surface of a cell (which may or may not be one which is capable of signal transduction, for example).

The antibody and chimeric protein of the invention are able to cause superagonistic signalling of a cell surface receptor when they bind to the receptor, typically according to the mechanism illustrated in FIG. 1. Thus the antibody or chimeric protein is able to cause activation of the receptor (i.e. cause the receptor to transduce a signal to the cytoplasm of the cell) without the need for additional costimulus of the receptor or cell. As mentioned above, in one embodiment the second type of chimeric protein comprises Fv regions able to bind to different types of receptors. Such a chimeric protein is preferably able to induce superagonistic signalling by both of the receptors which it binds.

The antibody and both types of chimeric protein bind the extracellular portion of the receptor at a membrane proximal region of the receptor, typically to a region of the receptor which is within 75 Å of the cell membrane, such as within 60 Å, 50 Å or 40 Å of the cell membrane. However the second type of chimeric protein of the invention typically also binds the extracellular portion of the second apposing receptor (as defined above), within 75 Å of the cell membrane, such as within 60 Å, 50 Å or 40 Å of the cell membrane.

Generally the antibody or chimeric protein will be capable of binding the native form of the receptor (at the extracellular regions discussed above) when the receptor is present on the surface of the cell where it occurs naturally.

The antibody or chimeric protein cause superagonistic signalling by sterically hindering the access of phosphatases (which tend to be large proteins), such as CD45, to the receptor (i.e. hindering contact of the phosphatase and receptor). In the case of the antibody or first type of chimeric protein such steric hindrance may be caused by the antibody binding to the receptor at one end (through the Fab of the antibody of the invention or the ligand sequence of the first type of chimeric protein) and typically binding to a protein on the surface of another cell (e.g. due to the Fc region of the antibody or chimeric protein binding to an Fc receptor expressed on a second cell), thus bringing the cell membrane of the two cells into close proximity in the region of the receptor.

For the second type of chimeric protein, one of the Fv fragments of the chimeric protein will bind to the receptor, and in the case where the other Fv fragment is specific for a second type of receptor expressed on another cell, the other Fv fragment will bind to the second receptor and thus bring the cell membranes of the two cells into close proximity in the region of the first receptor.

For the antibody and both types of chimeric protein, the close proximities of the cell membranes in the region of the first receptor will sterically hinder phosphatases from accessing the receptor, leading to signal transduction or "triggering" of the receptor. The antibody or chimeric protein are typically capable of bringing the cell membranes of two cells within 200 Å of each other, such as within 180 Å, 150 Å or 120 Å of each other.

The antibody or chimeric protein will preferably bind orthogonally to the main axis of the domain of the receptor which is bound, such as at more than 60 degrees from the main axis of the bound domain of the receptor, for example at more than 70, 80 or 90 degrees. The antibody or chimeric protein will preferably lie substantially parallel to the cell surface when bound to the receptor (to ensure the membranes are brought into close proximity).

The antibody or chimeric protein will bind to an extracellular region of the receptor, generally to amino acids of the receptor that are exposed at the surface of the protein. The amino acids in the receptor that are bound may be present in a loop region or a β-strand of the receptor. Preferred loops and strand sequences are shown for key examples in Table 1. The antibody or chimeric protein may bind to any of the epitopes or part thereof shown in Table 1 or an equivalent homologous sequence from the membrane proximal region of other receptors.

The antibody of the invention does not bind only to the C'-D loop of CD28, and thus in one embodiment will bind both the C'-D loop of CD28 and another region of CD28. The antibody may be one which does not bind any portion of the C'-D loop of CD28. The antibody may or may not bind to the C'-D loop (or the equivalent loop) of any other member of the CD28 family of proteins. The antibody of the invention may or may not bind to any or all of the sequences shown in Table 3.

The first type of chimeric protein of the invention may or may not bind to only the C'-D loop of CD28. The first type of chimeric protein may be one which does not bind to any portion of the C'-D loop of CD28. The first type of chimeric protein may or may not bind to the C'-D loop (or the equivalent loop) of any other member of the CD28 family of proteins. The first type of chimeric protein may or may not bind to any or all of the sequences shown in Table 3.

The second type of chimeric protein of the invention may or may not bind to only the C'-D loop of CD28. The second type of chimeric protein may be one which does not bind to any portion of the C'-D loop of CD28. The second type of chimeric protein may or may not bind to the C'-D loop (or the equivalent loop) of any other member of the CD28 family of proteins. The second type of protein may or may not bind to any or all of the sequences shown in Table 3.

Receptors Bound by the Antibody and Chimeric Protein

The receptors which are bound by the antibody or chimeric protein of the invention are expressed on the cell surface. The receptor is capable of being phosphorylated (typically at one or more tyrosine residues in the cytoplasmic region of the receptor), and phosphorylation of the receptor will typically lead to its activation. The receptor will comprise a cytoplasmic domain that is dependent on extrinsic protein kinases to be phosphorylated. Thus the receptor will not have an intrinsic enzymatic (kinase or phosphatase) activity. The receptor will typically comprise tyrosine-containing, activating ITAM motifs ($Yxx/Ix_{7-12}YxxL/I$), inhibitory ITIM motifs (I/V/L/SxYxxL/V) or "switch" (TxYxxV/I; activating and inhibitory) signalling motifs (where x is any amino acid). These motifs are phosphorylated by cytoplasmic tyrosine kinases, such as the Src kinases, in competition with antagonistic tyrosine phosphatases, such as CD45. The signalling character of the receptors is defined exclusively by the nature of these motifs (ITAM vs ITIM: activating vs inhibitory).

The receptor may be a member of any surface protein superfamily, but is typically a member of the immunoglobulin superfamily. The receptor may be a member of the CD28 superfamily. The receptor may be any of the specific receptors which are shown in Table 1 or 2 or may comprise a sequence which is homologous to the sequence of any of these specific receptors. The receptor may be CD28, CTLA-4, ICOS, PD-1 or BTLA or comprise a sequence which is homologous to the sequence of any of these specific receptors.

The receptor may be of any of the species that are mentioned herein, and thus may be a mammalian or avian, preferably rodent (such as mouse or rat) or primate (such as human) receptor.

The receptor may be naturally present on a cell of the immune system such as a T cell, B cell, myeloid cell, mast cell, NK cell or a granulocyte.

Screening Methods of the Invention

The invention provides a method of obtaining an agent which is capable of superagonising the above-mentioned receptor which binds to the antibody and chimeric protein of the invention. The method comprises determining whether a candidate agent has any of the properties discussed above possessed by the antibody or chimeric protein of the invention which allows them to induce superagonistic signalling by a receptor. Thus the method will generally comprise determining whether a candidate agent is able to bind to an extracellular membrane proximal region of the receptor, and may also determine whether a candidate agent is able to bind at a particular location from the cell membrane (such as within 75 Å of the cell membrane), to particular sequences (such as the sequences mentioned in Table 1), or in a manner (such as orthogonal to the main axis of the bound receptor domain) which is discussed above for binding of the antibody or chimeric protein of the invention.

Suitable extracellular membrane proximal regions of a receptor may be identified using a sequence database search algorithm (e.g. BLAST) to search for the solved structure most related to the receptor in the protein structural database (PDB). This structure would then be used to identify membrane proximal regions (preferably β-strands) in the receptor by sequence alignment. Whether or not a candidate agent binds to the identified sequences could be determined by taking the midpoint of the strand and the side chains of amino acids two- and three-residues below this mid-point could then be mutated. Mutant forms of the receptor mutated at each of these residues would then be expressed (e.g. on suitable target cells that can be transfected stably or transiently, such as 293T cells), and used to screen for candidate agents that bound the non-mutated receptor but failed to bind the mutant receptor, for example using fluorescence-activated cell sorting. It is envisaged that only every second strand in a conventional beta barrel protein would need to be mutated. In the case of a receptor which is a member of the immunoglobulin superfamily, this corresponds to 8-10 mutant lines being generated, in total. Examples of this process are shown in FIG. 2 for the immediate CD28 family members (ICOS and CTLA-4) and for the PD-1 protein, which is representative of receptors not related to CD28.

Agents that induce superagonistic signalling by a receptor may also be identified using a peptide which comprises sequence from the extracellular membrane proximal region of a receptor or homologous sequence thereto. Such a sequence is typically 5 to 20 amino acids long, such as 10 to 15 amino acids long. In one embodiment the agent is identified using peptide arrays. The mapping of discontinuous epitopes can be performed using overlapping peptides derived from the entire primary sequence of a protein. The whole protein sequence is generated in the form of short overlapping peptides (for example each shifted by 3 amino acids), e.g. prepared by standard spot synthesis (Automated Spot Synthesiser, Abimed, Langenfeld, Germany) on Whatman 50 filter paper (Whatman, Maidstone, England). The C-termini of the peptides may be attached to cellulose via a $(\beta\text{-Ala})_2$ spacer and the N-termini acetylated. The arrays may be subsequently probed either directly on the peptide membrane or after transfer to another surface (e.g. nitrocellulose) using the monoclonal antibody and a chemiluminescence-based detection system (ECL Western Blotting Detection System, Amersham Pharmacia Biotech).

Suitable candidate agents that can be tested in the above screening methods include antibody agents (for example, monoclonal and polyclonal antibodies, single chain antibodies, chimeric antibodies and CDR-grafted antibodies). Furthermore, combinatorial libraries, defined chemical identities, peptide and peptide mimetics, oligonucleotides and natural agent libraries, such as display libraries (e.g. phage display libraries) may also be tested. The candidate agents may be chemical compounds, which are typically derived from synthesis around small molecules. Batches of the candidate agents may be used in an initial screen of, for example, ten substances per assay, and the agents of batches which show the required property tested individually.

Obtaining a Superagonistic Antibody

The invention provides methods for obtaining a superagonistic antibody. In one embodiment the method comprises screening antibodies for the ability to superagonise a receptor, wherein the antibodies have been obtained either by immunizing an animal with the receptor or a homologue or fragment of the receptor, or from a combinatorial antibody library. Preferably the animal is immunized with a protein which comprises the sequences shown in Table 1, or a fragment thereof, or a homologue of such a sequence or fragment.

Whether or not an antibody is a superagonistic antibody may be ascertained by determining whether or not the antibody can bind an extracellular membrane proximal region of a receptor, for example using any of the suitable methods described above in the section of screening for superagonistic agents.

Alternatively the antibody can be tested in an activity assay to see whether or not it causes activation of the receptor. Receptors that are activated by the antibody will either transduce an activating signal or an inhibitory signal to the cell cytoplasm. In the case of receptors which transduce an activating signal, as in the case of CD28, the activity which is tested may be activation of the cell. This can be determined using functional screens based on, for example, cell proliferation, increased cellular calcium, enhanced tyrosine phosphorylation of proteins in the cell or the production of/release of substances by the cell, e.g. IL-2 production: In the case of receptors that transduce inhibitory signals when activated, activation of such receptors can be ascertained by detection of any of the changes which occur to the receptor or the cell when such a signal is transduced, such as changes in the extent of phosphorylation of one or more proteins in the cell.

The binding or activity assay may be carried out in vitro (inside or outside a cell) or in vivo.

In one embodiment of the method the antibody is obtained by immunising an animal with a peptide comprising a sequence of length 5 to 20 amino acids which represents an extracellular membrane proximal region of the receptor, or a homologue of such sequence, and obtaining the antibody produced by the animal against said sequence. Alternatively the antibody may be obtained by selecting an antibody from a combinatorial library based on its ability to bind a peptide comprising a sequence of length 5 to 20 amino acids which represents an extracellular membrane proximal region of the receptor, or a homologue of such sequence.

In one embodiment the peptide which is used to immunise the animal or select an antibody from a library only comprises sequence from the receptor, or a homologue thereof, and does not comprise any additional sequence. In this embodiment the peptide will only be 5 to 20 amino acids long. However in other embodiments the peptide comprises other sequence to the N-terminus and/or C-terminus of the receptor sequence, such as sequence which is different from (and typically not homologous to) receptor sequence.

Antibodies

Various types of antibodies are mentioned herein, including antibodies obtained by immunisation. Such antibodies may be raised against specific epitopes/sequences. An antibody, or other compound, "specifically binds" to a sequence when it binds with preferential or high affinity to the sequence for which it is specific but does not bind or binds with only low affinity to other sequences. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific sequence and its antibody and the measurement of complex formation.

Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising antibody in a host animal.

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified.

A method for producing a monoclonal antibody comprises immortalising cells which produce the desired antibody. Hybridoma cells may be produced by fusing spleen cells from an inoculated experimental animal with tumour cells (Kohler and Milstein (1975) *Nature* 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat, mouse, guinea pig, chicken, sheep or horse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

The Peptide of the Invention

The invention also provides a peptide of length 5 to 20 amino acids comprising a sequence which binds to the superagonistic antibody of the invention. The peptide may have a length of 10 to 15 amino acids. The peptide may comprise sequence from an extracellular membrane proximal region of any of the receptors mentioned herein or have a homologous sequence thereto (such sequence may have a length of 5 to 20 amino acids). The peptide may thus comprise any of the sequences shown in Table 1 or homologues of such sequences.

Therapeutic Aspects of the Invention

The invention provides substances which can be used to treat a patient. The patient is typically a human or animal, such as a mammal or bird, for example a cow, sheep, goat, pig, camel, horse, dog, cat, goose, duck or chicken.

The modulator of CD28 which is identified from a structural model or structural coordinates of CD28 can be used to modulate the immune system of a patient. Such modulators will either agonise or antagonize CD28 (i.e. cause or contribute to an increase or decrease, respectively, in CD28 signalling activity). Modulators which agonise CD28 may be used to stimulate the activity of T cells (which express CD28) and thus to stimulate an immune response against an antigen. Such modulators may therefore be used in the prevention or treatment of a disease caused by a pathogenic agent, such as a virus, microorganism (for example a bacterium) or multicellular organism; or in the prevention or treatment of a cancer.

Modulators which antagonise CD28 may be used to inhibit the activity of T cells, and thus to inhibit an immune response to an antigen. Such modulators may be used to prevent or treat an autoimmune disease (such as rheumatoid arthritis or asthma), allergy or transplantation rejection.

The superagonistic antibodies, chimeric proteins and agent described herein may also be used in the therapy of patients to prevent or treat a disease. These substances may be used to modulate the state of a cell on which the relevant receptor is present. Thus the substance may activate or inhibit cell activity depending on whether the activated receptor transduces a stimulatory or inhibitory signal to the cytoplasm of the cell. The modulation of the cell may thus be used to treat a disease caused by the cell or a disease which can be alleviated or prevented by the cell.

In a preferred embodiment the cell is a cell of the immune system (e.g. any such cell mentioned herein) and therefore superagonistic antibodies, chimeric proteins and agents may be used to modulate the immune response of a patient. Superagonistic antibodies, chimeric proteins and agents which stimulate an immune response may be used in the prevention or treatment of a disease caused by a pathogenic agent, such as a virus, microorganism (for example a bacterium) or multicellular organism; or in the prevention or treatment of a cancer. Superagonistic antibodies, chimeric proteins and agents which inhibit an immune response may be used to prevent or treat an autoimmune disease (such as rheumatoid arthritis or asthma), allergy or transplantation rejection.

The patient may also be treated by generating a superagonistic antibody response in the patient by immunisation with a peptide that stimulates the generation of such a response. The antibody that is generated will be specific to a sequence present in the peptide. The peptide will comprise sequence from the extracellular membrane proximal region of a receptor, or sequence which is homologous thereto. Such receptor sequence may be any of the membrane proximal sequences of a receptor (or homologues thereof) mentioned herein. Thus the peptide may be any of the peptides mentioned herein which comprise such sequence.

In one embodiment a nucleic acid capable of expressing any of the above-mentioned therapeutic substances is administered to the patient. Such nucleic acid typically comprises a region which encodes the therapeutic substance and a control region which causes expression of the coding sequence, such as a promoter. Thus the nucleic acid may be in the form of a vector.

The Substances Mentioned Herein

The modulators, antibodies, chimeric proteins, peptides and nucleic acids mentioned herein may be present in a substantially isolated form. They may be mixed with carriers or diluents which will not interfere with their intended use and still be regarded as substantially isolated. They may also be in a substantially purified form, in which case they will generally comprise at least 90%, e.g. at least 95%, 98% or 99%, of the proteins nucleic acids or dry mass of the preparation.

Homologues

Homologues of protein sequences are referred to herein. Such homologues typically have at least 50% homology, preferably at least 60%, 70%, 80, 90%, 95%, 97% or 99% homology, for example over a region of at least 15, 20, 30, 100 more contiguous amino acids. The homology may be calculated on the basis of amino acid identity (sometimes referred to as "hard homology").

For example the UWGCG Package provides the BESTFIT program which can be used to calculate homology (for example used on its default settings) (Devereux et al (1984) *Nucleic Acids Research* 12, p 387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information (http://www.ncbi.nhn.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.*, USA 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by at least 1, 2, 5, 10, 20 or more mutations (each of which may be a substitution, deletion or insertion of an amino acid). These mutations may be measured across any of the regions mentioned above in relation to calculating homology. The substitutions are preferably conservative substitutions. These are defined according to the following Table. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Administration

The formulation of any of the therapeutic substances mentioned herein will depend upon factors such as the nature of the substance and the condition to be treated. Any such substance may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. The substance may also be administered as suppositories. A physician will be able to determine the required route of administration for each particular patient.

Typically the substance is formulated for use with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in a known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

A therapeutically effective amount of substance is administered. The dose may be determined according to various parameters, especially according to the substance used; the age, weight and condition of the patient to be treated; the route of administration; and the required regimen. Again, a physician will be able to determine the required route of administration and dosage for any particular patient A typical daily dose is from about 0.1 to 50 mg per kg, preferably from about 1.0 mg per kg to 10 mg per kg of body weight, according to the activity of the specific therapeutic substance, the age, weight and condition of the subject to be treated, the type and severity of the disease and the frequency and route of administration. Preferably, daily dosage levels are from 5 mg to 2 g.

The following Examples illustrate the invention:

EXAMPLES

Overview of Crystallisation Strategy

In order to undertake crystallization trials with glycoproteins, such as the CD28 homodimer, it is generally necessary to produce large amounts of protein (>10 milligrams). For this the glutamine synthetase-based Chinese hamster ovary cell expression system (Lonza Biologics Plc, UK) was chosen, which is one of the few eukaryotic expression systems capable of glycoprotein production at this level. The Lec3.2.8.1 cell line was used as the expression host as this provides the option of enzymatically removing unnecessary glycosylation after protein folding and secretion has taken place; which generally favours crystallization. In order to enhance homodimerization, the protein was expressed in the form of a fusion protein with the Fc region of immunoglobulin, which is itself a homodimer. Because the link between the CD28 portion and the Fc is extremely flexible (which will generally discourage crystallization), the construct was prepared in a way that made it thrombin-cleavable.

It was found that producing active, thrombin-cleavable protein depended on the location of the cleavage site. When the cleavage site was too close to the ligand binding domain (to make a more compact protein for crystallization), the protein produced was mis-folded.

In general removal of the N-linked glycans from a glycoprotein substantially enhances its ability to crystallise. Unexpectedly, and in marked contrast to other cell surface glycoproteins, which are generally very stable and active after deglycosylation, the CD28 homodimer proved to be very unstable after deglycosylation with the enzyme endoglycosidase H at the slightly acidic pH at which this enzyme is active. Therefore it was necessary to leave the glycosylation of CD28 intact. The glycosylated form of the homodimer failed to crystallise in more than 100 trials.

To reduce the impact of the glycosylation, therefore, an alternative strategy was employed, in which Fab fragments of anti-CD28 antibodies were prepared and crystallised with CD28. Fab fragments are almost invariably unglycosylated, so the formation of complexes with the Fab can be expected to reduce the impact of the glycans by 80%, regardless of where they bind the protein of interest (a Fab is four times the size of the CD28 monomer). The likelihood that the complex of the Fab and protein of interest will crystallise depends on the overall shape of the complex, (i.e. its "compactness") and on the chemical properties of the surfaces of the complex involved in forming crystal lattice contacts. Because the surface of the complex that will form lattice contacts cannot be predicted a priori, it is impossible to predict whether a given Fab will give crystals when complexed with the protein. Not unexpectedly, therefore, the homodimer still failed to crystallize after being complexed with one Fab molecule per homodimer for two different antibodies (5.11A1 and 9D7), or two Fabs per homodimer for one of these antibodies (5.11A1), in >100 trials per complex.

In addition the stalk region was expected to create problems. The key to obtaining crystals was to prepare monomeric CD28 by gentle reduction and alkylation of the interchain disulphide bond in the stalk-like region of the homodimer. The expectation was that the presence of an intact disulphide in the stalk might rigidify the stalk making the overall structure less compact. Two complexes formed with the monomer and two different Fabs (5.11A1 and 9D7) gave crystals, but only one of these crystal forms (obtained with 5.11A1 Fab fragments) proved to be suitable for data collection. Other antibodies may also have been useful in crystallising CD28, including antibodies that bind to the same loop of CD28 as bound by 5.11A1 (the C'-D loop) or that bind to the ligand binding site of CD28. Suitable antibodies are described in US-A1-2003/0166860 and Luhder et al (2003) J. Exp. Med., 197, 955-66.

Preparation of CD28 Homodimer (i) Construct Generation

The polymerase chain reaction (PCR) was used to amplify complementary DNA (cDNA) encoding the signal peptide sequence of mouse immunoglobulin heavy chain and the extracellular domain of CD28 (residues 1-134 of the mature polypeptide; SEQ ID NO:1) from 44 ng of the plasmid, pKGe1145. The oligonucleotides used in the reaction added, at the 5' end, an Xba I cleavage site and 24 nt of the rat CD4 5' untranslated region and, at the 3' end, codons for the thrombin cleavage site, LVPRGS. The sequences of the oligonucleotide primers used for this were (oligonucleotide sequences are given in 5' to 3' direction) CD28T__5': TAG TAG TCT AGA CCC CAT CCG CTC AAG CAG GCC ACC ATG GAT TGG CTG CGG AAC TTG; and CD28T__3': CTA CCA CTA CCC CTG GGT ACC AGG GGC TTA G. In a second reaction, cDNA encoding the heavy chain constant (C) region-2 and C region-3 domains of murine Ig (residues 103-323 of the secreted protein) was amplified by PCR from 44 ng of pKGe1145. At the 3' end, the oligonucleotides added an Xba I restriction site to aid cloning. The NH2-terminus of the protein encoded by the Ig cDNA had the sequence GSKPSIS rather than GCKPCIC. The sequences of the oligonucleotide primers for this reaction were Ig__5': CTA AGC CCC TGG TAC CCA GGG GTA GTG GTA G; and Ig__3': CTA CTA TCT AGA TTA TTT ACC AGG AGA GTG GGA G. The PCR conditions for both reactions were: denaturation at 94° C. for 15 s, annealing at 59° C. for 30 s, extension at 68° C. for 210 s; 2.5 U of Accuzyme polymerase (Bioline Ltd, U.K.), 300 nM oligonucleotides and 200 µM dNTPs were used and the reactions run for 20 cycles.

In a third reaction, PCR was used to anneal the two initial products together to generate cDNA encoding a chimera consisting of the CD28 extracellular domain fused to murine IgGFc via a thrombin cleavable sequence (called the CD28TFc chimera; SEQ ID NO:2). Ten microlitres of each of the initial PCR reaction product mixtures was used as template and 300 nM of the CD28__5' and Ig__3' oligonucleotides was also added to the mix. The PCR conditions were otherwise identical to the first set except that they were run for only 4 cycles. The PCR product was gel-purified, cut with Xba I and cloned into the Xba I site of pEE14 for expression in the glutamine synthetase-based gene expression system (Lonza Biologics Plc, UK). The plasmid construct was then sequenced using dideoxy sequencing.

(ii) Expression of the CD28TFc Chimera

Lec3.2.8.1 cells, 2×10⁶/flask, were transfected with 20 µg of DNA/flask for 3 h using Pfx-8 lipids (Invitrogen Inc), and then the cells were cloned the following day by plating out at 2×10⁶ cells/96-well plate. After 2 weeks, the clones expressing the highest amounts of CD28TFc were selected by Western-blotting using the semi-quantitive ECL detection system (Amersham-Pharmacia, UK) and an anti-mouse Fc primary antibody (Sigma-Aldrich Co.). The best-expressing clone was expanded and grown to confluence in bulk culture in Cell Factories (Nunc A/S, Denmark) containing immunoglobulin-free medium (Invitrogen-Gibco Ltd, UK) in the presence of 2 mM sodium butyrate. The supernatant was harvested after approximately four weeks and clarified by centrifugation at 5,000 g.

(iii) CD28TFc Purification

The spent, clarified medium was concentrated to approximately ⅙ of the original volume using a Masterflex L/S concentrator (Helixx Technologies, Inc.). The sample was then buffer-exchanged against the original volume of 3 M NaCl, 1.5 M glycine, pH 8.5 high-salt buffer and the protein incubated with Protein A Sepharose beads (Sigma-Aldrich Co.) using 10 mls of swollen beads/litre of concentrated supernatant at 1 litre of supernatant/5 litre conical flask or beaker. The pH was adjusted to pH 8.5 with 2.75 M Tris, pH 8.5 to allow binding of the CD28TFc to Protein A overnight with gentle stirring at 4° C.

The beads were allowed to settle for 2 h prior to siphoning off the depleted supernatant. The settled beads were then transferred to 50 ml Falcon tubes (Becton Dickinson Biosciences, UK) and recovered by centrifugation at 200 g. The beads were transferred to a 30 ml column (Biorad, UK) and then washed with 300 mls of cold phosphate-buffered saline, 0.5 M NaCl, pH 8.3. The column was eluted with 0.1 M citric acid, pH 3.0 into 10×2 ml fractions in glass tubes containing 0.4 ml of 2.75M Tris, pH 8.5 for immediate neutralization of the citric acid. Fractions containing CD28TFc according to analysis by 12% sodium dodecyl sulphate polyacrylamide gel electrophoresis (SDS-PAGE) were concentrated to 0.5 ml or no higher concentration than 20 mg/ml using a Centriprep 10 concentrator (Millipore Corp). The protein was then applied to a Superdex 200 H/R gel filtration column (Amersham Biosciences) pre-equilibrated with 10 mM Hepes, 140 mM NaCl, pH 7.4 (HBS buffer) for up to three successive runs. Eluting fractions were monitored for absorbance at 280 nm. Protein-containing fractions were examined by SDS-PAGE. Each cycle of batch purification yielded ~9 mgs of CD28TFc; up to 7 batch purifications was required to deplete all the CD28TFc per set of 6 cell factories (~5 liters of starting tissue culture supernatant).

(iv) Thrombin Protease Cleavage of CD28TFc

The most-pure fractions containing CD28TFc were pooled for thrombin cleavage. Initial trial titrations dictated the use of the following conditions for large-scale cleavage of CD2TFc: lyophilized thrombin (Sigma-Aldrich Co.) was re-hydrated in HBS buffer to a concentration of 1 U/µl and this was then added to the CD28TFc at 0.11 µl/6 µg of protein for overnight digestion at 37° C. The reaction was stopped by addition of freshly re-hydrated benzamidine to a final concentration of 1 mM. A 12% non-reducing SDS-PAGE gel was used to confirm the extent of cleavage.

(v) Purification of the CD28 Homodimer

The pH of the thrombin-cleaved protein was adjusted to pH 8.5 using 2.75 M Tris pH 8.5, prior to concentration to 0.5 ml using a Centriprep 10 concentrator (Millipore Corp). Fresh Protein A beads were washed and rehydrated to a final volume of ~5 mls, prior to being packed into a 0.7 cm×20 cm Econo-column (Bio-Rad, U.K.) and then equilibriated with HBS, pH 8.5 at 4° C. The concentrated protein was then applied to the column, allowed to run into the bed, and then sequential fractions were eluted by addition of 0.5 ml of HBS, pH 8.5 to the top of the bed every 10 minutes for 2 h. The absorbance of each fraction was determined at 280 nm. The extent of separation of the Fc from the thrombin-released CD28 homodimer was determined by 12% SDS-PAGE analysis of the fractions under non-reducing conditions. The critical steps for good separation were (1) to allow the protein to pass slowly through the column and (2) to conduct the separation at 4° C. The homodimer was concentrated to 0.5 ml and subjected to gel-filtration on a Superdex 75 H/R column (Amersham Biosciences). The purified homodimer was used for crystallization trials, reduced and alkylated for other crystallization trials (see below), or frozen at −80° C. for future use.

Preparation of Fab Fragments of 5.11A1 Antibody

Fab fragments were prepared using the Pierce Biotechnology ImmunoPure® Fab Preparation Kit, as briefly outlined below.

(i) Fab Fragment Generation and Purification

Nine millilitres of whole, purified 5.11A1 antibody at 0.3 mg/ml in PBS was concentrated to 1 ml and then diluted to 10 mls with 20 mM sodium phosphate, 10 mM EDTA, pH 7 and then re-concentrated to 0.5 ml. To this was added 0.5 ml of 20 mM sodium phosphate, pH 7 containing 3.5 mg/ml cysteine●HCl. The 1 ml mixture was then added to 0.5 ml of a 50% slurry of Sepharose-immobilized Papain supplied with the kit, which had been pre-equilibrated with 20 mM sodium phosphate pH 7 containing 3.5 mg/ml cysteine-HCl. This was then incubated for 5 hours in a shaking water bath at 37° C. The cleaved Fab and Fc fragments and undigested IgG were separated from the Immobilized Papain beads by centrifugation at 1000 g and the beads rinsed with 1.5 ml of the ImmunoPure IgG Binding Buffer supplied with the kit. The wash was then combined with the crude digest and the mix applied to a Sepharose-immobilized Protein A column pre-equilibrated with 13 ml of ImmunoPure IgG Binding Buffer. The column was washed with 6.0 ml of the Binding Buffer and the eluate containing the Fab fragments collected (9 mls in total). The eluate was concentrated to 0.5 ml and applied to a Superdex 200 H/R gel filtration column (Amersham Biosciences) pre-equilibrated with HBS buffer. Eluting fractions were monitored for absorbance at 280 nm. Protein-containing fractions were examined by SDS-PAGE.

Preparation of a Crystallizable Form of CD28

(i) Reduction and Alkylation of CD28

CD28 has an interchain disulphide bond within the "stalk-like" region that is largely responsible for homodimerization. It was speculated that its location within the stalk would render it more sensitive to reducing agents than the "canonical" disulphide bond and one other disulphide buried within the ligand-binding domain. If true this meant that monomeric CD28 could be generated which was native-like and fully active for ligand and antibody binding. The minimum concentration of reducing agent required to release the monomer was ascertained by titrating the reducing agent, dithiothreitol (DTF). The reduced cysteines in the protein and excess DTT were each then inactivated by alkylation with a 2.2-fold molar excess of iodoacetamide (IAA). This titration indicated that the optimal conditions were 12.5 µM protein, 1.5 mM DTT and 3.3 mM IAA. The reduced protein sample, generally ~4 ml, was finally concentrated to 0.5 ml and separated from unreduced homodimer by gel-filtration on a Superdex 75 H/R column (Amersham Biosciences).

Crystallographic Methods (i) Crystallization and Data Collection

The CD28/5.11A1 Fab complex was formed by incubating a 2:1 molar ratio of CD28 and Fab, followed by concentration of the protein mixture to 15.6 mg/ml in HBS (the extinction coefficient, $\epsilon$, of CD28 is 1.7 and that of the Fab is 1.4). Crystals were grown at 18° C. in 0.2 µl hanging drops (0.1 µl of the protein mixture plus 0.1 µl of precipitating reagent) set up using a Cartesian Robot (APS Robotics & Integration, llc; Brown et al (2003) J. Appl. Cryst. 36, 315-18). The precipitating reagent consisted of a mixture of 0.2 M magnesium formate and 20% polyethylene glycol 3350 in water. Crystals appeared in 5-7 days and were cooled to 100K in the precipitating reagent with glycerol added to a final concentration of 10%, using a Cryojet liquid nitrogen system for data collection (Oxford Instruments, Abingdon, UK). Crystals belong to space group C2 with unit cell dimensions a=191.2, b=47.4, c=71.8 Å and a calculated solvent content of 56-58% for one CD28 monomer and one Fab molecule per asymmetric unit (ignoring the effects of glycosylation). The 2.7 Å resolution data were collected from a single crystal at 100K at Beamline ID2 at the European Synchrotron Radiation Facility using a FReLoN CCD. One hundred and fifty-eight 1° rotation images were collected and reduced with HKL2000 (Otwinowski and Minor (1997) Methods Enzym. 276, 307-26).

(ii) Structure Determination and Refinement

The structure was solved by molecular replacement in XPLOR v3.851 (Brünger (1992) X-PLOR Version 3.1. A system for X-ray crystallography and NMR. Yale University Press, New Haven, Conn.) using a set of search models generated from a single Fab structure (PDB accession no. 15c8) by varying the elbow angle in 2° steps using an XPLOR script. A single unambiguous solution was found when the elbow angle was altered by −8° as defined by the script. After rigid body refinement of each domain of the Fab in CNS (Brünger et al. (1998) Acta Cryst. D54, 905-21), the R-factor was 44.4%. Initial electron density maps phased with Fab alone showed very limited, if any, electron density for the CD28 molecule. The Fab model was mutated to the sequence of 5.11A1 before proceeding with two cycles of manual rebuilding in O (Jones et al (1990) O: A macromolecular modelling environment. Crystallographic and modeling methods in molecular design. Bugg and Ealick, Eds. Springer-Verlag Press 189-95) and positional refinement in CNS, reducing the R-factor to 36.4%. A molecular replacement solution for CD28 was then found by using only regions of human CTLA-4 (from PDB 1i81) with strong sequence homology to CD28, i.e. all the β-strands (except C') and the EF and FG loops, as a search model and by fixing the refined Fab structure. In order to avoid model bias, the refined constant regions of the Fab were replaced with the unaltered constant domains from PDB 15c8 by superposition using SHP (Stuart et al (1979) J. Mol. Biol. 134, 109-42), and the positions were fixed during refinement. The variable regions of the Fab and the CD28 monomer were refined in X-PLOR v3.851 using positional refinement followed by grouped and restrained individual B factor refinement along with manual rebuilding in O. All refinement procedures used data from 25.0-2.7 Å and excluded 5% of reflections randomly selected for generation of the $R_{free}$ data set. The anisotropy of the data was corrected for using X-PLOR and the data were sharpened for all but the last round of refinement. The current model has an R factor of 25.3% and an $R_{free}$ of 33.4% against all data to 2.7 Å. The model includes the CD28 monomer (excluding its C-terminal stalk) from residues 2 to 118, excluding residues Leu28 and Phe29, which are poorly ordered, and the Fab, but with none of the sugar chains built onto the CD28. The model has 76% of residues in the most favoured regions of the Ramachandran plot, with a further 21% in additionally allowed regions.

The Structure of a CD28-Superagonist Antibody Complex

The ligand-binding V-set IgSF domain of the CD28 monomer, solved in complex with 5.11A1 Fab, is very similar to the equivalent region of CTLA-4. Lattice contacts generate a plausible CD28 homodimer. Whilst this dimer is similar to the CTLA-4 homodimer (which is bivalent), the arrangement of the monomers in CD28 is sufficiently distinct to suggest an explanation for the apparent monovalence of CD28, i.e. the membrane proximal domains of ligands competing for each ligand binding site are likely to clash. Cryoelectron microscopic analyses show that both classes of antibodies are bivalent, ruling out aggregation-based explanations for the differential signalling effects of conventional versus superagonistic antibodies. The 5.11A1 Fab fragment binds orthogonally to the surface formed by the CC'C" strands of CD28, favouring the C'C" "edge" of the monomer. This places the two long axes of the Fabs parallel to each other and the cell surface. In contrast, the epitopes of the conventional antibodies are close to the ligand binding "top" of the homodimer.

Signalling by Receptors Dependent on Extrinsic Kinases

The existence of two classes of activating anti-CD28 antibodies, i.e. costimulatory antibodies and superagonists, greatly simplifies the analysis of signalling by this archetypal costimulatory receptor. The observation that the two antibody classes have homologous effects in two different species, and that these effects are predictable simply according to the location of their epitopes, rules out trivial explanations for the distinct signalling properties of these antibodies, e.g. affinity differences. Instead, the receptor-triggering problem is reduced to a comparison of the structural properties of the complexes that these two types of antibodies form with CD28.

From the present crystal structure of the complex of CD28 with a superagonistic antibody, it can be deduced that an antibody-induced increase in the net phosphorylation of the cytoplasmic domain of a given cell surface receptor, due to changes in the rates of phosphorylation and dephosphorylation of it, results in the triggering of that receptor (see FIG. 1). In more detail, the antibodies hold the cell surface at certain distances from an immobilizing substrate (i.e. other, Fc receptor-bearing cells, in vivo or plastic, in vitro), such that the membrane separation in the region of the immobilized antibody and receptor will differentially exclude, from the immediate vicinity of the receptor, other molecules whose extracellular domains are comparable in size or larger than CD28-antibody complexes, such as the tyrosine phosphatase, CD45. In contrast, tyrosine kinases, e.g. p56lck, will be unaffected because they are small and/or attached to the inner leaflet of the membrane. The result is that, overall, the phosphorylation of CD28 will be favoured over its de-phoshorylation (by CD45), with the net increase in phosphorylation amounting to receptor triggering. Superagonists are more potent than conventional antibodies because they bind epitopes close to the membrane rather than at the "top" of the molecule, leading to more efficient segregation of, e.g. CD45, and therefore a larger increase in the net phosphorylation of CD28.

The important corollary of this explanation is that antibodies that bind the membrane-proximal epitopes of the large number of other cell surface molecules not belonging to the CD28 subset of the immunoglobulin superfamily, but sharing the key signalling property of CD28-subset molecules, i.e. a reliance on extrinsic tyrosine kinases, for example PD-1 and BTLA, should also potently invoke the activating or inhibitory signalling properties of those molecules in precisely the same way, allowing the manipulation of cell behaviour with such antibodies.

PD-1 and BTLA

Programmed Death (PD)-1 protein modulates the responses of previously activated T- and B-cells in secondary lymphoid organs or peripheral (parenchymal) tissues. PD-1 is expressed on a subset of thymocytes and upregulated on activated T, B and myeloid cells. The PD-1 ligands, B7-H1 and B7-DC, are more widely expressed than those of CD28 family members and are induced by pro-inflammatory agents on monocytes and dendritic cells and on activated but not resting B cells. B7-DC is expressed in a variety of peripheral tissues, including heart, pancreas, lung and liver. The B and T lymphocyte attenuator (BTLA), is also expressed on activated T and B cells, but attenuates production of IL-2 after binding a different peripherally expressed B7-related protein, called B7x.

PD-1 and BTLA are structurally comparable to other members of the CD28 family only insofar as the proteins also consist of a single V-set IgSF domain supported on stalks, and the cytoplasmic domains contain immunoreceptor tyrosine-based motifs (inhibitory in these two cases). The sequences of the IgSF domains of PD-1 and BTLA indicate that these proteins are unrelated and do not belong to the same subset of the IgSF as CD28. Consistent with the view that PD-1 is involved in maintaining tolerance in normal T cells in the periphery, mice lacking the gene develop a variety of autoimmune-like diseases dependent on the genetic background, including lupus-like arthritis and glomerulonephritis, and have increased serum IgG3 and augmented B-cell proliferative responses to anti-IgM in vivo.

Activating signalling by PD-1 and BTLA, because these molecules are inhibitory, would be expected to dampen a variety of peripheral immune pathologies. Signalling of this type could be stimulated by the binding of superagonistic antibodies to the membrane proximal regions of these proteins. A set of additional molecules, each of which has inhibitory immunoreceptor tyrosine-based signalling motifs and are therefore targets for generating superagonists, is shown in Table 2.

Identifying Epitopes for Superagonists

The procedure is as follows. The "lower", membrane-proximal half of the membrane proximal domain of a given structure, e.g. CD28 in FIG. 2A, is identified by visual inspection of the structure. Superagonistic agents bind residues in this region. For identifying superagonistic agents in receptors closely related to the known structure, the equivalent regions are identified in an alignment of the sequence of the known structure with that of the related proteins as shown in FIG. 2A.

To identify the epitopes of superagonistic antibodies in other molecules that have the requisite signalling properties but for which there is no structure, e.g. PD-1 in FIG. 2B, a structural model is identified by alignment of the sequence with that of the most similar molecule of known structure in the Protein Data Bank (in the example in FIG. 2B, the variable domain of the Ig kappa chain is the structure with the most similar sequence to PD-1). The "lower", membrane proximal half of this domain is highlighted on the structure by visual inspection and the equivalent regions are identified in the sequence alignment. To screen for superagonists, the second and third residues "down" (i.e. toward the membrane) in the marked epitopes shown in parts A and B are identified as shown in FIGS. 2C and 2D. These residues, singly or together preferably form at least part of the epitopes of antibodies or other superagonistic agents, as binding to these residues will require that the binding of the agent is parallel with the cell membrane. These residues can therefore be mutated in proteins used for screening the superagonistic agents (i.e. agents binding to the unmutated protein but not the mutated protein, should be superagonistic).

TABLE 1

CD28 family superagonistic epitopes
Epitopes are named according to the strands from which they derive.

| Protein | A' | B | C-C' | C"-D | E | F | G |
|---|---|---|---|---|---|---|---|
| hCD28<br>hCTLA-4<br>hICOS | SPMLV<br>PAVVL<br>YEMFI<br>(SEQ ID NOs: 23, 24, 25) | AVNLS<br>GIASFV<br>GVQIL<br>(SEQ ID NOs: 26, 27, 28) | SLHKGLDSAVEVCV<br>TVLRQADSQVTEVCA<br>QLLKGGQILCD<br>(SEQ ID NOs: 29, 30, 31) | VYSKTGFNCDG<br>FLDDSICTG<br>VSIKSLKFCHS<br>(SEQ ID NOs: 32, 33, 34) | FYLQN<br>LTIQG<br>FFLYN<br>(SEQ ID NOs: 35, 36, 37) | TDIYFC<br>TGLYIC<br>ANYYFC<br>(SEQ ID NOs: 38, 39, 40) | NGTIIHV<br>NGTQIYV<br>TGGYLHI<br>(SEQ ID NOs: 41, 42, 43) |

PD-1 and BTLA superagonistic epitopes

| Protein | A | B | C-C' | C"-D | E | F | G |
|---|---|---|---|---|---|---|---|
| hpd-1<br>hBTLA | PALLVV<br>QSEHSI<br>(SEQ ID NOs: 44, 45) | DNATF<br>DPFEL<br>(SEQ ID NOs: 46, 47) | RMSPSNQTDK<br>KLNG<br>(SEQ ID NOs: 48, 49) | QPGQDCRFR<br>QTSWK<br>(SEQ ID NOs: 50, 51) | MSVVR<br>LHFEP<br>(SEQ ID NOs: 52, 53) | NDSGTY<br>NDNGSY<br>(SEQ ID NOs: 54, 55) | LRAELR<br>TTLYVT<br>(SEQ ID NOs: 56, 57) |

TABLE 3

| Protein | Sequence |
|---|---|
| hCD28 | GNYSQQLQVYSKTGF<br>(SEQ ID NO: 58) |
| hCTLA-4 | YMMGNELTFLDDS<br>(SEQ ID NO: 59) |
| hICOS | KTKGSGNTVSIKSLK<br>(SEQ ID NO: 60) |
| hPD-1 | LAAFPEDRSQPGQDCR<br>(SEQ ID NO: 61) |

TABLE 2

Targets of inhibitory superagonist antibodies

| Receptor | Chromosome | Expression | no. of ITIMs |
|---|---|---|---|
| FcRIIB | 1q23-24 | B, myeloid, mast | 1 |
| PILR | 7q22 | Myeloid | 2 |
| CD72 | 9p | B | 2 |
| CD5 | 11q13 | T, subset B | 1 |
| MAFA | 12p12-13 | Myeloid, mast, NK | 1 |
| NKG2A | 12p13.1-13.2 | NK, T | 2 |
| CD31 | 17q23 | Myeloid, etc | 1 |
| CMRF35H | 17q24 | Leukocytes | 3 |
| CD22 | 19q13.1 | B | 4 |
| CD66a | 19q13.2 | Granulocytes, etc | 2 |
| CD66d | 19q13.2 | Granulocytes | 1 |
| CD33 | 19q13.3 | Myeloid | 1 |
| SIGLEC5 | 19q13.3 | Myeloid | 1 |
| SIGLEC6 | 19q13.3 | B cells, myeloid | 1 |
| SIGLEC7 | 19q13.3 | NK, myeloid, etc | 1 |
| ILT2, 3, 4, 5 | 19q13.4 | Myeloid, B, etc | 4 |
| LIR8 | 19q13.4 | Myeloid, B, etc | 4 |
| LAIR-1 | 19q13.4 | Leukocytes | 2 |
| KIR2DL | 19q13.4 | NK, T | 2 |
| KIR3DL | 19q13.4 | NK, T | 2 |
| SIRP | 20p13 | Myeloid, etc | 2 |

TABLE 4

Co-ordinates of the CD28/5.11A1 crystal structure

```
REMARK FILENAME = "/mnt/safe6/ed/cd28/cd28_all/xplor/ref18/positionaln3.pdb"
REMARK R = 0.251035 from 25 to 2.7
REMARK DATE: Jan. 09, 2004 09:48:19 created by user: robert
ATOM      1  CB   ASP   1    122.280  49.781  38.327  1.00  64.18  L
ATOM      2  CG   ASP   1    123.319  49.071  37.463  1.00  67.78  L
ATOM      3  OD1  ASP   1    122.934  48.417  36.470  1.00  66.82  L
ATOM      4  OD2  ASP   1    124.524  49.162  37.779  1.00  54.04  L
ATOM      5  C    ASP   1    122.104  52.265  38.005  1.00  50.51  L
ATOM      6  O    ASP   1    122.541  53.057  37.163  1.00  41.52  L
ATOM      7  N    ASP   1    121.674  50.711  36.112  1.00  37.53  L
ATOM      8  CA   ASP   1    121.547  50.905  37.579  1.00  50.29  L
ATOM      9  N    ILE   2    122.073  52.527  39.314  1.00  51.24  L
ATOM     10  CA   ILE   2    122.567  53.783  39.890  1.00  50.84  L
ATOM     11  CB   ILE   2    121.842  54.094  41.240  1.00  22.62  L
ATOM     12  CG2  ILE   2    122.278  55.454  41.781  1.00  18.55  L
ATOM     13  CG1  ILE   2    120.327  54.081  41.022  1.00  30.61  L
ATOM     14  CD1  ILE   2    119.510  54.521  42.229  1.00  31.86  L
ATOM     15  C    ILE   2    124.086  53.714  40.119  1.00  54.91  L
ATOM     16  O    ILE   2    124.645  52.630  40.283  1.00  55.68  L
ATOM     17  N    GLN   3    124.749  54.869  40.136  1.00  58.93  L
ATOM     18  CA   GLN   3    126.204  54.923  40.322  1.00  56.95  L
ATOM     19  CB   GLN   3    126.847  55.679  39.145  1.00  60.02  L
ATOM     20  CG   GLN   3    127.010  54.851  37.863  1.00  63.51  L
ATOM     21  CD   GLN   3    126.479  55.552  36.615  1.00  65.36  L
ATOM     22  OE1  GLN   3    127.024  56.568  36.174  1.00  62.07  L
ATOM     23  NE2  GLN   3    125.412  55.003  36.038  1.00  72.37  L
ATOM     24  C    GLN   3    126.635  55.564  41.650  1.00  51.69  L
ATOM     25  O    GLN   3    126.179  56.649  42.004  1.00  54.63  L
ATOM     26  N    MET   4    127.522  54.889  42.376  1.00  42.42  L
ATOM     27  CA   MET   4    128.005  55.392  43.660  1.00  37.64  L
ATOM     28  CB   MET   4    128.066  54.248  44.671  1.00  54.55  L
ATOM     29  CG   MET   4    127.037  54.319  45.783  1.00  56.74  L
ATOM     30  SD   MET   4    125.360  54.633  45.189  1.00  76.06  L
ATOM     31  CE   MET   4    125.083  56.269  45.843  1.00  68.01  L
ATOM     32  C    MET   4    129.392  56.008  43.507  1.00  44.16  L
ATOM     33  O    MET   4    130.358  55.311  43.176  1.00  35.72  L
ATOM     34  N    ASN   5    129.496  57.310  43.750  1.00  50.40  L
ATOM     35  CA   ASN   5    130.779  57.996  43.624  1.00  58.90  L
ATOM     36  CB   ASN   5    130.703  59.060  42.521  1.00  67.94  L
ATOM     37  CG   ASN   5    130.113  58.517  41.233  1.00  59.91  L
ATOM     38  OD1  ASN   5    130.783  57.811  40.474  1.00  49.08  L
ATOM     39  ND2  ASN   5    128.848  58.839  40.981  1.00  56.43  L
ATOM     40  C    ASN   5    131.191  58.643  44.939  1.00  46.55  L
ATOM     41  O    ASN   5    130.612  59.637  45.368  1.00  40.94  L
ATOM     42  N    GLN   6    132.202  58.076  45.577  1.00  33.77  L
ATOM     43  CA   GLN   6    132.661  58.607  46.846  1.00  36.85  L
ATOM     44  CB   GLN   6    133.257  57.476  47.679  1.00  24.74  L
ATOM     45  CG   GLN   6    132.395  56.218  47.684  1.00  19.84  L
ATOM     46  CD   GLN   6    132.393  55.524  49.029  1.00  27.56  L
ATOM     47  OE1  GLN   6    132.925  56.048  50.013  1.00  30.84  L
ATOM     48  NE2  GLN   6    131.803  54.339  49.082  1.00  34.41  L
ATOM     49  C    GLN   6    133.677  59.725  46.647  1.00  43.10  L
ATOM     50  O    GLN   6    134.328  59.800  45.608  1.00  55.89  L
ATOM     51  N    SER   7    133.807  60.598  47.641  1.00  47.45  L
ATOM     52  CA   SER   7    134.736  61.714  47.543  1.00  54.98  L
ATOM     53  CB   SER   7    134.285  62.858  48.469  1.00  70.71  L
```

TABLE 4-continued

Co-ordinates of the CD28/5.11A1 crystal structure

| ATOM | 54 | OG | SER | 7 | 135.232 | 63.917 | 48.514 | 1.00 | 61.37 | L |
|---|---|---|---|---|---|---|---|---|---|---|
| ATOM | 55 | C | SER | 7 | 136.187 | 61.304 | 47.812 | 1.00 | 57.75 | L |
| ATOM | 56 | O | SER | 7 | 136.828 | 60.732 | 46.928 | 1.00 | 68.97 | L |
| ATOM | 57 | N | PRO | 8 | 136.722 | 61.540 | 49.029 | 1.00 | 48.65 | L |
| ATOM | 58 | CD | PRO | 8 | 136.250 | 62.116 | 50.300 | 1.00 | 21.82 | L |
| ATOM | 59 | CA | PRO | 8 | 138.118 | 61.109 | 49.140 | 1.00 | 47.63 | L |
| ATOM | 60 | CB | PRO | 8 | 138.515 | 61.533 | 50.559 | 1.00 | 29.91 | L |
| ATOM | 61 | CG | PRO | 8 | 137.525 | 62.576 | 50.933 | 1.00 | 26.41 | L |
| ATOM | 62 | C | PRO | 8 | 138.358 | 59.622 | 48.893 | 1.00 | 48.77 | L |
| ATOM | 63 | O | PRO | 8 | 137.820 | 58.772 | 49.604 | 1.00 | 63.86 | L |
| ATOM | 64 | N | SER | 9 | 139.161 | 59.318 | 47.876 | 1.00 | 33.02 | L |
| ATOM | 65 | CA | SER | 9 | 139.500 | 57.939 | 47.548 | 1.00 | 32.48 | L |
| ATOM | 66 | CB | SER | 9 | 140.151 | 57.864 | 46.169 | 1.00 | 30.85 | L |
| ATOM | 67 | OG | SER | 9 | 141.554 | 57.812 | 46.286 | 1.00 | 25.75 | L |
| ATOM | 68 | C | SER | 9 | 140.469 | 57.407 | 48.602 | 1.00 | 30.90 | L |
| ATOM | 69 | O | SER | 9 | 140.661 | 56.197 | 48.737 | 1.00 | 32.96 | L |
| ATOM | 70 | N | SER | 10 | 141.076 | 58.333 | 49.340 | 1.00 | 29.68 | L |
| ATOM | 71 | CA | SER | 10 | 142.022 | 58.018 | 50.412 | 1.00 | 35.34 | L |
| ATOM | 72 | CB | SER | 10 | 143.387 | 57.645 | 49.831 | 1.00 | 49.82 | L |
| ATOM | 73 | OG | SER | 10 | 144.392 | 58.538 | 50.289 | 1.00 | 81.38 | L |
| ATOM | 74 | C | SER | 10 | 142.161 | 59.254 | 51.308 | 1.00 | 31.04 | L |
| ATOM | 75 | O | SER | 10 | 141.964 | 60.379 | 50.839 | 1.00 | 35.88 | L |
| ATOM | 76 | N | LEU | 11 | 142.502 | 59.056 | 52.582 | 1.00 | 27.16 | L |
| ATOM | 77 | CA | LEU | 11 | 142.634 | 60.181 | 53.498 | 1.00 | 24.50 | L |
| ATOM | 78 | CB | LEU | 11 | 141.258 | 60.780 | 53.780 | 1.00 | 47.56 | L |
| ATOM | 79 | CG | LEU | 11 | 141.120 | 61.488 | 55.134 | 1.00 | 57.17 | L |
| ATOM | 80 | CD1 | LEU | 11 | 141.752 | 62.878 | 55.063 | 1.00 | 65.58 | L |
| ATOM | 81 | CD2 | LEU | 11 | 139.650 | 61.583 | 55.509 | 1.00 | 61.17 | L |
| ATOM | 82 | C | LEU | 11 | 143.308 | 59.884 | 54.831 | 1.00 | 22.63 | L |
| ATOM | 83 | O | LEU | 11 | 142.978 | 58.919 | 55.508 | 1.00 | 25.60 | L |
| ATOM | 84 | N | SER | 12 | 144.233 | 60.759 | 55.209 | 1.00 | 33.11 | L |
| ATOM | 85 | CA | SER | 12 | 144.965 | 60.653 | 56.466 | 1.00 | 35.62 | L |
| ATOM | 86 | CB | SER | 12 | 146.465 | 60.745 | 56.201 | 1.00 | 34.92 | L |
| ATOM | 87 | OG | SER | 12 | 147.186 | 60.895 | 57.409 | 1.00 | 29.53 | L |
| ATOM | 88 | C | SER | 12 | 144.534 | 61.798 | 57.392 | 1.00 | 38.38 | L |
| ATOM | 89 | O | SER | 12 | 144.226 | 62.894 | 56.928 | 1.00 | 46.48 | L |
| ATOM | 90 | N | ALA | 13 | 144.519 | 61.546 | 58.696 | 1.00 | 31.39 | L |
| ATOM | 91 | CA | ALA | 13 | 144.116 | 62.559 | 59.666 | 1.00 | 34.62 | L |
| ATOM | 92 | CB | ALA | 13 | 142.615 | 62.610 | 59.753 | 1.00 | 28.98 | L |
| ATOM | 93 | C | ALA | 13 | 144.706 | 62.178 | 61.012 | 1.00 | 38.12 | L |
| ATOM | 94 | O | ALA | 13 | 144.928 | 61.002 | 61.268 | 1.00 | 41.17 | L |
| ATOM | 95 | N | SER | 14 | 144.946 | 63.156 | 61.878 | 1.00 | 36.11 | L |
| ATOM | 96 | CA | SER | 14 | 145.553 | 62.865 | 63.177 | 1.00 | 42.50 | L |
| ATOM | 97 | CB | SER | 14 | 146.477 | 64.012 | 63.593 | 1.00 | 45.35 | L |
| ATOM | 98 | OG | SER | 14 | 147.608 | 63.522 | 64.299 | 1.00 | 51.37 | L |
| ATOM | 99 | C | SER | 14 | 144.618 | 62.553 | 64.343 | 1.00 | 36.84 | L |
| ATOM | 100 | O | SER | 14 | 143.395 | 62.586 | 64.217 | 1.00 | 30.77 | L |
| ATOM | 101 | N | LEU | 15 | 145.246 | 62.246 | 65.477 | 1.00 | 42.69 | L |
| ATOM | 102 | CA | LEU | 15 | 144.588 | 61.919 | 66.737 | 1.00 | 51.12 | L |
| ATOM | 103 | CB | LEU | 15 | 145.077 | 62.874 | 67.829 | 1.00 | 35.76 | L |
| ATOM | 104 | CG | LEU | 15 | 145.549 | 64.244 | 67.331 | 1.00 | 50.27 | L |
| ATOM | 105 | CD1 | LEU | 15 | 144.709 | 65.353 | 67.956 | 1.00 | 45.12 | L |
| ATOM | 106 | CD2 | LEU | 15 | 147.023 | 64.425 | 67.671 | 1.00 | 46.79 | L |
| ATOM | 107 | C | LEU | 15 | 143.071 | 61.968 | 66.666 | 1.00 | 63.00 | L |
| ATOM | 108 | O | LEU | 15 | 142.440 | 61.062 | 66.125 | 1.00 | 71.25 | L |
| ATOM | 109 | N | GLY | 16 | 142.495 | 63.029 | 67.229 | 1.00 | 61.62 | L |
| ATOM | 110 | CA | GLY | 16 | 141.052 | 63.182 | 67.225 | 1.00 | 58.47 | L |
| ATOM | 111 | C | GLY | 16 | 140.588 | 64.176 | 66.177 | 1.00 | 62.05 | L |
| ATOM | 112 | O | GLY | 16 | 139.827 | 65.094 | 66.481 | 1.00 | 59.73 | L |
| ATOM | 113 | N | ASP | 17 | 141.052 | 63.991 | 64.942 | 1.00 | 62.73 | L |
| ATOM | 114 | CA | ASP | 17 | 140.690 | 64.863 | 63.828 | 1.00 | 55.42 | L |
| ATOM | 115 | CB | ASP | 17 | 141.729 | 64.728 | 62.715 | 1.00 | 45.39 | L |
| ATOM | 116 | CG | ASP | 17 | 142.006 | 66.039 | 62.017 | 1.00 | 56.02 | L |
| ATOM | 117 | OD1 | ASP | 17 | 142.467 | 66.992 | 62.682 | 1.00 | 51.84 | L |
| ATOM | 118 | OD2 | ASP | 17 | 141.762 | 66.116 | 60.795 | 1.00 | 64.45 | L |
| ATOM | 119 | C | ASP | 17 | 139.313 | 64.470 | 63.298 | 1.00 | 54.85 | L |
| ATOM | 120 | O | ASP | 17 | 139.066 | 63.296 | 63.027 | 1.00 | 69.38 | L |
| ATOM | 121 | N | THR | 18 | 138.425 | 65.448 | 63.150 | 1.00 | 39.55 | L |
| ATOM | 122 | CA | THR | 18 | 137.073 | 65.189 | 62.661 | 1.00 | 35.18 | L |
| ATOM | 123 | CB | THR | 18 | 136.089 | 66.238 | 63.211 | 1.00 | 39.72 | L |
| ATOM | 124 | OG1 | THR | 18 | 136.155 | 66.250 | 64.644 | 1.00 | 36.21 | L |
| ATOM | 125 | CG2 | THR | 18 | 134.668 | 65.918 | 62.774 | 1.00 | 28.85 | L |
| ATOM | 126 | C | THR | 18 | 136.967 | 65.172 | 61.132 | 1.00 | 39.85 | L |
| ATOM | 127 | O | THR | 18 | 136.590 | 66.167 | 60.522 | 1.00 | 51.97 | L |
| ATOM | 128 | N | ILE | 19 | 137.289 | 64.035 | 60.521 | 1.00 | 38.56 | L |
| ATOM | 129 | CA | ILE | 19 | 137.233 | 63.881 | 59.065 | 1.00 | 40.49 | L |
| ATOM | 130 | CB | ILE | 19 | 137.917 | 62.579 | 58.621 | 1.00 | 43.22 | L |

TABLE 4-continued

Co-ordinates of the CD28/5.11A1 crystal structure

| ATOM | 131 | CG2 | ILE | 19 | 139.334 | 62.545 | 59.144 | 1.00 | 53.54 | L |
|---|---|---|---|---|---|---|---|---|---|---|
| ATOM | 132 | CG1 | ILE | 19 | 137.148 | 61.373 | 59.161 | 1.00 | 31.99 | L |
| ATOM | 133 | CD1 | ILE | 19 | 136.020 | 60.889 | 58.260 | 1.00 | 27.22 | L |
| ATOM | 134 | C | ILE | 19 | 135.811 | 63.857 | 58.519 | 1.00 | 41.63 | L |
| ATOM | 135 | O | ILE | 19 | 134.850 | 63.825 | 59.284 | 1.00 | 48.28 | L |
| ATOM | 136 | N | THR | 20 | 135.690 | 63.839 | 57.191 | 1.00 | 41.74 | L |
| ATOM | 137 | CA | THR | 20 | 134.388 | 63.814 | 56.517 | 1.00 | 46.28 | L |
| ATOM | 138 | CB | THR | 20 | 133.761 | 65.246 | 56.473 | 1.00 | 55.85 | L |
| ATOM | 139 | OG1 | THR | 20 | 132.666 | 65.316 | 57.396 | 1.00 | 68.15 | L |
| ATOM | 140 | CG2 | THR | 20 | 133.260 | 65.592 | 55.073 | 1.00 | 57.90 | L |
| ATOM | 141 | C | THR | 20 | 134.516 | 63.260 | 55.090 | 1.00 | 34.62 | L |
| ATOM | 142 | O | THR | 20 | 135.433 | 63.620 | 54.351 | 1.00 | 35.05 | L |
| ATOM | 143 | N | ILE | 21 | 133.592 | 62.385 | 54.706 | 1.00 | 27.66 | L |
| ATOM | 144 | CA | ILE | 21 | 133.613 | 61.793 | 53.371 | 1.00 | 40.68 | L |
| ATOM | 145 | CB | ILE | 21 | 133.646 | 60.260 | 53.466 | 1.00 | 45.17 | L |
| ATOM | 146 | CG2 | ILE | 21 | 133.946 | 59.641 | 52.110 | 1.00 | 58.28 | L |
| ATOM | 147 | CG1 | ILE | 21 | 134.757 | 59.849 | 54.432 | 1.00 | 37.17 | L |
| ATOM | 148 | CD1 | ILE | 21 | 134.556 | 58.489 | 55.038 | 1.00 | 30.25 | L |
| ATOM | 149 | C | ILE | 21 | 132.412 | 62.266 | 52.552 | 1.00 | 41.14 | L |
| ATOM | 150 | O | ILE | 21 | 131.706 | 63.173 | 52.978 | 1.00 | 52.31 | L |
| ATOM | 151 | N | THR | 22 | 132.176 | 61.669 | 51.386 | 1.00 | 37.16 | L |
| ATOM | 152 | CA | THR | 22 | 131.069 | 62.096 | 50.533 | 1.00 | 30.97 | L |
| ATOM | 153 | CB | THR | 22 | 131.426 | 63.392 | 49.791 | 1.00 | 33.17 | L |
| ATOM | 154 | OG1 | THR | 22 | 131.754 | 64.417 | 50.736 | 1.00 | 20.87 | L |
| ATOM | 155 | CG2 | THR | 22 | 130.270 | 63.832 | 48.913 | 1.00 | 26.45 | L |
| ATOM | 156 | C | THR | 22 | 130.703 | 61.078 | 49.462 | 1.00 | 45.82 | L |
| ATOM | 157 | O | THR | 22 | 131.563 | 60.656 | 48.694 | 1.00 | 54.24 | L |
| ATOM | 158 | N | CYS | 23 | 129.430 | 60.705 | 49.381 | 1.00 | 50.07 | L |
| ATOM | 159 | CA | CYS | 23 | 129.004 | 59.746 | 48.363 | 1.00 | 63.67 | L |
| ATOM | 160 | C | CYS | 23 | 127.790 | 60.230 | 47.570 | 1.00 | 68.93 | L |
| ATOM | 161 | O | CYS | 23 | 126.651 | 60.017 | 47.983 | 1.00 | 85.32 | L |
| ATOM | 162 | CB | CYS | 23 | 128.682 | 58.384 | 48.998 | 1.00 | 53.28 | L |
| ATOM | 163 | SG | CYS | 23 | 127.931 | 57.193 | 47.829 | 1.00 | 60.78 | L |
| ATOM | 164 | N | HIS | 24 | 128.035 | 60.874 | 46.432 | 1.00 | 62.30 | L |
| ATOM | 165 | CA | HIS | 24 | 126.958 | 61.376 | 45.581 | 1.00 | 55.79 | L |
| ATOM | 166 | CB | HIS | 24 | 127.438 | 62.585 | 44.766 | 1.00 | 66.11 | L |
| ATOM | 167 | CG | HIS | 24 | 127.210 | 63.903 | 45.443 | 1.00 | 94.47 | L |
| ATOM | 168 | CD2 | HIS | 24 | 127.360 | 64.280 | 46.736 | 1.00 | 100.00 | L |
| ATOM | 169 | ND1 | HIS | 24 | 126.760 | 65.020 | 44.771 | 1.00 | 99.99 | L |
| ATOM | 170 | CE1 | HIS | 24 | 126.647 | 66.029 | 45.618 | 1.00 | 96.64 | L |
| ATOM | 171 | NE2 | HIS | 24 | 127.005 | 65.605 | 46.818 | 1.00 | 100.00 | L |
| ATOM | 172 | C | HIS | 24 | 126.456 | 60.282 | 44.636 | 1.00 | 53.07 | L |
| ATOM | 173 | O | HIS | 24 | 127.232 | 59.442 | 44.174 | 1.00 | 50.30 | L |
| ATOM | 174 | N | ALA | 25 | 125.154 | 60.295 | 44.359 | 1.00 | 48.84 | L |
| ATOM | 175 | CA | ALA | 25 | 124.546 | 59.309 | 43.470 | 1.00 | 62.65 | L |
| ATOM | 176 | CB | ALA | 25 | 123.334 | 58.678 | 44.149 | 1.00 | 50.68 | L |
| ATOM | 177 | C | ALA | 25 | 124.135 | 59.923 | 42.124 | 1.00 | 71.88 | L |
| ATOM | 178 | O | ALA | 25 | 123.769 | 61.098 | 42.053 | 1.00 | 69.35 | L |
| ATOM | 179 | N | SER | 26 | 124.196 | 59.120 | 41.061 | 1.00 | 75.26 | L |
| ATOM | 180 | CA | SER | 26 | 123.833 | 59.585 | 39.724 | 1.00 | 65.26 | L |
| ATOM | 181 | CB | SER | 26 | 123.832 | 58.421 | 38.724 | 1.00 | 51.17 | L |
| ATOM | 182 | OG | SER | 26 | 122.779 | 57.511 | 38.981 | 1.00 | 34.32 | L |
| ATOM | 183 | C | SER | 26 | 122.466 | 60.247 | 39.755 | 1.00 | 68.59 | L |
| ATOM | 184 | O | SER | 26 | 122.329 | 61.422 | 39.413 | 1.00 | 70.72 | L |
| ATOM | 185 | N | GLN | 27 | 121.452 | 59.490 | 40.163 | 1.00 | 70.13 | L |
| ATOM | 186 | CA | GLN | 27 | 120.103 | 60.030 | 40.253 | 1.00 | 61.69 | L |
| ATOM | 187 | CB | GLN | 27 | 119.171 | 59.312 | 39.273 | 1.00 | 49.30 | L |
| ATOM | 188 | CG | GLN | 27 | 119.385 | 57.827 | 39.181 | 1.00 | 40.46 | L |
| ATOM | 189 | CD | GLN | 27 | 118.295 | 57.064 | 39.899 | 1.00 | 47.76 | L |
| ATOM | 190 | OE1 | GLN | 27 | 117.623 | 57.601 | 40.785 | 1.00 | 42.99 | L |
| ATOM | 191 | NE2 | GLN | 27 | 118.110 | 55.806 | 39.523 | 1.00 | 37.30 | L |
| ATOM | 192 | C | GLN | 27 | 119.568 | 59.937 | 41.690 | 1.00 | 59.24 | L |
| ATOM | 193 | O | GLN | 27 | 120.323 | 59.658 | 42.623 | 1.00 | 58.99 | L |
| ATOM | 194 | N | ASN | 28 | 118.268 | 60.160 | 41.859 | 1.00 | 54.50 | L |
| ATOM | 195 | CA | ASN | 28 | 117.628 | 60.162 | 43.176 | 1.00 | 48.17 | L |
| ATOM | 196 | CB | ASN | 28 | 116.286 | 60.871 | 43.058 | 1.00 | 28.87 | L |
| ATOM | 197 | CG | ASN | 28 | 115.671 | 61.159 | 44.397 | 1.00 | 25.62 | L |
| ATOM | 198 | OD1 | ASN | 28 | 116.346 | 61.607 | 45.321 | 1.00 | 43.90 | L |
| ATOM | 199 | ND2 | ASN | 28 | 114.383 | 60.894 | 44.518 | 1.00 | 47.96 | L |
| ATOM | 200 | C | ASN | 28 | 117.422 | 58.833 | 43.917 | 1.00 | 53.06 | L |
| ATOM | 201 | O | ASN | 28 | 116.727 | 57.939 | 43.431 | 1.00 | 50.76 | L |
| ATOM | 202 | N | ILE | 29 | 118.011 | 58.727 | 45.112 | 1.00 | 49.78 | L |
| ATOM | 203 | CA | ILE | 29 | 117.887 | 57.528 | 45.951 | 1.00 | 48.76 | L |
| ATOM | 204 | CB | ILE | 29 | 119.278 | 56.900 | 46.275 | 1.00 | 38.91 | L |
| ATOM | 205 | CG2 | ILE | 29 | 119.870 | 56.276 | 45.028 | 1.00 | 38.09 | L |
| ATOM | 206 | CG1 | ILE | 29 | 120.235 | 57.965 | 46.801 | 1.00 | 35.93 | L |
| ATOM | 207 | CD1 | ILE | 29 | 121.444 | 57.381 | 47.498 | 1.00 | 24.13 | L |

TABLE 4-continued

Co-ordinates of the CD28/5.11A1 crystal structure

| ATOM | 208 | C | ILE | 29 | 117.176 | 57.883 | 47.270 | 1.00 | 49.01 | L |
|---|---|---|---|---|---|---|---|---|---|---|
| ATOM | 209 | O | ILE | 29 | 117.043 | 57.056 | 48.183 | 1.00 | 28.15 | L |
| ATOM | 210 | N | TYR | 30 | 116.720 | 59.127 | 47.358 | 1.00 | 51.14 | L |
| ATOM | 211 | CA | TYR | 30 | 116.018 | 59.610 | 48.536 | 1.00 | 40.55 | L |
| ATOM | 212 | CB | TYR | 30 | 114.708 | 58.834 | 48.708 | 1.00 | 51.35 | L |
| ATOM | 213 | CG | TYR | 30 | 113.856 | 58.829 | 47.452 | 1.00 | 50.82 | L |
| ATOM | 214 | CD1 | TYR | 30 | 112.914 | 59.832 | 47.218 | 1.00 | 57.07 | L |
| ATOM | 215 | CE1 | TYR | 30 | 112.164 | 59.859 | 46.044 | 1.00 | 48.93 | L |
| ATOM | 216 | CD2 | TYR | 30 | 114.023 | 57.846 | 46.477 | 1.00 | 54.94 | L |
| ATOM | 217 | CE2 | TYR | 30 | 113.280 | 57.863 | 45.302 | 1.00 | 54.60 | L |
| ATOM | 218 | CZ | TYR | 30 | 112.354 | 58.872 | 45.089 | 1.00 | 54.60 | L |
| ATOM | 219 | OH | TYR | 30 | 111.641 | 58.906 | 43.914 | 1.00 | 46.05 | L |
| ATOM | 220 | C | TYR | 30 | 116.867 | 59.539 | 49.800 | 1.00 | 36.49 | L |
| ATOM | 221 | O | TYR | 30 | 117.747 | 60.377 | 50.007 | 1.00 | 36.08 | L |
| ATOM | 222 | N | VAL | 31 | 116.607 | 58.553 | 50.650 | 1.00 | 27.22 | L |
| ATOM | 223 | CA | VAL | 31 | 117.363 | 58.421 | 51.889 | 1.00 | 25.88 | L |
| ATOM | 224 | CB | VAL | 31 | 116.518 | 58.771 | 53.103 | 1.00 | 24.60 | L |
| ATOM | 225 | CG1 | VAL | 31 | 115.741 | 60.036 | 52.827 | 1.00 | 39.18 | L |
| ATOM | 226 | CG2 | VAL | 31 | 115.581 | 57.607 | 53.441 | 1.00 | 11.43 | L |
| ATOM | 227 | C | VAL | 31 | 117.815 | 57.001 | 52.068 | 1.00 | 30.74 | L |
| ATOM | 228 | O | VAL | 31 | 118.333 | 56.637 | 53.125 | 1.00 | 32.26 | L |
| ATOM | 229 | N | TRP | 32 | 117.612 | 56.202 | 51.028 | 1.00 | 34.27 | L |
| ATOM | 230 | CA | TRP | 32 | 117.978 | 54.796 | 51.064 | 1.00 | 29.66 | L |
| ATOM | 231 | CB | TRP | 32 | 117.016 | 53.999 | 50.173 | 1.00 | 37.57 | L |
| ATOM | 232 | CG | TRP | 32 | 115.569 | 54.306 | 50.497 | 1.00 | 45.16 | L |
| ATOM | 233 | CD2 | TRP | 32 | 114.858 | 53.921 | 51.677 | 1.00 | 28.80 | L |
| ATOM | 234 | CE2 | TRP | 32 | 113.571 | 54.493 | 51.597 | 1.00 | 36.20 | L |
| ATOM | 235 | CE3 | TRP | 32 | 115.183 | 53.149 | 52.798 | 1.00 | 25.93 | L |
| ATOM | 236 | CD1 | TRP | 32 | 114.706 | 55.074 | 49.765 | 1.00 | 47.52 | L |
| ATOM | 237 | NE1 | TRP | 32 | 113.504 | 55.193 | 50.418 | 1.00 | 36.87 | L |
| ATOM | 238 | CZ2 | TRP | 32 | 112.610 | 54.319 | 52.591 | 1.00 | 25.25 | L |
| ATOM | 239 | CZ3 | TRP | 32 | 114.229 | 52.978 | 53.788 | 1.00 | 21.98 | L |
| ATOM | 240 | CH2 | TRP | 32 | 112.954 | 53.563 | 53.677 | 1.00 | 2.00 | L |
| ATOM | 241 | C | TRP | 32 | 119.419 | 54.578 | 50.645 | 1.00 | 17.38 | L |
| ATOM | 242 | O | TRP | 32 | 119.697 | 54.267 | 49.491 | 1.00 | 20.83 | L |
| ATOM | 243 | N | LEU | 33 | 120.332 | 54.750 | 51.599 | 1.00 | 19.97 | L |
| ATOM | 244 | CA | LEU | 33 | 121.763 | 54.570 | 51.357 | 1.00 | 39.54 | L |
| ATOM | 245 | CB | LEU | 33 | 122.352 | 55.790 | 50.642 | 1.00 | 44.19 | L |
| ATOM | 246 | CG | LEU | 33 | 123.876 | 55.803 | 50.500 | 1.00 | 34.32 | L |
| ATOM | 247 | CD1 | LEU | 33 | 124.252 | 56.190 | 49.078 | 1.00 | 27.47 | L |
| ATOM | 248 | CD2 | LEU | 33 | 124.479 | 56.774 | 51.515 | 1.00 | 19.98 | L |
| ATOM | 249 | C | LEU | 33 | 122.481 | 54.371 | 52.685 | 1.00 | 39.15 | L |
| ATOM | 250 | O | LEU | 33 | 122.345 | 55.182 | 53.595 | 1.00 | 42.09 | L |
| ATOM | 251 | N | ASN | 34 | 123.262 | 53.303 | 52.785 | 1.00 | 38.96 | L |
| ATOM | 252 | CA | ASN | 34 | 123.969 | 53.008 | 54.017 | 1.00 | 33.81 | L |
| ATOM | 253 | CB | ASN | 34 | 123.635 | 51.588 | 54.470 | 1.00 | 29.67 | L |
| ATOM | 254 | CG | ASN | 34 | 122.323 | 51.104 | 53.908 | 1.00 | 18.96 | L |
| ATOM | 255 | OD1 | ASN | 34 | 121.252 | 51.484 | 54.384 | 1.00 | 22.09 | L |
| ATOM | 256 | ND2 | ASN | 34 | 122.396 | 50.269 | 52.883 | 1.00 | 22.68 | L |
| ATOM | 257 | C | ASN | 34 | 125.465 | 53.162 | 53.889 | 1.00 | 27.35 | L |
| ATOM | 258 | O | ASN | 34 | 125.996 | 53.215 | 52.785 | 1.00 | 25.60 | L |
| ATOM | 259 | N | TRP | 35 | 126.125 | 53.242 | 55.041 | 1.00 | 31.00 | L |
| ATOM | 260 | CA | TRP | 35 | 127.574 | 53.380 | 55.122 | 1.00 | 37.04 | L |
| ATOM | 261 | CB | TRP | 35 | 127.942 | 54.663 | 55.871 | 1.00 | 44.59 | L |
| ATOM | 262 | CG | TRP | 35 | 127.725 | 55.956 | 55.099 | 1.00 | 50.73 | L |
| ATOM | 263 | CD2 | TRP | 35 | 128.624 | 56.560 | 54.155 | 1.00 | 39.25 | L |
| ATOM | 264 | CE2 | TRP | 35 | 128.042 | 57.776 | 53.738 | 1.00 | 36.81 | L |
| ATOM | 265 | CE3 | TRP | 35 | 129.868 | 56.194 | 53.621 | 1.00 | 29.95 | L |
| ATOM | 266 | CD1 | TRP | 35 | 126.660 | 56.808 | 55.208 | 1.00 | 38.58 | L |
| ATOM | 267 | NE1 | TRP | 35 | 126.843 | 57.900 | 54.397 | 1.00 | 40.14 | L |
| ATOM | 268 | CZ2 | TRP | 35 | 128.655 | 58.629 | 52.812 | 1.00 | 36.05 | L |
| ATOM | 269 | CZ3 | TRP | 35 | 130.479 | 57.045 | 52.698 | 1.00 | 39.51 | L |
| ATOM | 270 | CH2 | TRP | 35 | 129.871 | 58.247 | 52.307 | 1.00 | 31.94 | L |
| ATOM | 271 | C | TRP | 35 | 128.118 | 52.168 | 55.885 | 1.00 | 32.85 | L |
| ATOM | 272 | O | TRP | 35 | 127.499 | 51.715 | 56.849 | 1.00 | 24.56 | L |
| ATOM | 273 | N | TYR | 36 | 129.271 | 51.654 | 55.451 | 1.00 | 29.03 | L |
| ATOM | 274 | CA | TYR | 36 | 129.894 | 50.488 | 56.080 | 1.00 | 24.01 | L |
| ATOM | 275 | CB | TYR | 36 | 129.760 | 49.256 | 55.178 | 1.00 | 24.57 | L |
| ATOM | 276 | CG | TYR | 36 | 128.341 | 48.844 | 54.845 | 1.00 | 36.78 | L |
| ATOM | 277 | CD1 | TYR | 36 | 127.740 | 47.745 | 55.469 | 1.00 | 45.66 | L |
| ATOM | 278 | CE1 | TYR | 36 | 126.439 | 47.350 | 55.138 | 1.00 | 29.26 | L |
| ATOM | 279 | CD2 | TYR | 36 | 127.606 | 49.536 | 53.885 | 1.00 | 43.28 | L |
| ATOM | 280 | CE2 | TYR | 36 | 126.314 | 49.153 | 53.550 | 1.00 | 29.25 | L |
| ATOM | 281 | CZ | TYR | 36 | 125.736 | 48.064 | 54.174 | 1.00 | 33.13 | L |
| ATOM | 282 | OH | TYR | 36 | 124.458 | 47.709 | 53.810 | 1.00 | 29.39 | L |
| ATOM | 283 | C | TYR | 36 | 131.379 | 50.683 | 56.401 | 1.00 | 34.79 | L |
| ATOM | 284 | O | TYR | 36 | 132.060 | 51.530 | 55.813 | 1.00 | 31.84 | L |

TABLE 4-continued

Co-ordinates of the CD28/5.11A1 crystal structure

| ATOM | 285 | N | GLN | 37 | 131.876 | 49.880 | 57.337 | 1.00 | 38.75 | L |
|---|---|---|---|---|---|---|---|---|---|---|
| ATOM | 286 | CA | GLN | 37 | 133.278 | 49.923 | 57.731 | 1.00 | 41.58 | L |
| ATOM | 287 | CB | GLN | 37 | 133.406 | 50.342 | 59.199 | 1.00 | 30.71 | L |
| ATOM | 288 | CG | GLN | 37 | 134.852 | 50.495 | 59.704 | 1.00 | 37.19 | L |
| ATOM | 289 | CD | GLN | 37 | 134.989 | 50.332 | 61.222 | 1.00 | 25.39 | L |
| ATOM | 290 | OE1 | GLN | 37 | 134.904 | 49.222 | 61.753 | 1.00 | 36.25 | L |
| ATOM | 291 | NE2 | GLN | 37 | 135.209 | 51.439 | 61.918 | 1.00 | 22.58 | L |
| ATOM | 292 | C | GLN | 37 | 133.884 | 48.528 | 57.528 | 1.00 | 39.79 | L |
| ATOM | 293 | O | GLN | 37 | 133.319 | 47.526 | 57.975 | 1.00 | 29.52 | L |
| ATOM | 294 | N | GLN | 38 | 135.022 | 48.465 | 56.839 | 1.00 | 29.65 | L |
| ATOM | 295 | CA | GLN | 38 | 135.695 | 47.195 | 56.596 | 1.00 | 31.00 | L |
| ATOM | 296 | CB | GLN | 38 | 135.471 | 46.738 | 55.155 | 1.00 | 37.06 | L |
| ATOM | 297 | CG | GLN | 38 | 136.385 | 45.597 | 54.724 | 1.00 | 37.85 | L |
| ATOM | 298 | CD | GLN | 38 | 135.973 | 44.992 | 53.401 | 1.00 | 51.91 | L |
| ATOM | 299 | OE1 | GLN | 38 | 135.856 | 45.693 | 52.399 | 1.00 | 56.78 | L |
| ATOM | 300 | NE2 | GLN | 38 | 135.753 | 43.683 | 53.390 | 1.00 | 47.92 | L |
| ATOM | 301 | C | GLN | 38 | 137.192 | 47.285 | 56.860 | 1.00 | 23.61 | L |
| ATOM | 302 | O | GLN | 38 | 137.952 | 47.630 | 55.963 | 1.00 | 30.06 | L |
| ATOM | 303 | N | LYS | 39 | 137.610 | 46.969 | 58.086 | 1.00 | 29.96 | L |
| ATOM | 304 | CA | LYS | 39 | 139.021 | 47.022 | 58.464 | 1.00 | 20.79 | L |
| ATOM | 305 | CB | LYS | 39 | 139.204 | 46.606 | 59.925 | 1.00 | 26.60 | L |
| ATOM | 306 | CG | LYS | 39 | 139.493 | 47.764 | 60.884 | 1.00 | 31.56 | L |
| ATOM | 307 | CD | LYS | 39 | 138.268 | 48.135 | 61.727 | 1.00 | 24.64 | L |
| ATOM | 308 | CE | LYS | 39 | 138.633 | 48.266 | 63.205 | 1.00 | 28.08 | L |
| ATOM | 309 | NZ | LYS | 39 | 137.922 | 47.293 | 64.094 | 1.00 | 32.42 | L |
| ATOM | 310 | C | LYS | 39 | 139.831 | 46.103 | 57.566 | 1.00 | 39.66 | L |
| ATOM | 311 | O | LYS | 39 | 139.272 | 45.238 | 56.886 | 1.00 | 49.56 | L |
| ATOM | 312 | N | PRO | 40 | 141.161 | 46.283 | 57.533 | 1.00 | 54.59 | L |
| ATOM | 313 | CD | PRO | 40 | 141.957 | 47.289 | 58.266 | 1.00 | 52.22 | L |
| ATOM | 314 | CA | PRO | 40 | 142.007 | 45.434 | 56.686 | 1.00 | 54.43 | L |
| ATOM | 315 | CB | PRO | 40 | 143.431 | 45.874 | 57.037 | 1.00 | 40.87 | L |
| ATOM | 316 | CG | PRO | 40 | 143.274 | 47.280 | 57.530 | 1.00 | 36.77 | L |
| ATOM | 317 | C | PRO | 40 | 141.792 | 43.935 | 56.895 | 1.00 | 53.33 | L |
| ATOM | 318 | O | PRO | 40 | 141.962 | 43.429 | 58.003 | 1.00 | 48.18 | L |
| ATOM | 319 | N | GLY | 41 | 141.403 | 43.244 | 55.825 | 1.00 | 56.47 | L |
| ATOM | 320 | CA | GLY | 41 | 141.178 | 41.807 | 55.889 | 1.00 | 46.36 | L |
| ATOM | 321 | C | GLY | 41 | 140.030 | 41.378 | 56.783 | 1.00 | 47.51 | L |
| ATOM | 322 | O | GLY | 41 | 139.890 | 40.195 | 57.103 | 1.00 | 42.82 | L |
| ATOM | 323 | N | ASN | 42 | 139.198 | 42.336 | 57.177 | 1.00 | 39.14 | L |
| ATOM | 324 | CA | ASN | 42 | 138.061 | 42.049 | 58.044 | 1.00 | 33.16 | L |
| ATOM | 325 | CB | ASN | 42 | 138.031 | 43.041 | 59.210 | 1.00 | 25.23 | L |
| ATOM | 326 | CG | ASN | 42 | 137.400 | 42.453 | 60.451 | 1.00 | 34.65 | L |
| ATOM | 327 | OD1 | ASN | 42 | 136.876 | 41.338 | 60.416 | 1.00 | 42.65 | L |
| ATOM | 328 | ND2 | ASN | 42 | 137.444 | 43.194 | 61.558 | 1.00 | 15.22 | L |
| ATOM | 329 | C | ASN | 42 | 136.743 | 42.123 | 57.287 | 1.00 | 36.43 | L |
| ATOM | 330 | O | ASN | 42 | 136.726 | 42.413 | 56.092 | 1.00 | 31.10 | L |
| ATOM | 331 | N | ILE | 43 | 135.648 | 41.852 | 57.993 | 1.00 | 46.04 | L |
| ATOM | 332 | CA | ILE | 43 | 134.310 | 41.894 | 57.407 | 1.00 | 55.78 | L |
| ATOM | 333 | CB | ILE | 43 | 133.340 | 40.879 | 58.089 | 1.00 | 55.57 | L |
| ATOM | 334 | CG2 | ILE | 43 | 134.038 | 39.554 | 58.323 | 1.00 | 47.83 | L |
| ATOM | 335 | CG1 | ILE | 43 | 132.828 | 41.439 | 59.423 | 1.00 | 61.00 | L |
| ATOM | 336 | CD1 | ILE | 43 | 131.656 | 40.662 | 60.017 | 1.00 | 68.36 | L |
| ATOM | 337 | C | ILE | 43 | 133.726 | 43.298 | 57.555 | 1.00 | 63.83 | L |
| ATOM | 338 | O | ILE | 43 | 134.037 | 44.010 | 58.513 | 1.00 | 72.13 | L |
| ATOM | 339 | N | PRO | 44 | 132.881 | 43.720 | 56.605 | 1.00 | 56.85 | L |
| ATOM | 340 | CD | PRO | 44 | 132.444 | 42.988 | 55.402 | 1.00 | 59.76 | L |
| ATOM | 341 | CA | PRO | 44 | 132.282 | 45.052 | 56.681 | 1.00 | 47.82 | L |
| ATOM | 342 | CB | PRO | 44 | 131.893 | 45.349 | 55.242 | 1.00 | 52.95 | L |
| ATOM | 343 | CG | PRO | 44 | 131.590 | 43.997 | 54.665 | 1.00 | 66.17 | L |
| ATOM | 344 | C | PRO | 44 | 131.079 | 45.064 | 57.613 | 1.00 | 41.70 | L |
| ATOM | 345 | O | PRO | 44 | 130.160 | 44.258 | 57.460 | 1.00 | 35.22 | L |
| ATOM | 346 | N | LYS | 45 | 131.095 | 45.982 | 58.575 | 1.00 | 33.96 | L |
| ATOM | 347 | CA | LYS | 45 | 130.010 | 46.106 | 59.537 | 1.00 | 39.65 | L |
| ATOM | 348 | CB | LYS | 45 | 130.576 | 46.225 | 60.953 | 1.00 | 36.05 | L |
| ATOM | 349 | CG | LYS | 45 | 132.096 | 46.222 | 61.012 | 1.00 | 44.96 | L |
| ATOM | 350 | CD | LYS | 45 | 132.651 | 45.003 | 61.752 | 1.00 | 53.54 | L |
| ATOM | 351 | CE | LYS | 45 | 134.060 | 45.269 | 62.297 | 1.00 | 58.35 | L |
| ATOM | 352 | NZ | LYS | 45 | 134.818 | 44.011 | 62.586 | 1.00 | 46.04 | L |
| ATOM | 353 | C | LYS | 45 | 129.162 | 47.329 | 59.218 | 1.00 | 37.07 | L |
| ATOM | 354 | O | LYS | 45 | 129.686 | 48.369 | 58.817 | 1.00 | 37.21 | L |
| ATOM | 355 | N | LEU | 46 | 127.850 | 47.205 | 59.385 | 1.00 | 22.26 | L |
| ATOM | 356 | CA | LEU | 46 | 126.969 | 48.326 | 59.107 | 1.00 | 28.40 | L |
| ATOM | 357 | CB | LEU | 46 | 125.505 | 47.904 | 59.239 | 1.00 | 32.99 | L |
| ATOM | 358 | CG | LEU | 46 | 124.429 | 48.756 | 58.541 | 1.00 | 40.56 | L |
| ATOM | 359 | CD1 | LEU | 46 | 123.264 | 48.947 | 59.508 | 1.00 | 53.21 | L |
| ATOM | 360 | CD2 | LEU | 46 | 124.987 | 50.114 | 58.096 | 1.00 | 41.53 | L |
| ATOM | 361 | C | LEU | 46 | 127.268 | 49.459 | 60.079 | 1.00 | 27.28 | L |

TABLE 4-continued

Co-ordinates of the CD28/5.11A1 crystal structure

| ATOM | 362 | O | LEU | 46 | 127.353 | 49.247 | 61.286 | 1.00 | 40.74 | L |
|---|---|---|---|---|---|---|---|---|---|---|
| ATOM | 363 | N | LEU | 47 | 127.414 | 50.666 | 59.548 | 1.00 | 31.54 | L |
| ATOM | 364 | CA | LEU | 47 | 127.719 | 51.837 | 60.362 | 1.00 | 26.31 | L |
| ATOM | 365 | CB | LEU | 47 | 128.915 | 52.562 | 59.755 | 1.00 | 25.09 | L |
| ATOM | 366 | CG | LEU | 47 | 130.100 | 52.926 | 60.636 | 1.00 | 16.21 | L |
| ATOM | 367 | CD1 | LEU | 47 | 130.727 | 51.676 | 61.198 | 1.00 | 17.63 | L |
| ATOM | 368 | CD2 | LEU | 47 | 131.094 | 53.701 | 59.805 | 1.00 | 2.00 | L |
| ATOM | 369 | C | LEU | 47 | 126.535 | 52.807 | 60.449 | 1.00 | 34.89 | L |
| ATOM | 370 | O | LEU | 47 | 126.190 | 53.282 | 61.535 | 1.00 | 26.31 | L |
| ATOM | 371 | N | ILE | 48 | 125.934 | 53.100 | 59.293 | 1.00 | 44.65 | L |
| ATOM | 372 | CA | ILE | 48 | 124.794 | 54.018 | 59.187 | 1.00 | 34.33 | L |
| ATOM | 373 | CB | ILE | 48 | 125.251 | 55.439 | 58.788 | 1.00 | 24.64 | L |
| ATOM | 374 | CG2 | ILE | 48 | 124.145 | 56.146 | 58.008 | 1.00 | 29.43 | L |
| ATOM | 375 | CG1 | ILE | 48 | 125.591 | 56.253 | 60.033 | 1.00 | 28.98 | L |
| ATOM | 376 | CD1 | ILE | 48 | 126.967 | 56.866 | 59.993 | 1.00 | 25.03 | L |
| ATOM | 377 | C | ILE | 48 | 123.775 | 53.576 | 58.133 | 1.00 | 29.31 | L |
| ATOM | 378 | O | ILE | 48 | 124.113 | 53.411 | 56.962 | 1.00 | 40.59 | L |
| ATOM | 379 | N | TYR | 49 | 122.527 | 53.405 | 58.547 | 1.00 | 15.91 | L |
| ATOM | 380 | CA | TYR | 49 | 121.485 | 53.018 | 57.613 | 1.00 | 21.27 | L |
| ATOM | 381 | CB | TYR | 49 | 120.762 | 51.748 | 58.087 | 1.00 | 36.34 | L |
| ATOM | 382 | CG | TYR | 49 | 119.779 | 51.925 | 59.231 | 1.00 | 35.16 | L |
| ATOM | 383 | CD1 | TYR | 49 | 118.408 | 52.066 | 58.986 | 1.00 | 25.01 | L |
| ATOM | 384 | CE1 | TYR | 49 | 117.498 | 52.216 | 60.028 | 1.00 | 28.72 | L |
| ATOM | 385 | CD2 | TYR | 49 | 120.214 | 51.934 | 60.560 | 1.00 | 28.85 | L |
| ATOM | 386 | CE2 | TYR | 49 | 119.308 | 52.084 | 61.614 | 1.00 | 30.37 | L |
| ATOM | 387 | CZ | TYR | 49 | 117.953 | 52.228 | 61.340 | 1.00 | 42.99 | L |
| ATOM | 388 | OH | TYR | 49 | 117.048 | 52.410 | 62.370 | 1.00 | 55.09 | L |
| ATOM | 389 | C | TYR | 49 | 120.510 | 54.172 | 57.486 | 1.00 | 24.72 | L |
| ATOM | 390 | O | TYR | 49 | 120.451 | 55.037 | 58.356 | 1.00 | 26.69 | L |
| ATOM | 391 | N | LYS | 50 | 119.762 | 54.189 | 56.392 | 1.00 | 25.34 | L |
| ATOM | 392 | CA | LYS | 50 | 118.786 | 55.241 | 56.132 | 1.00 | 19.61 | L |
| ATOM | 393 | CB | LYS | 50 | 117.611 | 55.134 | 57.108 | 1.00 | 42.59 | L |
| ATOM | 394 | CG | LYS | 50 | 116.426 | 54.345 | 56.566 | 1.00 | 36.91 | L |
| ATOM | 395 | CD | LYS | 50 | 115.124 | 55.118 | 56.723 | 1.00 | 40.28 | L |
| ATOM | 396 | CE | LYS | 50 | 114.289 | 54.568 | 57.865 | 1.00 | 33.03 | L |
| ATOM | 397 | NZ | LYS | 50 | 112.829 | 54.799 | 57.659 | 1.00 | 38.05 | L |
| ATOM | 398 | C | LYS | 50 | 119.368 | 56.645 | 56.192 | 1.00 | 22.01 | L |
| ATOM | 399 | O | LYS | 50 | 118.697 | 57.575 | 56.623 | 1.00 | 30.12 | L |
| ATOM | 400 | N | ALA | 51 | 120.622 | 56.790 | 55.779 | 1.00 | 32.92 | L |
| ATOM | 401 | CA | ALA | 51 | 121.275 | 58.094 | 55.749 | 1.00 | 27.76 | L |
| ATOM | 402 | CB | ALA | 51 | 120.346 | 59.117 | 55.100 | 1.00 | 14.79 | L |
| ATOM | 403 | C | ALA | 51 | 121.787 | 58.647 | 57.073 | 1.00 | 25.18 | L |
| ATOM | 404 | O | ALA | 51 | 122.949 | 59.026 | 57.173 | 1.00 | 28.58 | L |
| ATOM | 405 | N | SER | 52 | 120.927 | 58.714 | 58.081 | 1.00 | 22.15 | L |
| ATOM | 406 | CA | SER | 52 | 121.347 | 59.270 | 59.362 | 1.00 | 19.39 | L |
| ATOM | 407 | CB | SER | 52 | 120.690 | 60.632 | 59.599 | 1.00 | 25.09 | L |
| ATOM | 408 | OG | SER | 52 | 120.199 | 61.188 | 58.390 | 1.00 | 53.81 | L |
| ATOM | 409 | C | SER | 52 | 121.021 | 58.369 | 60.518 | 1.00 | 20.68 | L |
| ATOM | 410 | O | SER | 52 | 121.232 | 58.729 | 61.674 | 1.00 | 23.62 | L |
| ATOM | 411 | N | ASN | 53 | 120.497 | 57.194 | 60.209 | 1.00 | 25.87 | L |
| ATOM | 412 | CA | ASN | 53 | 120.157 | 56.253 | 61.254 | 1.00 | 27.39 | L |
| ATOM | 413 | CB | ASN | 53 | 118.992 | 55.387 | 60.811 | 1.00 | 27.54 | L |
| ATOM | 414 | CG | ASN | 53 | 117.668 | 55.895 | 61.323 | 1.00 | 28.84 | L |
| ATOM | 415 | OD1 | ASN | 53 | 116.619 | 55.656 | 60.729 | 1.00 | 26.55 | L |
| ATOM | 416 | ND2 | ASN | 53 | 117.713 | 56.607 | 62.450 | 1.00 | 36.37 | L |
| ATOM | 417 | C | ASN | 53 | 121.366 | 55.402 | 61.592 | 1.00 | 25.27 | L |
| ATOM | 418 | O | ASN | 53 | 121.809 | 54.592 | 60.783 | 1.00 | 34.60 | L |
| ATOM | 419 | N | LEU | 54 | 121.899 | 55.607 | 62.795 | 1.00 | 34.99 | L |
| ATOM | 420 | CA | LEU | 54 | 123.064 | 54.880 | 63.294 | 1.00 | 47.12 | L |
| ATOM | 421 | CB | LEU | 54 | 123.649 | 55.607 | 64.510 | 1.00 | 37.02 | L |
| ATOM | 422 | CG | LEU | 54 | 125.152 | 55.873 | 64.594 | 1.00 | 20.40 | L |
| ATOM | 423 | CD1 | LEU | 54 | 125.508 | 57.117 | 63.830 | 1.00 | 25.30 | L |
| ATOM | 424 | CD2 | LEU | 54 | 125.533 | 56.034 | 66.039 | 1.00 | 22.53 | L |
| ATOM | 425 | C | LEU | 54 | 122.660 | 53.468 | 63.705 | 1.00 | 56.63 | L |
| ATOM | 426 | O | LEU | 54 | 121.529 | 53.250 | 64.145 | 1.00 | 68.94 | L |
| ATOM | 427 | N | HIS | 55 | 123.578 | 52.513 | 63.573 | 1.00 | 51.79 | L |
| ATOM | 428 | CA | HIS | 55 | 123.267 | 51.142 | 63.948 | 1.00 | 38.57 | L |
| ATOM | 429 | CB | HIS | 55 | 124.091 | 50.139 | 63.137 | 1.00 | 36.54 | L |
| ATOM | 430 | CG | HIS | 55 | 123.551 | 48.742 | 63.186 | 1.00 | 27.93 | L |
| ATOM | 431 | CD2 | HIS | 55 | 122.338 | 48.268 | 63.551 | 1.00 | 31.02 | L |
| ATOM | 432 | ND1 | HIS | 55 | 124.303 | 47.639 | 62.841 | 1.00 | 36.74 | L |
| ATOM | 433 | CE1 | HIS | 55 | 123.573 | 46.545 | 62.993 | 1.00 | 43.03 | L |
| ATOM | 434 | NE2 | HIS | 55 | 122.376 | 46.902 | 63.423 | 1.00 | 37.77 | L |
| ATOM | 435 | C | HIS | 55 | 123.513 | 50.925 | 65.424 | 1.00 | 38.01 | L |
| ATOM | 436 | O | HIS | 55 | 124.296 | 51.634 | 66.058 | 1.00 | 47.97 | L |
| ATOM | 437 | N | THR | 56 | 122.832 | 49.930 | 65.966 | 1.00 | 33.15 | L |
| ATOM | 438 | CA | THR | 56 | 122.951 | 49.600 | 67.371 | 1.00 | 41.46 | L |

TABLE 4-continued

Co-ordinates of the CD28/5.11A1 crystal structure

| ATOM | 439 | CB | THR | 56 | 122.008 | 48.436 | 67.708 | 1.00 | 58.72 | L |
|---|---|---|---|---|---|---|---|---|---|---|
| ATOM | 440 | OG1 | THR | 56 | 121.601 | 47.787 | 66.495 | 1.00 | 57.81 | L |
| ATOM | 441 | CG2 | THR | 56 | 120.770 | 48.955 | 68.430 | 1.00 | 63.75 | L |
| ATOM | 442 | C | THR | 56 | 124.380 | 49.260 | 67.805 | 1.00 | 32.47 | L |
| ATOM | 443 | O | THR | 56 | 124.940 | 48.236 | 67.415 | 1.00 | 23.36 | L |
| ATOM | 444 | N | GLY | 57 | 124.967 | 50.136 | 68.612 | 1.00 | 28.03 | L |
| ATOM | 445 | CA | GLY | 57 | 126.311 | 49.893 | 69.101 | 1.00 | 36.90 | L |
| ATOM | 446 | C | GLY | 57 | 127.388 | 50.703 | 68.403 | 1.00 | 48.73 | L |
| ATOM | 447 | O | GLY | 57 | 128.584 | 50.506 | 68.641 | 1.00 | 45.48 | L |
| ATOM | 448 | N | VAL | 58 | 126.971 | 51.616 | 67.537 | 1.00 | 45.32 | L |
| ATOM | 449 | CA | VAL | 58 | 127.926 | 52.439 | 66.819 | 1.00 | 42.70 | L |
| ATOM | 450 | CB | VAL | 58 | 127.448 | 52.680 | 65.372 | 1.00 | 41.53 | L |
| ATOM | 451 | CG1 | VAL | 58 | 128.383 | 53.648 | 64.654 | 1.00 | 20.54 | L |
| ATOM | 452 | CG2 | VAL | 58 | 127.380 | 51.354 | 64.635 | 1.00 | 16.05 | L |
| ATOM | 453 | C | VAL | 58 | 128.129 | 53.768 | 67.546 | 1.00 | 40.96 | L |
| ATOM | 454 | O | VAL | 58 | 127.178 | 54.509 | 67.780 | 1.00 | 35.53 | L |
| ATOM | 455 | N | PRO | 59 | 129.378 | 54.059 | 67.951 | 1.00 | 38.91 | L |
| ATOM | 456 | CD | PRO | 59 | 130.553 | 53.187 | 67.788 | 1.00 | 42.54 | L |
| ATOM | 457 | CA | PRO | 59 | 129.717 | 55.296 | 68.658 | 1.00 | 38.07 | L |
| ATOM | 458 | CB | PRO | 59 | 131.253 | 55.289 | 68.706 | 1.00 | 34.29 | L |
| ATOM | 459 | CG | PRO | 59 | 131.698 | 54.148 | 67.847 | 1.00 | 25.37 | L |
| ATOM | 460 | C | PRO | 59 | 129.174 | 56.543 | 67.980 | 1.00 | 36.88 | L |
| ATOM | 461 | O | PRO | 59 | 129.273 | 56.694 | 66.762 | 1.00 | 38.73 | L |
| ATOM | 462 | N | SER | 60 | 128.605 | 57.437 | 68.782 | 1.00 | 35.30 | L |
| ATOM | 463 | CA | SER | 60 | 128.044 | 58.680 | 68.274 | 1.00 | 37.70 | L |
| ATOM | 464 | CB | SER | 60 | 127.466 | 59.513 | 69.424 | 1.00 | 47.02 | L |
| ATOM | 465 | OG | SER | 60 | 128.108 | 59.201 | 70.648 | 1.00 | 44.15 | L |
| ATOM | 466 | C | SER | 60 | 129.096 | 59.492 | 67.536 | 1.00 | 33.70 | L |
| ATOM | 467 | O | SER | 60 | 128.760 | 60.405 | 66.785 | 1.00 | 38.05 | L |
| ATOM | 468 | N | ARG | 61 | 130.369 | 59.175 | 67.758 | 1.00 | 31.36 | L |
| ATOM | 469 | CA | ARG | 61 | 131.440 | 59.887 | 67.068 | 1.00 | 40.37 | L |
| ATOM | 470 | CB | ARG | 61 | 132.801 | 59.241 | 67.361 | 1.00 | 45.69 | L |
| ATOM | 471 | CG | ARG | 61 | 133.316 | 58.277 | 66.278 | 1.00 | 69.44 | L |
| ATOM | 472 | CD | ARG | 61 | 134.854 | 58.263 | 66.188 | 1.00 | 56.63 | L |
| ATOM | 473 | NE | ARG | 61 | 135.482 | 57.895 | 67.458 | 1.00 | 41.22 | L |
| ATOM | 474 | CZ | ARG | 61 | 135.733 | 56.646 | 67.834 | 1.00 | 36.39 | L |
| ATOM | 475 | NH1 | ARG | 61 | 135.411 | 55.637 | 67.041 | 1.00 | 46.50 | L |
| ATOM | 476 | NH2 | ARG | 61 | 136.294 | 56.405 | 69.008 | 1.00 | 45.10 | L |
| ATOM | 477 | C | ARG | 61 | 131.137 | 59.822 | 65.573 | 1.00 | 39.44 | L |
| ATOM | 478 | O | ARG | 61 | 131.495 | 60.718 | 64.807 | 1.00 | 31.59 | L |
| ATOM | 479 | N | PHE | 62 | 130.468 | 58.744 | 65.176 | 1.00 | 29.20 | L |
| ATOM | 480 | CA | PHE | 62 | 130.083 | 58.534 | 63.795 | 1.00 | 21.62 | L |
| ATOM | 481 | CB | PHE | 62 | 129.922 | 57.038 | 63.507 | 1.00 | 15.95 | L |
| ATOM | 482 | CG | PHE | 62 | 131.216 | 56.325 | 63.248 | 1.00 | 28.60 | L |
| ATOM | 483 | CD1 | PHE | 62 | 131.770 | 56.303 | 61.975 | 1.00 | 25.81 | L |
| ATOM | 484 | CD2 | PHE | 62 | 131.884 | 55.661 | 64.277 | 1.00 | 34.71 | L |
| ATOM | 485 | CE1 | PHE | 62 | 132.973 | 55.629 | 61.730 | 1.00 | 25.28 | L |
| ATOM | 486 | CE2 | PHE | 62 | 133.086 | 54.987 | 64.039 | 1.00 | 17.13 | L |
| ATOM | 487 | CZ | PHE | 62 | 133.628 | 54.972 | 62.759 | 1.00 | 16.17 | L |
| ATOM | 488 | C | PHE | 62 | 128.749 | 59.223 | 63.574 | 1.00 | 27.58 | L |
| ATOM | 489 | O | PHE | 62 | 127.812 | 59.041 | 64.347 | 1.00 | 26.02 | L |
| ATOM | 490 | N | SER | 63 | 128.667 | 60.028 | 62.526 | 1.00 | 27.01 | L |
| ATOM | 491 | CA | SER | 63 | 127.432 | 60.724 | 62.194 | 1.00 | 29.21 | L |
| ATOM | 492 | CB | SER | 63 | 127.512 | 62.197 | 62.620 | 1.00 | 27.06 | L |
| ATOM | 493 | OG | SER | 63 | 127.604 | 63.059 | 61.501 | 1.00 | 46.67 | L |
| ATOM | 494 | C | SER | 63 | 127.271 | 60.609 | 60.689 | 1.00 | 31.69 | L |
| ATOM | 495 | O | SER | 63 | 128.247 | 60.359 | 59.983 | 1.00 | 35.00 | L |
| ATOM | 496 | N | GLY | 64 | 126.046 | 60.778 | 60.203 | 1.00 | 32.44 | L |
| ATOM | 497 | CA | GLY | 64 | 125.796 | 60.677 | 58.775 | 1.00 | 28.03 | L |
| ATOM | 498 | C | GLY | 64 | 124.656 | 61.567 | 58.325 | 1.00 | 36.15 | L |
| ATOM | 499 | O | GLY | 64 | 123.678 | 61.753 | 59.050 | 1.00 | 31.20 | L |
| ATOM | 500 | N | SER | 65 | 124.761 | 62.103 | 57.115 | 1.00 | 45.47 | L |
| ATOM | 501 | CA | SER | 65 | 123.723 | 62.993 | 56.612 | 1.00 | 43.02 | L |
| ATOM | 502 | CB | SER | 65 | 124.029 | 64.412 | 57.075 | 1.00 | 39.26 | L |
| ATOM | 503 | OG | SER | 65 | 125.378 | 64.487 | 57.510 | 1.00 | 49.79 | L |
| ATOM | 504 | C | SER | 65 | 123.566 | 62.975 | 55.097 | 1.00 | 33.50 | L |
| ATOM | 505 | O | SER | 65 | 124.401 | 62.428 | 54.373 | 1.00 | 35.77 | L |
| ATOM | 506 | N | GLY | 66 | 122.485 | 63.579 | 54.625 | 1.00 | 17.16 | L |
| ATOM | 507 | CA | GLY | 66 | 122.258 | 63.641 | 53.196 | 1.00 | 29.10 | L |
| ATOM | 508 | C | GLY | 66 | 120.920 | 63.081 | 52.769 | 1.00 | 35.42 | L |
| ATOM | 509 | O | GLY | 66 | 120.321 | 62.267 | 53.479 | 1.00 | 32.46 | L |
| ATOM | 510 | N | SER | 67 | 120.449 | 63.527 | 51.608 | 1.00 | 24.62 | L |
| ATOM | 511 | CA | SER | 67 | 119.184 | 63.062 | 51.061 | 1.00 | 28.74 | L |
| ATOM | 512 | CB | SER | 67 | 118.012 | 63.757 | 51.757 | 1.00 | 46.75 | L |
| ATOM | 513 | OG | SER | 67 | 116.780 | 63.142 | 51.412 | 1.00 | 59.32 | L |
| ATOM | 514 | C | SER | 67 | 119.129 | 63.343 | 49.567 | 1.00 | 32.92 | L |
| ATOM | 515 | O | SER | 67 | 119.579 | 64.391 | 49.113 | 1.00 | 35.08 | L |

TABLE 4-continued

Co-ordinates of the CD28/5.11A1 crystal structure

| ATOM | 516 | N | GLY | 68 | 118.589 | 62.399 | 48.803 | 1.00 | 32.00 | L |
|------|-----|-----|-----|----|---------|--------|--------|------|-------|---|
| ATOM | 517 | CA | GLY | 68 | 118.485 | 62.585 | 47.367 | 1.00 | 22.78 | L |
| ATOM | 518 | C | GLY | 68 | 119.712 | 62.129 | 46.604 | 1.00 | 35.09 | L |
| ATOM | 519 | O | GLY | 68 | 119.885 | 60.935 | 46.341 | 1.00 | 32.80 | L |
| ATOM | 520 | N | THR | 69 | 120.567 | 63.086 | 46.255 | 1.00 | 36.67 | L |
| ATOM | 521 | CA | THR | 69 | 121.784 | 62.805 | 45.505 | 1.00 | 36.14 | L |
| ATOM | 522 | CB | THR | 69 | 121.890 | 63.748 | 44.285 | 1.00 | 43.08 | L |
| ATOM | 523 | OG1 | THR | 69 | 120.775 | 63.516 | 43.414 | 1.00 | 47.12 | L |
| ATOM | 524 | CG2 | THR | 69 | 123.175 | 63.505 | 43.514 | 1.00 | 44.41 | L |
| ATOM | 525 | C | THR | 69 | 123.029 | 62.953 | 46.376 | 1.00 | 29.87 | L |
| ATOM | 526 | O | THR | 69 | 123.915 | 62.101 | 46.350 | 1.00 | 38.58 | L |
| ATOM | 527 | N | GLY | 70 | 123.082 | 64.022 | 47.160 | 1.00 | 31.63 | L |
| ATOM | 528 | CA | GLY | 70 | 124.234 | 64.256 | 48.016 | 1.00 | 42.61 | L |
| ATOM | 529 | C | GLY | 70 | 124.171 | 63.521 | 49.337 | 1.00 | 36.70 | L |
| ATOM | 530 | O | GLY | 70 | 123.119 | 63.471 | 49.965 | 1.00 | 45.53 | L |
| ATOM | 531 | N | PHE | 71 | 125.295 | 62.944 | 49.755 | 1.00 | 38.83 | L |
| ATOM | 532 | CA | PHE | 71 | 125.370 | 62.206 | 51.019 | 1.00 | 33.73 | L |
| ATOM | 533 | CB | PHE | 71 | 124.999 | 60.739 | 50.798 | 1.00 | 31.54 | L |
| ATOM | 534 | CG | PHE | 71 | 123.602 | 60.540 | 50.263 | 1.00 | 38.58 | L |
| ATOM | 535 | CD1 | PHE | 71 | 122.561 | 60.199 | 51.120 | 1.00 | 21.48 | L |
| ATOM | 536 | CD2 | PHE | 71 | 123.329 | 60.697 | 48.908 | 1.00 | 26.22 | L |
| ATOM | 537 | CE1 | PHE | 71 | 121.278 | 60.021 | 50.641 | 1.00 | 26.37 | L |
| ATOM | 538 | CE2 | PHE | 71 | 122.044 | 60.520 | 48.422 | 1.00 | 42.61 | L |
| ATOM | 539 | CZ | PHE | 71 | 121.016 | 60.183 | 49.286 | 1.00 | 24.00 | L |
| ATOM | 540 | C | PHE | 71 | 126.774 | 62.296 | 51.605 | 1.00 | 27.97 | L |
| ATOM | 541 | O | PHE | 71 | 127.760 | 62.212 | 50.877 | 1.00 | 31.31 | L |
| ATOM | 542 | N | THR | 72 | 126.866 | 62.457 | 52.921 | 1.00 | 26.78 | L |
| ATOM | 543 | CA | THR | 72 | 128.167 | 62.582 | 53.564 | 1.00 | 26.67 | L |
| ATOM | 544 | CB | THR | 72 | 128.520 | 64.069 | 53.781 | 1.00 | 32.81 | L |
| ATOM | 545 | OG1 | THR | 72 | 129.493 | 64.187 | 54.826 | 1.00 | 56.77 | L |
| ATOM | 546 | CG2 | THR | 72 | 127.288 | 64.856 | 54.164 | 1.00 | 32.03 | L |
| ATOM | 547 | C | THR | 72 | 128.291 | 61.866 | 54.903 | 1.00 | 27.04 | L |
| ATOM | 548 | O | THR | 72 | 127.308 | 61.722 | 55.635 | 1.00 | 23.90 | L |
| ATOM | 549 | N | LEU | 73 | 129.511 | 61.417 | 55.207 | 1.00 | 31.55 | L |
| ATOM | 550 | CA | LEU | 73 | 129.816 | 60.722 | 56.459 | 1.00 | 24.92 | L |
| ATOM | 551 | CB | LEU | 73 | 130.387 | 59.333 | 56.194 | 1.00 | 32.89 | L |
| ATOM | 552 | CG | LEU | 73 | 130.625 | 58.551 | 57.490 | 1.00 | 34.57 | L |
| ATOM | 553 | CD1 | LEU | 73 | 129.287 | 58.045 | 58.021 | 1.00 | 14.98 | L |
| ATOM | 554 | CD2 | LEU | 73 | 131.586 | 57.404 | 57.246 | 1.00 | 10.86 | L |
| ATOM | 555 | C | LEU | 73 | 130.826 | 61.512 | 57.274 | 1.00 | 25.60 | L |
| ATOM | 556 | O | LEU | 73 | 131.823 | 62.004 | 56.755 | 1.00 | 39.03 | L |
| ATOM | 557 | N | THR | 74 | 130.581 | 61.593 | 58.567 | 1.00 | 21.07 | L |
| ATOM | 558 | CA | THR | 74 | 131.443 | 62.362 | 59.436 | 1.00 | 25.98 | L |
| ATOM | 559 | CB | THR | 74 | 130.686 | 63.625 | 59.933 | 1.00 | 34.99 | L |
| ATOM | 560 | OG1 | THR | 74 | 130.181 | 64.351 | 58.808 | 1.00 | 35.85 | L |
| ATOM | 561 | CG2 | THR | 74 | 131.588 | 64.524 | 60.747 | 1.00 | 27.11 | L |
| ATOM | 562 | C | THR | 74 | 131.886 | 61.542 | 60.640 | 1.00 | 29.95 | L |
| ATOM | 563 | O | THR | 74 | 131.065 | 60.931 | 61.322 | 1.00 | 36.77 | L |
| ATOM | 564 | N | ILE | 75 | 133.186 | 61.522 | 60.896 | 1.00 | 24.95 | L |
| ATOM | 565 | CA | ILE | 75 | 133.706 | 60.813 | 62.052 | 1.00 | 23.49 | L |
| ATOM | 566 | CB | ILE | 75 | 134.723 | 59.737 | 61.659 | 1.00 | 21.59 | L |
| ATOM | 567 | CG2 | ILE | 75 | 135.597 | 59.401 | 62.847 | 1.00 | 7.06 | L |
| ATOM | 568 | CG1 | ILE | 75 | 133.988 | 58.479 | 61.198 | 1.00 | 33.47 | L |
| ATOM | 569 | CD1 | ILE | 75 | 133.840 | 58.343 | 59.687 | 1.00 | 25.94 | L |
| ATOM | 570 | C | ILE | 75 | 134.399 | 61.855 | 62.914 | 1.00 | 34.16 | L |
| ATOM | 571 | O | ILE | 75 | 135.440 | 62.381 | 62.537 | 1.00 | 28.63 | L |
| ATOM | 572 | N | SER | 76 | 133.803 | 62.167 | 64.059 | 1.00 | 42.00 | L |
| ATOM | 573 | CA | SER | 76 | 134.366 | 63.155 | 64.971 | 1.00 | 51.91 | L |
| ATOM | 574 | CB | SER | 76 | 133.251 | 63.762 | 65.829 | 1.00 | 67.85 | L |
| ATOM | 575 | OG | SER | 76 | 131.981 | 63.244 | 65.449 | 1.00 | 75.08 | L |
| ATOM | 576 | C | SER | 76 | 135.424 | 62.507 | 65.865 | 1.00 | 55.79 | L |
| ATOM | 577 | O | SER | 76 | 135.372 | 61.304 | 66.131 | 1.00 | 54.31 | L |
| ATOM | 578 | N | SER | 77 | 136.384 | 63.307 | 66.319 | 1.00 | 51.60 | L |
| ATOM | 579 | CA | SER | 77 | 137.459 | 62.818 | 67.177 | 1.00 | 51.14 | L |
| ATOM | 580 | CB | SER | 77 | 136.993 | 62.788 | 68.633 | 1.00 | 51.40 | L |
| ATOM | 581 | OG | SER | 77 | 136.336 | 63.998 | 68.967 | 1.00 | 52.89 | L |
| ATOM | 582 | C | SER | 77 | 137.938 | 61.433 | 66.755 | 1.00 | 49.10 | L |
| ATOM | 583 | O | SER | 77 | 137.515 | 60.422 | 67.311 | 1.00 | 47.48 | L |
| ATOM | 584 | N | LEU | 78 | 138.832 | 61.406 | 65.771 | 1.00 | 46.54 | L |
| ATOM | 585 | CA | LEU | 78 | 139.389 | 60.168 | 65.241 | 1.00 | 32.83 | L |
| ATOM | 586 | CB | LEU | 78 | 140.333 | 60.495 | 64.084 | 1.00 | 27.78 | L |
| ATOM | 587 | CG | LEU | 78 | 140.423 | 59.481 | 62.950 | 1.00 | 35.44 | L |
| ATOM | 588 | CD1 | LEU | 78 | 139.472 | 59.898 | 61.855 | 1.00 | 40.91 | L |
| ATOM | 589 | CD2 | LEU | 78 | 141.852 | 59.397 | 62.421 | 1.00 | 25.57 | L |
| ATOM | 590 | C | LEU | 78 | 140.134 | 59.314 | 66.268 | 1.00 | 28.27 | L |
| ATOM | 591 | O | LEU | 78 | 140.668 | 59.809 | 67.264 | 1.00 | 19.55 | L |
| ATOM | 592 | N | GLN | 79 | 140.163 | 58.016 | 65.999 | 1.00 | 30.85 | L |

TABLE 4-continued

Co-ordinates of the CD28/5.11A1 crystal structure

| ATOM | 593 | CA | GLN | 79 | 140.847 | 57.064 | 66.859 | 1.00 | 34.63 | L |
|------|-----|-----|-----|----|---------|--------|--------|------|-------|---|
| ATOM | 594 | CB | GLN | 79 | 139.855 | 56.338 | 67.763 | 1.00 | 47.40 | L |
| ATOM | 595 | CG | GLN | 79 | 139.162 | 57.238 | 68.764 | 1.00 | 66.32 | L |
| ATOM | 596 | CD | GLN | 79 | 140.118 | 57.793 | 69.791 | 1.00 | 51.70 | L |
| ATOM | 597 | OE1 | GLN | 79 | 141.184 | 57.229 | 70.022 | 1.00 | 38.18 | L |
| ATOM | 598 | NE2 | GLN | 79 | 139.740 | 58.901 | 70.419 | 1.00 | 50.52 | L |
| ATOM | 599 | C | GLN | 79 | 141.534 | 56.054 | 65.965 | 1.00 | 36.58 | L |
| ATOM | 600 | O | GLN | 79 | 141.056 | 55.755 | 64.869 | 1.00 | 30.40 | L |
| ATOM | 601 | N | PRO | 80 | 142.663 | 55.504 | 66.430 | 1.00 | 40.78 | L |
| ATOM | 602 | CD | PRO | 80 | 143.270 | 55.791 | 67.740 | 1.00 | 37.68 | L |
| ATOM | 603 | CA | PRO | 80 | 143.430 | 54.513 | 65.665 | 1.00 | 41.10 | L |
| ATOM | 604 | CB | PRO | 80 | 144.460 | 53.991 | 66.672 | 1.00 | 43.39 | L |
| ATOM | 605 | CG | PRO | 80 | 144.056 | 54.557 | 68.021 | 1.00 | 37.64 | L |
| ATOM | 606 | C | PRO | 80 | 142.532 | 53.398 | 65.149 | 1.00 | 46.35 | L |
| ATOM | 607 | O | PRO | 80 | 142.569 | 53.048 | 63.969 | 1.00 | 41.86 | L |
| ATOM | 608 | N | GLU | 81 | 141.721 | 52.859 | 66.056 | 1.00 | 57.27 | L |
| ATOM | 609 | CA | GLU | 81 | 140.793 | 51.773 | 65.761 | 1.00 | 58.29 | L |
| ATOM | 610 | CB | GLU | 81 | 139.870 | 51.548 | 66.967 | 1.00 | 54.76 | L |
| ATOM | 611 | CG | GLU | 81 | 138.677 | 52.498 | 67.042 | 1.00 | 71.46 | L |
| ATOM | 612 | CD | GLU | 81 | 138.507 | 53.125 | 68.419 | 1.00 | 74.52 | L |
| ATOM | 613 | OE1 | GLU | 81 | 137.390 | 53.039 | 68.983 | 1.00 | 60.52 | L |
| ATOM | 614 | OE2 | GLU | 81 | 139.489 | 53.703 | 68.934 | 1.00 | 65.39 | L |
| ATOM | 615 | C | GLU | 81 | 139.956 | 51.998 | 64.503 | 1.00 | 62.35 | L |
| ATOM | 616 | O | GLU | 81 | 139.618 | 51.052 | 63.794 | 1.00 | 64.51 | L |
| ATOM | 617 | N | ASP | 82 | 139.629 | 53.256 | 64.230 | 1.00 | 63.68 | L |
| ATOM | 618 | CA | ASP | 82 | 138.823 | 53.600 | 63.069 | 1.00 | 50.22 | L |
| ATOM | 619 | CB | ASP | 82 | 138.299 | 55.024 | 63.212 | 1.00 | 50.14 | L |
| ATOM | 620 | CG | ASP | 82 | 137.729 | 55.285 | 64.581 | 1.00 | 50.17 | L |
| ATOM | 621 | OD1 | ASP | 82 | 137.107 | 54.358 | 65.143 | 1.00 | 56.15 | L |
| ATOM | 622 | OD2 | ASP | 82 | 137.906 | 56.408 | 65.095 | 1.00 | 62.15 | L |
| ATOM | 623 | C | ASP | 82 | 139.583 | 53.462 | 61.761 | 1.00 | 47.40 | L |
| ATOM | 624 | O | ASP | 82 | 139.080 | 53.837 | 60.706 | 1.00 | 44.58 | L |
| ATOM | 625 | N | ILE | 83 | 140.801 | 52.935 | 61.830 | 1.00 | 43.70 | L |
| ATOM | 626 | CA | ILE | 83 | 141.586 | 52.738 | 60.621 | 1.00 | 38.44 | L |
| ATOM | 627 | CB | ILE | 83 | 142.991 | 52.194 | 60.932 | 1.00 | 41.83 | L |
| ATOM | 628 | CG2 | ILE | 83 | 143.428 | 51.225 | 59.846 | 1.00 | 41.86 | L |
| ATOM | 629 | CG1 | ILE | 83 | 143.982 | 53.356 | 61.025 | 1.00 | 52.87 | L |
| ATOM | 630 | CD1 | ILE | 83 | 145.232 | 53.032 | 61.826 | 1.00 | 47.10 | L |
| ATOM | 631 | C | ILE | 83 | 140.827 | 51.706 | 59.794 | 1.00 | 32.55 | L |
| ATOM | 632 | O | ILE | 83 | 140.588 | 50.594 | 60.263 | 1.00 | 26.83 | L |
| ATOM | 633 | N | ALA | 84 | 140.441 | 52.085 | 58.575 | 1.00 | 26.12 | L |
| ATOM | 634 | CA | ALA | 84 | 139.692 | 51.200 | 57.693 | 1.00 | 15.10 | L |
| ATOM | 635 | CB | ALA | 84 | 138.453 | 50.702 | 58.406 | 1.00 | 21.07 | L |
| ATOM | 636 | C | ALA | 84 | 139.290 | 51.913 | 56.414 | 1.00 | 12.91 | L |
| ATOM | 637 | O | ALA | 84 | 139.668 | 53.060 | 56.195 | 1.00 | 24.44 | L |
| ATOM | 638 | N | THR | 85 | 138.519 | 51.224 | 55.578 | 1.00 | 19.66 | L |
| ATOM | 639 | CA | THR | 85 | 138.025 | 51.774 | 54.320 | 1.00 | 17.95 | L |
| ATOM | 640 | CB | THR | 85 | 138.413 | 50.898 | 53.131 | 1.00 | 21.81 | L |
| ATOM | 641 | OG1 | THR | 85 | 137.552 | 51.197 | 52.024 | 1.00 | 45.12 | L |
| ATOM | 642 | CG2 | THR | 85 | 138.277 | 49.435 | 53.490 | 1.00 | 27.37 | L |
| ATOM | 643 | C | THR | 85 | 136.505 | 51.809 | 54.410 | 1.00 | 27.74 | L |
| ATOM | 644 | O | THR | 85 | 135.876 | 50.804 | 54.732 | 1.00 | 32.43 | L |
| ATOM | 645 | N | TYR | 86 | 135.914 | 52.960 | 54.116 | 1.00 | 37.25 | L |
| ATOM | 646 | CA | TYR | 86 | 134.469 | 53.109 | 54.213 | 1.00 | 33.34 | L |
| ATOM | 647 | CB | TYR | 86 | 134.153 | 54.363 | 55.028 | 1.00 | 25.32 | L |
| ATOM | 648 | CG | TYR | 86 | 134.852 | 54.381 | 56.372 | 1.00 | 28.51 | L |
| ATOM | 649 | CD1 | TYR | 86 | 134.151 | 54.118 | 57.547 | 1.00 | 44.83 | L |
| ATOM | 650 | CE1 | TYR | 86 | 134.801 | 54.071 | 58.789 | 1.00 | 21.36 | L |
| ATOM | 651 | CD2 | TYR | 86 | 136.226 | 54.607 | 56.467 | 1.00 | 14.36 | L |
| ATOM | 652 | CE2 | TYR | 86 | 136.884 | 54.561 | 57.705 | 1.00 | 22.98 | L |
| ATOM | 653 | CZ | TYR | 86 | 136.158 | 54.289 | 58.857 | 1.00 | 22.24 | L |
| ATOM | 654 | OH | TYR | 86 | 136.786 | 54.210 | 60.072 | 1.00 | 25.93 | L |
| ATOM | 655 | C | TYR | 86 | 133.766 | 53.159 | 52.868 | 1.00 | 44.00 | L |
| ATOM | 656 | O | TYR | 86 | 134.164 | 53.908 | 51.975 | 1.00 | 50.72 | L |
| ATOM | 657 | N | TYR | 87 | 132.712 | 52.353 | 52.748 | 1.00 | 51.03 | L |
| ATOM | 658 | CA | TYR | 87 | 131.910 | 52.248 | 51.526 | 1.00 | 48.37 | L |
| ATOM | 659 | CB | TYR | 87 | 131.795 | 50.780 | 51.108 | 1.00 | 25.20 | L |
| ATOM | 660 | CG | TYR | 87 | 133.108 | 50.126 | 50.753 | 1.00 | 41.42 | L |
| ATOM | 661 | CD1 | TYR | 87 | 133.551 | 50.080 | 49.427 | 1.00 | 38.02 | L |
| ATOM | 662 | CE1 | TYR | 87 | 134.769 | 49.484 | 49.096 | 1.00 | 42.21 | L |
| ATOM | 663 | CD2 | TYR | 87 | 133.918 | 49.555 | 51.742 | 1.00 | 33.37 | L |
| ATOM | 664 | CE2 | TYR | 87 | 135.137 | 48.957 | 51.418 | 1.00 | 33.81 | L |
| ATOM | 665 | CZ | TYR | 87 | 135.555 | 48.929 | 50.096 | 1.00 | 23.95 | L |
| ATOM | 666 | OH | TYR | 87 | 136.771 | 48.380 | 49.779 | 1.00 | 34.33 | L |
| ATOM | 667 | C | TYR | 87 | 130.493 | 52.813 | 51.687 | 1.00 | 52.12 | L |
| ATOM | 668 | O | TYR | 87 | 129.948 | 52.838 | 52.786 | 1.00 | 65.19 | L |
| ATOM | 669 | N | CYS | 88 | 129.895 | 53.250 | 50.582 | 1.00 | 47.34 | L |

TABLE 4-continued

Co-ordinates of the CD28/5.11A1 crystal structure

| ATOM | 670 | CA | CYS | 88 | 128.538 | 53.789 | 50.598 | 1.00 | 32.49 | L |
|---|---|---|---|---|---|---|---|---|---|---|
| ATOM | 671 | C | CYS | 88 | 127.715 | 52.920 | 49.661 | 1.00 | 32.31 | L |
| ATOM | 672 | O | CYS | 88 | 128.140 | 52.641 | 48.547 | 1.00 | 39.98 | L |
| ATOM | 673 | CB | CYS | 88 | 128.530 | 55.233 | 50.093 | 1.00 | 33.98 | L |
| ATOM | 674 | SG | CYS | 88 | 128.799 | 55.411 | 48.289 | 1.00 | 51.95 | L |
| ATOM | 675 | N | GLN | 89 | 126.549 | 52.476 | 50.109 | 1.00 | 22.59 | L |
| ATOM | 676 | CA | GLN | 89 | 125.709 | 51.648 | 49.260 | 1.00 | 21.84 | L |
| ATOM | 677 | CB | GLN | 89 | 125.810 | 50.179 | 49.700 | 1.00 | 31.57 | L |
| ATOM | 678 | CG | GLN | 89 | 124.788 | 49.740 | 50.735 | 1.00 | 42.44 | L |
| ATOM | 679 | CD | GLN | 89 | 123.613 | 48.982 | 50.132 | 1.00 | 34.76 | L |
| ATOM | 680 | OE1 | GLN | 89 | 122.664 | 48.637 | 50.834 | 1.00 | 26.74 | L |
| ATOM | 681 | NE2 | GLN | 89 | 123.671 | 48.723 | 48.831 | 1.00 | 46.97 | L |
| ATOM | 682 | C | GLN | 89 | 124.262 | 52.131 | 49.287 | 1.00 | 25.45 | L |
| ATOM | 683 | O | GLN | 89 | 123.783 | 52.603 | 50.313 | 1.00 | 20.31 | L |
| ATOM | 684 | N | GLN | 90 | 123.574 | 52.035 | 48.153 | 1.00 | 19.13 | L |
| ATOM | 685 | CA | GLN | 90 | 122.183 | 52.457 | 48.096 | 1.00 | 19.46 | L |
| ATOM | 686 | CB | GLN | 90 | 121.882 | 53.162 | 46.769 | 1.00 | 22.24 | L |
| ATOM | 687 | CG | GLN | 90 | 122.072 | 52.299 | 45.523 | 1.00 | 38.10 | L |
| ATOM | 688 | CD | GLN | 90 | 120.775 | 51.666 | 45.009 | 1.00 | 30.31 | L |
| ATOM | 689 | OE1 | GLN | 90 | 119.701 | 51.853 | 45.586 | 1.00 | 32.81 | L |
| ATOM | 690 | NE2 | GLN | 90 | 120.878 | 50.908 | 43.921 | 1.00 | 28.00 | L |
| ATOM | 691 | C | GLN | 90 | 121.257 | 51.250 | 48.267 | 1.00 | 30.72 | L |
| ATOM | 692 | O | GLN | 90 | 121.556 | 50.143 | 47.801 | 1.00 | 25.46 | L |
| ATOM | 693 | N | GLY | 91 | 120.137 | 51.473 | 48.951 | 1.00 | 34.63 | L |
| ATOM | 694 | CA | GLY | 91 | 119.166 | 50.416 | 49.179 | 1.00 | 33.97 | L |
| ATOM | 695 | C | GLY | 91 | 117.820 | 50.781 | 48.580 | 1.00 | 38.48 | L |
| ATOM | 696 | O | GLY | 91 | 116.762 | 50.335 | 49.035 | 1.00 | 28.43 | L |
| ATOM | 697 | N | GLN | 92 | 117.869 | 51.603 | 47.540 | 1.00 | 28.95 | L |
| ATOM | 698 | CA | GLN | 92 | 116.668 | 52.043 | 46.868 | 1.00 | 29.94 | L |
| ATOM | 699 | CB | GLN | 92 | 116.841 | 53.489 | 46.418 | 1.00 | 30.37 | L |
| ATOM | 700 | CG | GLN | 92 | 115.571 | 54.307 | 46.498 | 1.00 | 39.02 | L |
| ATOM | 701 | CD | GLN | 92 | 115.079 | 54.736 | 45.130 | 1.00 | 41.59 | L |
| ATOM | 702 | OE1 | GLN | 92 | 114.039 | 54.274 | 44.663 | 1.00 | 31.97 | L |
| ATOM | 703 | NE2 | GLN | 92 | 115.829 | 55.621 | 44.479 | 1.00 | 59.08 | L |
| ATOM | 704 | C | GLN | 92 | 116.352 | 51.144 | 45.680 | 1.00 | 41.66 | L |
| ATOM | 705 | O | GLN | 92 | 115.495 | 50.267 | 45.782 | 1.00 | 33.85 | L |
| ATOM | 706 | N | THR | 93 | 117.046 | 51.373 | 44.564 | 1.00 | 60.13 | L |
| ATOM | 707 | CA | THR | 93 | 116.866 | 50.596 | 43.327 | 1.00 | 66.93 | L |
| ATOM | 708 | CB | THR | 93 | 117.639 | 51.242 | 42.149 | 1.00 | 78.05 | L |
| ATOM | 709 | OG1 | THR | 93 | 117.362 | 52.647 | 42.104 | 1.00 | 79.52 | L |
| ATOM | 710 | CG2 | THR | 93 | 117.233 | 50.610 | 40.829 | 1.00 | 75.70 | L |
| ATOM | 711 | C | THR | 93 | 117.391 | 49.180 | 43.539 | 1.00 | 59.06 | L |
| ATOM | 712 | O | THR | 93 | 118.425 | 49.009 | 44.183 | 1.00 | 58.37 | L |
| ATOM | 713 | N | TYR | 94 | 116.703 | 48.173 | 42.993 | 1.00 | 50.92 | L |
| ATOM | 714 | CA | TYP | 94 | 117.127 | 46.791 | 43.209 | 1.00 | 52.81 | L |
| ATOM | 715 | CB | TYR | 94 | 116.119 | 45.793 | 42.646 | 1.00 | 55.69 | L |
| ATOM | 716 | CG | TYR | 94 | 115.809 | 44.706 | 43.658 | 1.00 | 64.81 | L |
| ATOM | 717 | CD1 | TYR | 94 | 116.742 | 44.361 | 44.643 | 1.00 | 66.44 | L |
| ATOM | 718 | CE1 | TYR | 94 | 116.451 | 43.413 | 45.622 | 1.00 | 61.74 | L |
| ATOM | 719 | CD2 | TYR | 94 | 114.573 | 44.066 | 43.676 | 1.00 | 65.08 | L |
| ATOM | 720 | CE2 | TYR | 94 | 114.269 | 43.112 | 44.654 | 1.00 | 75.90 | L |
| ATOM | 721 | CZ | TYR | 94 | 115.214 | 42.796 | 45.623 | 1.00 | 73.24 | L |
| ATOM | 722 | OH | TYR | 94 | 114.918 | 41.877 | 46.603 | 1.00 | 71.00 | L |
| ATOM | 723 | C | TYR | 94 | 118.530 | 46.372 | 42.797 | 1.00 | 58.78 | L |
| ATOM | 724 | O | TYR | 94 | 119.146 | 45.561 | 43.487 | 1.00 | 72.46 | L |
| ATOM | 725 | N | PRO | 95 | 119.045 | 46.851 | 41.650 | 1.00 | 50.22 | L |
| ATOM | 726 | CD | PRO | 95 | 118.550 | 47.719 | 40.573 | 1.00 | 29.17 | L |
| ATOM | 727 | CA | PRO | 95 | 120.412 | 46.375 | 41.404 | 1.00 | 45.68 | L |
| ATOM | 728 | CB | PRO | 95 | 120.673 | 46.762 | 39.946 | 1.00 | 19.42 | L |
| ATOM | 729 | CG | PRO | 95 | 119.780 | 47.938 | 39.712 | 1.00 | 25.27 | L |
| ATOM | 730 | C | PRO | 95 | 121.286 | 47.156 | 42.398 | 1.00 | 43.53 | L |
| ATOM | 731 | O | PRO | 95 | 121.936 | 48.131 | 42.027 | 1.00 | 52.07 | L |
| ATOM | 732 | N | TYR | 96 | 121.253 | 46.734 | 43.667 | 1.00 | 32.53 | L |
| ATOM | 733 | CA | TYR | 96 | 122.000 | 47.378 | 44.748 | 1.00 | 29.95 | L |
| ATOM | 734 | CB | TYR | 96 | 122.099 | 46.463 | 45.971 | 1.00 | 35.33 | L |
| ATOM | 735 | CG | TYR | 96 | 120.833 | 46.317 | 46.792 | 1.00 | 28.60 | L |
| ATOM | 736 | CD1 | TYR | 96 | 120.678 | 45.244 | 47.663 | 1.00 | 33.58 | L |
| ATOM | 737 | CE1 | TYR | 96 | 119.523 | 45.087 | 48.430 | 1.00 | 23.02 | L |
| ATOM | 738 | CD2 | TYR | 96 | 119.792 | 47.244 | 46.701 | 1.00 | 29.21 | L |
| ATOM | 739 | CE2 | TYR | 96 | 118.625 | 47.096 | 47.466 | 1.00 | 29.26 | L |
| ATOM | 740 | CZ | TYR | 96 | 118.506 | 46.011 | 48.329 | 1.00 | 29.92 | L |
| ATOM | 741 | OH | TYR | 96 | 117.383 | 45.853 | 49.102 | 1.00 | 25.77 | L |
| ATOM | 742 | C | TYR | 96 | 123.392 | 47.712 | 44.281 | 1.00 | 29.68 | L |
| ATOM | 743 | O | TYR | 96 | 123.980 | 46.954 | 43.511 | 1.00 | 37.11 | L |
| ATOM | 744 | N | THR | 97 | 123.926 | 48.830 | 44.770 | 1.00 | 36.89 | L |
| ATOM | 745 | CA | THR | 97 | 125.259 | 49.280 | 44.372 | 1.00 | 40.63 | L |
| ATOM | 746 | CB | THR | 97 | 125.153 | 50.181 | 43.141 | 1.00 | 46.47 | L |

TABLE 4-continued

Co-ordinates of the CD28/5.11A1 crystal structure

| ATOM | 747 | OG1 | THR | 97  | 123.945 | 50.951 | 43.228 | 1.00 | 49.45 | L |
|------|-----|-----|-----|-----|---------|--------|--------|------|-------|---|
| ATOM | 748 | CG2 | THR | 97  | 125.123 | 49.342 | 41.874 | 1.00 | 48.22 | L |
| ATOM | 749 | C   | THR | 97  | 126.017 | 50.049 | 45.458 | 1.00 | 34.47 | L |
| ATOM | 750 | O   | THR | 97  | 125.473 | 50.975 | 46.062 | 1.00 | 27.32 | L |
| ATOM | 751 | N   | PHE | 98  | 127.268 | 49.662 | 45.700 | 1.00 | 24.58 | L |
| ATOM | 752 | CA  | PHE | 98  | 128.097 | 50.338 | 46.689 | 1.00 | 19.63 | L |
| ATOM | 753 | CB  | PHE | 98  | 129.009 | 49.369 | 47.458 | 1.00 | 21.69 | L |
| ATOM | 754 | CG  | PHE | 98  | 128.386 | 48.051 | 47.780 | 1.00 | 22.09 | L |
| ATOM | 755 | CD1 | PHE | 98  | 128.078 | 47.719 | 49.098 | 1.00 | 28.14 | L |
| ATOM | 756 | CD2 | PHE | 98  | 128.145 | 47.117 | 46.780 | 1.00 | 29.87 | L |
| ATOM | 757 | CE1 | PHE | 98  | 127.543 | 46.481 | 49.409 | 1.00 | 20.31 | L |
| ATOM | 758 | CE2 | PHE | 98  | 127.610 | 45.877 | 47.080 | 1.00 | 20.97 | L |
| ATOM | 759 | CZ  | PHE | 98  | 127.308 | 45.556 | 48.397 | 1.00 | 35.93 | L |
| ATOM | 760 | C   | PHE | 98  | 128.994 | 51.317 | 45.947 | 1.00 | 27.49 | L |
| ATOM | 761 | O   | PHE | 98  | 128.868 | 51.493 | 44.738 | 1.00 | 15.09 | L |
| ATOM | 762 | N   | GLY | 99  | 129.912 | 51.931 | 46.689 | 1.00 | 32.03 | L |
| ATOM | 763 | CA  | GLY | 99  | 130.839 | 52.878 | 46.106 | 1.00 | 37.27 | L |
| ATOM | 764 | C   | GLY | 99  | 132.207 | 52.250 | 45.927 | 1.00 | 44.52 | L |
| ATOM | 765 | O   | GLY | 99  | 132.319 | 51.038 | 45.717 | 1.00 | 42.71 | L |
| ATOM | 766 | N   | GLY | 100 | 133.246 | 53.077 | 46.008 | 1.00 | 42.44 | L |
| ATOM | 767 | CA  | GLY | 100 | 134.600 | 52.584 | 45.848 | 1.00 | 51.35 | L |
| ATOM | 768 | C   | GLY | 100 | 135.344 | 52.448 | 47.164 | 1.00 | 53.12 | L |
| ATOM | 769 | O   | GLY | 100 | 136.390 | 51.791 | 47.241 | 1.00 | 49.35 | L |
| ATOM | 770 | N   | GLY | 101 | 134.799 | 53.067 | 48.204 | 1.00 | 43.66 | L |
| ATOM | 771 | CA  | GLY | 101 | 135.430 | 53.013 | 49.504 | 1.00 | 26.42 | L |
| ATOM | 772 | C   | GLY | 101 | 136.368 | 54.181 | 49.696 | 1.00 | 21.78 | L |
| ATOM | 773 | O   | GLY | 101 | 136.710 | 54.886 | 48.747 | 1.00 | 23.28 | L |
| ATOM | 774 | N   | THR | 102 | 136.787 | 54.392 | 50.933 | 1.00 | 17.65 | L |
| ATOM | 775 | CA  | THR | 102 | 137.682 | 55.489 | 51.221 | 1.00 | 39.10 | L |
| ATOM | 776 | CB  | THR | 102 | 136.869 | 56.745 | 51.644 | 1.00 | 49.68 | L |
| ATOM | 777 | OG1 | THR | 102 | 137.738 | 57.731 | 52.224 | 1.00 | 42.53 | L |
| ATOM | 778 | CG2 | THR | 102 | 135.780 | 56.357 | 52.630 | 1.00 | 55.18 | L |
| ATOM | 779 | C   | THR | 102 | 138.659 | 55.072 | 52.311 | 1.00 | 37.54 | L |
| ATOM | 780 | O   | THR | 102 | 138.295 | 54.948 | 53.478 | 1.00 | 44.36 | L |
| ATOM | 781 | N   | LYS | 103 | 139.903 | 54.830 | 51.911 | 1.00 | 34.42 | L |
| ATOM | 782 | CA  | LYS | 103 | 140.943 | 54.427 | 52.850 | 1.00 | 33.42 | L |
| ATOM | 783 | CB  | LYS | 103 | 142.245 | 54.118 | 52.095 | 1.00 | 27.82 | L |
| ATOM | 784 | CG  | LYS | 103 | 143.518 | 54.210 | 52.937 | 1.00 | 32.59 | L |
| ATOM | 785 | CD  | LYS | 103 | 144.038 | 55.649 | 53.036 | 1.00 | 39.07 | L |
| ATOM | 786 | CE  | LYS | 103 | 145.366 | 55.734 | 53.790 | 1.00 | 45.98 | L |
| ATOM | 787 | NZ  | LYS | 103 | 146.255 | 56.817 | 53.258 | 1.00 | 37.43 | L |
| ATOM | 788 | C   | LYS | 103 | 141.185 | 55.531 | 53.868 | 1.00 | 23.38 | L |
| ATOM | 789 | O   | LYS | 103 | 140.842 | 56.687 | 53.637 | 1.00 | 30.72 | L |
| ATOM | 790 | N   | LEU | 104 | 141.770 | 55.171 | 55.002 | 1.00 | 32.38 | L |
| ATOM | 791 | CA  | LEU | 104 | 142.077 | 56.159 | 56.021 | 1.00 | 38.59 | L |
| ATOM | 792 | CB  | LEU | 104 | 140.904 | 56.368 | 56.966 | 1.00 | 25.66 | L |
| ATOM | 793 | CG  | LEU | 104 | 141.378 | 57.265 | 58.113 | 1.00 | 32.02 | L |
| ATOM | 794 | CD1 | LEU | 104 | 140.804 | 58.658 | 57.944 | 1.00 | 23.79 | L |
| ATOM | 795 | CD2 | LEU | 104 | 140.996 | 56.648 | 59.452 | 1.00 | 29.54 | L |
| ATOM | 796 | C   | LEU | 104 | 143.300 | 55.784 | 56.841 | 1.00 | 45.89 | L |
| ATOM | 797 | O   | LEU | 104 | 143.525 | 54.612 | 57.154 | 1.00 | 45.41 | L |
| ATOM | 798 | N   | GLU | 105 | 144.080 | 56.799 | 57.197 | 1.00 | 40.34 | L |
| ATOM | 799 | CA  | GLU | 105 | 145.280 | 56.597 | 57.979 | 1.00 | 35.75 | L |
| ATOM | 800 | CB  | GLU | 105 | 146.510 | 56.674 | 57.064 | 1.00 | 52.11 | L |
| ATOM | 801 | CG  | GLU | 105 | 147.798 | 57.154 | 57.728 | 1.00 | 69.87 | L |
| ATOM | 802 | CD  | GLU | 105 | 148.876 | 57.513 | 56.712 | 1.00 | 84.87 | L |
| ATOM | 803 | OE1 | GLU | 105 | 150.027 | 57.054 | 56.875 | 1.00 | 87.68 | L |
| ATOM | 804 | OE2 | GLU | 105 | 148.578 | 58.251 | 55.748 | 1.00 | 91.43 | L |
| ATOM | 805 | C   | GLU | 105 | 145.365 | 57.644 | 59.076 | 1.00 | 23.69 | L |
| ATOM | 806 | O   | GLU | 105 | 145.640 | 58.804 | 58.808 | 1.00 | 36.93 | L |
| ATOM | 807 | N   | ILE | 106 | 145.088 | 57.241 | 60.311 | 1.00 | 29.41 | L |
| ATOM | 808 | CA  | ILE | 106 | 145.199 | 58.168 | 61.425 | 1.00 | 38.27 | L |
| ATOM | 809 | CB  | ILE | 106 | 144.723 | 57.513 | 62.769 | 1.00 | 40.94 | L |
| ATOM | 810 | CG2 | ILE | 106 | 145.030 | 56.026 | 62.766 | 1.00 | 31.48 | L |
| ATOM | 811 | CG1 | ILE | 106 | 145.387 | 58.193 | 63.971 | 1.00 | 37.37 | L |
| ATOM | 812 | CD1 | ILE | 106 | 144.571 | 59.336 | 64.579 | 1.00 | 27.37 | L |
| ATOM | 813 | C   | ILE | 106 | 146.702 | 58.441 | 61.434 | 1.00 | 40.57 | L |
| ATOM | 814 | O   | ILE | 106 | 147.497 | 57.506 | 61.438 | 1.00 | 41.72 | L |
| ATOM | 815 | N   | LYS | 107 | 147.088 | 59.716 | 61.399 | 1.00 | 48.16 | L |
| ATOM | 816 | CA  | LYS | 107 | 148.500 | 60.100 | 61.364 | 1.00 | 42.60 | L |
| ATOM | 817 | CB  | LYS | 107 | 148.640 | 61.486 | 60.736 | 1.00 | 20.26 | L |
| ATOM | 818 | CG  | LYS | 107 | 150.043 | 62.069 | 60.819 | 1.00 | 43.13 | L |
| ATOM | 819 | CD  | LYS | 107 | 150.034 | 63.572 | 60.590 | 1.00 | 34.99 | L |
| ATOM | 820 | CE  | LYS | 107 | 149.967 | 63.895 | 59.108 | 1.00 | 38.89 | L |
| ATOM | 821 | NZ  | LYS | 107 | 148.581 | 63.791 | 58.588 | 1.00 | 13.28 | L |
| ATOM | 822 | C   | LYS | 107 | 149.186 | 60.089 | 62.729 | 1.00 | 51.65 | L |
| ATOM | 823 | O   | LYS | 107 | 148.643 | 60.592 | 63.713 | 1.00 | 65.04 | L |

TABLE 4-continued

Co-ordinates of the CD28/5.11A1 crystal structure

| ATOM | 824 | N | ARG | 108 | 150.388 | 59.519 | 62.781 | 1.00 | 52.66 | L |
|---|---|---|---|---|---|---|---|---|---|---|
| ATOM | 825 | CA | ARG | 108 | 151.147 | 59.450 | 64.028 | 1.00 | 39.90 | L |
| ATOM | 826 | CB | ARG | 108 | 151.199 | 58.007 | 64.553 | 1.00 | 33.40 | L |
| ATOM | 827 | CG | ARG | 108 | 152.127 | 57.083 | 63.771 | 1.00 | 28.54 | L |
| ATOM | 828 | CD | ARG | 108 | 152.649 | 55.957 | 64.635 | 1.00 | 25.73 | L |
| ATOM | 829 | NE | ARG | 108 | 153.934 | 56.297 | 65.246 | 1.00 | 34.47 | L |
| ATOM | 830 | CZ | ARG | 108 | 154.303 | 55.928 | 66.471 | 1.00 | 34.06 | L |
| ATOM | 831 | NH1 | ARG | 108 | 153.489 | 55.205 | 67.224 | 1.00 | 57.79 | L |
| ATOM | 832 | NH2 | ARG | 108 | 155.484 | 56.280 | 66.947 | 1.00 | 31.28 | L |
| ATOM | 833 | C | ARG | 108 | 152.566 | 59.974 | 63.858 | 1.00 | 41.80 | L |
| ATOM | 834 | O | ARG | 108 | 153.071 | 60.102 | 62.733 | 1.00 | 36.52 | L |
| ATOM | 835 | N | ALA | 109 | 153.193 | 60.271 | 64.996 | 1.00 | 49.39 | L |
| ATOM | 836 | CA | ALA | 109 | 154.557 | 60.774 | 65.040 | 1.00 | 56.62 | L |
| ATOM | 837 | CB | ALA | 109 | 155.042 | 60.822 | 66.479 | 1.00 | 33.22 | L |
| ATOM | 838 | C | ALA | 109 | 155.479 | 59.894 | 64.209 | 1.00 | 68.35 | L |
| ATOM | 839 | O | ALA | 109 | 155.350 | 58.667 | 64.213 | 1.00 | 79.99 | L |
| ATOM | 840 | N | ASP | 110 | 156.403 | 60.524 | 63.492 | 1.00 | 75.21 | L |
| ATOM | 841 | CA | ASP | 110 | 157.350 | 59.784 | 62.673 | 1.00 | 65.78 | L |
| ATOM | 842 | CB | ASP | 110 | 158.395 | 60.740 | 62.082 | 1.00 | 68.55 | L |
| ATOM | 843 | CG | ASP | 110 | 157.861 | 61.528 | 60.889 | 1.00 | 84.17 | L |
| ATOM | 844 | OD1 | ASP | 110 | 156.656 | 61.399 | 60.580 | 1.00 | 78.11 | L |
| ATOM | 845 | OD2 | ASP | 110 | 158.641 | 62.277 | 60.256 | 1.00 | 94.16 | L |
| ATOM | 846 | C | ASP | 110 | 158.022 | 58.731 | 63.551 | 1.00 | 60.38 | L |
| ATOM | 847 | O | ASP | 110 | 158.093 | 58.882 | 64.776 | 1.00 | 54.97 | L |
| ATOM | 848 | N | ALA | 111 | 158.487 | 57.651 | 62.932 | 1.00 | 55.72 | L |
| ATOM | 849 | CA | ALA | 111 | 159.151 | 56.577 | 63.661 | 1.00 | 59.37 | L |
| ATOM | 850 | CB | ALA | 111 | 158.123 | 55.633 | 64.272 | 1.00 | 55.98 | L |
| ATOM | 851 | C | ALA | 111 | 160.074 | 55.815 | 62.730 | 1.00 | 51.95 | L |
| ATOM | 852 | O | ALA | 111 | 159.669 | 55.363 | 61.658 | 1.00 | 59.98 | L |
| ATOM | 853 | N | ALA | 112 | 161.328 | 55.685 | 63.141 | 1.00 | 47.00 | L |
| ATOM | 854 | CA | ALA | 112 | 162.318 | 54.977 | 62.348 | 1.00 | 42.20 | L |
| ATOM | 855 | CB | ALA | 112 | 163.712 | 55.266 | 62.887 | 1.00 | 43.77 | L |
| ATOM | 856 | C | ALA | 112 | 162.043 | 53.476 | 62.376 | 1.00 | 42.23 | L |
| ATOM | 857 | O | ALA | 112 | 161.447 | 52.957 | 63.325 | 1.00 | 45.43 | L |
| ATOM | 858 | N | PRO | 113 | 162.464 | 52.761 | 61.325 | 1.00 | 51.11 | L |
| ATOM | 859 | CD | PRO | 113 | 163.153 | 53.256 | 60.117 | 1.00 | 52.49 | L |
| ATOM | 860 | CA | PRO | 113 | 162.250 | 51.316 | 61.269 | 1.00 | 49.74 | L |
| ATOM | 861 | CB | PRO | 113 | 162.267 | 51.018 | 59.776 | 1.00 | 32.76 | L |
| ATOM | 862 | CG | PRO | 113 | 163.223 | 52.029 | 59.220 | 1.00 | 41.64 | L |
| ATOM | 863 | C | PRO | 113 | 163.356 | 50.568 | 61.997 | 1.00 | 45.33 | L |
| ATOM | 864 | O | PRO | 113 | 164.511 | 50.988 | 61.974 | 1.00 | 53.16 | L |
| ATOM | 865 | N | THR | 114 | 163.006 | 49.475 | 62.661 | 1.00 | 36.71 | L |
| ATOM | 866 | CA | THR | 114 | 164.009 | 48.675 | 63.341 | 1.00 | 39.49 | L |
| ATOM | 867 | CB | THR | 114 | 163.505 | 48.159 | 64.706 | 1.00 | 34.54 | L |
| ATOM | 868 | OG1 | THR | 114 | 162.504 | 47.153 | 64.511 | 1.00 | 38.54 | L |
| ATOM | 869 | CG2 | THR | 114 | 162.926 | 49.305 | 65.518 | 1.00 | 31.63 | L |
| ATOM | 870 | C | THR | 114 | 164.322 | 47.515 | 62.406 | 1.00 | 42.88 | L |
| ATOM | 871 | O | THR | 114 | 163.527 | 46.585 | 62.247 | 1.00 | 35.53 | L |
| ATOM | 872 | N | VAL | 115 | 165.488 | 47.596 | 61.769 | 1.00 | 36.33 | L |
| ATOM | 873 | CA | VAL | 115 | 165.939 | 46.594 | 60.815 | 1.00 | 42.49 | L |
| ATOM | 874 | CB | VAL | 115 | 166.973 | 47.210 | 59.839 | 1.00 | 46.96 | L |
| ATOM | 875 | CG1 | VAL | 115 | 167.217 | 46.269 | 58.670 | 1.00 | 26.72 | L |
| ATOM | 876 | CG2 | VAL | 115 | 166.470 | 48.555 | 59.338 | 1.00 | 30.46 | L |
| ATOM | 877 | C | VAL | 115 | 166.544 | 45.324 | 61.424 | 1.00 | 38.71 | L |
| ATOM | 878 | O | VAL | 115 | 167.064 | 45.327 | 62.541 | 1.00 | 36.49 | L |
| ATOM | 879 | N | SER | 116 | 166.458 | 44.237 | 60.659 | 1.00 | 44.76 | L |
| ATOM | 880 | CA | SER | 116 | 166.988 | 42.939 | 61.053 | 1.00 | 51.12 | L |
| ATOM | 881 | CB | SER | 116 | 165.975 | 42.188 | 61.913 | 1.00 | 55.78 | L |
| ATOM | 882 | OG | SER | 116 | 165.653 | 42.932 | 63.068 | 1.00 | 58.23 | L |
| ATOM | 883 | C | SER | 116 | 167.292 | 42.130 | 59.799 | 1.00 | 44.61 | L |
| ATOM | 884 | O | SER | 116 | 166.413 | 41.891 | 58.976 | 1.00 | 53.07 | L |
| ATOM | 885 | N | ILE | 117 | 168.547 | 41.726 | 59.641 | 1.00 | 40.79 | L |
| ATOM | 886 | CA | ILE | 117 | 168.935 | 40.929 | 58.487 | 1.00 | 35.02 | L |
| ATOM | 887 | CB | ILE | 117 | 170.299 | 41.393 | 57.902 | 1.00 | 20.96 | L |
| ATOM | 888 | CG2 | ILE | 117 | 171.426 | 41.040 | 58.848 | 1.00 | 28.48 | L |
| ATOM | 889 | CG1 | ILE | 117 | 170.529 | 40.742 | 56.537 | 1.00 | 16.89 | L |
| ATOM | 890 | CD1 | ILE | 117 | 171.461 | 41.625 | 55.632 | 1.00 | 18.50 | L |
| ATOM | 891 | C | ILE | 117 | 169.039 | 39.484 | 58.952 | 1.00 | 32.15 | L |
| ATOM | 892 | O | ILE | 117 | 169.467 | 39.212 | 60.076 | 1.00 | 40.81 | L |
| ATOM | 893 | N | PHE | 118 | 168.626 | 38.560 | 58.091 | 1.00 | 28.82 | L |
| ATOM | 894 | CA | PHE | 118 | 168.671 | 37.145 | 58.423 | 1.00 | 22.76 | L |
| ATOM | 895 | CB | PHE | 118 | 167.260 | 36.601 | 58.654 | 1.00 | 32.60 | L |
| ATOM | 896 | CG | PHE | 118 | 166.589 | 37.174 | 59.858 | 1.00 | 32.33 | L |
| ATOM | 897 | CD1 | PHE | 118 | 165.845 | 38.339 | 59.761 | 1.00 | 32.14 | L |
| ATOM | 898 | CD2 | PHE | 118 | 166.731 | 36.572 | 61.100 | 1.00 | 30.97 | L |
| ATOM | 899 | CE1 | PHE | 118 | 165.262 | 38.902 | 60.884 | 1.00 | 43.45 | L |
| ATOM | 900 | CE2 | PHE | 118 | 166.148 | 37.128 | 62.230 | 1.00 | 24.60 | L |

TABLE 4-continued

Co-ordinates of the CD28/5.11A1 crystal structure

| ATOM | 901 | CZ | PHE | 118 | 165.411 | 38.294 | 62.124 | 1.00 | 41.49 | L |
|---|---|---|---|---|---|---|---|---|---|---|
| ATOM | 902 | C | PHE | 118 | 169.339 | 36.332 | 57.329 | 1.00 | 26.66 | L |
| ATOM | 903 | O | PHE | 118 | 168.928 | 36.370 | 56.170 | 1.00 | 29.78 | L |
| ATOM | 904 | N | PRO | 119 | 170.402 | 35.602 | 57.685 | 1.00 | 34.94 | L |
| ATOM | 905 | CD | PRO | 119 | 170.999 | 35.559 | 59.027 | 1.00 | 32.83 | L |
| ATOM | 906 | CA | PRO | 119 | 171.136 | 34.763 | 56.734 | 1.00 | 37.60 | L |
| ATOM | 907 | CB | PRO | 119 | 172.400 | 34.369 | 57.497 | 1.00 | 31.28 | L |
| ATOM | 908 | CG | PRO | 119 | 172.428 | 35.261 | 58.732 | 1.00 | 32.18 | L |
| ATOM | 909 | C | PRO | 119 | 170.278 | 33.551 | 56.389 | 1.00 | 36.29 | L |
| ATOM | 910 | O | PRO | 119 | 169.297 | 33.266 | 57.079 | 1.00 | 43.06 | L |
| ATOM | 911 | N | PRO | 120 | 170.628 | 32.822 | 55.321 | 1.00 | 33.16 | L |
| ATOM | 912 | CD | PRO | 120 | 171.752 | 33.046 | 54.401 | 1.00 | 35.66 | L |
| ATOM | 913 | CA | PRO | 120 | 169.838 | 31.645 | 54.944 | 1.00 | 27.25 | L |
| ATOM | 914 | CB | PRO | 120 | 170.543 | 31.110 | 53.699 | 1.00 | 23.84 | L |
| ATOM | 915 | CG | PRO | 120 | 171.345 | 32.258 | 53.186 | 1.00 | 47.85 | L |
| ATOM | 916 | C | PRO | 120 | 169.771 | 30.597 | 56.052 | 1.00 | 47.51 | L |
| ATOM | 917 | O | PRO | 120 | 170.408 | 30.733 | 57.097 | 1.00 | 61.24 | L |
| ATOM | 918 | N | SER | 121 | 168.990 | 29.552 | 55.812 | 1.00 | 46.49 | L |
| ATOM | 919 | CA | SER | 121 | 168.836 | 28.481 | 56.781 | 1.00 | 35.79 | L |
| ATOM | 920 | CB | SER | 121 | 167.366 | 28.091 | 56.908 | 1.00 | 39.97 | L |
| ATOM | 921 | OG | SER | 121 | 166.848 | 28.512 | 58.153 | 1.00 | 61.95 | L |
| ATOM | 922 | C | SER | 121 | 169.643 | 27.264 | 56.366 | 1.00 | 35.14 | L |
| ATOM | 923 | O | SER | 121 | 169.776 | 26.970 | 55.178 | 1.00 | 54.90 | L |
| ATOM | 924 | N | SER | 122 | 170.190 | 26.566 | 57.352 | 1.00 | 34.00 | L |
| ATOM | 925 | CA | SER | 122 | 170.964 | 25.367 | 57.078 | 1.00 | 43.67 | L |
| ATOM | 926 | CB | SER | 122 | 171.319 | 24.661 | 58.385 | 1.00 | 55.34 | L |
| ATOM | 927 | OG | SER | 122 | 170.845 | 25.401 | 59.496 | 1.00 | 66.58 | L |
| ATOM | 928 | C | SER | 122 | 170.038 | 24.496 | 56.265 | 1.00 | 39.48 | L |
| ATOM | 929 | O | SER | 122 | 170.345 | 24.107 | 55.139 | 1.00 | 38.43 | L |
| ATOM | 930 | N | GLU | 123 | 168.878 | 24.223 | 56.850 | 1.00 | 39.62 | L |
| ATOM | 931 | CA | GLU | 123 | 167.865 | 23.412 | 56.208 | 1.00 | 42.31 | L |
| ATOM | 932 | CB | GLU | 123 | 166.569 | 23.487 | 57.012 | 1.00 | 49.13 | L |
| ATOM | 933 | CG | GLU | 123 | 165.364 | 22.895 | 56.294 | 1.00 | 85.24 | L |
| ATOM | 934 | CD | GLU | 123 | 164.237 | 22.520 | 57.240 | 1.00 | 100.00 | L |
| ATOM | 935 | OE1 | GLU | 123 | 164.458 | 22.525 | 58.473 | 1.00 | 99.99 | L |
| ATOM | 936 | OE2 | GLU | 123 | 163.127 | 22.221 | 56.742 | 1.00 | 99.98 | L |
| ATOM | 937 | C | GLU | 123 | 167.627 | 23.885 | 54.774 | 1.00 | 34.58 | L |
| ATOM | 938 | O | GLU | 123 | 167.599 | 23.079 | 53.843 | 1.00 | 33.93 | L |
| ATOM | 939 | N | GLN | 124 | 167.467 | 25.193 | 54.588 | 1.00 | 36.30 | L |
| ATOM | 940 | CA | GLN | 124 | 167.228 | 25.719 | 53.254 | 1.00 | 21.55 | L |
| ATOM | 941 | CB | GLN | 124 | 166.875 | 27.207 | 53.289 | 1.00 | 32.12 | L |
| ATOM | 942 | CG | GLN | 124 | 167.075 | 27.854 | 51.927 | 1.00 | 35.77 | L |
| ATOM | 943 | CD | GLN | 124 | 166.351 | 29.160 | 51.766 | 1.00 | 35.92 | L |
| ATOM | 944 | OE1 | GLN | 124 | 166.349 | 29.995 | 52.669 | 1.00 | 37.01 | L |
| ATOM | 945 | NE2 | GLN | 124 | 165.739 | 29.355 | 50.603 | 1.00 | 40.10 | L |
| ATOM | 946 | C | GLN | 124 | 168.441 | 25.534 | 52.353 | 1.00 | 29.80 | L |
| ATOM | 947 | O | GLN | 124 | 168.308 | 25.269 | 51.159 | 1.00 | 40.34 | L |
| ATOM | 948 | N | LEU | 125 | 169.626 | 25.691 | 52.921 | 1.00 | 29.81 | L |
| ATOM | 949 | CA | LEU | 125 | 170.837 | 25.538 | 52.142 | 1.00 | 30.50 | L |
| ATOM | 950 | CB | LEU | 125 | 172.047 | 25.907 | 52.998 | 1.00 | 28.95 | L |
| ATOM | 951 | CG | LEU | 125 | 172.296 | 27.418 | 53.004 | 1.00 | 38.05 | L |
| ATOM | 952 | CD1 | LEU | 125 | 173.275 | 27.794 | 54.099 | 1.00 | 45.58 | L |
| ATOM | 953 | CD2 | LEU | 125 | 172.814 | 27.836 | 51.636 | 1.00 | 18.04 | L |
| ATOM | 954 | C | LEU | 125 | 170.952 | 24.108 | 51.630 | 1.00 | 31.63 | L |
| ATOM | 955 | O | LEU | 125 | 171.396 | 23.873 | 50.503 | 1.00 | 28.04 | L |
| ATOM | 956 | N | THR | 126 | 170.530 | 23.156 | 52.454 | 1.00 | 34.33 | L |
| ATOM | 957 | CA | THR | 126 | 170.570 | 21.741 | 52.094 | 1.00 | 40.34 | L |
| ATOM | 958 | CB | THR | 126 | 169.981 | 20.876 | 53.226 | 1.00 | 47.29 | L |
| ATOM | 959 | OG1 | THR | 126 | 170.445 | 21.364 | 54.490 | 1.00 | 38.65 | L |
| ATOM | 960 | CG2 | THR | 126 | 170.397 | 19.426 | 53.063 | 1.00 | 58.05 | L |
| ATOM | 961 | C | THR | 126 | 169.806 | 21.444 | 50.796 | 1.00 | 47.30 | L |
| ATOM | 962 | O | THR | 126 | 170.142 | 20.515 | 50.063 | 1.00 | 54.95 | L |
| ATOM | 963 | N | SER | 127 | 168.779 | 22.236 | 50.513 | 1.00 | 57.73 | L |
| ATOM | 964 | CA | SER | 127 | 167.985 | 22.042 | 49.308 | 1.00 | 63.60 | L |
| ATOM | 965 | CB | SER | 127 | 166.551 | 22.525 | 49.542 | 1.00 | 63.78 | L |
| ATOM | 966 | OG | SER | 127 | 166.528 | 23.787 | 50.186 | 1.00 | 64.66 | L |
| ATOM | 967 | C | SER | 127 | 168.581 | 22.760 | 48.096 | 1.00 | 67.39 | L |
| ATOM | 968 | O | SER | 127 | 168.031 | 22.693 | 46.994 | 1.00 | 73.65 | L |
| ATOM | 969 | N | GLY | 128 | 169.701 | 23.446 | 48.303 | 1.00 | 60.63 | L |
| ATOM | 970 | CA | GLY | 128 | 170.350 | 24.154 | 47.209 | 1.00 | 50.24 | L |
| ATOM | 971 | C | GLY | 128 | 169.838 | 25.563 | 46.947 | 1.00 | 51.09 | L |
| ATOM | 972 | O | GLY | 128 | 170.151 | 26.169 | 45.917 | 1.00 | 49.56 | L |
| ATOM | 973 | N | GLY | 129 | 169.043 | 26.083 | 47.877 | 1.00 | 48.06 | L |
| ATOM | 974 | CA | GLY | 129 | 168.507 | 27.425 | 47.731 | 1.00 | 48.39 | L |
| ATOM | 975 | C | GLY | 129 | 168.926 | 28.261 | 48.919 | 1.00 | 45.57 | L |
| ATOM | 976 | O | GLY | 129 | 169.221 | 27.719 | 49.986 | 1.00 | 58.83 | L |
| ATOM | 977 | N | ALA | 130 | 168.964 | 29.577 | 48.746 | 1.00 | 44.51 | L |

TABLE 4-continued

Co-ordinates of the CD28/5.11A1 crystal structure

| ATOM | 978 | CA | ALA | 130 | 169.368 | 30.467 | 49.834 | 1.00 | 42.67 | L |
|---|---|---|---|---|---|---|---|---|---|---|
| ATOM | 979 | CB | ALA | 130 | 170.868 | 30.721 | 49.766 | 1.00 | 41.38 | L |
| ATOM | 980 | C | ALA | 130 | 168.612 | 31.784 | 49.784 | 1.00 | 38.53 | L |
| ATOM | 981 | O | ALA | 130 | 168.661 | 32.506 | 48.783 | 1.00 | 43.66 | L |
| ATOM | 982 | N | SER | 131 | 167.923 | 32.103 | 50.872 | 1.00 | 34.81 | L |
| ATOM | 983 | CA | SER | 131 | 167.154 | 33.334 | 50.936 | 1.00 | 28.61 | L |
| ATOM | 984 | CB | SER | 131 | 165.662 | 33.019 | 51.035 | 1.00 | 29.28 | L |
| ATOM | 985 | OG | SER | 131 | 165.165 | 32.494 | 49.817 | 1.00 | 65.36 | L |
| ATOM | 986 | C | SER | 131 | 167.568 | 34.177 | 52.118 | 1.00 | 17.56 | L |
| ATOM | 987 | O | SER | 131 | 167.547 | 33.714 | 53.259 | 1.00 | 23.33 | L |
| ATOM | 988 | N | VAL | 132 | 167.958 | 35.413 | 51.842 | 1.00 | 21.04 | L |
| ATOM | 989 | CA | VAL | 132 | 168.353 | 36.345 | 52.891 | 1.00 | 22.72 | L |
| ATOM | 990 | CB | VAL | 132 | 169.558 | 37.211 | 52.474 | 1.00 | 24.09 | L |
| ATOM | 991 | CG1 | VAL | 132 | 170.321 | 37.669 | 53.711 | 1.00 | 37.12 | L |
| ATOM | 992 | CG2 | VAL | 132 | 170.468 | 36.420 | 51.535 | 1.00 | 26.09 | L |
| ATOM | 993 | C | VAL | 132 | 167.143 | 37.238 | 53.115 | 1.00 | 27.45 | L |
| ATOM | 994 | O | VAL | 132 | 166.609 | 37.836 | 52.179 | 1.00 | 34.77 | L |
| ATOM | 995 | N | VAL | 133 | 166.701 | 37.314 | 54.360 | 1.00 | 21.35 | L |
| ATOM | 996 | CA | VAL | 133 | 165.532 | 38.101 | 54.688 | 1.00 | 15.87 | L |
| ATOM | 997 | CB | VAL | 133 | 164.483 | 37.235 | 55.426 | 1.00 | 18.41 | L |
| ATOM | 998 | CG1 | VAL | 133 | 163.382 | 38.111 | 56.010 | 1.00 | 41.56 | L |
| ATOM | 999 | CG2 | VAL | 133 | 163.900 | 36.211 | 54.466 | 1.00 | 38.08 | L |
| ATOM | 1000 | C | VAL | 133 | 165.870 | 39.296 | 55.548 | 1.00 | 10.26 | L |
| ATOM | 1001 | O | VAL | 133 | 166.701 | 39.222 | 56.454 | 1.00 | 24.39 | L |
| ATOM | 1002 | N | CYS | 134 | 165.206 | 40.404 | 55.254 | 1.00 | 24.79 | L |
| ATOM | 1003 | CA | CYS | 134 | 165.412 | 41.626 | 55.999 | 1.00 | 33.03 | L |
| ATOM | 1004 | C | CYS | 134 | 164.070 | 42.163 | 56.444 | 1.00 | 34.77 | L |
| ATOM | 1005 | O | CYS | 134 | 163.166 | 42.338 | 55.631 | 1.00 | 37.02 | L |
| ATOM | 1006 | CB | CYS | 134 | 166.104 | 42.660 | 55.127 | 1.00 | 37.32 | L |
| ATOM | 1007 | SG | CYS | 134 | 166.705 | 44.083 | 56.077 | 1.00 | 64.48 | L |
| ATOM | 1008 | N | PHE | 135 | 163.946 | 42.420 | 57.737 | 1.00 | 28.41 | L |
| ATOM | 1009 | CA | PHE | 135 | 162.710 | 42.949 | 58.296 | 1.00 | 35.98 | L |
| ATOM | 1010 | CB | PHE | 135 | 162.297 | 42.152 | 59.536 | 1.00 | 23.45 | L |
| ATOM | 1011 | CG | PHE | 135 | 161.854 | 40.746 | 59.244 | 1.00 | 41.99 | L |
| ATOM | 1012 | CD1 | PHE | 135 | 160.991 | 40.472 | 58.187 | 1.00 | 58.79 | L |
| ATOM | 1013 | CD2 | PHE | 135 | 162.280 | 39.696 | 60.049 | 1.00 | 38.90 | L |
| ATOM | 1014 | CE1 | PHE | 135 | 160.555 | 39.170 | 57.939 | 1.00 | 56.32 | L |
| ATOM | 1015 | CE2 | PHE | 135 | 161.849 | 38.391 | 59.810 | 1.00 | 57.18 | L |
| ATOM | 1016 | CZ | PHE | 135 | 160.987 | 38.127 | 58.753 | 1.00 | 46.58 | L |
| ATOM | 1017 | C | PHE | 135 | 162.880 | 44.412 | 58.696 | 1.00 | 37.21 | L |
| ATOM | 1018 | O | PHE | 135 | 163.841 | 44.773 | 59.373 | 1.00 | 31.75 | L |
| ATOM | 1019 | N | LEU | 136 | 161.951 | 45.253 | 58.264 | 1.00 | 38.27 | L |
| ATOM | 1020 | CA | LEU | 136 | 161.968 | 46.665 | 58.622 | 1.00 | 33.10 | L |
| ATOM | 1021 | CB | LEU | 136 | 162.049 | 47.531 | 57.369 | 1.00 | 23.62 | L |
| ATOM | 1022 | CG | LEU | 136 | 163.303 | 47.259 | 56.534 | 1.00 | 17.58 | L |
| ATOM | 1023 | CD1 | LEU | 136 | 163.055 | 46.103 | 55.572 | 1.00 | 17.79 | L |
| ATOM | 1024 | CD2 | LEU | 136 | 163.686 | 48.512 | 55.770 | 1.00 | 29.81 | L |
| ATOM | 1025 | C | LEU | 136 | 160.632 | 46.839 | 59.319 | 1.00 | 30.65 | L |
| ATOM | 1026 | O | LEU | 136 | 159.600 | 47.002 | 58.673 | 1.00 | 30.43 | L |
| ATOM | 1027 | N | ASN | 137 | 160.651 | 46.779 | 60.643 | 1.00 | 35.92 | L |
| ATOM | 1028 | CA | ASN | 137 | 159.421 | 46.873 | 61.400 | 1.00 | 43.25 | L |
| ATOM | 1029 | CB | ASN | 137 | 159.387 | 45.751 | 62.433 | 1.00 | 42.56 | L |
| ATOM | 1030 | CG | ASN | 137 | 159.308 | 44.384 | 61.793 | 1.00 | 30.61 | L |
| ATOM | 1031 | OD1 | ASN | 137 | 159.471 | 43.356 | 62.454 | 1.00 | 37.72 | L |
| ATOM | 1032 | ND2 | ASN | 137 | 159.057 | 44.363 | 60.490 | 1.00 | 39.03 | L |
| ATOM | 1033 | C | ASN | 137 | 159.101 | 48.199 | 62.075 | 1.00 | 40.01 | L |
| ATOM | 1034 | O | ASN | 137 | 159.975 | 49.028 | 62.305 | 1.00 | 39.51 | L |
| ATOM | 1035 | N | ASN | 138 | 157.813 | 48.362 | 62.370 | 1.00 | 41.07 | L |
| ATOM | 1036 | CA | ASN | 138 | 157.239 | 49.526 | 63.036 | 1.00 | 38.43 | L |
| ATOM | 1037 | CB | ASN | 138 | 157.227 | 49.273 | 64.540 | 1.00 | 34.91 | L |
| ATOM | 1038 | CG | ASN | 138 | 156.667 | 47.916 | 64.883 | 1.00 | 33.75 | L |
| ATOM | 1039 | OD1 | ASN | 138 | 155.592 | 47.806 | 65.459 | 1.00 | 29.26 | L |
| ATOM | 1040 | ND2 | ASN | 138 | 157.402 | 46.864 | 64.537 | 1.00 | 33.12 | L |
| ATOM | 1041 | C | ASN | 138 | 157.838 | 50.898 | 62.749 | 1.00 | 31.73 | L |
| ATOM | 1042 | O | ASN | 138 | 158.582 | 51.447 | 63.559 | 1.00 | 39.37 | L |
| ATOM | 1043 | N | PHE | 139 | 157.492 | 51.458 | 61.599 | 1.00 | 32.60 | L |
| ATOM | 1044 | CA | PHE | 139 | 157.982 | 52.770 | 61.227 | 1.00 | 34.36 | L |
| ATOM | 1045 | CB | PHE | 139 | 159.138 | 52.644 | 60.237 | 1.00 | 37.95 | L |
| ATOM | 1046 | CG | PHE | 139 | 158.770 | 51.972 | 58.946 | 1.00 | 21.99 | L |
| ATOM | 1047 | CD1 | PHE | 139 | 158.295 | 52.716 | 57.869 | 1.00 | 28.23 | L |
| ATOM | 1048 | CD2 | PHE | 139 | 158.941 | 50.597 | 58.792 | 1.00 | 23.34 | L |
| ATOM | 1049 | CE1 | PHE | 139 | 157.998 | 52.102 | 56.651 | 1.00 | 22.39 | L |
| ATOM | 1050 | CE2 | PHE | 139 | 158.646 | 49.969 | 57.578 | 1.00 | 15.56 | L |
| ATOM | 1051 | CZ | PHE | 139 | 158.175 | 50.723 | 56.505 | 1.00 | 21.70 | L |
| ATOM | 1052 | C | PHE | 139 | 156.868 | 53.626 | 60.627 | 1.00 | 42.27 | L |
| ATOM | 1053 | O | PHE | 139 | 155.772 | 53.142 | 60.350 | 1.00 | 50.50 | L |
| ATOM | 1054 | N | TYR | 140 | 157.158 | 54.906 | 60.444 | 1.00 | 53.69 | L |

TABLE 4-continued

Co-ordinates of the CD28/5.11A1 crystal structure

| ATOM | 1055 | CA | TYR | 140 | 156.205 | 55.847 | 59.883 | 1.00 | 47.40 | L |
|---|---|---|---|---|---|---|---|---|---|---|
| ATOM | 1056 | CB | TYR | 140 | 155.193 | 56.266 | 60.942 | 1.00 | 53.56 | L |
| ATOM | 1057 | CG | TYR | 140 | 154.002 | 56.979 | 60.360 | 1.00 | 71.75 | L |
| ATOM | 1058 | CD1 | TYR | 140 | 154.072 | 58.331 | 60.029 | 1.00 | 76.99 | L |
| ATOM | 1059 | CE1 | TYR | 140 | 152.978 | 58.991 | 59.471 | 1.00 | 91.66 | L |
| ATOM | 1060 | CD2 | TYR | 140 | 152.809 | 56.301 | 60.119 | 1.00 | 85.47 | L |
| ATOM | 1061 | CE2 | TYR | 140 | 151.712 | 56.948 | 59.562 | 1.00 | 96.08 | L |
| ATOM | 1062 | CZ | TYR | 140 | 151.803 | 58.293 | 59.242 | 1.00 | 93.77 | L |
| ATOM | 1063 | OH | TYR | 140 | 150.716 | 58.946 | 58.706 | 1.00 | 99.99 | L |
| ATOM | 1064 | C | TYR | 140 | 156.981 | 57.065 | 59.410 | 1.00 | 31.82 | L |
| ATOM | 1065 | O | TYR | 140 | 157.900 | 57.515 | 60.088 | 1.00 | 34.79 | L |
| ATOM | 1066 | N | PRO | 141 | 156.631 | 57.613 | 58.240 | 1.00 | 33.26 | L |
| ATOM | 1067 | CD | PRO | 141 | 157.366 | 58.764 | 57.691 | 1.00 | 26.57 | L |
| ATOM | 1068 | CA | PRO | 141 | 155.566 | 57.178 | 57.336 | 1.00 | 39.66 | L |
| ATOM | 1069 | CB | PRO | 141 | 155.450 | 58.321 | 56.323 | 1.00 | 45.22 | L |
| ATOM | 1070 | CG | PRO | 141 | 156.359 | 59.402 | 56.804 | 1.00 | 34.28 | L |
| ATOM | 1071 | C | PRO | 141 | 155.882 | 55.860 | 56.651 | 1.00 | 32.49 | L |
| ATOM | 1072 | O | PRO | 141 | 156.913 | 55.244 | 56.913 | 1.00 | 34.82 | L |
| ATOM | 1073 | N | LYS | 142 | 154.986 | 55.438 | 55.762 | 1.00 | 33.41 | L |
| ATOM | 1074 | CA | LYS | 142 | 155.157 | 54.191 | 55.033 | 1.00 | 45.13 | L |
| ATOM | 1075 | CB | LYS | 142 | 153.862 | 53.816 | 54.304 | 1.00 | 63.72 | L |
| ATOM | 1076 | CG | LYS | 142 | 152.851 | 54.942 | 54.200 | 1.00 | 82.02 | L |
| ATOM | 1077 | CD | LYS | 142 | 152.005 | 54.806 | 52.943 | 1.00 | 86.08 | L |
| ATOM | 1078 | CE | LYS | 142 | 152.031 | 56.087 | 52.114 | 1.00 | 97.81 | L |
| ATOM | 1079 | NZ | LYS | 142 | 153.221 | 56.173 | 51.209 | 1.00 | 100.00 | L |
| ATOM | 1080 | C | LYS | 142 | 156.290 | 54.308 | 54.029 | 1.00 | 47.94 | L |
| ATOM | 1081 | O | LYS | 142 | 156.926 | 53.320 | 53.679 | 1.00 | 60.89 | L |
| ATOM | 1082 | N | ASP | 143 | 156.543 | 55.523 | 53.565 | 1.00 | 61.49 | L |
| ATOM | 1083 | CA | ASP | 143 | 157.605 | 55.725 | 52.603 | 1.00 | 70.17 | L |
| ATOM | 1084 | CB | ASP | 143 | 157.730 | 57.203 | 52.259 | 1.00 | 86.10 | L |
| ATOM | 1085 | CG | ASP | 143 | 156.674 | 57.656 | 51.286 | 1.00 | 99.99 | L |
| ATOM | 1086 | OD1 | ASP | 143 | 155.526 | 57.891 | 51.727 | 1.00 | 98.78 | L |
| ATOM | 1087 | OD2 | ASP | 143 | 156.992 | 57.769 | 50.080 | 1.00 | 99.96 | L |
| ATOM | 1088 | C | ASP | 143 | 158.923 | 55.207 | 53.148 | 1.00 | 62.40 | L |
| ATOM | 1089 | O | ASP | 143 | 159.344 | 55.564 | 54.251 | 1.00 | 47.98 | L |
| ATOM | 1090 | N | ILE | 144 | 159.563 | 54.348 | 52.363 | 1.00 | 59.85 | L |
| ATOM | 1091 | CA | ILE | 144 | 160.839 | 53.752 | 52.722 | 1.00 | 51.41 | L |
| ATOM | 1092 | CB | ILE | 144 | 160.664 | 52.644 | 53.785 | 1.00 | 41.53 | L |
| ATOM | 1093 | CG2 | ILE | 144 | 160.074 | 51.392 | 53.155 | 1.00 | 34.89 | L |
| ATOM | 1094 | CG1 | ILE | 144 | 162.011 | 52.320 | 54.427 | 1.00 | 24.47 | L |
| ATOM | 1095 | CD1 | ILE | 144 | 161.892 | 51.470 | 55.671 | 1.00 | 21.68 | L |
| ATOM | 1096 | C | ILE | 144 | 161.441 | 53.160 | 51.460 | 1.00 | 48.41 | L |
| ATOM | 1097 | O | ILE | 144 | 160.719 | 52.739 | 50.557 | 1.00 | 31.96 | L |
| ATOM | 1098 | N | ASN | 145 | 162.765 | 53.142 | 51.387 | 1.00 | 56.85 | L |
| ATOM | 1099 | CA | ASN | 145 | 163.447 | 52.603 | 50.221 | 1.00 | 62.49 | L |
| ATOM | 1100 | CB | ASN | 145 | 164.063 | 53.730 | 49.399 | 1.00 | 75.48 | L |
| ATOM | 1101 | CG | ASN | 145 | 164.104 | 53.413 | 47.922 | 1.00 | 98.08 | L |
| ATOM | 1102 | OD1 | ASN | 145 | 163.684 | 54.221 | 47.094 | 1.00 | 99.97 | L |
| ATOM | 1103 | ND2 | ASN | 145 | 164.612 | 52.231 | 47.579 | 1.00 | 99.99 | L |
| ATOM | 1104 | C | ASN | 145 | 164.531 | 51.633 | 50.650 | 1.00 | 52.75 | L |
| ATOM | 1105 | O | ASN | 145 | 165.530 | 52.024 | 51.251 | 1.00 | 46.53 | L |
| ATOM | 1106 | N | VAL | 146 | 164.324 | 50.362 | 50.330 | 1.00 | 60.86 | L |
| ATOM | 1107 | CA | VAL | 146 | 165.283 | 49.327 | 50.683 | 1.00 | 55.40 | L |
| ATOM | 1108 | CB | VAL | 146 | 164.572 | 48.048 | 51.171 | 1.00 | 51.60 | L |
| ATOM | 1109 | CG1 | VAL | 146 | 165.593 | 47.066 | 51.728 | 1.00 | 23.45 | L |
| ATOM | 1110 | CG2 | VAL | 146 | 163.545 | 48.397 | 52.234 | 1.00 | 57.40 | L |
| ATOM | 1111 | C | VAL | 146 | 166.158 | 48.975 | 49.490 | 1.00 | 53.23 | L |
| ATOM | 1112 | O | VAL | 146 | 165.707 | 48.977 | 48.341 | 1.00 | 69.79 | L |
| ATOM | 1113 | N | LYS | 147 | 167.421 | 48.679 | 49.775 | 1.00 | 49.86 | L |
| ATOM | 1114 | CA | LYS | 147 | 168.378 | 48.312 | 48.746 | 1.00 | 42.42 | L |
| ATOM | 1115 | CB | LYS | 147 | 169.281 | 49.499 | 48.413 | 1.00 | 47.62 | L |
| ATOM | 1116 | CG | LYS | 147 | 168.754 | 50.388 | 47.302 | 1.00 | 79.82 | L |
| ATOM | 1117 | CD | LYS | 147 | 169.895 | 51.010 | 46.512 | 1.00 | 86.84 | L |
| ATOM | 1118 | CE | LYS | 147 | 169.939 | 52.524 | 46.691 | 1.00 | 93.63 | L |
| ATOM | 1119 | NZ | LYS | 147 | 170.983 | 52.943 | 47.671 | 1.00 | 75.73 | L |
| ATOM | 1120 | C | LYS | 147 | 169.222 | 47.159 | 49.265 | 1.00 | 35.56 | L |
| ATOM | 1121 | O | LYS | 147 | 169.545 | 47.103 | 50.451 | 1.00 | 22.60 | L |
| ATOM | 1122 | N | TRP | 148 | 169.566 | 46.236 | 48.375 | 1.00 | 43.57 | L |
| ATOM | 1123 | CA | TRP | 148 | 170.386 | 45.095 | 48.758 | 1.00 | 34.06 | L |
| ATOM | 1124 | CB | TRP | 148 | 169.782 | 43.796 | 48.214 | 1.00 | 32.94 | L |
| ATOM | 1125 | CG | TRP | 148 | 168.782 | 43.185 | 49.150 | 1.00 | 47.82 | L |
| ATOM | 1126 | CD2 | TRP | 148 | 169.062 | 42.433 | 50.338 | 1.00 | 46.07 | L |
| ATOM | 1127 | CE2 | TRP | 148 | 167.822 | 42.096 | 50.923 | 1.00 | 40.42 | L |
| ATOM | 1128 | CE3 | TRP | 148 | 170.243 | 42.012 | 50.967 | 1.00 | 64.21 | L |
| ATOM | 1129 | CD1 | TRP | 148 | 167.420 | 43.270 | 49.065 | 1.00 | 34.71 | L |
| ATOM | 1130 | NE1 | TRP | 148 | 166.838 | 42.621 | 50.125 | 1.00 | 38.06 | L |
| ATOM | 1131 | CZ2 | TRP | 148 | 167.725 | 41.357 | 52.109 | 1.00 | 15.75 | L |

TABLE 4-continued

Co-ordinates of the CD28/5.11A1 crystal structure

| ATOM | 1132 | CZ3 | TRP | 148 | 170.146 | 41.277 | 52.148 | 1.00 | 72.60 | L |
|---|---|---|---|---|---|---|---|---|---|---|
| ATOM | 1133 | CH2 | TRP | 148 | 168.894 | 40.958 | 52.705 | 1.00 | 49.76 | L |
| ATOM | 1134 | C | TRP | 148 | 171.793 | 45.269 | 48.217 | 1.00 | 36.36 | L |
| ATOM | 1135 | O | TRP | 148 | 171.984 | 45.624 | 47.055 | 1.00 | 34.43 | L |
| ATOM | 1136 | N | LYS | 149 | 172.784 | 45.027 | 49.062 | 1.00 | 44.04 | L |
| ATOM | 1137 | CA | LYS | 149 | 174.157 | 45.161 | 48.623 | 1.00 | 41.49 | L |
| ATOM | 1138 | CB | LYS | 149 | 174.820 | 46.341 | 49.321 | 1.00 | 34.89 | L |
| ATOM | 1139 | CG | LYS | 149 | 175.080 | 47.515 | 48.400 | 1.00 | 38.34 | L |
| ATOM | 1140 | CD | LYS | 149 | 174.417 | 48.774 | 48.915 | 1.00 | 36.55 | L |
| ATOM | 1141 | CE | LYS | 149 | 175.294 | 49.986 | 48.667 | 1.00 | 43.94 | L |
| ATOM | 1142 | NZ | LYS | 149 | 175.270 | 50.930 | 49.819 | 1.00 | 55.84 | L |
| ATOM | 1143 | C | LYS | 149 | 174.937 | 43.893 | 48.896 | 1.00 | 38.62 | L |
| ATOM | 1144 | O | LYS | 149 | 175.125 | 43.505 | 50.045 | 1.00 | 42.16 | L |
| ATOM | 1145 | N | ILE | 150 | 175.372 | 43.241 | 47.825 | 1.00 | 22.84 | L |
| ATOM | 1146 | CA | ILE | 150 | 176.157 | 42.020 | 47.938 | 1.00 | 24.90 | L |
| ATOM | 1147 | CB | ILE | 150 | 175.675 | 40.954 | 46.958 | 1.00 | 42.14 | L |
| ATOM | 1148 | CG2 | ILE | 150 | 176.371 | 39.642 | 47.255 | 1.00 | 38.41 | L |
| ATOM | 1149 | CG1 | ILE | 150 | 174.159 | 40.812 | 47.060 | 1.00 | 42.99 | L |
| ATOM | 1150 | CD1 | ILE | 150 | 173.598 | 39.635 | 46.309 | 1.00 | 32.26 | L |
| ATOM | 1151 | C | ILE | 150 | 177.600 | 42.361 | 47.614 | 1.00 | 23.92 | L |
| ATOM | 1152 | O | ILE | 150 | 177.975 | 42.479 | 46.443 | 1.00 | 24.95 | L |
| ATOM | 1153 | N | ASP | 151 | 178.404 | 42.527 | 48.658 | 1.00 | 48.84 | L |
| ATOM | 1154 | CA | ASP | 151 | 179.805 | 42.886 | 48.488 | 1.00 | 63.98 | L |
| ATOM | 1155 | CB | ASP | 151 | 180.507 | 41.896 | 47.547 | 1.00 | 74.75 | L |
| ATOM | 1156 | CG | ASP | 151 | 180.844 | 40.574 | 48.223 | 1.00 | 76.70 | L |
| ATOM | 1157 | OD1 | ASP | 151 | 180.681 | 40.465 | 49.460 | 1.00 | 79.84 | L |
| ATOM | 1158 | OD2 | ASP | 151 | 181.274 | 39.638 | 47.508 | 1.00 | 56.23 | L |
| ATOM | 1159 | C | ASP | 151 | 179.854 | 44.300 | 47.905 | 1.00 | 70.87 | L |
| ATOM | 1160 | O | ASP | 151 | 180.483 | 44.536 | 46.868 | 1.00 | 70.42 | L |
| ATOM | 1161 | N | GLY | 152 | 179.172 | 45.226 | 48.577 | 1.00 | 76.86 | L |
| ATOM | 1162 | CA | GLY | 152 | 179.139 | 46.613 | 48.139 | 1.00 | 67.78 | L |
| ATOM | 1163 | C | GLY | 152 | 178.418 | 46.840 | 46.824 | 1.00 | 70.46 | L |
| ATOM | 1164 | O | GLY | 152 | 178.156 | 47.980 | 46.438 | 1.00 | 79.32 | L |
| ATOM | 1165 | N | SER | 153 | 178.098 | 45.754 | 46.131 | 1.00 | 62.96 | L |
| ATOM | 1166 | CA | SER | 153 | 177.409 | 45.845 | 44.856 | 1.00 | 60.58 | L |
| ATOM | 1167 | CB | SER | 153 | 177.840 | 44.693 | 43.947 | 1.00 | 68.60 | L |
| ATOM | 1168 | OG | SER | 153 | 178.171 | 45.160 | 42.653 | 1.00 | 71.40 | L |
| ATOM | 1169 | C | SER | 153 | 175.902 | 45.800 | 45.063 | 1.00 | 61.38 | L |
| ATOM | 1170 | O | SER | 153 | 175.401 | 45.044 | 45.895 | 1.00 | 59.28 | L |
| ATOM | 1171 | N | GLU | 154 | 175.183 | 46.620 | 44.304 | 1.00 | 59.43 | L |
| ATOM | 1172 | CA | GLU | 154 | 173.731 | 46.677 | 44.393 | 1.00 | 66.09 | L |
| ATOM | 1173 | CB | GLU | 154 | 173.222 | 47.987 | 43.793 | 1.00 | 81.88 | L |
| ATOM | 1174 | CG | GLU | 154 | 172.299 | 48.776 | 44.700 | 1.00 | 78.09 | L |
| ATOM | 1175 | CD | GLU | 154 | 171.857 | 50.087 | 44.079 | 1.00 | 85.76 | L |
| ATOM | 1176 | OE1 | GLU | 154 | 170.891 | 50.074 | 43.283 | 1.00 | 65.69 | L |
| ATOM | 1177 | OE2 | GLU | 154 | 172.476 | 51.131 | 44.385 | 1.00 | 98.75 | L |
| ATOM | 1178 | C | GLU | 154 | 173.123 | 45.505 | 43.635 | 1.00 | 78.80 | L |
| ATOM | 1179 | O | GLU | 154 | 173.476 | 45.248 | 42.485 | 1.00 | 87.43 | L |
| ATOM | 1180 | N | ARG | 155 | 172.211 | 44.791 | 44.288 | 1.00 | 78.61 | L |
| ATOM | 1181 | CA | ARG | 155 | 171.552 | 43.654 | 43.669 | 1.00 | 72.18 | L |
| ATOM | 1182 | CB | ARG | 155 | 171.904 | 42.371 | 44.411 | 1.00 | 57.25 | L |
| ATOM | 1183 | CG | ARG | 155 | 172.051 | 41.177 | 43.500 | 1.00 | 53.97 | L |
| ATOM | 1184 | CD | ARG | 155 | 170.868 | 40.250 | 43.648 | 1.00 | 47.95 | L |
| ATOM | 1185 | NE | ARG | 155 | 170.680 | 39.401 | 42.474 | 1.00 | 59.26 | L |
| ATOM | 1186 | CZ | ARG | 155 | 171.533 | 38.459 | 42.084 | 1.00 | 47.18 | L |
| ATOM | 1187 | NH1 | ARG | 155 | 172.644 | 38.239 | 42.776 | 1.00 | 58.65 | L |
| ATOM | 1188 | NH2 | ARG | 155 | 171.272 | 37.731 | 41.007 | 1.00 | 62.18 | L |
| ATOM | 1189 | C | ARG | 155 | 170.049 | 43.862 | 43.692 | 1.00 | 76.06 | L |
| ATOM | 1190 | O | ARG | 155 | 169.470 | 44.142 | 44.741 | 1.00 | 79.59 | L |
| ATOM | 1191 | N | GLN | 156 | 169.426 | 43.726 | 42.527 | 1.00 | 81.46 | L |
| ATOM | 1192 | CA | GLN | 156 | 167.984 | 43.913 | 42.395 | 1.00 | 75.51 | L |
| ATOM | 1193 | CB | GLN | 156 | 167.702 | 45.122 | 41.510 | 1.00 | 76.21 | L |
| ATOM | 1194 | CG | GLN | 156 | 168.779 | 46.179 | 41.579 | 1.00 | 86.59 | L |
| ATOM | 1195 | CD | GLN | 156 | 168.216 | 47.575 | 41.514 | 1.00 | 82.98 | L |
| ATOM | 1196 | OE1 | GLN | 156 | 167.460 | 47.912 | 40.597 | 1.00 | 74.92 | L |
| ATOM | 1197 | NE2 | GLN | 156 | 168.579 | 48.402 | 42.486 | 1.00 | 79.96 | L |
| ATOM | 1198 | C | GLN | 156 | 167.308 | 42.690 | 41.799 | 1.00 | 75.18 | L |
| ATOM | 1199 | O | GLN | 156 | 166.094 | 42.663 | 41.629 | 1.00 | 78.45 | L |
| ATOM | 1200 | N | ASN | 157 | 168.106 | 41.681 | 41.485 | 1.00 | 69.92 | L |
| ATOM | 1201 | CA | ASN | 157 | 167.577 | 40.460 | 40.909 | 1.00 | 62.62 | L |
| ATOM | 1202 | CB | ASN | 157 | 168.587 | 39.880 | 39.912 | 1.00 | 83.40 | L |
| ATOM | 1203 | CG | ASN | 157 | 168.058 | 38.656 | 39.189 | 1.00 | 96.73 | L |
| ATOM | 1204 | OD1 | ASN | 157 | 168.142 | 37.534 | 39.692 | 1.00 | 99.98 | L |
| ATOM | 1205 | ND2 | ASN | 157 | 167.509 | 38.865 | 38.000 | 1.00 | 96.79 | L |
| ATOM | 1206 | C | ASN | 157 | 167.270 | 39.440 | 42.009 | 1.00 | 43.07 | L |
| ATOM | 1207 | O | ASN | 157 | 168.169 | 38.978 | 42.711 | 1.00 | 51.60 | L |
| ATOM | 1208 | N | GLY | 158 | 165.994 | 39.103 | 42.166 | 1.00 | 37.93 | L |

TABLE 4-continued

Co-ordinates of the CD28/5.11A1 crystal structure

| ATOM | 1209 | CA | GLY | 158 | 165.613 | 38.126 | 43.168 | 1.00 | 45.50 | L |
|---|---|---|---|---|---|---|---|---|---|---|
| ATOM | 1210 | C | GLY | 158 | 165.052 | 38.719 | 44.441 | 1.00 | 46.88 | L |
| ATOM | 1211 | O | GLY | 158 | 164.905 | 38.016 | 45.438 | 1.00 | 46.67 | L |
| ATOM | 1212 | N | VAL | 159 | 164.730 | 40.005 | 44.409 | 1.00 | 46.40 | L |
| ATOM | 1213 | CA | VAL | 159 | 164.191 | 40.668 | 45.582 | 1.00 | 48.04 | L |
| ATOM | 1214 | CB | VAL | 159 | 164.746 | 42.089 | 45.707 | 1.00 | 46.84 | L |
| ATOM | 1215 | CG1 | VAL | 159 | 164.497 | 42.616 | 47.106 | 1.00 | 49.41 | L |
| ATOM | 1216 | CG2 | VAL | 159 | 166.234 | 42.091 | 45.398 | 1.00 | 31.32 | L |
| ATOM | 1217 | C | VAL | 159 | 162.668 | 40.738 | 45.570 | 1.00 | 50.14 | L |
| ATOM | 1218 | O | VAL | 159 | 162.065 | 41.111 | 44.563 | 1.00 | 70.43 | L |
| ATOM | 1219 | N | LEU | 160 | 162.060 | 40.371 | 46.699 | 1.00 | 47.07 | L |
| ATOM | 1220 | CA | LEU | 160 | 160.606 | 40.379 | 46.862 | 1.00 | 40.66 | L |
| ATOM | 1221 | CB | LEU | 160 | 160.060 | 38.958 | 46.894 | 1.00 | 28.04 | L |
| ATOM | 1222 | CG | LEU | 160 | 160.148 | 38.197 | 45.577 | 1.00 | 32.43 | L |
| ATOM | 1223 | CD1 | LEU | 160 | 159.270 | 36.965 | 45.669 | 1.00 | 37.34 | L |
| ATOM | 1224 | CD2 | LEU | 160 | 159.722 | 39.095 | 44.413 | 1.00 | 7.94 | L |
| ATOM | 1225 | C | LEU | 160 | 160.204 | 41.077 | 48.151 | 1.00 | 42.42 | L |
| ATOM | 1226 | O | LEU | 160 | 160.474 | 40.583 | 49.250 | 1.00 | 48.94 | L |
| ATOM | 1227 | N | ASN | 161 | 159.545 | 42.220 | 48.011 | 1.00 | 40.58 | L |
| ATOM | 1228 | CA | ASN | 161 | 159.109 | 42.996 | 49.161 | 1.00 | 26.69 | L |
| ATOM | 1229 | CB | ASN | 161 | 159.377 | 44.477 | 48.917 | 1.00 | 24.90 | L |
| ATOM | 1230 | CG | ASN | 161 | 160.804 | 44.746 | 48.500 | 1.00 | 36.23 | L |
| ATOM | 1231 | OD1 | ASN | 161 | 161.743 | 44.301 | 49.153 | 1.00 | 55.57 | L |
| ATOM | 1232 | ND2 | ASN | 161 | 160.975 | 45.475 | 47.407 | 1.00 | 47.35 | L |
| ATOM | 1233 | C | ASN | 161 | 157.637 | 42.792 | 49.471 | 1.00 | 32.25 | L |
| ATOM | 1234 | O | ASN | 161 | 156.850 | 42.415 | 48.605 | 1.00 | 34.73 | L |
| ATOM | 1235 | N | SER | 162 | 157.276 | 43.052 | 50.722 | 1.00 | 28.82 | L |
| ATOM | 1236 | CA | SER | 162 | 155.908 | 42.907 | 51.179 | 1.00 | 30.10 | L |
| ATOM | 1237 | CB | SER | 162 | 155.655 | 41.470 | 51.623 | 1.00 | 25.07 | L |
| ATOM | 1238 | OG | SER | 162 | 154.368 | 41.341 | 52.203 | 1.00 | 34.98 | L |
| ATOM | 1239 | C | SER | 162 | 155.687 | 43.855 | 52.349 | 1.00 | 28.22 | L |
| ATOM | 1240 | O | SER | 162 | 156.542 | 43.949 | 53.231 | 1.00 | 28.01 | L |
| ATOM | 1241 | N | TRP | 163 | 154.556 | 44.560 | 52.346 | 1.00 | 44.68 | L |
| ATOM | 1242 | CA | TRP | 163 | 154.217 | 45.502 | 53.413 | 1.00 | 47.01 | L |
| ATOM | 1243 | CB | TRP | 163 | 153.977 | 46.914 | 52.865 | 1.00 | 47.04 | L |
| ATOM | 1244 | CG | TRP | 163 | 155.114 | 47.542 | 52.139 | 1.00 | 50.28 | L |
| ATOM | 1245 | CD2 | TRP | 163 | 155.581 | 47.209 | 50.824 | 1.00 | 47.77 | L |
| ATOM | 1246 | CE2 | TRP | 163 | 156.655 | 48.079 | 50.529 | 1.00 | 47.30 | L |
| ATOM | 1247 | CE3 | TRP | 163 | 155.193 | 46.258 | 49.865 | 1.00 | 36.64 | L |
| ATOM | 1248 | CD1 | TRP | 163 | 155.899 | 48.573 | 52.578 | 1.00 | 61.33 | L |
| ATOM | 1249 | NE1 | TRP | 163 | 156.828 | 48.901 | 51.615 | 1.00 | 51.73 | L |
| ATOM | 1250 | CZ2 | TRP | 163 | 157.349 | 48.028 | 49.313 | 1.00 | 41.27 | L |
| ATOM | 1251 | CZ3 | TRP | 163 | 155.882 | 46.206 | 48.655 | 1.00 | 43.64 | L |
| ATOM | 1252 | CH2 | TRP | 163 | 156.950 | 47.089 | 48.391 | 1.00 | 31.42 | L |
| ATOM | 1253 | C | TRP | 163 | 152.937 | 45.087 | 54.111 | 1.00 | 47.66 | L |
| ATOM | 1254 | O | TRP | 163 | 152.056 | 44.487 | 53.504 | 1.00 | 46.95 | L |
| ATOM | 1255 | N | THR | 164 | 152.831 | 45.420 | 55.389 | 1.00 | 42.09 | L |
| ATOM | 1256 | CA | THR | 164 | 151.623 | 45.119 | 56.141 | 1.00 | 39.34 | L |
| ATOM | 1257 | CB | THR | 164 | 151.927 | 44.805 | 57.604 | 1.00 | 40.04 | L |
| ATOM | 1258 | OG1 | THR | 164 | 152.625 | 45.911 | 58.185 | 1.00 | 45.73 | L |
| ATOM | 1259 | CG2 | THR | 164 | 152.770 | 43.552 | 57.720 | 1.00 | 45.43 | L |
| ATOM | 1260 | C | THR | 164 | 150.804 | 46.400 | 56.099 | 1.00 | 33.70 | L |
| ATOM | 1261 | O | THR | 164 | 151.268 | 47.424 | 55.597 | 1.00 | 27.93 | L |
| ATOM | 1262 | N | ASP | 165 | 149.584 | 46.349 | 56.620 | 1.00 | 29.63 | L |
| ATOM | 1263 | CA | ASP | 165 | 148.739 | 47.533 | 56.649 | 1.00 | 37.94 | L |
| ATOM | 1264 | CB | ASP | 165 | 147.261 | 47.141 | 56.673 | 1.00 | 57.52 | L |
| ATOM | 1265 | CG | ASP | 165 | 146.784 | 46.574 | 55.352 | 1.00 | 78.24 | L |
| ATOM | 1266 | OD1 | ASP | 165 | 147.303 | 47.005 | 54.302 | 1.00 | 92.25 | L |
| ATOM | 1267 | OD2 | ASP | 165 | 145.891 | 45.698 | 55.364 | 1.00 | 85.65 | L |
| ATOM | 1268 | C | ASP | 165 | 149.078 | 48.282 | 57.923 | 1.00 | 47.66 | L |
| ATOM | 1269 | O | ASP | 165 | 149.760 | 47.746 | 58.792 | 1.00 | 50.50 | L |
| ATOM | 1270 | N | GLN | 166 | 148.609 | 49.516 | 58.030 | 1.00 | 47.56 | L |
| ATOM | 1271 | CA | GLN | 166 | 148.850 | 50.319 | 59.220 | 1.00 | 42.28 | L |
| ATOM | 1272 | CB | GLN | 166 | 147.982 | 51.570 | 59.185 | 1.00 | 44.46 | L |
| ATOM | 1273 | CG | GLN | 166 | 148.213 | 52.541 | 60.320 | 1.00 | 29.22 | L |
| ATOM | 1274 | CD | GLN | 166 | 147.967 | 53.965 | 59.885 | 1.00 | 17.51 | L |
| ATOM | 1275 | OE1 | GLN | 166 | 146.909 | 54.283 | 59.343 | 1.00 | 43.27 | L |
| ATOM | 1276 | NE2 | GLN | 166 | 148.949 | 54.830 | 60.103 | 1.00 | 25.31 | L |
| ATOM | 1277 | C | GLN | 166 | 148.462 | 49.478 | 60.422 | 1.00 | 38.24 | L |
| ATOM | 1278 | O | GLN | 166 | 147.361 | 48.934 | 60.465 | 1.00 | 28.20 | L |
| ATOM | 1279 | N | ASP | 167 | 149.361 | 49.364 | 61.393 | 1.00 | 47.65 | L |
| ATOM | 1280 | CA | ASP | 167 | 149.072 | 48.577 | 62.576 | 1.00 | 59.05 | L |
| ATOM | 1281 | CB | ASP | 167 | 150.200 | 48.691 | 63.591 | 1.00 | 40.82 | L |
| ATOM | 1282 | CG | ASP | 167 | 150.022 | 47.742 | 64.752 | 1.00 | 39.12 | L |
| ATOM | 1283 | OD1 | ASP | 167 | 149.966 | 46.517 | 64.510 | 1.00 | 57.63 | L |
| ATOM | 1284 | OD2 | ASP | 167 | 149.927 | 48.214 | 65.902 | 1.00 | 58.29 | L |
| ATOM | 1285 | C | ASP | 167 | 147.768 | 49.040 | 63.205 | 1.00 | 68.64 | L |

TABLE 4-continued

Co-ordinates of the CD28/5.11A1 crystal structure

| ATOM | 1286 | O   | ASP | 167 | 147.482 | 50.237 | 63.274 | 1.00 | 62.87 | L |
|------|------|-----|-----|-----|---------|--------|--------|------|-------|---|
| ATOM | 1287 | N   | SER | 168 | 146.978 | 48.079 | 63.658 | 1.00 | 81.22 | L |
| ATOM | 1288 | CA  | SER | 168 | 145.695 | 48.374 | 64.271 | 1.00 | 77.38 | L |
| ATOM | 1289 | CB  | SER | 168 | 144.865 | 47.095 | 64.370 | 1.00 | 77.42 | L |
| ATOM | 1290 | OG  | SER | 168 | 145.397 | 46.080 | 63.532 | 1.00 | 89.64 | L |
| ATOM | 1291 | C   | SER | 168 | 145.839 | 48.994 | 65.651 | 1.00 | 79.26 | L |
| ATOM | 1292 | O   | SER | 168 | 144.922 | 49.650 | 66.139 | 1.00 | 85.04 | L |
| ATOM | 1293 | N   | LYS | 169 | 146.990 | 48.792 | 66.282 | 1.00 | 71.82 | L |
| ATOM | 1294 | CA  | LYS | 169 | 147.210 | 49.330 | 67.617 | 1.00 | 55.95 | L |
| ATOM | 1295 | CB  | LYS | 169 | 147.785 | 48.247 | 68.534 | 1.00 | 74.95 | L |
| ATOM | 1296 | CG  | LYS | 169 | 147.259 | 46.849 | 68.253 | 1.00 | 84.17 | L |
| ATOM | 1297 | CD  | LYS | 169 | 148.379 | 45.938 | 67.762 | 1.00 | 83.79 | L |
| ATOM | 1298 | CE  | LYS | 169 | 147.843 | 44.810 | 66.885 | 1.00 | 85.61 | L |
| ATOM | 1299 | NZ  | LYS | 169 | 148.678 | 44.588 | 65.665 | 1.00 | 81.34 | L |
| ATOM | 1300 | C   | LYS | 169 | 148.114 | 50.556 | 67.658 | 1.00 | 46.88 | L |
| ATOM | 1301 | O   | LYS | 169 | 147.720 | 51.614 | 68.145 | 1.00 | 59.39 | L |
| ATOM | 1302 | N   | ASP | 170 | 149.331 | 50.418 | 67.142 | 1.00 | 40.42 | L |
| ATOM | 1303 | CA  | ASP | 170 | 150.269 | 51.532 | 67.164 | 1.00 | 32.11 | L |
| ATOM | 1304 | CB  | ASP | 170 | 151.647 | 51.033 | 67.620 | 1.00 | 37.35 | L |
| ATOM | 1305 | CG  | ASP | 170 | 152.505 | 50.537 | 66.479 | 1.00 | 58.55 | L |
| ATOM | 1306 | OD1 | ASP | 170 | 152.200 | 49.471 | 65.909 | 1.00 | 65.81 | L |
| ATOM | 1307 | OD2 | ASP | 170 | 153.500 | 51.221 | 66.162 | 1.00 | 76.15 | L |
| ATOM | 1308 | C   | ASP | 170 | 150.370 | 52.309 | 65.856 | 1.00 | 34.80 | L |
| ATOM | 1309 | O   | ASP | 170 | 151.246 | 53.159 | 65.693 | 1.00 | 26.65 | L |
| ATOM | 1310 | N   | SER | 171 | 149.466 | 52.024 | 64.927 | 1.00 | 29.78 | L |
| ATOM | 1311 | CA  | SER | 171 | 149.429 | 52.719 | 63.648 | 1.00 | 32.11 | L |
| ATOM | 1312 | CB  | SER | 171 | 148.876 | 54.135 | 63.845 | 1.00 | 36.91 | L |
| ATOM | 1313 | OG  | SER | 171 | 147.612 | 54.105 | 64.486 | 1.00 | 87.97 | L |
| ATOM | 1314 | C   | SER | 171 | 150.750 | 52.809 | 62.894 | 1.00 | 34.11 | L |
| ATOM | 1315 | O   | SER | 171 | 151.004 | 53.807 | 62.223 | 1.00 | 25.60 | L |
| ATOM | 1316 | N   | THR | 172 | 151.591 | 51.783 | 62.993 | 1.00 | 30.87 | L |
| ATOM | 1317 | CA  | THR | 172 | 152.866 | 51.788 | 62.271 | 1.00 | 19.30 | L |
| ATOM | 1318 | CB  | THR | 172 | 154.046 | 51.292 | 63.129 | 1.00 | 41.47 | L |
| ATOM | 1319 | OG1 | THR | 172 | 153.590 | 50.286 | 64.039 | 1.00 | 61.43 | L |
| ATOM | 1320 | CG2 | THR | 172 | 154.686 | 52.449 | 63.876 | 1.00 | 35.62 | L |
| ATOM | 1321 | C   | THR | 172 | 152.807 | 50.877 | 61.058 | 1.00 | 25.70 | L |
| ATOM | 1322 | O   | THR | 172 | 151.812 | 50.189 | 60.826 | 1.00 | 23.98 | L |
| ATOM | 1323 | N   | TYR | 173 | 153.892 | 50.871 | 60.295 | 1.00 | 30.31 | L |
| ATOM | 1324 | CA  | TYR | 173 | 153.985 | 50.042 | 59.109 | 1.00 | 21.84 | L |
| ATOM | 1325 | CB  | TYR | 173 | 154.167 | 50.911 | 57.863 | 1.00 | 39.03 | L |
| ATOM | 1326 | CG  | TYR | 173 | 152.916 | 51.668 | 57.487 | 1.00 | 42.99 | L |
| ATOM | 1327 | CD1 | TYR | 173 | 151.794 | 50.994 | 57.008 | 1.00 | 41.83 | L |
| ATOM | 1328 | CE1 | TYR | 173 | 150.621 | 51.678 | 56.709 | 1.00 | 59.78 | L |
| ATOM | 1329 | CD2 | TYR | 173 | 152.834 | 53.050 | 57.651 | 1.00 | 48.81 | L |
| ATOM | 1330 | CE2 | TYR | 173 | 151.663 | 53.745 | 57.355 | 1.00 | 38.39 | L |
| ATOM | 1331 | CZ  | TYR | 173 | 150.560 | 53.052 | 56.888 | 1.00 | 60.04 | L |
| ATOM | 1332 | OH  | TYR | 173 | 149.392 | 53.723 | 56.607 | 1.00 | 65.26 | L |
| ATOM | 1333 | C   | TYR | 173 | 155.160 | 49.098 | 59.245 | 1.00 | 30.15 | L |
| ATOM | 1334 | O   | TYR | 173 | 156.089 | 49.350 | 60.009 | 1.00 | 35.37 | L |
| ATOM | 1335 | N   | SER | 174 | 155.111 | 48.005 | 58.505 | 1.00 | 26.54 | L |
| ATOM | 1336 | CA  | SER | 174 | 156.184 | 47.035 | 58.539 | 1.00 | 25.11 | L |
| ATOM | 1337 | CB  | SER | 174 | 155.832 | 45.874 | 59.467 | 1.00 | 32.70 | L |
| ATOM | 1338 | OG  | SER | 174 | 156.004 | 46.246 | 60.824 | 1.00 | 23.41 | L |
| ATOM | 1339 | C   | SER | 174 | 156.394 | 46.518 | 57.136 | 1.00 | 28.29 | L |
| ATOM | 1340 | O   | SER | 174 | 155.475 | 46.515 | 56.314 | 1.00 | 22.73 | L |
| ATOM | 1341 | N   | MET | 175 | 157.614 | 46.093 | 56.857 | 1.00 | 29.61 | L |
| ATOM | 1342 | CA  | MET | 175 | 157.925 | 45.571 | 55.552 | 1.00 | 24.86 | L |
| ATOM | 1343 | CB  | MET | 175 | 158.423 | 46.693 | 54.646 | 1.00 | 16.99 | L |
| ATOM | 1344 | CG  | MET | 175 | 159.379 | 46.232 | 53.575 | 1.00 | 9.33  | L |
| ATOM | 1345 | SD  | MET | 175 | 159.949 | 47.595 | 52.577 | 1.00 | 36.70 | L |
| ATOM | 1346 | CE  | MET | 175 | 160.270 | 46.761 | 51.036 | 1.00 | 45.25 | L |
| ATOM | 1347 | C   | MET | 175 | 158.986 | 44.498 | 55.686 | 1.00 | 31.31 | L |
| ATOM | 1348 | O   | MET | 175 | 159.800 | 44.522 | 56.615 | 1.00 | 32.20 | L |
| ATOM | 1349 | N   | SER | 176 | 158.947 | 43.544 | 54.765 | 1.00 | 27.89 | L |
| ATOM | 1350 | CA  | SER | 176 | 159.916 | 42.462 | 54.737 | 1.00 | 33.91 | L |
| ATOM | 1351 | CB  | SER | 176 | 159.263 | 41.137 | 55.135 | 1.00 | 32.59 | L |
| ATOM | 1352 | OG  | SER | 176 | 159.019 | 40.331 | 53.997 | 1.00 | 35.30 | L |
| ATOM | 1353 | C   | SER | 176 | 160.435 | 42.382 | 53.312 | 1.00 | 22.54 | L |
| ATOM | 1354 | O   | SER | 176 | 159.669 | 42.497 | 52.356 | 1.00 | 28.72 | L |
| ATOM | 1355 | N   | SER | 177 | 161.743 | 42.210 | 53.169 | 1.00 | 21.03 | L |
| ATOM | 1356 | CA  | SER | 177 | 162.355 | 42.107 | 51.856 | 1.00 | 27.57 | L |
| ATOM | 1357 | CB  | SER | 177 | 163.231 | 43.320 | 51.574 | 1.00 | 32.40 | L |
| ATOM | 1358 | OG  | SER | 177 | 163.713 | 43.272 | 50.245 | 1.00 | 27.68 | L |
| ATOM | 1359 | C   | SER | 177 | 163.196 | 40.847 | 51.802 | 1.00 | 22.76 | L |
| ATOM | 1360 | O   | SER | 177 | 164.047 | 40.621 | 52.661 | 1.00 | 33.72 | L |
| ATOM | 1361 | N   | THR | 178 | 162.956 | 40.026 | 50.788 | 1.00 | 18.89 | L |
| ATOM | 1362 | CA  | THR | 178 | 163.687 | 38.780 | 50.656 | 1.00 | 16.96 | L |

TABLE 4-continued

Co-ordinates of the CD28/5.11A1 crystal structure

| ATOM | 1363 | CB  | THR | 178 | 162.740 | 37.580 | 50.740 | 1.00 | 21.10 | L |
| ---- | ---- | --- | --- | --- | ------- | ------ | ------ | ---- | ----- | - |
| ATOM | 1364 | OG1 | THR | 178 | 161.938 | 37.681 | 51.922 | 1.00 | 36.63 | L |
| ATOM | 1365 | CG2 | THR | 178 | 163.533 | 36.285 | 50.782 | 1.00 | 22.64 | L |
| ATOM | 1366 | C   | THR | 178 | 164.481 | 38.675 | 49.362 | 1.00 | 21.04 | L |
| ATOM | 1367 | O   | THR | 178 | 163.949 | 38.878 | 48.266 | 1.00 | 32.90 | L |
| ATOM | 1368 | N   | LEU | 179 | 165.764 | 38.358 | 49.515 | 1.00 | 23.97 | L |
| ATOM | 1369 | CA  | LEU | 179 | 166.679 | 38.183 | 48.395 | 1.00 | 27.62 | L |
| ATOM | 1370 | CB  | LEU | 179 | 168.000 | 38.899 | 48.669 | 1.00 | 25.50 | L |
| ATOM | 1371 | CG  | LEU | 179 | 169.043 | 38.856 | 47.557 | 1.00 | 25.95 | L |
| ATOM | 1372 | CD1 | LEU | 179 | 168.487 | 39.491 | 46.291 | 1.00 | 44.04 | L |
| ATOM | 1373 | CD2 | LEU | 179 | 170.289 | 39.591 | 48.025 | 1.00 | 24.41 | L |
| ATOM | 1374 | C   | LEU | 179 | 166.920 | 36.687 | 48.293 | 1.00 | 22.54 | L |
| ATOM | 1375 | O   | LEU | 179 | 167.417 | 36.070 | 49.236 | 1.00 | 16.26 | L |
| ATOM | 1376 | N   | THR | 180 | 166.558 | 36.110 | 47.153 | 1.00 | 27.81 | L |
| ATOM | 1377 | CA  | THR | 180 | 166.699 | 34.675 | 46.941 | 1.00 | 38.84 | L |
| ATOM | 1378 | CB  | THR | 180 | 165.343 | 34.060 | 46.531 | 1.00 | 58.84 | L |
| ATOM | 1379 | OG1 | THR | 180 | 164.391 | 34.253 | 47.585 | 1.00 | 69.01 | L |
| ATOM | 1380 | CG2 | THR | 180 | 165.489 | 32.571 | 46.243 | 1.00 | 65.13 | L |
| ATOM | 1381 | C   | THR | 180 | 167.744 | 34.304 | 45.893 | 1.00 | 38.32 | L |
| ATOM | 1382 | O   | THR | 180 | 167.658 | 34.715 | 44.733 | 1.00 | 23.89 | L |
| ATOM | 1383 | N   | LEU | 181 | 168.726 | 33.515 | 46.318 | 1.00 | 50.48 | L |
| ATOM | 1384 | CA  | LEU | 181 | 169.796 | 33.059 | 45.439 | 1.00 | 54.78 | L |
| ATOM | 1385 | CB  | LEU | 181 | 171.118 | 33.751 | 45.782 | 1.00 | 57.52 | L |
| ATOM | 1386 | CG  | LEU | 181 | 171.097 | 35.239 | 46.126 | 1.00 | 52.16 | L |
| ATOM | 1387 | CD1 | LEU | 181 | 171.777 | 35.466 | 47.468 | 1.00 | 64.66 | L |
| ATOM | 1388 | CD2 | LEU | 181 | 171.800 | 36.017 | 45.032 | 1.00 | 59.17 | L |
| ATOM | 1389 | C   | LEU | 181 | 169.978 | 31.558 | 45.595 | 1.00 | 45.72 | L |
| ATOM | 1390 | O   | LEU | 181 | 169.250 | 30.904 | 46.347 | 1.00 | 53.82 | L |
| ATOM | 1391 | N   | THR | 182 | 170.964 | 31.021 | 44.882 | 1.00 | 33.32 | L |
| ATOM | 1392 | CA  | THR | 182 | 171.268 | 29.601 | 44.935 | 1.00 | 32.86 | L |
| ATOM | 1393 | CB  | THR | 182 | 171.740 | 29.086 | 43.571 | 1.00 | 35.79 | L |
| ATOM | 1394 | OG1 | THR | 182 | 172.994 | 29.694 | 43.241 | 1.00 | 51.80 | L |
| ATOM | 1395 | CG2 | THR | 182 | 170.726 | 29.434 | 42.497 | 1.00 | 10.97 | L |
| ATOM | 1396 | C   | THR | 182 | 172.371 | 29.340 | 45.955 | 1.00 | 31.89 | L |
| ATOM | 1397 | O   | THR | 182 | 173.084 | 30.256 | 46.366 | 1.00 | 22.49 | L |
| ATOM | 1398 | N   | LYS | 183 | 172.498 | 28.086 | 46.369 | 1.00 | 18.19 | L |
| ATOM | 1399 | CA  | LYS | 183 | 173.521 | 27.703 | 47.326 | 1.00 | 22.39 | L |
| ATOM | 1400 | CB  | LYS | 183 | 173.539 | 26.186 | 47.492 | 1.00 | 27.09 | L |
| ATOM | 1401 | CG  | LYS | 183 | 173.959 | 25.715 | 48.868 | 1.00 | 21.06 | L |
| ATOM | 1402 | CD  | LYS | 183 | 174.795 | 24.443 | 48.785 | 1.00 | 28.23 | L |
| ATOM | 1403 | CE  | LYS | 183 | 175.371 | 24.075 | 50.148 | 1.00 | 65.45 | L |
| ATOM | 1404 | NZ  | LYS | 183 | 176.860 | 24.085 | 50.151 | 1.00 | 66.90 | L |
| ATOM | 1405 | C   | LYS | 183 | 174.847 | 28.168 | 46.750 | 1.00 | 30.33 | L |
| ATOM | 1406 | O   | LYS | 183 | 175.732 | 28.640 | 47.462 | 1.00 | 47.79 | L |
| ATOM | 1407 | N   | ASP | 184 | 174.957 | 28.044 | 45.436 | 1.00 | 33.23 | L |
| ATOM | 1408 | CA  | ASP | 184 | 176.162 | 28.422 | 44.729 | 1.00 | 32.28 | L |
| ATOM | 1409 | CB  | ASP | 184 | 176.089 | 27.931 | 43.290 | 1.00 | 41.02 | L |
| ATOM | 1410 | CG  | ASP | 184 | 176.041 | 26.424 | 43.199 | 1.00 | 63.85 | L |
| ATOM | 1411 | OD1 | ASP | 184 | 176.516 | 25.754 | 44.147 | 1.00 | 80.57 | L |
| ATOM | 1412 | OD2 | ASP | 184 | 175.530 | 25.907 | 42.185 | 1.00 | 76.42 | L |
| ATOM | 1413 | C   | ASP | 184 | 176.443 | 29.910 | 44.747 | 1.00 | 37.31 | L |
| ATOM | 1414 | O   | ASP | 184 | 177.250 | 30.379 | 45.547 | 1.00 | 58.28 | L |
| ATOM | 1415 | N   | GLU | 185 | 175.770 | 30.652 | 43.873 | 1.00 | 33.24 | L |
| ATOM | 1416 | CA  | GLU | 185 | 175.994 | 32.088 | 43.781 | 1.00 | 36.62 | L |
| ATOM | 1417 | CB  | GLU | 185 | 175.088 | 32.691 | 42.702 | 1.00 | 37.34 | L |
| ATOM | 1418 | CG  | GLU | 185 | 173.899 | 33.484 | 43.198 | 1.00 | 71.02 | L |
| ATOM | 1419 | CD  | GLU | 185 | 172.973 | 33.876 | 42.058 | 1.00 | 78.07 | L |
| ATOM | 1420 | OE1 | GLU | 185 | 173.399 | 34.680 | 41.198 | 1.00 | 94.70 | L |
| ATOM | 1421 | OE2 | GLU | 185 | 171.826 | 33.378 | 42.020 | 1.00 | 82.48 | L |
| ATOM | 1422 | C   | GLU | 185 | 175.870 | 32.849 | 45.095 | 1.00 | 40.77 | L |
| ATOM | 1423 | O   | GLU | 185 | 176.154 | 34.039 | 45.144 | 1.00 | 28.19 | L |
| ATOM | 1424 | N   | TYR | 186 | 175.455 | 32.171 | 46.160 | 1.00 | 45.72 | L |
| ATOM | 1425 | CA  | TYR | 186 | 175.357 | 32.824 | 47.461 | 1.00 | 31.13 | L |
| ATOM | 1426 | CB  | TYR | 186 | 174.183 | 32.284 | 48.271 | 1.00 | 29.29 | L |
| ATOM | 1427 | CG  | TYR | 186 | 174.394 | 32.396 | 49.769 | 1.00 | 30.13 | L |
| ATOM | 1428 | CD1 | TYR | 186 | 174.131 | 33.590 | 50.447 | 1.00 | 33.39 | L |
| ATOM | 1429 | CE1 | TYR | 186 | 174.314 | 33.694 | 51.833 | 1.00 | 36.37 | L |
| ATOM | 1430 | CD2 | TYR | 186 | 174.850 | 31.310 | 50.509 | 1.00 | 34.49 | L |
| ATOM | 1431 | CE2 | TYR | 186 | 175.036 | 31.402 | 51.893 | 1.00 | 18.79 | L |
| ATOM | 1432 | CZ  | TYR | 186 | 174.766 | 32.594 | 52.549 | 1.00 | 34.18 | L |
| ATOM | 1433 | OH  | TYR | 186 | 174.933 | 32.673 | 53.913 | 1.00 | 39.71 | L |
| ATOM | 1434 | C   | TYR | 186 | 176.641 | 32.530 | 48.224 | 1.00 | 25.69 | L |
| ATOM | 1435 | O   | TYR | 186 | 177.138 | 33.358 | 48.985 | 1.00 | 46.65 | L |
| ATOM | 1436 | N   | GLU | 187 | 177.163 | 31.327 | 48.025 | 1.00 | 33.86 | L |
| ATOM | 1437 | CA  | GLU | 187 | 178.380 | 30.916 | 48.695 | 1.00 | 30.31 | L |
| ATOM | 1438 | CB  | GLU | 187 | 178.478 | 29.394 | 48.707 | 1.00 | 51.43 | L |
| ATOM | 1439 | CG  | GLU | 187 | 177.688 | 28.757 | 49.831 | 1.00 | 68.32 | L |

TABLE 4-continued

Co-ordinates of the CD28/5.11A1 crystal structure

| ATOM | 1440 | CD  | GLU | 187 | 177.931 | 27.269 | 49.944 | 1.00 | 84.34  | L |
| ---- | ---- | --- | --- | --- | ------- | ------ | ------ | ---- | ------ | - |
| ATOM | 1441 | OE1 | GLU | 187 | 178.505 | 26.681 | 49.000 | 1.00 | 72.88  | L |
| ATOM | 1442 | OE2 | GLU | 187 | 177.540 | 26.690 | 50.980 | 1.00 | 92.94  | L |
| ATOM | 1443 | C   | GLU | 187 | 179.608 | 31.516 | 48.021 | 1.00 | 25.34  | L |
| ATOM | 1444 | O   | GLU | 187 | 180.731 | 31.319 | 48.476 | 1.00 | 33.80  | L |
| ATOM | 1445 | N   | ARG | 188 | 179.393 | 32.255 | 46.937 | 1.00 | 25.18  | L |
| ATOM | 1446 | CA  | ARG | 188 | 180.504 | 32.887 | 46.238 | 1.00 | 28.26  | L |
| ATOM | 1447 | CB  | ARG | 188 | 180.430 | 32.583 | 44.732 | 1.00 | 50.64  | L |
| ATOM | 1448 | CG  | ARG | 188 | 179.374 | 33.352 | 43.952 | 1.00 | 42.62  | L |
| ATOM | 1449 | CD  | ARG | 188 | 179.332 | 32.895 | 42.493 | 1.00 | 43.87  | L |
| ATOM | 1450 | NE  | ARG | 188 | 179.213 | 31.440 | 42.378 | 1.00 | 93.56  | L |
| ATOM | 1451 | CZ  | ARG | 188 | 180.106 | 30.659 | 41.779 | 1.00 | 99.99  | L |
| ATOM | 1452 | NH1 | ARG | 188 | 181.192 | 31.187 | 41.230 | 1.00 | 99.99  | L |
| ATOM | 1453 | NH2 | ARG | 188 | 179.918 | 29.345 | 41.733 | 1.00 | 99.98  | L |
| ATOM | 1454 | C   | ARG | 188 | 180.549 | 34.399 | 46.490 | 1.00 | 22.65  | L |
| ATOM | 1455 | O   | ARG | 188 | 181.077 | 35.160 | 45.679 | 1.00 | 30.16  | L |
| ATOM | 1456 | N   | HIS | 189 | 180.001 | 34.819 | 47.626 | 1.00 | 27.86  | L |
| ATOM | 1457 | CA  | HIS | 189 | 179.979 | 36.223 | 48.023 | 1.00 | 21.88  | L |
| ATOM | 1458 | CB  | HIS | 189 | 178.650 | 36.871 | 47.650 | 1.00 | 40.07  | L |
| ATOM | 1459 | CG  | HIS | 189 | 178.480 | 37.107 | 46.182 | 1.00 | 47.15  | L |
| ATOM | 1460 | CD2 | HIS | 189 | 178.796 | 38.171 | 45.405 | 1.00 | 55.79  | L |
| ATOM | 1461 | ND1 | HIS | 189 | 177.891 | 36.185 | 45.342 | 1.00 | 63.86  | L |
| ATOM | 1462 | CE1 | HIS | 189 | 177.849 | 36.672 | 44.115 | 1.00 | 61.64  | L |
| ATOM | 1463 | NE2 | HIS | 189 | 178.391 | 37.876 | 44.127 | 1.00 | 60.31  | L |
| ATOM | 1464 | C   | HIS | 189 | 180.152 | 36.239 | 49.531 | 1.00 | 29.34  | L |
| ATOM | 1465 | O   | HIS | 189 | 179.750 | 35.291 | 50.205 | 1.00 | 34.87  | L |
| ATOM | 1466 | N   | ASN | 190 | 180.729 | 37.309 | 50.067 | 1.00 | 37.34  | L |
| ATOM | 1467 | CA  | ASN | 190 | 180.961 | 37.379 | 51.507 | 1.00 | 47.66  | L |
| ATOM | 1468 | CB  | ASN | 190 | 182.388 | 37.855 | 51.795 | 1.00 | 68.12  | L |
| ATOM | 1469 | CG  | ASN | 190 | 183.417 | 37.167 | 50.930 | 1.00 | 100.00 | L |
| ATOM | 1470 | OD1 | ASN | 190 | 183.407 | 35.945 | 50.784 | 1.00 | 99.97  | L |
| ATOM | 1471 | ND2 | ASN | 190 | 184.320 | 37.954 | 50.350 | 1.00 | 99.98  | L |
| ATOM | 1472 | C   | ASN | 190 | 180.001 | 38.252 | 52.290 | 1.00 | 42.97  | L |
| ATOM | 1473 | O   | ASN | 190 | 179.383 | 37.797 | 53.259 | 1.00 | 33.80  | L |
| ATOM | 1474 | N   | SER | 191 | 179.885 | 39.511 | 51.892 | 1.00 | 39.67  | L |
| ATOM | 1475 | CA  | SER | 191 | 179.010 | 40.419 | 52.614 | 1.00 | 30.33  | L |
| ATOM | 1476 | CB  | SER | 191 | 179.698 | 41.774 | 52.801 | 1.00 | 31.09  | L |
| ATOM | 1477 | OG  | SER | 191 | 179.887 | 42.056 | 54.177 | 1.00 | 59.06  | L |
| ATOM | 1478 | C   | SER | 191 | 177.655 | 40.634 | 51.967 | 1.00 | 34.40  | L |
| ATOM | 1479 | O   | SER | 191 | 177.550 | 40.836 | 50.753 | 1.00 | 48.04  | L |
| ATOM | 1480 | N   | TYR | 192 | 176.620 | 40.574 | 52.802 | 1.00 | 25.05  | L |
| ATOM | 1481 | CA  | TYR | 192 | 175.246 | 40.785 | 52.361 | 1.00 | 22.04  | L |
| ATOM | 1482 | CB  | TYR | 192 | 174.420 | 39.517 | 52.582 | 1.00 | 16.56  | L |
| ATOM | 1483 | CG  | TYR | 192 | 174.807 | 38.444 | 51.598 | 1.00 | 33.82  | L |
| ATOM | 1484 | CD1 | TYR | 192 | 174.383 | 38.511 | 50.273 | 1.00 | 39.72  | L |
| ATOM | 1485 | CE1 | TYR | 192 | 174.829 | 37.592 | 49.330 | 1.00 | 33.77  | L |
| ATOM | 1486 | CD2 | TYR | 192 | 175.683 | 37.417 | 51.961 | 1.00 | 36.76  | L |
| ATOM | 1487 | CE2 | TYR | 192 | 176.135 | 36.492 | 51.024 | 1.00 | 36.40  | L |
| ATOM | 1488 | CZ  | TYR | 192 | 175.707 | 36.587 | 49.711 | 1.00 | 39.55  | L |
| ATOM | 1489 | OH  | TYR | 192 | 176.164 | 35.693 | 48.766 | 1.00 | 31.96  | L |
| ATOM | 1490 | C   | TYR | 192 | 174.705 | 41.961 | 53.160 | 1.00 | 26.50  | L |
| ATOM | 1491 | O   | TYR | 192 | 174.749 | 41.970 | 54.389 | 1.00 | 26.85  | L |
| ATOM | 1492 | N   | THR | 193 | 174.205 | 42.959 | 52.443 | 1.00 | 42.59  | L |
| ATOM | 1493 | CA  | THR | 193 | 173.716 | 44.165 | 53.086 | 1.00 | 49.57  | L |
| ATOM | 1494 | CB  | THR | 193 | 174.621 | 45.362 | 52.738 | 1.00 | 59.55  | L |
| ATOM | 1495 | OG1 | THR | 193 | 175.983 | 45.025 | 53.025 | 1.00 | 51.20  | L |
| ATOM | 1496 | CG2 | THR | 193 | 174.219 | 46.592 | 53.536 | 1.00 | 59.94  | L |
| ATOM | 1497 | C   | THR | 193 | 172.285 | 44.574 | 52.777 | 1.00 | 46.91  | L |
| ATOM | 1498 | O   | THR | 193 | 171.848 | 44.573 | 51.621 | 1.00 | 57.88  | L |
| ATOM | 1499 | N   | CYS | 194 | 171.578 | 44.946 | 53.836 | 1.00 | 40.06  | L |
| ATOM | 1500 | CA  | CYS | 194 | 170.208 | 45.409 | 53.738 | 1.00 | 39.66  | L |
| ATOM | 1501 | C   | CYS | 194 | 170.229 | 46.894 | 54.090 | 1.00 | 50.91  | L |
| ATOM | 1502 | O   | CYS | 194 | 170.419 | 47.263 | 55.253 | 1.00 | 50.44  | L |
| ATOM | 1503 | CB  | CYS | 194 | 169.326 | 44.652 | 54.719 | 1.00 | 56.36  | L |
| ATOM | 1504 | SG  | CYS | 194 | 167.606 | 45.219 | 54.662 | 1.00 | 57.55  | L |
| ATOM | 1505 | N   | GLU | 195 | 170.039 | 47.734 | 53.080 | 1.00 | 62.99  | L |
| ATOM | 1506 | CA  | GLU | 195 | 170.066 | 49.182 | 53.262 | 1.00 | 56.68  | L |
| ATOM | 1507 | CB  | GLU | 195 | 171.006 | 49.802 | 52.231 | 1.00 | 67.85  | L |
| ATOM | 1508 | CG  | GLU | 195 | 171.618 | 51.121 | 52.650 | 1.00 | 75.89  | L |
| ATOM | 1509 | CD  | GLU | 195 | 172.492 | 51.711 | 51.560 | 1.00 | 66.08  | L |
| ATOM | 1510 | OE1 | GLU | 195 | 171.941 | 52.170 | 50.533 | 1.00 | 83.91  | L |
| ATOM | 1511 | OE2 | GLU | 195 | 173.731 | 51.710 | 51.731 | 1.00 | 69.63  | L |
| ATOM | 1512 | C   | GLU | 195 | 168.689 | 49.812 | 53.128 | 1.00 | 41.96  | L |
| ATOM | 1513 | O   | GLU | 195 | 167.926 | 49.466 | 52.224 | 1.00 | 46.93  | L |
| ATOM | 1514 | N   | ALA | 196 | 168.381 | 50.755 | 54.014 | 1.00 | 39.48  | L |
| ATOM | 1515 | CA  | ALA | 196 | 167.085 | 51.419 | 53.983 | 1.00 | 55.44  | L |
| ATOM | 1516 | CB  | ALA | 196 | 166.114 | 50.674 | 54.880 | 1.00 | 62.95  | L |

TABLE 4-continued

Co-ordinates of the CD28/5.11A1 crystal structure

| ATOM | 1517 | C | ALA | 196 | 167.111 | 52.897 | 54.375 | 1.00 | 56.78 | L |
|---|---|---|---|---|---|---|---|---|---|---|
| ATOM | 1518 | O | ALA | 196 | 167.572 | 53.254 | 55.460 | 1.00 | 57.46 | L |
| ATOM | 1519 | N | THR | 197 | 166.606 | 53.748 | 53.484 | 1.00 | 59.26 | L |
| ATOM | 1520 | CA | THR | 197 | 166.532 | 55.186 | 53.738 | 1.00 | 71.50 | L |
| ATOM | 1521 | CB | THR | 197 | 166.971 | 56.023 | 52.502 | 1.00 | 77.13 | L |
| ATOM | 1522 | OG1 | THR | 197 | 166.548 | 55.374 | 51.295 | 1.00 | 83.37 | L |
| ATOM | 1523 | CG2 | THR | 197 | 168.486 | 56.185 | 52.483 | 1.00 | 62.62 | L |
| ATOM | 1524 | C | THR | 197 | 165.086 | 55.538 | 54.086 | 1.00 | 73.26 | L |
| ATOM | 1525 | O | THR | 197 | 164.155 | 55.182 | 53.362 | 1.00 | 73.27 | L |
| ATOM | 1526 | N | HIS | 198 | 164.901 | 56.233 | 55.200 | 1.00 | 66.28 | L |
| ATOM | 1527 | CA | HIS | 198 | 163.570 | 56.617 | 55.655 | 1.00 | 65.29 | L |
| ATOM | 1528 | CB | HIS | 198 | 163.203 | 55.777 | 56.889 | 1.00 | 59.65 | L |
| ATOM | 1529 | CG | HIS | 198 | 161.802 | 55.976 | 57.386 | 1.00 | 50.05 | L |
| ATOM | 1530 | CD2 | HIS | 198 | 161.333 | 56.281 | 58.619 | 1.00 | 10.46 | L |
| ATOM | 1531 | ND1 | HIS | 198 | 160.691 | 55.811 | 56.586 | 1.00 | 23.72 | L |
| ATOM | 1532 | CE1 | HIS | 198 | 159.601 | 56.009 | 57.306 | 1.00 | 8.26 | L |
| ATOM | 1533 | NE2 | HIS | 198 | 159.962 | 56.295 | 58.545 | 1.00 | 26.12 | L |
| ATOM | 1534 | C | HIS | 198 | 163.611 | 58.101 | 56.001 | 1.00 | 65.53 | L |
| ATOM | 1535 | O | HIS | 198 | 164.642 | 58.601 | 56.446 | 1.00 | 44.38 | L |
| ATOM | 1536 | N | LYS | 199 | 162.501 | 58.804 | 55.776 | 1.00 | 69.60 | L |
| ATOM | 1537 | CA | LYS | 199 | 162.407 | 60.235 | 56.078 | 1.00 | 62.83 | L |
| ATOM | 1538 | CB | LYS | 199 | 160.940 | 60.665 | 56.214 | 1.00 | 59.10 | L |
| ATOM | 1539 | CG | LYS | 199 | 160.168 | 60.725 | 54.908 | 1.00 | 66.79 | L |
| ATOM | 1540 | CD | LYS | 199 | 159.541 | 59.376 | 54.566 | 1.00 | 77.11 | L |
| ATOM | 1541 | CE | LYS | 199 | 160.458 | 58.543 | 53.670 | 1.00 | 66.29 | L |
| ATOM | 1542 | NZ | LYS | 199 | 160.372 | 58.922 | 52.226 | 1.00 | 71.28 | L |
| ATOM | 1543 | C | LYS | 199 | 163.100 | 60.459 | 57.409 | 1.00 | 54.65 | L |
| ATOM | 1544 | O | LYS | 199 | 163.853 | 61.418 | 57.596 | 1.00 | 52.78 | L |
| ATOM | 1545 | N | THR | 200 | 162.823 | 59.538 | 58.322 | 1.00 | 59.05 | L |
| ATOM | 1546 | CA | THR | 200 | 163.361 | 59.542 | 59.668 | 1.00 | 72.79 | L |
| ATOM | 1547 | CB | THR | 200 | 162.896 | 58.262 | 60.404 | 1.00 | 72.74 | L |
| ATOM | 1548 | OG1 | THR | 200 | 162.485 | 58.594 | 61.732 | 1.00 | 81.55 | L |
| ATOM | 1549 | CG2 | THR | 200 | 164.002 | 57.222 | 60.439 | 1.00 | 67.03 | L |
| ATOM | 1550 | C | THR | 200 | 164.890 | 59.648 | 59.712 | 1.00 | 77.51 | L |
| ATOM | 1551 | O | THR | 200 | 165.479 | 59.774 | 60.785 | 1.00 | 76.37 | L |
| ATOM | 1552 | N | SER | 201 | 165.536 | 59.607 | 58.550 | 1.00 | 82.04 | L |
| ATOM | 1553 | CA | SER | 201 | 166.991 | 59.696 | 58.521 | 1.00 | 77.00 | L |
| ATOM | 1554 | CB | SER | 201 | 167.599 | 58.411 | 59.082 | 1.00 | 70.20 | L |
| ATOM | 1555 | OG | SER | 201 | 168.828 | 58.678 | 59.728 | 1.00 | 48.40 | L |
| ATOM | 1556 | C | SER | 201 | 167.583 | 59.967 | 57.145 | 1.00 | 75.86 | L |
| ATOM | 1557 | O | SER | 201 | 167.126 | 59.436 | 56.129 | 1.00 | 78.72 | L |
| ATOM | 1558 | N | THR | 202 | 168.617 | 60.802 | 57.128 | 1.00 | 79.38 | L |
| ATOM | 1559 | CA | THR | 202 | 169.317 | 61.144 | 55.897 | 1.00 | 85.40 | L |
| ATOM | 1560 | CB | THR | 202 | 169.864 | 62.586 | 55.942 | 1.00 | 82.98 | L |
| ATOM | 1561 | OG1 | THR | 202 | 170.536 | 62.807 | 57.190 | 1.00 | 58.44 | L |
| ATOM | 1562 | CG2 | THR | 202 | 168.725 | 63.591 | 55.800 | 1.00 | 81.93 | L |
| ATOM | 1563 | C | THR | 202 | 170.481 | 60.165 | 55.752 | 1.00 | 87.12 | L |
| ATOM | 1564 | O | THR | 202 | 171.106 | 60.069 | 54.697 | 1.00 | 90.15 | L |
| ATOM | 1565 | N | SER | 203 | 170.757 | 59.442 | 56.835 | 1.00 | 85.15 | L |
| ATOM | 1566 | CA | SER | 203 | 171.826 | 58.452 | 56.866 | 1.00 | 85.74 | L |
| ATOM | 1567 | CB | SER | 203 | 172.589 | 58.538 | 58.194 | 1.00 | 91.67 | L |
| ATOM | 1568 | OG | SER | 203 | 172.049 | 59.540 | 59.041 | 1.00 | 86.93 | L |
| ATOM | 1569 | C | SER | 203 | 171.203 | 57.069 | 56.719 | 1.00 | 87.87 | L |
| ATOM | 1570 | O | SER | 203 | 170.682 | 56.508 | 57.686 | 1.00 | 84.65 | L |
| ATOM | 1571 | N | PRO | 204 | 171.244 | 56.501 | 55.502 | 1.00 | 89.56 | L |
| ATOM | 1572 | CD | PRO | 204 | 171.858 | 57.072 | 54.292 | 1.00 | 93.06 | L |
| ATOM | 1573 | CA | PRO | 204 | 170.672 | 55.176 | 55.244 | 1.00 | 82.77 | L |
| ATOM | 1574 | CB | PRO | 204 | 171.269 | 54.772 | 53.888 | 1.00 | 81.38 | L |
| ATOM | 1575 | CG | PRO | 204 | 172.262 | 55.855 | 53.525 | 1.00 | 78.75 | L |
| ATOM | 1576 | C | PRO | 204 | 171.002 | 54.167 | 56.335 | 1.00 | 76.12 | L |
| ATOM | 1577 | O | PRO | 204 | 172.169 | 53.960 | 56.656 | 1.00 | 79.62 | L |
| ATOM | 1578 | N | ILE | 205 | 169.971 | 53.557 | 56.911 | 1.00 | 69.79 | L |
| ATOM | 1579 | CA | ILE | 205 | 170.172 | 52.556 | 57.953 | 1.00 | 59.52 | L |
| ATOM | 1580 | CB | ILE | 205 | 168.862 | 52.224 | 58.675 | 1.00 | 59.30 | L |
| ATOM | 1581 | CG2 | ILE | 205 | 169.124 | 51.192 | 59.763 | 1.00 | 62.73 | L |
| ATOM | 1582 | CG1 | ILE | 205 | 168.264 | 53.503 | 59.263 | 1.00 | 51.85 | L |
| ATOM | 1583 | CD1 | ILE | 205 | 166.912 | 53.310 | 59.921 | 1.00 | 48.97 | L |
| ATOM | 1584 | C | ILE | 205 | 170.711 | 51.294 | 57.294 | 1.00 | 58.53 | L |
| ATOM | 1585 | O | ILE | 205 | 170.225 | 50.873 | 56.241 | 1.00 | 60.90 | L |
| ATOM | 1586 | N | VAL | 206 | 171.719 | 50.691 | 57.918 | 1.00 | 53.53 | L |
| ATOM | 1587 | CA | VAL | 206 | 172.332 | 49.498 | 57.356 | 1.00 | 41.22 | L |
| ATOM | 1588 | CB | VAL | 206 | 173.739 | 49.825 | 56.810 | 1.00 | 18.34 | L |
| ATOM | 1589 | CG1 | VAL | 206 | 174.486 | 48.548 | 56.467 | 1.00 | 13.15 | L |
| ATOM | 1590 | CG2 | VAL | 206 | 173.618 | 50.706 | 55.580 | 1.00 | 13.65 | L |
| ATOM | 1591 | C | VAL | 206 | 172.442 | 48.336 | 58.331 | 1.00 | 44.96 | L |
| ATOM | 1592 | O | VAL | 206 | 172.747 | 48.517 | 59.509 | 1.00 | 44.72 | L |
| ATOM | 1593 | N | LYS | 207 | 172.180 | 47.137 | 57.818 | 1.00 | 51.44 | L |

TABLE 4-continued

Co-ordinates of the CD28/5.11A1 crystal structure

| ATOM | 1594 | CA | LYS | 207 | 172.269 | 45.915 | 58.598 | 1.00 | 52.57 | L |
|------|------|-----|-----|-----|---------|--------|--------|------|--------|---|
| ATOM | 1595 | CB | LYS | 207 | 170.882 | 45.438 | 59.020 | 1.00 | 54.70 | L |
| ATOM | 1596 | CG | LYS | 207 | 170.800 | 45.038 | 60.479 | 1.00 | 47.68 | L |
| ATOM | 1597 | CD | LYS | 207 | 171.141 | 46.206 | 61.394 | 1.00 | 42.68 | L |
| ATOM | 1598 | CE | LYS | 207 | 170.477 | 46.060 | 62.758 | 1.00 | 53.93 | L |
| ATOM | 1599 | NZ | LYS | 207 | 170.763 | 44.740 | 63.395 | 1.00 | 56.72 | L |
| ATOM | 1600 | C | LYS | 207 | 172.906 | 44.900 | 57.671 | 1.00 | 51.25 | L |
| ATOM | 1601 | O | LYS | 207 | 172.357 | 44.592 | 56.610 | 1.00 | 57.87 | L |
| ATOM | 1602 | N | SER | 208 | 174.072 | 44.396 | 58.059 | 1.00 | 48.56 | L |
| ATOM | 1603 | CA | SER | 208 | 174.780 | 43.429 | 57.230 | 1.00 | 44.28 | L |
| ATOM | 1604 | CB | SER | 208 | 175.956 | 44.095 | 56.525 | 1.00 | 43.06 | L |
| ATOM | 1605 | OG | SER | 208 | 175.511 | 45.119 | 55.659 | 1.00 | 64.64 | L |
| ATOM | 1606 | C | SER | 208 | 175.301 | 42.236 | 58.003 | 1.00 | 46.92 | L |
| ATOM | 1607 | O | SER | 208 | 175.121 | 42.129 | 59.221 | 1.00 | 49.18 | L |
| ATOM | 1608 | N | PHE | 209 | 175.950 | 41.342 | 57.269 | 1.00 | 47.47 | L |
| ATOM | 1609 | CA | PHE | 209 | 176.539 | 40.152 | 57.850 | 1.00 | 48.36 | L |
| ATOM | 1610 | CB | PHE | 209 | 175.443 | 39.170 | 58.296 | 1.00 | 58.47 | L |
| ATOM | 1611 | CG | PHE | 209 | 174.804 | 38.414 | 57.168 | 1.00 | 68.93 | L |
| ATOM | 1612 | CD1 | PHE | 209 | 173.734 | 38.960 | 56.471 | 1.00 | 77.87 | L |
| ATOM | 1613 | CD2 | PHE | 209 | 175.280 | 37.161 | 56.793 | 1.00 | 73.00 | L |
| ATOM | 1614 | CE1 | PHE | 209 | 173.148 | 38.270 | 55.411 | 1.00 | 71.56 | L |
| ATOM | 1615 | CE2 | PHE | 209 | 174.703 | 36.461 | 55.736 | 1.00 | 64.61 | L |
| ATOM | 1616 | CZ | PHE | 209 | 173.633 | 37.017 | 55.043 | 1.00 | 71.74 | L |
| ATOM | 1617 | C | PHE | 209 | 177.481 | 39.498 | 56.851 | 1.00 | 44.99 | L |
| ATOM | 1618 | O | PHE | 209 | 177.336 | 39.658 | 55.637 | 1.00 | 35.92 | L |
| ATOM | 1619 | N | ASN | 210 | 178.463 | 38.782 | 57.384 | 1.00 | 56.65 | L |
| ATOM | 1620 | CA | ASN | 210 | 179.444 | 38.079 | 56.572 | 1.00 | 60.29 | L |
| ATOM | 1621 | CB | ASN | 210 | 180.853 | 38.402 | 57.064 | 1.00 | 70.34 | L |
| ATOM | 1622 | CG | ASN | 210 | 181.925 | 37.920 | 56.112 | 1.00 | 100.00 | L |
| ATOM | 1623 | OD1 | ASN | 210 | 182.386 | 38.670 | 55.250 | 1.00 | 99.98 | L |
| ATOM | 1624 | ND2 | ASN | 210 | 182.328 | 36.658 | 56.258 | 1.00 | 100.00 | L |
| ATOM | 1625 | C | ASN | 210 | 179.165 | 36.592 | 56.741 | 1.00 | 63.50 | L |
| ATOM | 1626 | O | ASN | 210 | 178.624 | 36.183 | 57.763 | 1.00 | 79.33 | L |
| ATOM | 1627 | N | ARG | 211 | 179.524 | 35.780 | 55.756 | 1.00 | 60.96 | L |
| ATOM | 1628 | CA | ARG | 211 | 179.284 | 34.350 | 55.872 | 1.00 | 67.53 | L |
| ATOM | 1629 | CB | ARG | 211 | 179.672 | 33.644 | 54.576 | 1.00 | 53.17 | L |
| ATOM | 1630 | CG | ARG | 211 | 178.475 | 33.141 | 53.792 | 1.00 | 46.30 | L |
| ATOM | 1631 | CD | ARG | 211 | 178.602 | 33.466 | 52.320 | 1.00 | 24.02 | L |
| ATOM | 1632 | NE | ARG | 211 | 179.366 | 32.449 | 51.606 | 1.00 | 24.23 | L |
| ATOM | 1633 | CZ | ARG | 211 | 180.693 | 32.431 | 51.527 | 1.00 | 46.60 | L |
| ATOM | 1634 | NH1 | ARG | 211 | 181.411 | 33.377 | 52.118 | 1.00 | 74.04 | L |
| ATOM | 1635 | NH2 | ARG | 211 | 181.307 | 31.466 | 50.863 | 1.00 | 58.03 | L |
| ATOM | 1636 | C | ARG | 211 | 180.041 | 33.746 | 57.060 | 1.00 | 78.01 | L |
| ATOM | 1637 | O | ARG | 211 | 181.277 | 33.714 | 57.080 | 1.00 | 62.45 | L |
| ATOM | 1638 | N | ASN | 212 | 179.264 | 33.284 | 58.046 | 1.00 | 96.28 | L |
| ATOM | 1639 | CA | ASN | 212 | 179.747 | 32.661 | 59.288 | 1.00 | 99.99 | L |
| ATOM | 1640 | CB | ASN | 212 | 181.065 | 31.915 | 59.055 | 1.00 | 99.98 | L |
| ATOM | 1641 | CG | ASN | 212 | 181.130 | 30.602 | 59.816 | 1.00 | 100.00 | L |
| ATOM | 1642 | OD1 | ASN | 212 | 180.343 | 30.360 | 60.738 | 1.00 | 94.94 | L |
| ATOM | 1643 | ND2 | ASN | 212 | 182.070 | 29.743 | 59.434 | 1.00 | 99.99 | L |
| ATOM | 1644 | C | ASN | 212 | 179.918 | 33.640 | 60.455 | 1.00 | 99.98 | L |
| ATOM | 1645 | O | ASN | 212 | 180.791 | 34.533 | 60.359 | 1.00 | 99.99 | L |
| ATOM | 1646 | OT | ASN | 212 | 181.064 | 34.157 | 61.055 | 1.00 | 99.99 | L |
| ATOM | 1647 | CB | VAL | 2 | 121.621 | 36.267 | 64.620 | 1.00 | 37.38 | H |
| ATOM | 1648 | CG1 | VAL | 2 | 120.401 | 36.241 | 65.515 | 1.00 | 27.71 | H |
| ATOM | 1649 | CG2 | VAL | 2 | 122.281 | 37.627 | 64.680 | 1.00 | 34.18 | H |
| ATOM | 1650 | C | VAL | 2 | 123.855 | 35.223 | 64.193 | 1.00 | 42.92 | H |
| ATOM | 1651 | O | VAL | 2 | 124.332 | 36.300 | 63.840 | 1.00 | 42.57 | H |
| ATOM | 1652 | N | VAL | 2 | 122.979 | 35.304 | 66.494 | 1.00 | 47.65 | H |
| ATOM | 1653 | CA | VAL | 2 | 122.610 | 35.160 | 65.057 | 1.00 | 44.59 | H |
| ATOM | 1654 | N | GLN | 3 | 124.382 | 34.056 | 63.852 | 1.00 | 45.14 | H |
| ATOM | 1655 | CA | GLN | 3 | 125.594 | 33.990 | 63.047 | 1.00 | 47.76 | H |
| ATOM | 1656 | CB | GLN | 3 | 126.585 | 33.018 | 63.684 | 1.00 | 47.79 | H |
| ATOM | 1657 | CG | GLN | 3 | 128.013 | 33.216 | 63.226 | 1.00 | 70.50 | H |
| ATOM | 1658 | CD | GLN | 3 | 128.654 | 31.926 | 62.768 | 1.00 | 77.13 | H |
| ATOM | 1659 | OE1 | GLN | 3 | 128.477 | 30.879 | 63.392 | 1.00 | 89.69 | H |
| ATOM | 1660 | NE2 | GLN | 3 | 129.403 | 31.990 | 61.671 | 1.00 | 74.80 | H |
| ATOM | 1661 | C | GLN | 3 | 125.324 | 33.576 | 61.605 | 1.00 | 43.77 | H |
| ATOM | 1662 | O | GLN | 3 | 124.223 | 33.144 | 61.264 | 1.00 | 28.11 | H |
| ATOM | 1663 | N | LEU | 4 | 126.341 | 33.721 | 60.761 | 1.00 | 43.76 | H |
| ATOM | 1664 | CA | LEU | 4 | 126.231 | 33.358 | 59.356 | 1.00 | 47.78 | H |
| ATOM | 1665 | CB | LEU | 4 | 126.061 | 34.620 | 58.502 | 1.00 | 41.23 | H |
| ATOM | 1666 | CG | LEU | 4 | 125.041 | 34.700 | 57.351 | 1.00 | 30.41 | H |
| ATOM | 1667 | CD1 | LEU | 4 | 124.005 | 33.592 | 57.439 | 1.00 | 25.02 | H |
| ATOM | 1668 | CD2 | LEU | 4 | 124.353 | 36.059 | 57.404 | 1.00 | 18.34 | H |
| ATOM | 1669 | C | LEU | 4 | 127.499 | 32.620 | 58.945 | 1.00 | 47.69 | H |
| ATOM | 1670 | O | LEU | 4 | 128.468 | 33.245 | 58.524 | 1.00 | 52.13 | H |

TABLE 4-continued

Co-ordinates of the CD28/5.11A1 crystal structure

| ATOM | 1671 | N   | GLN | 5  | 127.500 | 31.296 | 59.081 | 1.00 | 46.16 | H |
|------|------|-----|-----|----|---------|--------|--------|------|-------|---|
| ATOM | 1672 | CA  | GLN | 5  | 128.669 | 30.500 | 58.706 | 1.00 | 47.49 | H |
| ATOM | 1673 | CB  | GLN | 5  | 128.591 | 29.109 | 59.335 | 1.00 | 47.97 | H |
| ATOM | 1674 | CG  | GLN | 5  | 129.142 | 29.029 | 60.747 | 1.00 | 41.56 | H |
| ATOM | 1675 | CD  | GLN | 5  | 128.328 | 28.100 | 61.633 | 1.00 | 64.06 | H |
| ATOM | 1676 | OE1 | GLN | 5  | 128.475 | 26.874 | 61.573 | 1.00 | 60.56 | H |
| ATOM | 1677 | NE2 | GLN | 5  | 127.459 | 28.681 | 62.459 | 1.00 | 60.41 | H |
| ATOM | 1678 | C   | GLN | 5  | 128.764 | 30.379 | 57.187 | 1.00 | 36.59 | H |
| ATOM | 1679 | O   | GLN | 5  | 127.760 | 30.146 | 56.519 | 1.00 | 31.08 | H |
| ATOM | 1680 | N   | GLN | 6  | 129.978 | 30.531 | 56.659 | 1.00 | 35.83 | H |
| ATOM | 1681 | CA  | GLN | 6  | 130.214 | 30.460 | 55.220 | 1.00 | 33.41 | H |
| ATOM | 1682 | CB  | GLN | 6  | 130.697 | 31.824 | 54.715 | 1.00 | 15.61 | H |
| ATOM | 1683 | CG  | GLN | 6  | 130.089 | 32.252 | 53.377 | 1.00 | 48.11 | H |
| ATOM | 1684 | CD  | GLN | 6  | 130.061 | 33.762 | 53.195 | 1.00 | 44.23 | H |
| ATOM | 1685 | OE1 | GLN | 6  | 129.429 | 34.480 | 53.971 | 1.00 | 44.77 | H |
| ATOM | 1686 | NE2 | GLN | 6  | 130.750 | 34.251 | 52.164 | 1.00 | 43.09 | H |
| ATOM | 1687 | C   | GLN | 6  | 131.230 | 29.393 | 54.818 | 1.00 | 39.29 | H |
| ATOM | 1688 | O   | GLN | 6  | 131.746 | 28.655 | 55.659 | 1.00 | 47.11 | H |
| ATOM | 1689 | N   | SER | 7  | 131.492 | 29.318 | 53.514 | 1.00 | 52.14 | H |
| ATOM | 1690 | CA  | SER | 7  | 132.464 | 28.402 | 52.913 | 1.00 | 45.28 | H |
| ATOM | 1691 | CB  | SER | 7  | 133.561 | 28.037 | 53.913 | 1.00 | 30.02 | H |
| ATOM | 1692 | OG  | SER | 7  | 134.775 | 27.764 | 53.240 | 1.00 | 36.01 | H |
| ATOM | 1693 | C   | SER | 7  | 131.963 | 27.125 | 52.255 | 1.00 | 53.29 | H |
| ATOM | 1694 | O   | SER | 7  | 130.825 | 26.691 | 52.435 | 1.00 | 41.78 | H |
| ATOM | 1695 | N   | GLY | 8  | 132.873 | 26.546 | 51.478 | 1.00 | 74.11 | H |
| ATOM | 1696 | CA  | GLY | 8  | 132.656 | 25.313 | 50.744 | 1.00 | 86.06 | H |
| ATOM | 1697 | C   | GLY | 8  | 133.987 | 25.088 | 50.046 | 1.00 | 96.74 | H |
| ATOM | 1698 | O   | GLY | 8  | 135.032 | 25.207 | 50.691 | 1.00 | 99.99 | H |
| ATOM | 1699 | N   | PRO | 9  | 133.999 | 24.757 | 48.739 | 1.00 | 99.99 | H |
| ATOM | 1700 | CD  | PRO | 9  | 132.851 | 24.529 | 47.850 | 1.00 | 99.99 | H |
| ATOM | 1701 | CA  | PRO | 9  | 135.283 | 24.547 | 48.047 | 1.00 | 95.17 | H |
| ATOM | 1702 | CB  | PRO | 9  | 134.873 | 23.925 | 46.702 | 1.00 | 99.99 | H |
| ATOM | 1703 | CG  | PRO | 9  | 133.404 | 23.557 | 46.852 | 1.00 | 99.98 | H |
| ATOM | 1704 | C   | PRO | 9  | 136.019 | 25.882 | 47.872 | 1.00 | 83.28 | H |
| ATOM | 1705 | O   | PRO | 9  | 135.387 | 26.937 | 47.793 | 1.00 | 73.84 | H |
| ATOM | 1706 | N   | GLU | 10 | 137.349 | 25.847 | 47.811 | 1.00 | 73.05 | H |
| ATOM | 1707 | CA  | GLU | 10 | 138.109 | 27.087 | 47.672 | 1.00 | 56.11 | H |
| ATOM | 1708 | CB  | GLU | 10 | 139.003 | 27.279 | 48.898 | 1.00 | 43.53 | H |
| ATOM | 1709 | CG  | GLU | 10 | 138.487 | 26.554 | 50.136 | 1.00 | 30.69 | H |
| ATOM | 1710 | CD  | GLU | 10 | 137.988 | 27.497 | 51.217 | 1.00 | 42.43 | H |
| ATOM | 1711 | OE1 | GLU | 10 | 138.782 | 28.352 | 51.678 | 1.00 | 16.81 | H |
| ATOM | 1712 | OE2 | GLU | 10 | 136.803 | 27.374 | 51.612 | 1.00 | 22.46 | H |
| ATOM | 1713 | C   | GLU | 10 | 138.939 | 27.223 | 46.393 | 1.00 | 47.28 | H |
| ATOM | 1714 | O   | GLU | 10 | 139.302 | 28.336 | 46.017 | 1.00 | 48.73 | H |
| ATOM | 1715 | N   | LEU | 11 | 139.239 | 26.106 | 45.730 | 1.00 | 37.54 | H |
| ATOM | 1716 | CA  | LEU | 11 | 140.012 | 26.137 | 44.486 | 1.00 | 30.14 | H |
| ATOM | 1717 | CB  | LEU | 11 | 141.398 | 25.517 | 44.676 | 1.00 | 20.14 | H |
| ATOM | 1718 | CG  | LEU | 11 | 142.591 | 26.256 | 44.045 | 1.00 | 23.62 | H |
| ATOM | 1719 | CD1 | LEU | 11 | 143.477 | 25.265 | 43.309 | 1.00 | 18.85 | H |
| ATOM | 1720 | CD2 | LEU | 11 | 142.110 | 27.357 | 43.100 | 1.00 | 23.67 | H |
| ATOM | 1721 | C   | LEU | 11 | 139.306 | 25.400 | 43.357 | 1.00 | 44.95 | H |
| ATOM | 1722 | O   | LEU | 11 | 138.867 | 24.257 | 43.519 | 1.00 | 54.63 | H |
| ATOM | 1723 | N   | VAL | 12 | 139.210 | 26.057 | 42.207 | 1.00 | 41.04 | H |
| ATOM | 1724 | CA  | VAL | 12 | 138.564 | 25.466 | 41.042 | 1.00 | 44.92 | H |
| ATOM | 1725 | CB  | VAL | 12 | 137.198 | 26.116 | 40.760 | 1.00 | 55.40 | H |
| ATOM | 1726 | CG1 | VAL | 12 | 136.166 | 25.600 | 41.736 | 1.00 | 60.33 | H |
| ATOM | 1727 | CG2 | VAL | 12 | 137.324 | 27.631 | 40.849 | 1.00 | 67.40 | H |
| ATOM | 1728 | C   | VAL | 12 | 139.428 | 25.687 | 39.824 | 1.00 | 38.99 | H |
| ATOM | 1729 | O   | VAL | 12 | 140.065 | 26.727 | 39.702 | 1.00 | 23.16 | H |
| ATOM | 1730 | N   | LYS | 13 | 139.451 | 24.705 | 38.928 | 1.00 | 56.02 | H |
| ATOM | 1731 | CA  | LYS | 13 | 140.230 | 24.817 | 37.701 | 1.00 | 61.99 | H |
| ATOM | 1732 | CB  | LYS | 13 | 140.577 | 23.430 | 37.154 | 1.00 | 47.53 | H |
| ATOM | 1733 | CG  | LYS | 13 | 142.054 | 23.066 | 37.259 | 1.00 | 29.92 | H |
| ATOM | 1734 | CD  | LYS | 13 | 142.364 | 21.831 | 36.416 | 1.00 | 39.21 | H |
| ATOM | 1735 | CE  | LYS | 13 | 143.629 | 22.007 | 35.596 | 1.00 | 40.05 | H |
| ATOM | 1736 | NZ  | LYS | 13 | 144.804 | 21.337 | 36.230 | 1.00 | 30.64 | H |
| ATOM | 1737 | C   | LYS | 13 | 139.365 | 25.595 | 36.706 | 1.00 | 60.22 | H |
| ATOM | 1738 | O   | LYS | 13 | 138.184 | 25.287 | 36.513 | 1.00 | 48.99 | H |
| ATOM | 1739 | N   | PRO | 14 | 139.951 | 26.619 | 36.066 | 1.00 | 55.96 | H |
| ATOM | 1740 | CD  | PRO | 14 | 141.359 | 27.003 | 36.236 | 1.00 | 55.17 | H |
| ATOM | 1741 | CA  | PRO | 14 | 139.270 | 27.477 | 35.091 | 1.00 | 63.02 | H |
| ATOM | 1742 | CB  | PRO | 14 | 140.412 | 28.234 | 34.404 | 1.00 | 59.73 | H |
| ATOM | 1743 | CG  | PRO | 14 | 141.685 | 27.633 | 34.929 | 1.00 | 60.43 | H |
| ATOM | 1744 | C   | PRO | 14 | 138.356 | 26.766 | 34.096 | 1.00 | 61.60 | H |
| ATOM | 1745 | O   | PRO | 14 | 138.802 | 25.957 | 33.275 | 1.00 | 63.48 | H |
| ATOM | 1746 | N   | GLY | 15 | 137.069 | 27.093 | 34.185 | 1.00 | 55.03 | H |
| ATOM | 1747 | CA  | GLY | 15 | 136.077 | 26.503 | 33.307 | 1.00 | 55.23 | H |

TABLE 4-continued

Co-ordinates of the CD28/5.11A1 crystal structure

| ATOM | 1748 | C   | GLY | 15 | 134.961 | 25.815 | 34.071 | 1.00 | 49.69 | H |
|------|------|-----|-----|----|---------|--------|--------|------|-------|---|
| ATOM | 1749 | O   | GLY | 15 | 133.800 | 25.865 | 33.670 | 1.00 | 45.93 | H |
| ATOM | 1750 | N   | THR | 16 | 135.304 | 25.176 | 35.182 | 1.00 | 46.88 | H |
| ATOM | 1751 | CA  | THR | 16 | 134.303 | 24.480 | 35.969 | 1.00 | 46.72 | H |
| ATOM | 1752 | CB  | THR | 16 | 134.946 | 23.549 | 36.992 | 1.00 | 53.32 | H |
| ATOM | 1753 | OG1 | THR | 16 | 135.914 | 24.275 | 37.758 | 1.00 | 63.69 | H |
| ATOM | 1754 | CG2 | THR | 16 | 135.615 | 22.387 | 36.286 | 1.00 | 61.76 | H |
| ATOM | 1755 | C   | THR | 16 | 133.361 | 25.415 | 36.700 | 1.00 | 42.84 | H |
| ATOM | 1756 | O   | THR | 16 | 133.391 | 26.626 | 36.505 | 1.00 | 35.33 | H |
| ATOM | 1757 | N   | SER | 17 | 132.535 | 24.829 | 37.559 | 1.00 | 46.34 | H |
| ATOM | 1758 | CA  | SER | 17 | 131.543 | 25.570 | 38.320 | 1.00 | 44.29 | H |
| ATOM | 1759 | CB  | SER | 17 | 130.190 | 25.458 | 37.621 | 1.00 | 43.09 | H |
| ATOM | 1760 | OG  | SER | 17 | 130.349 | 25.482 | 36.211 | 1.00 | 37.03 | H |
| ATOM | 1761 | C   | SER | 17 | 131.408 | 25.051 | 39.742 | 1.00 | 45.39 | H |
| ATOM | 1762 | O   | SER | 17 | 131.124 | 23.872 | 39.956 | 1.00 | 51.18 | H |
| ATOM | 1763 | N   | VAL | 18 | 131.599 | 25.938 | 40.713 | 1.00 | 43.96 | H |
| ATOM | 1764 | CA  | VAL | 18 | 131.483 | 25.564 | 42.119 | 1.00 | 45.50 | H |
| ATOM | 1765 | CB  | VAL | 18 | 132.723 | 25.989 | 42.932 | 1.00 | 47.04 | H |
| ATOM | 1766 | CG1 | VAL | 18 | 132.979 | 27.469 | 42.756 | 1.00 | 45.76 | H |
| ATOM | 1767 | CG2 | VAL | 18 | 132.513 | 25.665 | 44.400 | 1.00 | 36.17 | H |
| ATOM | 1768 | C   | VAL | 18 | 130.257 | 26.218 | 42.742 | 1.00 | 46.62 | H |
| ATOM | 1769 | O   | VAL | 18 | 129.772 | 27.240 | 42.258 | 1.00 | 24.82 | H |
| ATOM | 1770 | N   | ARG | 19 | 129.758 | 25.610 | 43.813 | 1.00 | 53.11 | H |
| ATOM | 1771 | CA  | ARG | 19 | 128.589 | 26.122 | 44.518 | 1.00 | 58.98 | H |
| ATOM | 1772 | CB  | ARG | 19 | 127.414 | 25.157 | 44.354 | 1.00 | 48.17 | H |
| ATOM | 1773 | CG  | ARG | 19 | 126.252 | 25.443 | 45.280 | 1.00 | 32.81 | H |
| ATOM | 1774 | CD  | ARG | 19 | 125.479 | 24.167 | 45.605 | 1.00 | 61.51 | H |
| ATOM | 1775 | NE  | ARG | 19 | 126.212 | 23.302 | 46.530 | 1.00 | 70.76 | H |
| ATOM | 1776 | CZ  | ARG | 19 | 125.661 | 22.352 | 47.283 | 1.00 | 68.17 | H |
| ATOM | 1777 | NH1 | ARG | 19 | 124.353 | 22.124 | 47.232 | 1.00 | 41.10 | H |
| ATOM | 1778 | NH2 | ARG | 19 | 126.428 | 21.625 | 48.090 | 1.00 | 47.54 | H |
| ATOM | 1779 | C   | ARG | 19 | 128.912 | 26.282 | 46.000 | 1.00 | 57.70 | H |
| ATOM | 1780 | O   | ARG | 19 | 129.050 | 25.294 | 46.716 | 1.00 | 66.45 | H |
| ATOM | 1781 | N   | ILE | 20 | 129.043 | 27.523 | 46.456 | 1.00 | 53.34 | H |
| ATOM | 1782 | CA  | ILE | 20 | 129.345 | 27.780 | 47.860 | 1.00 | 52.34 | H |
| ATOM | 1783 | CB  | ILE | 20 | 130.052 | 29.137 | 48.067 | 1.00 | 45.51 | H |
| ATOM | 1784 | CG2 | ILE | 20 | 131.474 | 29.053 | 47.565 | 1.00 | 47.12 | H |
| ATOM | 1785 | CG1 | ILE | 20 | 129.280 | 30.243 | 47.353 | 1.00 | 39.21 | H |
| ATOM | 1786 | CD1 | ILE | 20 | 129.929 | 31.606 | 47.466 | 1.00 | 37.76 | H |
| ATOM | 1787 | C   | ILE | 20 | 128.059 | 27.800 | 48.666 | 1.00 | 55.83 | H |
| ATOM | 1788 | O   | ILE | 20 | 126.960 | 27.764 | 48.113 | 1.00 | 48.41 | H |
| ATOM | 1789 | N   | SER | 21 | 128.208 | 27.860 | 49.981 | 1.00 | 65.06 | H |
| ATOM | 1790 | CA  | SER | 21 | 127.058 | 27.892 | 50.863 | 1.00 | 70.97 | H |
| ATOM | 1791 | CB  | SER | 21 | 126.810 | 26.503 | 51.468 | 1.00 | 72.43 | H |
| ATOM | 1792 | OG  | SER | 21 | 127.562 | 26.314 | 52.654 | 1.00 | 60.74 | H |
| ATOM | 1793 | C   | SER | 21 | 127.260 | 28.917 | 51.968 | 1.00 | 69.87 | H |
| ATOM | 1794 | O   | SER | 21 | 128.288 | 29.599 | 52.026 | 1.00 | 70.39 | H |
| ATOM | 1795 | N   | CYS | 22 | 126.262 | 29.013 | 52.839 | 1.00 | 69.21 | H |
| ATOM | 1796 | CA  | CYS | 22 | 126.263 | 29.940 | 53.963 | 1.00 | 61.84 | H |
| ATOM | 1797 | C   | CYS | 22 | 124.996 | 29.635 | 54.745 | 1.00 | 52.88 | H |
| ATOM | 1798 | O   | CYS | 22 | 123.890 | 29.845 | 54.249 | 1.00 | 52.20 | H |
| ATOM | 1799 | CB  | CYS | 22 | 126.233 | 31.379 | 53.461 | 1.00 | 52.16 | H |
| ATOM | 1800 | SG  | CYS | 22 | 125.483 | 32.535 | 54.637 | 1.00 | 54.59 | H |
| ATOM | 1801 | N   | GLU | 23 | 125.154 | 29.147 | 55.968 | 1.00 | 40.82 | H |
| ATOM | 1802 | CA  | GLU | 23 | 123.998 | 28.783 | 56.767 | 1.00 | 43.24 | H |
| ATOM | 1803 | CB  | GLU | 23 | 124.140 | 27.339 | 57.230 | 1.00 | 55.82 | H |
| ATOM | 1804 | CG  | GLU | 23 | 125.578 | 26.915 | 57.456 | 1.00 | 76.19 | H |
| ATOM | 1805 | CD  | GLU | 23 | 125.807 | 26.370 | 58.853 | 1.00 | 92.47 | H |
| ATOM | 1806 | OE1 | GLU | 23 | 124.810 | 26.025 | 59.525 | 1.00 | 98.93 | H |
| ATOM | 1807 | OE2 | GLU | 23 | 126.982 | 26.286 | 59.278 | 1.00 | 99.99 | H |
| ATOM | 1808 | C   | GLU | 23 | 123.723 | 29.675 | 57.962 | 1.00 | 47.05 | H |
| ATOM | 1809 | O   | GLU | 23 | 124.610 | 29.940 | 58.777 | 1.00 | 50.01 | H |
| ATOM | 1810 | N   | ALA | 24 | 122.472 | 30.117 | 58.060 | 1.00 | 39.44 | H |
| ATOM | 1811 | CA  | ALA | 24 | 122.022 | 30.980 | 59.143 | 1.00 | 43.91 | H |
| ATOM | 1812 | CB  | ALA | 24 | 120.770 | 31.729 | 58.709 | 1.00 | 40.39 | H |
| ATOM | 1813 | C   | ALA | 24 | 121.745 | 30.197 | 60.429 | 1.00 | 49.01 | H |
| ATOM | 1814 | O   | ALA | 24 | 121.532 | 28.983 | 60.398 | 1.00 | 44.02 | H |
| ATOM | 1815 | N   | SER | 25 | 121.752 | 30.909 | 61.555 | 1.00 | 60.65 | H |
| ATOM | 1816 | CA  | SER | 25 | 121.504 | 30.321 | 62.872 | 1.00 | 64.10 | H |
| ATOM | 1817 | CB  | SER | 25 | 122.557 | 29.250 | 63.192 | 1.00 | 76.12 | H |
| ATOM | 1818 | OG  | SER | 25 | 123.782 | 29.512 | 62.529 | 1.00 | 87.44 | H |
| ATOM | 1819 | C   | SER | 25 | 121.514 | 31.391 | 63.966 | 1.00 | 53.28 | H |
| ATOM | 1820 | O   | SER | 25 | 122.520 | 32.068 | 64.188 | 1.00 | 50.41 | H |
| ATOM | 1821 | N   | GLY | 26 | 120.384 | 31.533 | 64.651 | 1.00 | 46.94 | H |
| ATOM | 1822 | CA  | GLY | 26 | 120.275 | 32.520 | 65.708 | 1.00 | 30.92 | H |
| ATOM | 1823 | C   | GLY | 26 | 119.044 | 33.377 | 65.502 | 1.00 | 32.69 | H |
| ATOM | 1824 | O   | GLY | 26 | 118.711 | 34.201 | 66.349 | 1.00 | 19.54 | H |

TABLE 4-continued

Co-ordinates of the CD28/5.11A1 crystal structure

| ATOM | 1825 | N | TYR | 27 | 118.372 | 33.167 | 64.370 | 1.00 | 42.28 | H |
|---|---|---|---|---|---|---|---|---|---|---|
| ATOM | 1826 | CA | TYR | 27 | 117.163 | 33.909 | 64.012 | 1.00 | 45.58 | H |
| ATOM | 1827 | CB | TYR | 27 | 117.546 | 35.240 | 63.346 | 1.00 | 51.85 | H |
| ATOM | 1828 | CG | TYR | 27 | 118.025 | 35.116 | 61.907 | 1.00 | 59.01 | H |
| ATOM | 1829 | CD1 | TYR | 27 | 117.155 | 35.345 | 60.838 | 1.00 | 52.27 | H |
| ATOM | 1830 | CE1 | TYR | 27 | 117.595 | 35.261 | 59.514 | 1.00 | 42.40 | H |
| ATOM | 1831 | CD2 | TYR | 27 | 119.355 | 34.794 | 61.614 | 1.00 | 52.66 | H |
| ATOM | 1832 | CE2 | TYR | 27 | 119.804 | 34.710 | 60.293 | 1.00 | 46.26 | H |
| ATOM | 1833 | CZ | TYR | 27 | 118.919 | 34.947 | 59.250 | 1.00 | 50.61 | H |
| ATOM | 1834 | OH | TYR | 27 | 119.363 | 34.893 | 57.947 | 1.00 | 42.85 | H |
| ATOM | 1835 | C | TYR | 27 | 116.250 | 33.109 | 63.072 | 1.00 | 48.20 | H |
| ATOM | 1836 | O | TYR | 27 | 116.553 | 31.963 | 62.712 | 1.00 | 30.85 | H |
| ATOM | 1837 | N | THR | 28 | 115.131 | 33.722 | 62.684 | 1.00 | 47.35 | H |
| ATOM | 1838 | CA | THR | 28 | 114.176 | 33.088 | 61.776 | 1.00 | 41.83 | H |
| ATOM | 1839 | CB | THR | 28 | 112.786 | 33.737 | 61.871 | 1.00 | 39.96 | H |
| ATOM | 1840 | OG1 | THR | 28 | 112.270 | 33.577 | 63.197 | 1.00 | 50.93 | H |
| ATOM | 1841 | CG2 | THR | 28 | 111.830 | 33.084 | 60.878 | 1.00 | 45.16 | H |
| ATOM | 1842 | C | THR | 28 | 114.653 | 33.204 | 60.328 | 1.00 | 40.89 | H |
| ATOM | 1843 | O | THR | 28 | 114.619 | 34.280 | 59.739 | 1.00 | 31.24 | H |
| ATOM | 1844 | N | PHE | 29 | 115.095 | 32.084 | 59.766 | 1.00 | 41.61 | H |
| ATOM | 1845 | CA | PHE | 29 | 115.591 | 32.035 | 58.399 | 1.00 | 41.45 | H |
| ATOM | 1846 | CB | PHE | 29 | 115.946 | 30.593 | 58.034 | 1.00 | 30.51 | H |
| ATOM | 1847 | CG | PHE | 29 | 116.611 | 30.449 | 56.696 | 1.00 | 37.17 | H |
| ATOM | 1848 | CD1 | PHE | 29 | 117.833 | 31.065 | 56.439 | 1.00 | 30.37 | H |
| ATOM | 1849 | CD2 | PHE | 29 | 116.032 | 29.667 | 55.700 | 1.00 | 36.28 | H |
| ATOM | 1850 | CE1 | PHE | 29 | 118.469 | 30.904 | 55.214 | 1.00 | 21.32 | H |
| ATOM | 1851 | CE2 | PHE | 29 | 116.666 | 29.500 | 54.463 | 1.00 | 41.18 | H |
| ATOM | 1852 | CZ | PHE | 29 | 117.889 | 30.122 | 54.225 | 1.00 | 35.05 | H |
| ATOM | 1853 | C | PHE | 29 | 114.594 | 32.572 | 57.379 | 1.00 | 54.24 | H |
| ATOM | 1854 | O | PHE | 29 | 114.952 | 33.331 | 56.480 | 1.00 | 66.70 | H |
| ATOM | 1855 | N | THR | 30 | 113.342 | 32.164 | 57.527 | 1.00 | 55.99 | H |
| ATOM | 1856 | CA | THR | 30 | 112.276 | 32.557 | 56.615 | 1.00 | 52.36 | H |
| ATOM | 1857 | CB | THR | 30 | 111.052 | 31.652 | 56.824 | 1.00 | 53.76 | H |
| ATOM | 1858 | OG1 | THR | 30 | 110.733 | 31.583 | 58.225 | 1.00 | 35.56 | H |
| ATOM | 1859 | CG2 | THR | 30 | 111.357 | 30.244 | 56.304 | 1.00 | 44.72 | H |
| ATOM | 1860 | C | THR | 30 | 111.829 | 34.016 | 56.703 | 1.00 | 47.50 | H |
| ATOM | 1861 | O | THR | 30 | 110.914 | 34.426 | 55.996 | 1.00 | 53.11 | H |
| ATOM | 1862 | N | SER | 31 | 112.470 | 34.804 | 57.554 | 1.00 | 46.37 | H |
| ATOM | 1863 | CA | SER | 31 | 112.094 | 36.207 | 57.697 | 1.00 | 45.74 | H |
| ATOM | 1864 | CB | SER | 31 | 111.832 | 36.521 | 59.167 | 1.00 | 29.27 | H |
| ATOM | 1865 | OG | SER | 31 | 110.583 | 37.159 | 59.337 | 1.00 | 47.69 | H |
| ATOM | 1866 | C | SER | 31 | 113.143 | 37.175 | 57.150 | 1.00 | 47.78 | H |
| ATOM | 1867 | O | SER | 31 | 113.149 | 38.358 | 57.509 | 1.00 | 46.57 | H |
| ATOM | 1868 | N | TYR | 32 | 114.027 | 36.683 | 56.286 | 1.00 | 31.83 | H |
| ATOM | 1869 | CA | TYR | 32 | 115.068 | 37.530 | 55.720 | 1.00 | 30.55 | H |
| ATOM | 1870 | CB | TYR | 32 | 116.287 | 37.556 | 56.642 | 1.00 | 32.62 | H |
| ATOM | 1871 | CG | TYR | 32 | 116.075 | 38.248 | 57.963 | 1.00 | 37.51 | H |
| ATOM | 1872 | CD1 | TYR | 32 | 115.494 | 37.579 | 59.031 | 1.00 | 33.89 | H |
| ATOM | 1873 | CE1 | TYR | 32 | 115.358 | 38.184 | 60.266 | 1.00 | 35.72 | H |
| ATOM | 1874 | CD2 | TYR | 32 | 116.510 | 39.556 | 58.166 | 1.00 | 39.03 | H |
| ATOM | 1875 | CE2 | TYR | 32 | 116.378 | 40.173 | 59.401 | 1.00 | 40.85 | H |
| ATOM | 1876 | CZ | TYR | 32 | 115.803 | 39.476 | 60.449 | 1.00 | 43.40 | H |
| ATOM | 1877 | OH | TYR | 32 | 115.693 | 40.053 | 61.695 | 1.00 | 55.17 | H |
| ATOM | 1878 | C | TYR | 32 | 115.526 | 37.071 | 54.342 | 1.00 | 42.11 | H |
| ATOM | 1879 | O | TYR | 32 | 115.438 | 35.889 | 54.012 | 1.00 | 37.33 | H |
| ATOM | 1880 | N | TYR | 33 | 116.021 | 38.017 | 53.545 | 1.00 | 52.12 | H |
| ATOM | 1881 | CA | TYR | 33 | 116.544 | 37.721 | 52.210 | 1.00 | 50.02 | H |
| ATOM | 1882 | CB | TYR | 33 | 116.576 | 38.960 | 51.309 | 1.00 | 42.85 | H |
| ATOM | 1883 | CG | TYR | 33 | 115.263 | 39.601 | 50.944 | 1.00 | 58.80 | H |
| ATOM | 1884 | CD1 | TYR | 33 | 114.637 | 39.313 | 49.730 | 1.00 | 66.77 | H |
| ATOM | 1885 | CE1 | TYR | 33 | 113.466 | 39.968 | 49.345 | 1.00 | 69.61 | H |
| ATOM | 1886 | CD2 | TYR | 33 | 114.683 | 40.558 | 51.771 | 1.00 | 76.77 | H |
| ATOM | 1887 | CE2 | TYR | 33 | 113.513 | 41.220 | 51.398 | 1.00 | 80.20 | H |
| ATOM | 1888 | CZ | TYR | 33 | 112.909 | 40.921 | 50.185 | 1.00 | 74.03 | H |
| ATOM | 1889 | OH | TYR | 33 | 111.746 | 41.574 | 49.830 | 1.00 | 56.44 | H |
| ATOM | 1890 | C | TYR | 33 | 118.000 | 37.359 | 52.441 | 1.00 | 53.48 | H |
| ATOM | 1891 | O | TYR | 33 | 118.601 | 37.825 | 53.411 | 1.00 | 55.64 | H |
| ATOM | 1892 | N | ILE | 34 | 118.574 | 36.538 | 51.570 | 1.00 | 39.36 | H |
| ATOM | 1893 | CA | ILE | 34 | 119.991 | 36.237 | 51.705 | 1.00 | 36.92 | H |
| ATOM | 1894 | CB | ILE | 34 | 120.310 | 34.720 | 51.687 | 1.00 | 41.72 | H |
| ATOM | 1895 | CG2 | ILE | 34 | 121.831 | 34.515 | 51.776 | 1.00 | 24.87 | H |
| ATOM | 1896 | CG1 | ILE | 34 | 119.647 | 34.023 | 52.879 | 1.00 | 33.33 | H |
| ATOM | 1897 | CD1 | ILE | 34 | 120.435 | 34.137 | 54.177 | 1.00 | 29.68 | H |
| ATOM | 1898 | C | ILE | 34 | 120.629 | 36.900 | 50.490 | 1.00 | 33.61 | H |
| ATOM | 1899 | O | ILE | 34 | 120.304 | 36.568 | 49.351 | 1.00 | 36.71 | H |
| ATOM | 1900 | N | HIS | 35 | 121.506 | 37.864 | 50.739 | 1.00 | 34.93 | H |
| ATOM | 1901 | CA | HIS | 35 | 122.185 | 38.573 | 49.666 | 1.00 | 29.41 | H |

TABLE 4-continued

Co-ordinates of the CD28/5.11A1 crystal structure

| ATOM | 1902 | CB | HIS | 35 | 122.300 | 40.062 | 49.990 | 1.00 | 22.47 | H |
|---|---|---|---|---|---|---|---|---|---|---|
| ATOM | 1903 | CG | HIS | 35 | 120.983 | 40.768 | 50.047 | 1.00 | 28.34 | H |
| ATOM | 1904 | CD2 | HIS | 35 | 120.082 | 40.885 | 51.049 | 1.00 | 17.42 | H |
| ATOM | 1905 | ND1 | HIS | 35 | 120.446 | 41.427 | 48.965 | 1.00 | 34.24 | H |
| ATOM | 1906 | CE1 | HIS | 35 | 119.266 | 41.924 | 49.298 | 1.00 | 35.85 | H |
| ATOM | 1907 | NE2 | HIS | 35 | 119.023 | 41.609 | 50.556 | 1.00 | 28.90 | H |
| ATOM | 1908 | C | HIS | 35 | 123.574 | 38.000 | 49.482 | 1.00 | 24.58 | H |
| ATOM | 1909 | O | HIS | 35 | 124.156 | 37.437 | 50.403 | 1.00 | 40.74 | H |
| ATOM | 1910 | N | TRP | 36 | 124.104 | 38.149 | 48.282 | 1.00 | 18.85 | H |
| ATOM | 1911 | CA | TRP | 36 | 125.430 | 37.664 | 47.984 | 1.00 | 25.49 | H |
| ATOM | 1912 | CB | TRP | 36 | 125.334 | 36.410 | 47.104 | 1.00 | 38.00 | H |
| ATOM | 1913 | CG | TRP | 36 | 125.226 | 35.122 | 47.882 | 1.00 | 42.56 | H |
| ATOM | 1914 | CD2 | TRP | 36 | 126.288 | 34.433 | 48.564 | 1.00 | 28.82 | H |
| ATOM | 1915 | CE2 | TRP | 36 | 125.730 | 33.274 | 49.146 | 1.00 | 18.67 | H |
| ATOM | 1916 | CE3 | TRP | 36 | 127.658 | 34.687 | 48.737 | 1.00 | 34.82 | H |
| ATOM | 1917 | CD1 | TRP | 36 | 124.097 | 34.368 | 48.075 | 1.00 | 40.81 | H |
| ATOM | 1918 | NE1 | TRP | 36 | 124.394 | 33.257 | 48.834 | 1.00 | 30.56 | H |
| ATOM | 1919 | CZ2 | TRP | 36 | 126.492 | 32.368 | 49.889 | 1.00 | 44.00 | H |
| ATOM | 1920 | CZ3 | TRP | 36 | 128.418 | 33.786 | 49.479 | 1.00 | 41.71 | H |
| ATOM | 1921 | CH2 | TRP | 36 | 127.832 | 32.641 | 50.045 | 1.00 | 49.64 | H |
| ATOM | 1922 | C | TRP | 36 | 126.189 | 38.784 | 47.269 | 1.00 | 22.21 | H |
| ATOM | 1923 | O | TRP | 36 | 125.658 | 39.410 | 46.352 | 1.00 | 20.33 | H |
| ATOM | 1924 | N | VAL | 37 | 127.420 | 39.044 | 47.703 | 1.00 | 21.22 | H |
| ATOM | 1925 | CA | VAL | 37 | 128.237 | 40.085 | 47.089 | 1.00 | 29.63 | H |
| ATOM | 1926 | CB | VAL | 37 | 128.157 | 41.414 | 47.887 | 1.00 | 30.69 | H |
| ATOM | 1927 | CG1 | VAL | 37 | 126.874 | 41.453 | 48.701 | 1.00 | 7.82 | H |
| ATOM | 1928 | CG2 | VAL | 37 | 129.366 | 41.569 | 48.780 | 1.00 | 16.02 | H |
| ATOM | 1929 | C | VAL | 37 | 129.693 | 39.641 | 46.984 | 1.00 | 33.49 | H |
| ATOM | 1930 | O | VAL | 37 | 130.223 | 39.017 | 47.900 | 1.00 | 17.14 | H |
| ATOM | 1931 | N | LYS | 38 | 130.330 | 39.970 | 45.862 | 1.00 | 43.70 | H |
| ATOM | 1932 | CA | LYS | 38 | 131.720 | 39.591 | 45.619 | 1.00 | 47.72 | H |
| ATOM | 1933 | CB | LYS | 38 | 131.849 | 38.932 | 44.233 | 1.00 | 55.60 | H |
| ATOM | 1934 | CG | LYS | 38 | 132.592 | 39.756 | 43.175 | 1.00 | 55.19 | H |
| ATOM | 1935 | CD | LYS | 38 | 133.109 | 38.890 | 42.022 | 1.00 | 50.50 | H |
| ATOM | 1936 | CE | LYS | 38 | 131.967 | 38.347 | 41.155 | 1.00 | 51.42 | H |
| ATOM | 1937 | NZ | LYS | 38 | 132.372 | 37.162 | 40.335 | 1.00 | 38.13 | H |
| ATOM | 1938 | C | LYS | 38 | 132.699 | 40.757 | 45.732 | 1.00 | 48.64 | H |
| ATOM | 1939 | O | LYS | 38 | 132.467 | 41.837 | 45.189 | 1.00 | 52.35 | H |
| ATOM | 1940 | N | GLN | 39 | 133.798 | 40.525 | 46.439 | 1.00 | 38.36 | H |
| ATOM | 1941 | CA | GLN | 39 | 134.819 | 41.545 | 46.621 | 1.00 | 30.47 | H |
| ATOM | 1942 | CB | GLN | 39 | 134.969 | 41.879 | 48.103 | 1.00 | 40.49 | H |
| ATOM | 1943 | CG | GLN | 39 | 136.078 | 42.863 | 48.409 | 1.00 | 23.44 | H |
| ATOM | 1944 | CD | GLN | 39 | 135.965 | 43.424 | 49.803 | 1.00 | 27.61 | H |
| ATOM | 1945 | OE1 | GLN | 39 | 135.386 | 44.485 | 50.004 | 1.00 | 26.42 | H |
| ATOM | 1946 | NE2 | GLN | 39 | 136.517 | 42.709 | 50.781 | 1.00 | 31.89 | H |
| ATOM | 1947 | C | GLN | 39 | 136.142 | 41.029 | 46.074 | 1.00 | 29.22 | H |
| ATOM | 1948 | O | GLN | 39 | 136.781 | 40.160 | 46.672 | 1.00 | 19.00 | H |
| ATOM | 1949 | N | ARG | 40 | 136.548 | 41.560 | 44.928 | 1.00 | 41.18 | H |
| ATOM | 1950 | CA | ARG | 40 | 137.794 | 41.139 | 44.310 | 1.00 | 48.75 | H |
| ATOM | 1951 | CB | ARG | 40 | 137.805 | 41.496 | 42.819 | 1.00 | 47.54 | H |
| ATOM | 1952 | CG | ARG | 40 | 137.203 | 40.422 | 41.923 | 1.00 | 39.67 | H |
| ATOM | 1953 | CD | ARG | 40 | 137.409 | 40.741 | 40.448 | 1.00 | 63.74 | H |
| ATOM | 1954 | NE | ARG | 40 | 138.762 | 40.415 | 39.997 | 1.00 | 66.96 | H |
| ATOM | 1955 | CZ | ARG | 40 | 139.215 | 39.178 | 39.816 | 1.00 | 59.13 | H |
| ATOM | 1956 | NH1 | ARG | 40 | 138.426 | 38.137 | 40.046 | 1.00 | 49.49 | H |
| ATOM | 1957 | NH2 | ARG | 40 | 140.459 | 38.982 | 39.400 | 1.00 | 64.52 | H |
| ATOM | 1958 | C | ARG | 40 | 138.971 | 41.791 | 45.024 | 1.00 | 49.05 | H |
| ATOM | 1959 | O | ARG | 40 | 138.955 | 42.989 | 45.312 | 1.00 | 41.67 | H |
| ATOM | 1960 | N | PRO | 41 | 140.007 | 40.996 | 45.329 | 1.00 | 49.95 | H |
| ATOM | 1961 | CD | PRO | 41 | 140.102 | 39.557 | 45.022 | 1.00 | 60.26 | H |
| ATOM | 1962 | CA | PRO | 41 | 141.200 | 41.485 | 46.013 | 1.00 | 40.75 | H |
| ATOM | 1963 | CB | PRO | 41 | 142.268 | 40.476 | 45.625 | 1.00 | 50.53 | H |
| ATOM | 1964 | CG | PRO | 41 | 141.516 | 39.202 | 45.415 | 1.00 | 62.82 | H |
| ATOM | 1965 | C | PRO | 41 | 141.558 | 42.888 | 45.576 | 1.00 | 38.02 | H |
| ATOM | 1966 | O | PRO | 41 | 141.769 | 43.147 | 44.392 | 1.00 | 47.09 | H |
| ATOM | 1967 | N | GLY | 42 | 141.614 | 43.794 | 46.542 | 1.00 | 36.72 | H |
| ATOM | 1968 | CA | GLY | 42 | 141.952 | 45.170 | 46.241 | 1.00 | 31.35 | H |
| ATOM | 1969 | C | GLY | 42 | 140.726 | 45.981 | 45.900 | 1.00 | 40.05 | H |
| ATOM | 1970 | O | GLY | 42 | 140.468 | 47.014 | 46.514 | 1.00 | 41.40 | H |
| ATOM | 1971 | N | GLN | 43 | 139.975 | 45.502 | 44.913 | 1.00 | 58.75 | H |
| ATOM | 1972 | CA | GLN | 43 | 138.752 | 46.163 | 44.468 | 1.00 | 67.06 | H |
| ATOM | 1973 | CB | GLN | 43 | 138.192 | 45.449 | 43.227 | 1.00 | 64.21 | H |
| ATOM | 1974 | CG | GLN | 43 | 137.035 | 46.178 | 42.540 | 1.00 | 71.56 | H |
| ATOM | 1975 | CD | GLN | 43 | 135.900 | 45.251 | 42.130 | 1.00 | 71.51 | H |
| ATOM | 1976 | OE1 | GLN | 43 | 135.330 | 44.540 | 42.963 | 1.00 | 67.00 | H |
| ATOM | 1977 | NE2 | GLN | 43 | 135.566 | 45.255 | 40.842 | 1.00 | 53.00 | H |
| ATOM | 1978 | C | GLN | 43 | 137.701 | 46.158 | 45.581 | 1.00 | 68.90 | H |

TABLE 4-continued

Co-ordinates of the CD28/5.11A1 crystal structure

| ATOM | 1979 | O | GLN | 43 | 137.782 | 45.366 | 46.521 | 1.00 | 72.87 | H |
|---|---|---|---|---|---|---|---|---|---|---|
| ATOM | 1980 | N | GLY | 44 | 136.723 | 47.055 | 45.471 | 1.00 | 67.47 | H |
| ATOM | 1981 | CA | GLY | 44 | 135.661 | 47.119 | 46.458 | 1.00 | 54.03 | H |
| ATOM | 1982 | C | GLY | 44 | 134.746 | 45.927 | 46.268 | 1.00 | 52.55 | H |
| ATOM | 1983 | O | GLY | 44 | 135.191 | 44.881 | 45.794 | 1.00 | 65.13 | H |
| ATOM | 1984 | N | LEU | 45 | 133.474 | 46.062 | 46.623 | 1.00 | 38.94 | H |
| ATOM | 1985 | CA | LEU | 45 | 132.552 | 44.946 | 46.456 | 1.00 | 50.12 | H |
| ATOM | 1986 | CB | LEU | 45 | 132.197 | 44.339 | 47.819 | 1.00 | 44.25 | H |
| ATOM | 1987 | CG | LEU | 45 | 131.306 | 45.109 | 48.790 | 1.00 | 36.87 | H |
| ATOM | 1988 | CD1 | LEU | 45 | 131.661 | 44.692 | 50.212 | 1.00 | 34.38 | H |
| ATOM | 1989 | CD2 | LEU | 45 | 131.480 | 46.605 | 48.597 | 1.00 | 31.30 | H |
| ATOM | 1990 | C | LEU | 45 | 131.283 | 45.315 | 45.689 | 1.00 | 47.35 | H |
| ATOM | 1991 | O | LEU | 45 | 130.876 | 46.475 | 45.656 | 1.00 | 52.97 | H |
| ATOM | 1992 | N | GLU | 46 | 130.673 | 44.311 | 45.066 | 1.00 | 38.18 | H |
| ATOM | 1993 | CA | GLU | 46 | 129.468 | 44.497 | 44.275 | 1.00 | 32.36 | H |
| ATOM | 1994 | CB | GLU | 46 | 129.779 | 44.312 | 42.787 | 1.00 | 54.58 | H |
| ATOM | 1995 | CG | GLU | 46 | 131.106 | 43.601 | 42.502 | 1.00 | 70.14 | H |
| ATOM | 1996 | CD | GLU | 46 | 131.544 | 43.722 | 41.050 | 1.00 | 59.62 | H |
| ATOM | 1997 | OE1 | GLU | 46 | 132.769 | 43.760 | 40.796 | 1.00 | 60.49 | H |
| ATOM | 1998 | OE2 | GLU | 46 | 130.660 | 43.778 | 40.171 | 1.00 | 62.64 | H |
| ATOM | 1999 | C | GLU | 46 | 128.400 | 43.506 | 44.686 | 1.00 | 33.28 | H |
| ATOM | 2000 | O | GLU | 46 | 128.697 | 42.477 | 45.293 | 1.00 | 22.50 | H |
| ATOM | 2001 | N | TRP | 47 | 127.157 | 43.818 | 44.329 | 1.00 | 30.17 | H |
| ATOM | 2002 | CA | TRP | 47 | 126.010 | 42.982 | 44.661 | 1.00 | 39.51 | H |
| ATOM | 2003 | CB | TRP | 47 | 124.794 | 43.881 | 44.906 | 1.00 | 50.31 | H |
| ATOM | 2004 | CG | TRP | 47 | 123.538 | 43.163 | 45.304 | 1.00 | 46.71 | H |
| ATOM | 2005 | CD2 | TRP | 47 | 122.417 | 42.881 | 44.459 | 1.00 | 46.71 | H |
| ATOM | 2006 | CE2 | TRP | 47 | 121.440 | 42.259 | 45.262 | 1.00 | 40.21 | H |
| ATOM | 2007 | CE3 | TRP | 47 | 122.148 | 43.096 | 43.104 | 1.00 | 44.16 | H |
| ATOM | 2008 | CD1 | TRP | 47 | 123.204 | 42.709 | 46.547 | 1.00 | 44.85 | H |
| ATOM | 2009 | NE1 | TRP | 47 | 121.942 | 42.165 | 46.533 | 1.00 | 44.22 | H |
| ATOM | 2010 | CZ2 | TRP | 47 | 120.205 | 41.852 | 44.750 | 1.00 | 48.68 | H |
| ATOM | 2011 | CZ3 | TRP | 47 | 120.924 | 42.689 | 42.597 | 1.00 | 48.92 | H |
| ATOM | 2012 | CH2 | TRP | 47 | 119.969 | 42.073 | 43.420 | 1.00 | 39.77 | H |
| ATOM | 2013 | C | TRP | 47 | 125.692 | 41.936 | 43.592 | 1.00 | 45.09 | H |
| ATOM | 2014 | O | TRP | 47 | 125.359 | 42.260 | 42.449 | 1.00 | 45.19 | H |
| ATOM | 2015 | N | ILE | 48 | 125.800 | 40.671 | 43.981 | 1.00 | 45.61 | H |
| ATOM | 2016 | CA | ILE | 48 | 125.529 | 39.562 | 43.080 | 1.00 | 37.68 | H |
| ATOM | 2017 | CB | ILE | 48 | 126.185 | 38.266 | 43.601 | 1.00 | 25.87 | H |
| ATOM | 2018 | CG2 | ILE | 48 | 125.479 | 37.039 | 43.036 | 1.00 | 23.09 | H |
| ATOM | 2019 | CG1 | ILE | 48 | 127.657 | 38.249 | 43.202 | 1.00 | 15.27 | H |
| ATOM | 2020 | CD1 | ILE | 48 | 128.449 | 37.133 | 43.847 | 1.00 | 20.12 | H |
| ATOM | 2021 | C | ILE | 48 | 124.028 | 39.356 | 42.936 | 1.00 | 35.05 | H |
| ATOM | 2022 | O | ILE | 48 | 123.461 | 39.591 | 41.870 | 1.00 | 41.96 | H |
| ATOM | 2023 | N | GLY | 49 | 123.388 | 38.918 | 44.013 | 1.00 | 32.61 | H |
| ATOM | 2024 | CA | GLY | 49 | 121.953 | 38.689 | 43.986 | 1.00 | 30.75 | H |
| ATOM | 2025 | C | GLY | 49 | 121.432 | 38.298 | 45.359 | 1.00 | 38.37 | H |
| ATOM | 2026 | O | GLY | 49 | 122.161 | 38.327 | 46.349 | 1.00 | 41.94 | H |
| ATOM | 2027 | N | CYS | 50 | 120.163 | 37.931 | 45.431 | 1.00 | 37.54 | H |
| ATOM | 2028 | CA | CYS | 50 | 119.587 | 37.540 | 46.705 | 1.00 | 38.40 | H |
| ATOM | 2029 | CB | CYS | 50 | 119.095 | 38.774 | 47.462 | 1.00 | 51.77 | H |
| ATOM | 2030 | SG | CYS | 50 | 117.500 | 39.407 | 46.877 | 1.00 | 50.59 | H |
| ATOM | 2031 | C | CYS | 50 | 118.438 | 36.577 | 46.500 | 1.00 | 42.42 | H |
| ATOM | 2032 | O | CYS | 50 | 117.835 | 36.535 | 45.431 | 1.00 | 50.09 | H |
| ATOM | 2033 | N | ILE | 51 | 118.146 | 35.804 | 47.537 | 1.00 | 42.92 | H |
| ATOM | 2034 | CA | ILE | 51 | 117.059 | 34.837 | 47.502 | 1.00 | 37.44 | H |
| ATOM | 2035 | CB | ILE | 51 | 117.596 | 33.380 | 47.377 | 1.00 | 28.69 | H |
| ATOM | 2036 | CG2 | ILE | 51 | 118.648 | 33.111 | 48.440 | 1.00 | 29.15 | H |
| ATOM | 2037 | CG1 | ILE | 51 | 116.448 | 32.382 | 47.521 | 1.00 | 22.13 | H |
| ATOM | 2038 | CD1 | ILE | 51 | 115.840 | 31.963 | 46.201 | 1.00 | 43.28 | H |
| ATOM | 2039 | C | ILE | 51 | 116.277 | 34.989 | 48.800 | 1.00 | 42.00 | H |
| ATOM | 2040 | O | ILE | 51 | 116.861 | 35.219 | 49.868 | 1.00 | 34.19 | H |
| ATOM | 2041 | N | TYR | 52 | 114.957 | 34.886 | 48.706 | 1.00 | 38.73 | H |
| ATOM | 2042 | CA | TYR | 52 | 114.124 | 35.013 | 49.888 | 1.00 | 34.95 | H |
| ATOM | 2043 | CB | TYR | 52 | 112.954 | 35.960 | 49.643 | 1.00 | 26.98 | H |
| ATOM | 2044 | CG | TYR | 52 | 112.041 | 36.049 | 50.840 | 1.00 | 28.39 | H |
| ATOM | 2045 | CD1 | TYR | 52 | 112.571 | 36.155 | 52.132 | 1.00 | 31.39 | H |
| ATOM | 2046 | CE1 | TYR | 52 | 111.752 | 36.193 | 53.244 | 1.00 | 43.44 | H |
| ATOM | 2047 | CD2 | TYR | 52 | 110.660 | 35.986 | 50.695 | 1.00 | 19.91 | H |
| ATOM | 2048 | CE2 | TYR | 52 | 109.821 | 36.022 | 51.800 | 1.00 | 43.98 | H |
| ATOM | 2049 | CZ | TYR | 52 | 110.376 | 36.124 | 53.075 | 1.00 | 56.97 | H |
| ATOM | 2050 | OH | TYR | 52 | 109.556 | 36.153 | 54.178 | 1.00 | 67.54 | H |
| ATOM | 2051 | C | TYR | 52 | 113.578 | 33.674 | 50.350 | 1.00 | 39.53 | H |
| ATOM | 2052 | O | TYR | 52 | 112.611 | 33.161 | 49.791 | 1.00 | 45.44 | H |
| ATOM | 2053 | N | PRO | 53 | 114.191 | 33.092 | 51.386 | 1.00 | 46.32 | H |
| ATOM | 2054 | CD | PRO | 53 | 115.347 | 33.610 | 52.137 | 1.00 | 58.13 | H |
| ATOM | 2055 | CA | PRO | 53 | 113.728 | 31.803 | 51.900 | 1.00 | 36.81 | H |

TABLE 4-continued

Co-ordinates of the CD28/5.11A1 crystal structure

| ATOM | 2056 | CB | PRO | 53 | 114.599 | 31.566 | 53.126 | 1.00 | 38.59 | H |
|------|------|-----|-----|----|---------|--------|--------|------|-------|---|
| ATOM | 2057 | CG | PRO | 53 | 115.817 | 32.404 | 52.894 | 1.00 | 59.97 | H |
| ATOM | 2058 | C | PRO | 53 | 112.279 | 31.971 | 52.275 | 1.00 | 35.25 | H |
| ATOM | 2059 | O | PRO | 53 | 111.926 | 32.927 | 52.959 | 1.00 | 37.50 | H |
| ATOM | 2060 | N | GLY | 54 | 111.441 | 31.055 | 51.815 | 1.00 | 43.54 | H |
| ATOM | 2061 | CA | GLY | 54 | 110.027 | 31.142 | 52.120 | 1.00 | 53.47 | H |
| ATOM | 2062 | C | GLY | 54 | 109.200 | 31.023 | 50.860 | 1.00 | 58.70 | H |
| ATOM | 2063 | O | GLY | 54 | 108.726 | 29.936 | 50.530 | 1.00 | 74.82 | H |
| ATOM | 2064 | N | ASN | 55 | 109.021 | 32.132 | 50.150 | 1.00 | 48.62 | H |
| ATOM | 2065 | CA | ASN | 55 | 108.248 | 32.116 | 48.917 | 1.00 | 45.89 | H |
| ATOM | 2066 | CB | ASN | 55 | 107.602 | 33.482 | 48.675 | 1.00 | 46.66 | H |
| ATOM | 2067 | CG | ASN | 55 | 108.344 | 34.312 | 47.658 | 1.00 | 46.59 | H |
| ATOM | 2068 | OD1 | ASN | 55 | 109.183 | 35.138 | 48.009 | 1.00 | 50.93 | H |
| ATOM | 2069 | ND2 | ASN | 55 | 108.027 | 34.107 | 46.384 | 1.00 | 65.32 | H |
| ATOM | 2070 | C | ASN | 55 | 109.177 | 31.740 | 47.777 | 1.00 | 59.93 | H |
| ATOM | 2071 | O | ASN | 55 | 108.738 | 31.536 | 46.645 | 1.00 | 70.19 | H |
| ATOM | 2072 | N | VAL | 56 | 110.466 | 31.644 | 48.110 | 1.00 | 68.48 | H |
| ATOM | 2073 | CA | VAL | 56 | 111.541 | 31.269 | 47.182 | 1.00 | 68.32 | H |
| ATOM | 2074 | CB | VAL | 56 | 111.181 | 29.960 | 46.416 | 1.00 | 73.69 | H |
| ATOM | 2075 | CG1 | VAL | 56 | 110.739 | 30.271 | 44.989 | 1.00 | 75.39 | H |
| ATOM | 2076 | CG2 | VAL | 56 | 112.377 | 29.021 | 46.415 | 1.00 | 57.36 | H |
| ATOM | 2077 | C | VAL | 56 | 111.958 | 32.352 | 46.182 | 1.00 | 64.26 | H |
| ATOM | 2078 | O | VAL | 56 | 112.859 | 32.142 | 45.366 | 1.00 | 50.69 | H |
| ATOM | 2079 | N | ASN | 57 | 111.307 | 33.511 | 46.258 | 1.00 | 70.60 | H |
| ATOM | 2080 | CA | ASN | 57 | 111.610 | 34.622 | 45.366 | 1.00 | 62.78 | H |
| ATOM | 2081 | CB | ASN | 57 | 110.996 | 35.913 | 45.898 | 1.00 | 76.22 | H |
| ATOM | 2082 | CG | ASN | 57 | 109.868 | 36.422 | 45.032 | 1.00 | 82.20 | H |
| ATOM | 2083 | OD1 | ASN | 57 | 109.018 | 37.191 | 45.486 | 1.00 | 72.33 | H |
| ATOM | 2084 | ND2 | ASN | 57 | 109.849 | 35.989 | 43.772 | 1.00 | 72.74 | H |
| ATOM | 2085 | C | ASN | 57 | 113.110 | 34.795 | 45.242 | 1.00 | 63.32 | H |
| ATOM | 2086 | O | ASN | 57 | 113.857 | 34.515 | 46.181 | 1.00 | 68.16 | H |
| ATOM | 2087 | N | THR | 58 | 113.553 | 35.267 | 44.084 | 1.00 | 54.53 | H |
| ATOM | 2088 | CA | THR | 58 | 114.974 | 35.465 | 43.859 | 1.00 | 52.32 | H |
| ATOM | 2089 | CB | THR | 58 | 115.597 | 34.191 | 43.279 | 1.00 | 48.24 | H |
| ATOM | 2090 | OG1 | THR | 58 | 116.806 | 34.523 | 42.594 | 1.00 | 45.77 | H |
| ATOM | 2091 | CG2 | THR | 58 | 114.628 | 33.516 | 42.314 | 1.00 | 53.99 | H |
| ATOM | 2092 | C | THR | 58 | 115.243 | 36.641 | 42.921 | 1.00 | 52.31 | H |
| ATOM | 2093 | O | THR | 58 | 114.436 | 36.935 | 42.039 | 1.00 | 59.83 | H |
| ATOM | 2094 | N | ASN | 59 | 116.375 | 37.313 | 43.117 | 1.00 | 40.59 | H |
| ATOM | 2095 | CA | ASN | 59 | 116.730 | 38.462 | 42.290 | 1.00 | 38.18 | H |
| ATOM | 2096 | CB | ASN | 59 | 116.330 | 39.758 | 42.998 | 1.00 | 53.76 | H |
| ATOM | 2097 | CG | ASN | 59 | 114.928 | 40.217 | 42.632 | 1.00 | 53.44 | H |
| ATOM | 2098 | OD1 | ASN | 59 | 114.712 | 40.809 | 41.572 | 1.00 | 58.59 | H |
| ATOM | 2099 | ND2 | ASN | 59 | 113.970 | 39.951 | 43.512 | 1.00 | 44.63 | H |
| ATOM | 2100 | C | ASN | 59 | 118.217 | 38.505 | 41.970 | 1.00 | 30.27 | H |
| ATOM | 2101 | O | ASN | 59 | 119.049 | 38.423 | 42.873 | 1.00 | 35.55 | H |
| ATOM | 2102 | N | TYR | 60 | 118.544 | 38.661 | 40.687 | 1.00 | 19.72 | H |
| ATOM | 2103 | CA | TYR | 60 | 119.935 | 38.710 | 40.243 | 1.00 | 29.52 | H |
| ATOM | 2104 | CB | TYR | 60 | 120.213 | 37.596 | 39.227 | 1.00 | 27.47 | H |
| ATOM | 2105 | CG | TYR | 60 | 119.809 | 36.215 | 39.675 | 1.00 | 25.29 | H |
| ATOM | 2106 | CD1 | TYR | 60 | 120.762 | 35.233 | 39.929 | 1.00 | 18.79 | H |
| ATOM | 2107 | CE1 | TYR | 60 | 120.382 | 33.951 | 40.325 | 1.00 | 40.31 | H |
| ATOM | 2108 | CD2 | TYR | 60 | 118.468 | 35.883 | 39.825 | 1.00 | 40.64 | H |
| ATOM | 2109 | CE2 | TYR | 60 | 118.077 | 34.611 | 40.217 | 1.00 | 47.25 | H |
| ATOM | 2110 | CZ | TYR | 60 | 119.033 | 33.647 | 40.469 | 1.00 | 51.22 | H |
| ATOM | 2111 | OH | TYR | 60 | 118.621 | 32.391 | 40.883 | 1.00 | 56.18 | H |
| ATOM | 2112 | C | TYR | 60 | 120.367 | 40.034 | 39.618 | 1.00 | 25.63 | H |
| ATOM | 2113 | O | TYR | 60 | 119.574 | 40.746 | 39.008 | 1.00 | 17.78 | H |
| ATOM | 2114 | N | ASN | 61 | 121.645 | 40.354 | 39.789 | 1.00 | 31.77 | H |
| ATOM | 2115 | CA | ASN | 61 | 122.224 | 41.551 | 39.213 | 1.00 | 30.42 | H |
| ATOM | 2116 | CB | ASN | 61 | 123.542 | 41.891 | 39.907 | 1.00 | 26.96 | H |
| ATOM | 2117 | CG | ASN | 61 | 124.176 | 43.155 | 39.367 | 1.00 | 28.98 | H |
| ATOM | 2118 | OD1 | ASN | 61 | 124.721 | 43.964 | 40.120 | 1.00 | 39.03 | H |
| ATOM | 2119 | ND2 | ASN | 61 | 124.105 | 43.335 | 38.052 | 1.00 | 39.88 | H |
| ATOM | 2120 | C | ASN | 61 | 122.480 | 41.102 | 37.787 | 1.00 | 42.86 | H |
| ATOM | 2121 | O | ASN | 61 | 123.062 | 40.041 | 37.571 | 1.00 | 56.00 | H |
| ATOM | 2122 | N | GLU | 62 | 122.045 | 41.889 | 36.812 | 1.00 | 46.51 | H |
| ATOM | 2123 | CA | GLU | 62 | 122.224 | 41.498 | 35.424 | 1.00 | 52.07 | H |
| ATOM | 2124 | CB | GLU | 62 | 121.511 | 42.490 | 34.504 | 1.00 | 57.39 | H |
| ATOM | 2125 | CG | GLU | 62 | 120.513 | 41.839 | 33.531 | 1.00 | 76.62 | H |
| ATOM | 2126 | CD | GLU | 62 | 119.280 | 41.242 | 34.214 | 1.00 | 81.14 | H |
| ATOM | 2127 | OE1 | GLU | 62 | 119.442 | 40.484 | 35.197 | 1.00 | 79.43 | H |
| ATOM | 2128 | OE2 | GLU | 62 | 118.148 | 41.528 | 33.759 | 1.00 | 70.90 | H |
| ATOM | 2129 | C | GLU | 62 | 123.678 | 41.327 | 35.000 | 1.00 | 53.65 | H |
| ATOM | 2130 | O | GLU | 62 | 123.953 | 40.991 | 33.847 | 1.00 | 75.05 | H |
| ATOM | 2131 | N | LYS | 63 | 124.610 | 41.543 | 35.922 | 1.00 | 36.05 | H |
| ATOM | 2132 | CA | LYS | 63 | 126.025 | 41.379 | 35.604 | 1.00 | 35.02 | H |

TABLE 4-continued

Co-ordinates of the CD28/5.11A1 crystal structure

| ATOM | 2133 | CB | LYS | 63 | 126.862 | 42.421 | 36.353 | 1.00 | 26.34 | H |
|---|---|---|---|---|---|---|---|---|---|---|
| ATOM | 2134 | CG | LYS | 63 | 127.215 | 43.653 | 35.532 | 1.00 | 49.15 | H |
| ATOM | 2135 | CD | LYS | 63 | 126.773 | 44.948 | 36.217 | 1.00 | 45.62 | H |
| ATOM | 2136 | CE | LYS | 63 | 127.938 | 45.619 | 36.920 | 1.00 | 40.94 | H |
| ATOM | 2137 | NZ | LYS | 63 | 128.652 | 44.625 | 37.772 | 1.00 | 39.59 | H |
| ATOM | 2138 | C | LYS | 63 | 126.506 | 39.969 | 35.961 | 1.00 | 40.58 | H |
| ATOM | 2139 | O | LYS | 63 | 127.618 | 39.576 | 35.611 | 1.00 | 45.93 | H |
| ATOM | 2140 | N | PHE | 64 | 125.657 | 39.214 | 36.658 | 1.00 | 47.98 | H |
| ATOM | 2141 | CA | PHE | 64 | 125.975 | 37.849 | 37.073 | 1.00 | 42.86 | H |
| ATOM | 2142 | CB | PHE | 64 | 126.263 | 37.789 | 38.579 | 1.00 | 42.85 | H |
| ATOM | 2143 | CG | PHE | 64 | 127.177 | 38.872 | 39.068 | 1.00 | 44.03 | H |
| ATOM | 2144 | CD1 | PHE | 64 | 128.538 | 38.831 | 38.791 | 1.00 | 50.59 | H |
| ATOM | 2145 | CD2 | PHE | 64 | 126.680 | 39.929 | 39.817 | 1.00 | 38.08 | H |
| ATOM | 2146 | CE1 | PHE | 64 | 129.388 | 39.830 | 39.255 | 1.00 | 45.27 | H |
| ATOM | 2147 | CE2 | PHE | 64 | 127.524 | 40.933 | 40.284 | 1.00 | 43.09 | H |
| ATOM | 2148 | CZ | PHE | 64 | 128.877 | 40.883 | 40.004 | 1.00 | 31.11 | H |
| ATOM | 2149 | C | PHE | 64 | 124.823 | 36.908 | 36.768 | 1.00 | 43.11 | H |
| ATOM | 2150 | O | PHE | 64 | 124.560 | 35.988 | 37.535 | 1.00 | 47.33 | H |
| ATOM | 2151 | N | LYS | 65 | 124.148 | 37.128 | 35.644 | 1.00 | 55.21 | H |
| ATOM | 2152 | CA | LYS | 65 | 123.005 | 36.302 | 35.259 | 1.00 | 59.07 | H |
| ATOM | 2153 | CB | LYS | 65 | 122.383 | 36.806 | 33.949 | 1.00 | 45.97 | H |
| ATOM | 2154 | CG | LYS | 65 | 123.146 | 37.914 | 33.251 | 1.00 | 49.55 | H |
| ATOM | 2155 | CD | LYS | 65 | 124.165 | 37.363 | 32.270 | 1.00 | 46.70 | H |
| ATOM | 2156 | CE | LYS | 65 | 125.116 | 38.461 | 31.811 | 1.00 | 50.30 | H |
| ATOM | 2157 | NZ | LYS | 65 | 125.548 | 38.271 | 30.398 | 1.00 | 58.93 | H |
| ATOM | 2158 | C | LYS | 65 | 123.279 | 34.802 | 35.118 | 1.00 | 67.16 | H |
| ATOM | 2159 | O | LYS | 65 | 122.598 | 33.984 | 35.741 | 1.00 | 70.12 | H |
| ATOM | 2160 | N | ASP | 66 | 124.267 | 34.440 | 34.304 | 1.00 | 69.41 | H |
| ATOM | 2161 | CA | ASP | 66 | 124.579 | 33.031 | 34.073 | 1.00 | 66.83 | H |
| ATOM | 2162 | CB | ASP | 66 | 125.508 | 32.898 | 32.872 | 1.00 | 66.07 | H |
| ATOM | 2163 | CG | ASP | 66 | 124.747 | 32.712 | 31.580 | 1.00 | 66.45 | H |
| ATOM | 2164 | OD1 | ASP | 66 | 124.869 | 31.628 | 30.973 | 1.00 | 66.35 | H |
| ATOM | 2165 | OD2 | ASP | 66 | 124.023 | 33.649 | 31.177 | 1.00 | 50.12 | H |
| ATOM | 2166 | C | ASP | 66 | 125.168 | 32.265 | 35.251 | 1.00 | 70.25 | H |
| ATOM | 2167 | O | ASP | 66 | 124.514 | 31.365 | 35.792 | 1.00 | 72.29 | H |
| ATOM | 2168 | N | LYS | 67 | 126.399 | 32.605 | 35.637 | 1.00 | 62.38 | H |
| ATOM | 2169 | CA | LYS | 67 | 127.071 | 31.934 | 36.750 | 1.00 | 49.02 | H |
| ATOM | 2170 | CB | LYS | 67 | 128.374 | 32.653 | 37.115 | 1.00 | 25.39 | H |
| ATOM | 2171 | CG | LYS | 67 | 128.541 | 34.034 | 36.489 | 1.00 | 48.63 | H |
| ATOM | 2172 | CD | LYS | 67 | 129.958 | 34.579 | 36.675 | 1.00 | 21.16 | H |
| ATOM | 2173 | CE | LYS | 67 | 130.912 | 34.018 | 35.624 | 1.00 | 43.17 | H |
| ATOM | 2174 | NZ | LYS | 67 | 132.251 | 33.618 | 36.179 | 1.00 | 34.20 | H |
| ATOM | 2175 | C | LYS | 67 | 126.178 | 31.887 | 37.977 | 1.00 | 59.48 | H |
| ATOM | 2176 | O | LYS | 67 | 125.721 | 30.816 | 38.390 | 1.00 | 51.12 | H |
| ATOM | 2177 | N | ALA | 68 | 125.929 | 33.066 | 38.545 | 1.00 | 67.14 | H |
| ATOM | 2178 | CA | ALA | 68 | 125.104 | 33.220 | 39.741 | 1.00 | 54.74 | H |
| ATOM | 2179 | CB | ALA | 68 | 125.017 | 34.688 | 40.108 | 1.00 | 54.84 | H |
| ATOM | 2180 | C | ALA | 68 | 123.701 | 32.631 | 39.631 | 1.00 | 49.40 | H |
| ATOM | 2181 | O | ALA | 68 | 122.851 | 33.136 | 38.896 | 1.00 | 58.08 | H |
| ATOM | 2182 | N | THR | 69 | 123.473 | 31.564 | 40.387 | 1.00 | 32.05 | H |
| ATOM | 2183 | CA | THR | 69 | 122.192 | 30.874 | 40.429 | 1.00 | 37.56 | H |
| ATOM | 2184 | CB | THR | 69 | 122.284 | 29.541 | 39.655 | 1.00 | 35.94 | H |
| ATOM | 2185 | OG1 | THR | 69 | 122.392 | 29.821 | 38.253 | 1.00 | 40.10 | H |
| ATOM | 2186 | CG2 | THR | 69 | 121.065 | 28.676 | 39.908 | 1.00 | 26.92 | H |
| ATOM | 2187 | C | THR | 69 | 121.915 | 30.626 | 41.914 | 1.00 | 43.54 | H |
| ATOM | 2188 | O | THR | 69 | 122.595 | 29.823 | 42.550 | 1.00 | 40.52 | H |
| ATOM | 2189 | N | LEU | 70 | 120.924 | 31.319 | 42.469 | 1.00 | 45.97 | H |
| ATOM | 2190 | CA | LEU | 70 | 120.622 | 31.189 | 43.893 | 1.00 | 46.62 | H |
| ATOM | 2191 | CB | LEU | 70 | 120.166 | 32.536 | 44.445 | 1.00 | 47.28 | H |
| ATOM | 2192 | CG | LEU | 70 | 121.305 | 33.331 | 45.091 | 1.00 | 55.81 | H |
| ATOM | 2193 | CD1 | LEU | 70 | 121.133 | 34.805 | 44.767 | 1.00 | 43.73 | H |
| ATOM | 2194 | CD2 | LEU | 70 | 121.322 | 33.094 | 46.611 | 1.00 | 43.94 | H |
| ATOM | 2195 | C | LEU | 70 | 119.636 | 30.107 | 44.312 | 1.00 | 43.94 | H |
| ATOM | 2196 | O | LEU | 70 | 118.496 | 30.070 | 43.849 | 1.00 | 42.32 | H |
| ATOM | 2197 | N | ILE | 71 | 120.103 | 29.247 | 45.218 | 1.00 | 44.21 | H |
| ATOM | 2198 | CA | ILE | 71 | 119.333 | 28.125 | 45.755 | 1.00 | 49.89 | H |
| ATOM | 2199 | CB | ILE | 71 | 120.026 | 26.770 | 45.430 | 1.00 | 51.60 | H |
| ATOM | 2200 | CG2 | ILE | 71 | 119.259 | 25.616 | 46.072 | 1.00 | 29.06 | H |
| ATOM | 2201 | CG1 | ILE | 71 | 120.107 | 26.573 | 43.911 | 1.00 | 54.43 | H |
| ATOM | 2202 | CD1 | ILE | 71 | 121.184 | 27.402 | 43.222 | 1.00 | 43.28 | H |
| ATOM | 2203 | C | ILE | 71 | 119.203 | 28.255 | 47.278 | 1.00 | 52.79 | H |
| ATOM | 2204 | O | ILE | 71 | 120.103 | 28.779 | 47.939 | 1.00 | 62.18 | H |
| ATOM | 2205 | N | VAL | 72 | 118.093 | 27.768 | 47.830 | 1.00 | 50.92 | H |
| ATOM | 2206 | CA | VAL | 72 | 117.837 | 27.843 | 49.269 | 1.00 | 52.77 | H |
| ATOM | 2207 | CB | VAL | 72 | 116.551 | 28.677 | 49.549 | 1.00 | 47.96 | H |
| ATOM | 2208 | CG1 | VAL | 72 | 115.313 | 27.828 | 49.317 | 1.00 | 44.08 | H |
| ATOM | 2209 | CG2 | VAL | 72 | 116.569 | 29.224 | 50.967 | 1.00 | 43.63 | H |

TABLE 4-continued

Co-ordinates of the CD28/5.11A1 crystal structure

| ATOM | 2210 | C   | VAL | 72 | 117.687 | 26.437 | 49.861 | 1.00 | 56.26 | H |
|------|------|-----|-----|----|---------|--------|--------|------|-------|---|
| ATOM | 2211 | O   | VAL | 72 | 117.627 | 25.457 | 49.123 | 1.00 | 65.48 | H |
| ATOM | 2212 | N   | ASP | 73 | 117.638 | 26.344 | 51.191 | 1.00 | 56.09 | H |
| ATOM | 2213 | CA  | ASP | 73 | 117.492 | 25.064 | 51.891 | 1.00 | 50.35 | H |
| ATOM | 2214 | CB  | ASP | 73 | 118.848 | 24.365 | 51.995 | 1.00 | 53.65 | H |
| ATOM | 2215 | CG  | ASP | 73 | 118.721 | 22.907 | 52.384 | 1.00 | 57.99 | H |
| ATOM | 2216 | OD1 | ASP | 73 | 118.119 | 22.616 | 53.443 | 1.00 | 57.92 | H |
| ATOM | 2217 | OD2 | ASP | 73 | 119.229 | 22.055 | 51.625 | 1.00 | 61.79 | H |
| ATOM | 2218 | C   | ASP | 73 | 116.932 | 25.313 | 53.290 | 1.00 | 50.51 | H |
| ATOM | 2219 | O   | ASP | 73 | 117.664 | 25.288 | 54.280 | 1.00 | 43.10 | H |
| ATOM | 2220 | N   | THR | 74 | 115.624 | 25.535 | 53.352 | 1.00 | 56.54 | H |
| ATOM | 2221 | CA  | THR | 74 | 114.913 | 25.836 | 54.593 | 1.00 | 66.24 | H |
| ATOM | 2222 | CB  | THR | 74 | 113.421 | 26.020 | 54.296 | 1.00 | 71.27 | H |
| ATOM | 2223 | OG1 | THR | 74 | 113.183 | 25.793 | 52.901 | 1.00 | 71.81 | H |
| ATOM | 2224 | CG2 | THR | 74 | 112.979 | 27.430 | 54.659 | 1.00 | 81.34 | H |
| ATOM | 2225 | C   | THR | 74 | 115.054 | 24.876 | 55.785 | 1.00 | 71.66 | H |
| ATOM | 2226 | O   | THR | 74 | 114.662 | 25.220 | 56.902 | 1.00 | 67.59 | H |
| ATOM | 2227 | N   | SER | 75 | 115.610 | 23.689 | 55.559 | 1.00 | 75.40 | H |
| ATOM | 2228 | CA  | SER | 75 | 115.775 | 22.712 | 56.634 | 1.00 | 69.25 | H |
| ATOM | 2229 | CB  | SER | 75 | 115.833 | 21.292 | 56.063 | 1.00 | 76.48 | H |
| ATOM | 2230 | OG  | SER | 75 | 116.615 | 20.445 | 56.891 | 1.00 | 75.33 | H |
| ATOM | 2231 | C   | SER | 75 | 117.024 | 22.961 | 57.474 | 1.00 | 60.40 | H |
| ATOM | 2232 | O   | SER | 75 | 116.949 | 23.066 | 58.703 | 1.00 | 51.38 | H |
| ATOM | 2233 | N   | SER | 76 | 118.171 | 23.040 | 56.807 | 1.00 | 45.77 | H |
| ATOM | 2234 | CA  | SER | 76 | 119.435 | 23.282 | 57.498 | 1.00 | 44.97 | H |
| ATOM | 2235 | CB  | SER | 76 | 120.585 | 22.601 | 56.749 | 1.00 | 51.28 | H |
| ATOM | 2236 | OG  | SER | 76 | 120.106 | 21.807 | 55.676 | 1.00 | 43.07 | H |
| ATOM | 2237 | C   | SER | 76 | 119.691 | 24.781 | 57.589 | 1.00 | 34.83 | H |
| ATOM | 2238 | O   | SER | 76 | 120.755 | 25.221 | 58.008 | 1.00 | 28.11 | H |
| ATOM | 2239 | N   | ASN | 77 | 118.697 | 25.563 | 57.194 | 1.00 | 46.96 | H |
| ATOM | 2240 | CA  | ASN | 77 | 118.826 | 27.009 | 57.222 | 1.00 | 38.99 | H |
| ATOM | 2241 | CB  | ASN | 77 | 118.847 | 27.513 | 58.665 | 1.00 | 41.25 | H |
| ATOM | 2242 | CG  | ASN | 77 | 117.459 | 27.785 | 59.206 | 1.00 | 39.52 | H |
| ATOM | 2243 | OD1 | ASN | 77 | 116.470 | 27.731 | 58.468 | 1.00 | 40.29 | H |
| ATOM | 2244 | ND2 | ASN | 77 | 117.377 | 28.082 | 60.496 | 1.00 | 23.39 | H |
| ATOM | 2245 | C   | ASN | 77 | 120.111 | 27.395 | 56.515 | 1.00 | 34.49 | H |
| ATOM | 2246 | O   | ASN | 77 | 120.971 | 28.067 | 57.077 | 1.00 | 45.69 | H |
| ATOM | 2247 | N   | THR | 78 | 120.240 | 26.944 | 55.275 | 1.00 | 39.07 | H |
| ATOM | 2248 | CA  | THR | 78 | 121.417 | 27.244 | 54.481 | 1.00 | 43.99 | H |
| ATOM | 2249 | CB  | THR | 78 | 122.340 | 26.001 | 54.336 | 1.00 | 47.54 | H |
| ATOM | 2250 | OG1 | THR | 78 | 121.955 | 25.239 | 53.189 | 1.00 | 23.72 | H |
| ATOM | 2251 | CG2 | THR | 78 | 122.244 | 25.122 | 55.568 | 1.00 | 19.39 | H |
| ATOM | 2252 | C   | THR | 78 | 121.030 | 27.761 | 53.100 | 1.00 | 35.58 | H |
| ATOM | 2253 | O   | THR | 78 | 120.107 | 27.255 | 52.465 | 1.00 | 41.21 | H |
| ATOM | 2254 | N   | ALA | 79 | 121.738 | 28.791 | 52.658 | 1.00 | 32.09 | H |
| ATOM | 2255 | CA  | ALA | 79 | 121.498 | 29.399 | 51.361 | 1.00 | 45.71 | H |
| ATOM | 2256 | CB  | ALA | 79 | 121.265 | 30.903 | 51.520 | 1.00 | 20.04 | H |
| ATOM | 2257 | C   | ALA | 79 | 122.734 | 29.148 | 50.509 | 1.00 | 54.97 | H |
| ATOM | 2258 | O   | ALA | 79 | 123.854 | 29.447 | 50.927 | 1.00 | 71.91 | H |
| ATOM | 2259 | N   | TYR | 80 | 122.550 | 28.589 | 49.321 | 1.00 | 37.02 | H |
| ATOM | 2260 | CA  | TYR | 80 | 123.697 | 28.329 | 48.480 | 1.00 | 32.51 | H |
| ATOM | 2261 | CB  | TYR | 80 | 123.635 | 26.921 | 47.920 | 1.00 | 27.41 | H |
| ATOM | 2262 | CG  | TYR | 80 | 123.465 | 25.846 | 48.950 | 1.00 | 28.36 | H |
| ATOM | 2263 | CD1 | TYR | 80 | 124.539 | 25.049 | 49.332 | 1.00 | 30.12 | H |
| ATOM | 2264 | CE1 | TYR | 80 | 124.371 | 24.000 | 50.232 | 1.00 | 47.45 | H |
| ATOM | 2265 | CD2 | TYR | 80 | 122.212 | 25.575 | 49.495 | 1.00 | 29.76 | H |
| ATOM | 2266 | CE2 | TYR | 80 | 122.028 | 24.529 | 50.394 | 1.00 | 40.26 | H |
| ATOM | 2267 | CZ  | TYR | 80 | 123.111 | 23.742 | 50.759 | 1.00 | 45.55 | H |
| ATOM | 2268 | OH  | TYR | 80 | 122.933 | 22.695 | 51.643 | 1.00 | 45.67 | H |
| ATOM | 2269 | C   | TYR | 80 | 123.819 | 29.307 | 47.327 | 1.00 | 47.49 | H |
| ATOM | 2270 | O   | TYR | 80 | 122.870 | 30.010 | 46.974 | 1.00 | 54.32 | H |
| ATOM | 2271 | N   | MET | 81 | 125.012 | 29.328 | 46.744 | 1.00 | 58.24 | H |
| ATOM | 2272 | CA  | MET | 81 | 125.340 | 30.175 | 45.609 | 1.00 | 51.28 | H |
| ATOM | 2273 | CB  | MET | 81 | 126.117 | 31.401 | 46.073 | 1.00 | 47.13 | H |
| ATOM | 2274 | CG  | MET | 81 | 127.250 | 31.794 | 45.151 | 1.00 | 49.47 | H |
| ATOM | 2275 | SD  | MET | 81 | 126.890 | 33.310 | 44.268 | 1.00 | 52.80 | H |
| ATOM | 2276 | CE  | MET | 81 | 127.508 | 34.508 | 45.421 | 1.00 | 52.92 | H |
| ATOM | 2277 | C   | MET | 81 | 126.220 | 29.327 | 44.699 | 1.00 | 51.47 | H |
| ATOM | 2278 | O   | MET | 81 | 127.342 | 28.976 | 45.065 | 1.00 | 48.72 | H |
| ATOM | 2279 | N   | GLN | 82 | 125.707 | 28.981 | 43.525 | 1.00 | 46.87 | H |
| ATOM | 2280 | CA  | GLN | 82 | 126.476 | 28.175 | 42.595 | 1.00 | 45.38 | H |
| ATOM | 2281 | CB  | GLN | 82 | 125.589 | 27.113 | 41.943 | 1.00 | 71.53 | H |
| ATOM | 2282 | CG  | GLN | 82 | 125.978 | 26.739 | 40.511 | 1.00 | 89.74 | H |
| ATOM | 2283 | CD  | GLN | 82 | 127.278 | 25.955 | 40.433 | 1.00 | 96.73 | H |
| ATOM | 2284 | OE1 | GLN | 82 | 127.925 | 25.699 | 41.448 | 1.00 | 98.73 | H |
| ATOM | 2285 | NE2 | GLN | 82 | 127.665 | 25.572 | 39.220 | 1.00 | 94.58 | H |
| ATOM | 2286 | C   | GLN | 82 | 127.075 | 29.065 | 41.530 | 1.00 | 44.59 | H |

TABLE 4-continued

Co-ordinates of the CD28/5.11A1 crystal structure

| ATOM | 2287 | O | GLN | 82 | 126.366 | 29.787 | 40.833 | 1.00 | 42.20 | H |
|---|---|---|---|---|---|---|---|---|---|---|
| ATOM | 2288 | N | LEU | 83 | 128.394 | 29.014 | 41.422 | 1.00 | 49.17 | H |
| ATOM | 2289 | CA | LEU | 83 | 129.114 | 29.797 | 40.434 | 1.00 | 46.27 | H |
| ATOM | 2290 | CB | LEU | 83 | 130.369 | 30.398 | 41.067 | 1.00 | 32.33 | H |
| ATOM | 2291 | CG | LEU | 83 | 130.033 | 31.416 | 42.160 | 1.00 | 31.17 | H |
| ATOM | 2292 | CD1 | LEU | 83 | 131.119 | 31.455 | 43.252 | 1.00 | 6.90 | H |
| ATOM | 2293 | CD2 | LEU | 83 | 129.865 | 32.766 | 41.496 | 1.00 | 18.19 | H |
| ATOM | 2294 | C | LEU | 83 | 129.471 | 28.845 | 39.298 | 1.00 | 45.11 | H |
| ATOM | 2295 | O | LEU | 83 | 130.201 | 27.870 | 39.496 | 1.00 | 36.84 | H |
| ATOM | 2296 | N | SER | 84 | 128.925 | 29.118 | 38.117 | 1.00 | 44.08 | H |
| ATOM | 2297 | CA | SER | 84 | 129.160 | 28.280 | 36.948 | 1.00 | 46.97 | H |
| ATOM | 2298 | CB | SER | 84 | 127.829 | 27.869 | 36.323 | 1.00 | 54.37 | H |
| ATOM | 2299 | OG | SER | 84 | 127.604 | 28.576 | 35.118 | 1.00 | 64.19 | H |
| ATOM | 2300 | C | SER | 84 | 130.037 | 28.942 | 35.896 | 1.00 | 49.55 | H |
| ATOM | 2301 | O | SER | 84 | 129.905 | 30.137 | 35.617 | 1.00 | 47.92 | H |
| ATOM | 2302 | N | ARG | 85 | 130.925 | 28.146 | 35.306 | 1.00 | 48.23 | H |
| ATOM | 2303 | CA | ARG | 85 | 131.842 | 28.637 | 34.294 | 1.00 | 41.86 | H |
| ATOM | 2304 | CB | ARG | 85 | 131.057 | 29.141 | 33.082 | 1.00 | 46.21 | H |
| ATOM | 2305 | CG | ARG | 85 | 130.474 | 28.012 | 32.236 | 1.00 | 41.59 | H |
| ATOM | 2306 | CD | ARG | 85 | 129.125 | 28.393 | 31.630 | 1.00 | 68.47 | H |
| ATOM | 2307 | NE | ARG | 85 | 129.174 | 28.406 | 30.170 | 1.00 | 68.50 | H |
| ATOM | 2308 | CZ | ARG | 85 | 128.142 | 28.126 | 29.381 | 1.00 | 60.66 | H |
| ATOM | 2309 | NH1 | ARG | 85 | 126.962 | 27.808 | 29.906 | 1.00 | 56.39 | H |
| ATOM | 2310 | NH2 | ARG | 85 | 128.293 | 28.166 | 28.065 | 1.00 | 55.47 | H |
| ATOM | 2311 | C | ARG | 85 | 132.670 | 29.752 | 34.912 | 1.00 | 40.27 | H |
| ATOM | 2312 | O | ARG | 85 | 132.430 | 30.939 | 34.669 | 1.00 | 37.17 | H |
| ATOM | 2313 | N | MET | 86 | 133.645 | 29.350 | 35.722 | 1.00 | 35.41 | H |
| ATOM | 2314 | CA | MET | 86 | 134.518 | 30.288 | 36.412 | 1.00 | 32.72 | H |
| ATOM | 2315 | CB | MET | 86 | 134.974 | 29.684 | 37.733 | 1.00 | 38.34 | H |
| ATOM | 2316 | CG | MET | 86 | 134.091 | 28.551 | 38.215 | 1.00 | 45.32 | H |
| ATOM | 2317 | SD | MET | 86 | 133.310 | 28.856 | 39.804 | 1.00 | 63.97 | H |
| ATOM | 2318 | CE | MET | 86 | 133.680 | 30.599 | 40.068 | 1.00 | 45.50 | H |
| ATOM | 2319 | C | MET | 86 | 135.733 | 30.691 | 35.592 | 1.00 | 33.88 | H |
| ATOM | 2320 | O | MET | 86 | 136.097 | 30.018 | 34.627 | 1.00 | 28.01 | H |
| ATOM | 2321 | N | THR | 87 | 136.357 | 31.794 | 35.996 | 1.00 | 37.82 | H |
| ATOM | 2322 | CA | THR | 87 | 137.525 | 32.330 | 35.310 | 1.00 | 39.63 | H |
| ATOM | 2323 | CB | THR | 87 | 137.081 | 33.070 | 34.035 | 1.00 | 31.11 | H |
| ATOM | 2324 | OG1 | THR | 87 | 136.455 | 32.132 | 33.153 | 1.00 | 44.08 | H |
| ATOM | 2325 | CG2 | THR | 87 | 138.263 | 33.706 | 33.324 | 1.00 | 41.18 | H |
| ATOM | 2326 | C | THR | 87 | 138.299 | 33.282 | 36.232 | 1.00 | 49.08 | H |
| ATOM | 2327 | O | THR | 87 | 137.797 | 33.684 | 37.278 | 1.00 | 56.80 | H |
| ATOM | 2328 | N | SER | 88 | 139.523 | 33.634 | 35.845 | 1.00 | 59.16 | H |
| ATOM | 2329 | CA | SER | 88 | 140.362 | 34.539 | 36.633 | 1.00 | 63.45 | H |
| ATOM | 2330 | CB | SER | 88 | 141.693 | 34.780 | 35.911 | 1.00 | 64.98 | H |
| ATOM | 2331 | OG | SER | 88 | 142.614 | 33.729 | 36.165 | 1.00 | 44.05 | H |
| ATOM | 2332 | C | SER | 88 | 139.672 | 35.878 | 36.897 | 1.00 | 61.47 | H |
| ATOM | 2333 | O | SER | 88 | 140.291 | 36.838 | 37.356 | 1.00 | 63.13 | H |
| ATOM | 2334 | N | GLU | 89 | 138.384 | 35.928 | 36.586 | 1.00 | 61.96 | H |
| ATOM | 2335 | CA | GLU | 89 | 137.567 | 37.114 | 36.791 | 1.00 | 60.40 | H |
| ATOM | 2336 | CB | GLU | 89 | 136.888 | 37.517 | 35.483 | 1.00 | 58.39 | H |
| ATOM | 2337 | CG | GLU | 89 | 136.045 | 36.410 | 34.861 | 1.00 | 65.30 | H |
| ATOM | 2338 | CD | GLU | 89 | 134.607 | 36.832 | 34.614 | 1.00 | 74.02 | H |
| ATOM | 2339 | OE1 | GLU | 89 | 134.227 | 36.969 | 33.430 | 1.00 | 59.34 | H |
| ATOM | 2340 | OE2 | GLU | 89 | 133.858 | 37.028 | 35.604 | 1.00 | 71.55 | H |
| ATOM | 2341 | C | GLU | 89 | 136.518 | 36.725 | 37.822 | 1.00 | 58.77 | H |
| ATOM | 2342 | O | GLU | 89 | 135.492 | 37.388 | 37.971 | 1.00 | 54.85 | H |
| ATOM | 2343 | N | ASP | 90 | 136.788 | 35.624 | 38.514 | 1.00 | 59.98 | H |
| ATOM | 2344 | CA | ASP | 90 | 135.898 | 35.102 | 39.544 | 1.00 | 62.69 | H |
| ATOM | 2345 | CB | ASP | 90 | 135.475 | 33.664 | 39.211 | 1.00 | 63.78 | H |
| ATOM | 2346 | CG | ASP | 90 | 134.268 | 33.601 | 38.293 | 1.00 | 63.07 | H |
| ATOM | 2347 | OD1 | ASP | 90 | 133.728 | 32.488 | 38.109 | 1.00 | 51.98 | H |
| ATOM | 2348 | OD2 | ASP | 90 | 133.864 | 34.653 | 37.757 | 1.00 | 64.25 | H |
| ATOM | 2349 | C | ASP | 90 | 136.653 | 35.105 | 40.867 | 1.00 | 58.67 | H |
| ATOM | 2350 | O | ASP | 90 | 136.052 | 35.098 | 41.939 | 1.00 | 60.42 | H |
| ATOM | 2351 | N | SER | 91 | 137.979 | 35.102 | 40.783 | 1.00 | 57.82 | H |
| ATOM | 2352 | CA | SER | 91 | 138.806 | 35.113 | 41.978 | 1.00 | 51.69 | H |
| ATOM | 2353 | CB | SER | 91 | 140.285 | 35.096 | 41.597 | 1.00 | 44.52 | H |
| ATOM | 2354 | OG | SER | 91 | 140.598 | 33.935 | 40.846 | 1.00 | 46.65 | H |
| ATOM | 2355 | C | SER | 91 | 138.487 | 36.362 | 42.787 | 1.00 | 53.31 | H |
| ATOM | 2356 | O | SER | 91 | 138.881 | 37.471 | 42.427 | 1.00 | 45.71 | H |
| ATOM | 2357 | N | ALA | 92 | 137.755 | 36.167 | 43.877 | 1.00 | 53.93 | H |
| ATOM | 2358 | CA | ALA | 92 | 137.356 | 37.257 | 44.755 | 1.00 | 50.72 | H |
| ATOM | 2359 | CB | ALA | 92 | 136.133 | 37.967 | 44.177 | 1.00 | 48.61 | H |
| ATOM | 2360 | C | ALA | 92 | 137.045 | 36.691 | 46.143 | 1.00 | 46.86 | H |
| ATOM | 2361 | O | ALA | 92 | 137.638 | 35.690 | 46.545 | 1.00 | 49.03 | H |
| ATOM | 2362 | N | VAL | 93 | 136.116 | 37.313 | 46.868 | 1.00 | 46.02 | H |
| ATOM | 2363 | CA | VAL | 93 | 135.775 | 36.842 | 48.207 | 1.00 | 44.17 | H |

TABLE 4-continued

Co-ordinates of the CD28/5.11A1 crystal structure

| ATOM | 2364 | CB  | VAL | 93  | 136.116 | 37.909 | 49.272 | 1.00 | 39.83 | H |
|------|------|-----|-----|-----|---------|--------|--------|------|-------|---|
| ATOM | 2365 | CG1 | VAL | 93  | 136.006 | 37.299 | 50.663 | 1.00 | 31.85 | H |
| ATOM | 2366 | CG2 | VAL | 93  | 137.523 | 38.450 | 49.049 | 1.00 | 37.20 | H |
| ATOM | 2367 | C   | VAL | 93  | 134.330 | 36.371 | 48.439 | 1.00 | 45.91 | H |
| ATOM | 2368 | O   | VAL | 93  | 134.092 | 35.525 | 49.301 | 1.00 | 48.37 | H |
| ATOM | 2369 | N   | TYR | 94  | 133.373 | 36.916 | 47.691 | 1.00 | 38.60 | H |
| ATOM | 2370 | CA  | TYR | 94  | 131.963 | 36.524 | 47.825 | 1.00 | 49.33 | H |
| ATOM | 2371 | CB  | TYR | 94  | 131.706 | 35.189 | 47.125 | 1.00 | 40.10 | H |
| ATOM | 2372 | CG  | TYR | 94  | 132.160 | 35.137 | 45.692 | 1.00 | 31.43 | H |
| ATOM | 2373 | CD1 | TYR | 94  | 131.372 | 35.660 | 44.675 | 1.00 | 29.40 | H |
| ATOM | 2374 | CE1 | TYR | 94  | 131.758 | 35.556 | 43.344 | 1.00 | 41.76 | H |
| ATOM | 2375 | CD2 | TYR | 94  | 133.355 | 34.512 | 45.346 | 1.00 | 33.02 | H |
| ATOM | 2376 | CE2 | TYR | 94  | 133.750 | 34.402 | 44.025 | 1.00 | 31.73 | H |
| ATOM | 2377 | CZ  | TYR | 94  | 132.949 | 34.922 | 43.028 | 1.00 | 46.94 | H |
| ATOM | 2378 | OH  | TYR | 94  | 133.336 | 34.796 | 41.711 | 1.00 | 62.64 | H |
| ATOM | 2379 | C   | TYR | 94  | 131.450 | 36.407 | 49.267 | 1.00 | 50.08 | H |
| ATOM | 2380 | O   | TYR | 94  | 131.708 | 35.413 | 49.953 | 1.00 | 34.70 | H |
| ATOM | 2381 | N   | PHE | 95  | 130.688 | 37.408 | 49.703 | 1.00 | 50.03 | H |
| ATOM | 2382 | CA  | PHE | 95  | 130.140 | 37.431 | 51.051 | 1.00 | 34.71 | H |
| ATOM | 2383 | CB  | PHE | 95  | 130.292 | 38.814 | 51.671 | 1.00 | 32.84 | H |
| ATOM | 2384 | CG  | PHE | 95  | 131.646 | 39.077 | 52.243 | 1.00 | 19.95 | H |
| ATOM | 2385 | CD1 | PHE | 95  | 131.966 | 38.638 | 53.516 | 1.00 | 6.35  | H |
| ATOM | 2386 | CD2 | PHE | 95  | 132.600 | 39.780 | 51.508 | 1.00 | 14.02 | H |
| ATOM | 2387 | CE1 | PHE | 95  | 133.219 | 38.892 | 54.057 | 1.00 | 29.11 | H |
| ATOM | 2388 | CE2 | PHE | 95  | 133.849 | 40.037 | 52.041 | 1.00 | 21.81 | H |
| ATOM | 2389 | CZ  | PHE | 95  | 134.162 | 39.592 | 53.321 | 1.00 | 20.98 | H |
| ATOM | 2390 | C   | PHE | 95  | 128.678 | 37.082 | 51.077 | 1.00 | 37.58 | H |
| ATOM | 2391 | O   | PHE | 95  | 127.941 | 37.378 | 50.146 | 1.00 | 40.29 | H |
| ATOM | 2392 | N   | CYS | 96  | 128.272 | 36.455 | 52.168 | 1.00 | 47.35 | H |
| ATOM | 2393 | CA  | CYS | 96  | 126.888 | 36.080 | 52.375 | 1.00 | 48.56 | H |
| ATOM | 2394 | C   | CYS | 96  | 126.368 | 37.062 | 53.415 | 1.00 | 47.93 | H |
| ATOM | 2395 | O   | CYS | 96  | 127.035 | 37.326 | 54.420 | 1.00 | 49.37 | H |
| ATOM | 2396 | CB  | CYS | 96  | 126.796 | 34.652 | 52.911 | 1.00 | 45.82 | H |
| ATOM | 2397 | SG  | CYS | 96  | 125.140 | 34.190 | 53.511 | 1.00 | 75.54 | H |
| ATOM | 2398 | N   | THR | 97  | 125.188 | 37.614 | 53.168 | 1.00 | 37.05 | H |
| ATOM | 2399 | CA  | THR | 97  | 124.595 | 38.575 | 54.086 | 1.00 | 35.84 | H |
| ATOM | 2400 | CB  | THR | 97  | 125.127 | 40.008 | 53.807 | 1.00 | 33.55 | H |
| ATOM | 2401 | OG1 | THR | 97  | 124.832 | 40.851 | 54.922 | 1.00 | 24.79 | H |
| ATOM | 2402 | CG2 | THR | 97  | 124.517 | 40.584 | 52.542 | 1.00 | 23.01 | H |
| ATOM | 2403 | C   | THR | 97  | 123.085 | 38.518 | 53.931 | 1.00 | 34.60 | H |
| ATOM | 2404 | O   | THR | 97  | 122.584 | 37.860 | 53.026 | 1.00 | 34.26 | H |
| ATOM | 2405 | N   | ARG | 98  | 122.356 | 39.192 | 54.814 | 1.00 | 46.98 | H |
| ATOM | 2406 | CA  | ARG | 98  | 120.896 | 39.158 | 54.752 | 1.00 | 49.01 | H |
| ATOM | 2407 | CB  | ARG | 98  | 120.352 | 38.157 | 55.795 | 1.00 | 38.44 | H |
| ATOM | 2408 | CG  | ARG | 98  | 119.596 | 38.781 | 56.963 | 1.00 | 40.81 | H |
| ATOM | 2409 | CD  | ARG | 98  | 120.319 | 38.594 | 58.296 | 1.00 | 27.38 | H |
| ATOM | 2410 | NE  | ARG | 98  | 119.849 | 39.546 | 59.307 | 1.00 | 53.08 | H |
| ATOM | 2411 | CZ  | ARG | 98  | 119.540 | 39.230 | 60.563 | 1.00 | 40.53 | H |
| ATOM | 2412 | NH1 | ARG | 98  | 119.651 | 37.977 | 60.980 | 1.00 | 58.43 | H |
| ATOM | 2413 | NH2 | ARG | 98  | 119.113 | 40.167 | 61.403 | 1.00 | 33.33 | H |
| ATOM | 2414 | C   | ARG | 98  | 120.229 | 40.507 | 54.938 | 1.00 | 39.44 | H |
| ATOM | 2415 | O   | ARG | 98  | 120.740 | 41.377 | 55.637 | 1.00 | 41.38 | H |
| ATOM | 2416 | N   | SER | 99  | 119.079 | 40.666 | 54.296 | 1.00 | 35.04 | H |
| ATOM | 2417 | CA  | SER | 99  | 118.299 | 41.889 | 54.388 | 1.00 | 24.81 | H |
| ATOM | 2418 | CB  | SER | 99  | 117.920 | 42.396 | 53.004 | 1.00 | 14.04 | H |
| ATOM | 2419 | OG  | SER | 99  | 117.671 | 43.780 | 53.039 | 1.00 | 29.22 | H |
| ATOM | 2420 | C   | SER | 99  | 117.050 | 41.455 | 55.106 | 1.00 | 28.87 | H |
| ATOM | 2421 | O   | SER | 99  | 116.660 | 40.294 | 55.009 | 1.00 | 36.12 | H |
| ATOM | 2422 | N   | HIS | 100 | 116.418 | 42.367 | 55.829 | 1.00 | 34.54 | H |
| ATOM | 2423 | CA  | HIS | 100 | 115.209 | 41.998 | 56.541 | 1.00 | 40.60 | H |
| ATOM | 2424 | CB  | HIS | 100 | 114.976 | 42.943 | 57.714 | 1.00 | 35.00 | H |
| ATOM | 2425 | CG  | HIS | 100 | 113.731 | 42.641 | 58.492 | 1.00 | 48.41 | H |
| ATOM | 2426 | CD2 | HIS | 100 | 113.141 | 41.463 | 58.812 | 1.00 | 45.56 | H |
| ATOM | 2427 | ND1 | HIS | 100 | 112.947 | 43.625 | 59.057 | 1.00 | 32.49 | H |
| ATOM | 2428 | CE1 | HIS | 100 | 111.930 | 43.069 | 59.687 | 1.00 | 29.00 | H |
| ATOM | 2429 | NE2 | HIS | 100 | 112.023 | 41.759 | 59.557 | 1.00 | 33.71 | H |
| ATOM | 2430 | C   | HIS | 100 | 114.037 | 42.072 | 55.584 | 1.00 | 41.32 | H |
| ATOM | 2431 | O   | HIS | 100 | 113.824 | 43.110 | 54.964 | 1.00 | 48.72 | H |
| ATOM | 2432 | N   | TYR | 101 | 113.295 | 40.976 | 55.438 | 1.00 | 35.01 | H |
| ATOM | 2433 | CA  | TYR | 101 | 112.136 | 41.001 | 54.551 | 1.00 | 39.86 | H |
| ATOM | 2434 | CB  | TYR | 101 | 111.509 | 39.606 | 54.408 | 1.00 | 26.52 | H |
| ATOM | 2435 | CG  | TYR | 101 | 110.507 | 39.496 | 53.267 | 1.00 | 26.05 | H |
| ATOM | 2436 | CD1 | TYR | 101 | 110.933 | 39.404 | 51.945 | 1.00 | 40.86 | H |
| ATOM | 2437 | CE1 | TYR | 101 | 110.024 | 39.324 | 50.885 | 1.00 | 27.58 | H |
| ATOM | 2438 | CD2 | TYR | 101 | 109.135 | 39.502 | 53.507 | 1.00 | 33.96 | H |
| ATOM | 2439 | CE2 | TYR | 101 | 108.216 | 39.422 | 52.450 | 1.00 | 40.43 | H |
| ATOM | 2440 | CZ  | TYR | 101 | 108.673 | 39.336 | 51.145 | 1.00 | 27.74 | H |

TABLE 4-continued

Co-ordinates of the CD28/5.11A1 crystal structure

| ATOM | 2441 | OH  | TYR | 101 | 107.779 | 39.275 | 50.100 | 1.00 | 40.21 | H |
|------|------|-----|-----|-----|---------|--------|--------|------|-------|---|
| ATOM | 2442 | C   | TYR | 101 | 111.167 | 41.950 | 55.247 | 1.00 | 55.50 | H |
| ATOM | 2443 | O   | TYR | 101 | 111.013 | 41.892 | 56.470 | 1.00 | 73.70 | H |
| ATOM | 2444 | N   | GLY | 102 | 110.525 | 42.828 | 54.482 | 1.00 | 45.70 | H |
| ATOM | 2445 | CA  | GLY | 102 | 109.611 | 43.790 | 55.079 | 1.00 | 43.01 | H |
| ATOM | 2446 | C   | GLY | 102 | 110.364 | 45.094 | 55.237 | 1.00 | 39.11 | H |
| ATOM | 2447 | O   | GLY | 102 | 110.169 | 46.028 | 54.464 | 1.00 | 47.90 | H |
| ATOM | 2448 | N   | LEU | 103 | 111.229 | 45.155 | 56.243 | 1.00 | 31.80 | H |
| ATOM | 2449 | CA  | LEU | 103 | 112.062 | 46.331 | 56.475 | 1.00 | 34.98 | H |
| ATOM | 2450 | CB  | LEU | 103 | 112.270 | 46.554 | 57.975 | 1.00 | 47.24 | H |
| ATOM | 2451 | CG  | LEU | 103 | 111.258 | 47.406 | 58.750 | 1.00 | 56.12 | H |
| ATOM | 2452 | CD1 | LEU | 103 | 109.959 | 47.593 | 57.956 | 1.00 | 31.67 | H |
| ATOM | 2453 | CD2 | LEU | 103 | 110.993 | 46.730 | 60.092 | 1.00 | 44.52 | H |
| ATOM | 2454 | C   | LEU | 103 | 113.394 | 46.019 | 55.807 | 1.00 | 31.85 | H |
| ATOM | 2455 | O   | LEU | 103 | 114.392 | 45.736 | 56.471 | 1.00 | 32.76 | H |
| ATOM | 2456 | N   | ASP | 104 | 113.368 | 46.045 | 54.477 | 1.00 | 33.42 | H |
| ATOM | 2457 | CA  | ASP | 104 | 114.512 | 45.757 | 53.625 | 1.00 | 20.79 | H |
| ATOM | 2458 | CB  | ASP | 104 | 113.992 | 45.202 | 52.295 | 1.00 | 32.02 | H |
| ATOM | 2459 | CG  | ASP | 104 | 115.093 | 44.901 | 51.298 | 1.00 | 55.62 | H |
| ATOM | 2460 | OD1 | ASP | 104 | 114.753 | 44.583 | 50.136 | 1.00 | 38.63 | H |
| ATOM | 2461 | OD2 | ASP | 104 | 116.286 | 44.985 | 51.663 | 1.00 | 61.09 | H |
| ATOM | 2462 | C   | ASP | 104 | 115.255 | 47.067 | 53.415 | 1.00 | 29.02 | H |
| ATOM | 2463 | O   | ASP | 104 | 115.021 | 47.775 | 52.440 | 1.00 | 33.69 | H |
| ATOM | 2464 | N   | TRP | 105 | 116.148 | 47.386 | 54.346 | 1.00 | 37.55 | H |
| ATOM | 2465 | CA  | TRP | 105 | 116.907 | 48.628 | 54.288 | 1.00 | 32.28 | H |
| ATOM | 2466 | CB  | TRP | 105 | 116.599 | 49.484 | 55.518 | 1.00 | 42.44 | H |
| ATOM | 2467 | CG  | TRP | 105 | 115.123 | 49.751 | 55.717 | 1.00 | 44.69 | H |
| ATOM | 2468 | CD2 | TRP | 105 | 114.456 | 50.028 | 56.955 | 1.00 | 43.59 | H |
| ATOM | 2469 | CE2 | TRP | 105 | 113.091 | 50.217 | 56.662 | 1.00 | 39.38 | H |
| ATOM | 2470 | CE3 | TRP | 105 | 114.887 | 50.136 | 58.285 | 1.00 | 53.16 | H |
| ATOM | 2471 | CD1 | TRP | 105 | 114.157 | 49.780 | 54.751 | 1.00 | 25.93 | H |
| ATOM | 2472 | NE1 | TRP | 105 | 112.942 | 50.059 | 55.313 | 1.00 | 37.01 | H |
| ATOM | 2473 | CZ2 | TRP | 105 | 112.144 | 50.507 | 57.650 | 1.00 | 45.54 | H |
| ATOM | 2474 | CZ3 | TRP | 105 | 113.945 | 50.425 | 59.270 | 1.00 | 48.69 | H |
| ATOM | 2475 | CH2 | TRP | 105 | 112.588 | 50.609 | 58.945 | 1.00 | 55.24 | H |
| ATOM | 2476 | C   | TRP | 105 | 118.405 | 48.421 | 54.187 | 1.00 | 40.80 | H |
| ATOM | 2477 | O   | TRP | 105 | 119.063 | 49.042 | 53.352 | 1.00 | 47.85 | H |
| ATOM | 2478 | N   | ASN | 106 | 118.952 | 47.556 | 55.038 | 1.00 | 49.48 | H |
| ATOM | 2479 | CA  | ASN | 106 | 120.389 | 47.305 | 55.013 | 1.00 | 46.39 | H |
| ATOM | 2480 | CB  | ASN | 106 | 121.103 | 48.280 | 55.951 | 1.00 | 36.85 | H |
| ATOM | 2481 | CG  | ASN | 106 | 120.869 | 47.961 | 57.408 | 1.00 | 28.91 | H |
| ATOM | 2482 | OD1 | ASN | 106 | 119.909 | 48.434 | 58.013 | 1.00 | 32.97 | H |
| ATOM | 2483 | ND2 | ASN | 106 | 121.744 | 47.152 | 57.981 | 1.00 | 41.71 | H |
| ATOM | 2484 | C   | ASN | 106 | 120.786 | 45.877 | 55.363 | 1.00 | 48.25 | H |
| ATOM | 2485 | O   | ASN | 106 | 119.950 | 45.059 | 55.760 | 1.00 | 46.92 | H |
| ATOM | 2486 | N   | PHE | 107 | 122.079 | 45.602 | 55.202 | 1.00 | 47.37 | H |
| ATOM | 2487 | CA  | PHE | 107 | 122.665 | 44.294 | 55.489 | 1.00 | 47.06 | H |
| ATOM | 2488 | CB  | PHE | 107 | 123.589 | 43.862 | 54.341 | 1.00 | 51.22 | H |
| ATOM | 2489 | CG  | PHE | 107 | 123.004 | 44.052 | 52.954 | 1.00 | 36.58 | H |
| ATOM | 2490 | CD1 | PHE | 107 | 121.628 | 44.053 | 52.737 | 1.00 | 43.99 | H |
| ATOM | 2491 | CD2 | PHE | 107 | 123.847 | 44.180 | 51.851 | 1.00 | 35.28 | H |
| ATOM | 2492 | CE1 | PHE | 107 | 121.107 | 44.175 | 51.449 | 1.00 | 41.51 | H |
| ATOM | 2493 | CE2 | PHE | 107 | 123.334 | 44.301 | 50.561 | 1.00 | 20.31 | H |
| ATOM | 2494 | CZ  | PHE | 107 | 121.965 | 44.296 | 50.362 | 1.00 | 40.17 | H |
| ATOM | 2495 | C   | PHE | 107 | 123.479 | 44.386 | 56.787 | 1.00 | 45.87 | H |
| ATOM | 2496 | O   | PHE | 107 | 124.641 | 44.805 | 56.765 | 1.00 | 38.80 | H |
| ATOM | 2497 | N   | ASP | 108 | 122.874 | 43.982 | 57.905 | 1.00 | 44.31 | H |
| ATOM | 2498 | CA  | ASP | 108 | 123.528 | 44.053 | 59.215 | 1.00 | 40.48 | H |
| ATOM | 2499 | CB  | ASP | 108 | 122.479 | 44.243 | 60.325 | 1.00 | 54.96 | H |
| ATOM | 2500 | CG  | ASP | 108 | 121.048 | 44.057 | 59.833 | 1.00 | 66.26 | H |
| ATOM | 2501 | OD1 | ASP | 108 | 120.304 | 45.059 | 59.790 | 1.00 | 56.03 | H |
| ATOM | 2502 | OD2 | ASP | 108 | 120.664 | 42.914 | 59.494 | 1.00 | 63.18 | H |
| ATOM | 2503 | C   | ASP | 108 | 124.445 | 42.889 | 59.600 | 1.00 | 27.53 | H |
| ATOM | 2504 | O   | ASP | 108 | 125.418 | 43.077 | 60.328 | 1.00 | 16.20 | H |
| ATOM | 2505 | N   | VAL | 109 | 124.133 | 41.690 | 59.128 | 1.00 | 18.58 | H |
| ATOM | 2506 | CA  | VAL | 109 | 124.946 | 40.527 | 59.458 | 1.00 | 20.11 | H |
| ATOM | 2507 | CB  | VAL | 109 | 124.072 | 39.410 | 60.037 | 1.00 | 25.57 | H |
| ATOM | 2508 | CG1 | VAL | 109 | 124.936 | 38.353 | 60.691 | 1.00 | 22.40 | H |
| ATOM | 2509 | CG2 | VAL | 109 | 123.098 | 39.998 | 61.038 | 1.00 | 21.93 | H |
| ATOM | 2510 | C   | VAL | 109 | 125.704 | 39.984 | 58.246 | 1.00 | 26.64 | H |
| ATOM | 2511 | O   | VAL | 109 | 125.110 | 39.594 | 57.248 | 1.00 | 34.79 | H |
| ATOM | 2512 | N   | TRP | 110 | 127.023 | 39.949 | 58.336 | 1.00 | 27.30 | H |
| ATOM | 2513 | CA  | TRP | 110 | 127.818 | 39.459 | 57.229 | 1.00 | 27.28 | H |
| ATOM | 2514 | CB  | TRP | 110 | 128.834 | 40.519 | 56.810 | 1.00 | 33.78 | H |
| ATOM | 2515 | CG  | TRP | 110 | 128.248 | 41.738 | 56.167 | 1.00 | 36.21 | H |
| ATOM | 2516 | CD2 | TRP | 110 | 128.440 | 42.162 | 54.813 | 1.00 | 25.48 | H |
| ATOM | 2517 | CE2 | TRP | 110 | 127.801 | 43.411 | 54.669 | 1.00 | 33.24 | H |

TABLE 4-continued

Co-ordinates of the CD28/5.11A1 crystal structure

| ATOM | 2518 | CE3 | TRP | 110 | 129.097 | 41.609 | 53.711 | 1.00 | 13.14 | H |
|---|---|---|---|---|---|---|---|---|---|---|
| ATOM | 2519 | CD1 | TRP | 110 | 127.511 | 42.715 | 56.770 | 1.00 | 42.55 | H |
| ATOM | 2520 | NE1 | TRP | 110 | 127.236 | 43.728 | 55.879 | 1.00 | 36.86 | H |
| ATOM | 2521 | CZ2 | TRP | 110 | 127.795 | 44.115 | 53.467 | 1.00 | 25.21 | H |
| ATOM | 2522 | CZ3 | TRP | 110 | 129.096 | 42.314 | 52.511 | 1.00 | 30.00 | H |
| ATOM | 2523 | CH2 | TRP | 110 | 128.449 | 43.553 | 52.402 | 1.00 | 26.50 | H |
| ATOM | 2524 | C | TRP | 110 | 128.566 | 38.187 | 57.601 | 1.00 | 29.69 | H |
| ATOM | 2525 | O | TRP | 110 | 128.946 | 37.993 | 58.753 | 1.00 | 39.20 | H |
| ATOM | 2526 | N | GLY | 111 | 128.774 | 37.317 | 56.621 | 1.00 | 26.69 | H |
| ATOM | 2527 | CA | GLY | 111 | 129.523 | 36.110 | 56.880 | 1.00 | 15.66 | H |
| ATOM | 2528 | C | GLY | 111 | 130.988 | 36.505 | 56.847 | 1.00 | 32.31 | H |
| ATOM | 2529 | O | GLY | 111 | 131.327 | 37.622 | 56.451 | 1.00 | 24.60 | H |
| ATOM | 2530 | N | ALA | 112 | 131.867 | 35.604 | 57.261 | 1.00 | 41.72 | H |
| ATOM | 2531 | CA | ALA | 112 | 133.287 | 35.907 | 57.249 | 1.00 | 41.34 | H |
| ATOM | 2532 | CB | ALA | 112 | 134.033 | 34.911 | 58.119 | 1.00 | 39.24 | H |
| ATOM | 2533 | C | ALA | 112 | 133.857 | 35.896 | 55.826 | 1.00 | 45.93 | H |
| ATOM | 2534 | O | ALA | 112 | 134.902 | 36.492 | 55.568 | 1.00 | 49.85 | H |
| ATOM | 2535 | N | GLY | 113 | 133.178 | 35.217 | 54.906 | 1.00 | 45.09 | H |
| ATOM | 2536 | CA | GLY | 113 | 133.665 | 35.161 | 53.538 | 1.00 | 44.98 | H |
| ATOM | 2537 | C | GLY | 113 | 134.180 | 33.798 | 53.099 | 1.00 | 44.48 | H |
| ATOM | 2538 | O | GLY | 113 | 134.273 | 32.862 | 53.894 | 1.00 | 40.99 | H |
| ATOM | 2539 | N | THR | 114 | 134.519 | 33.690 | 51.819 | 1.00 | 44.31 | H |
| ATOM | 2540 | CA | THR | 114 | 135.019 | 32.446 | 51.242 | 1.00 | 31.88 | H |
| ATOM | 2541 | CB | THR | 114 | 133.845 | 31.530 | 50.772 | 1.00 | 20.38 | H |
| ATOM | 2542 | OG1 | THR | 114 | 133.279 | 30.861 | 51.900 | 1.00 | 35.87 | H |
| ATOM | 2543 | CG2 | THR | 114 | 134.328 | 30.478 | 49.789 | 1.00 | 32.39 | H |
| ATOM | 2544 | C | THR | 114 | 135.865 | 32.814 | 50.032 | 1.00 | 33.60 | H |
| ATOM | 2545 | O | THR | 114 | 135.325 | 33.054 | 48.953 | 1.00 | 42.98 | H |
| ATOM | 2546 | N | THR | 115 | 137.182 | 32.880 | 50.208 | 1.00 | 35.92 | H |
| ATOM | 2547 | CA | THR | 115 | 138.055 | 33.208 | 49.089 | 1.00 | 33.21 | H |
| ATOM | 2548 | CB | THR | 115 | 139.525 | 33.317 | 49.499 | 1.00 | 43.78 | H |
| ATOM | 2549 | OG1 | THR | 115 | 139.649 | 34.185 | 50.632 | 1.00 | 41.45 | H |
| ATOM | 2550 | CG2 | THR | 115 | 140.351 | 33.867 | 48.332 | 1.00 | 43.50 | H |
| ATOM | 2551 | C | THR | 115 | 137.938 | 32.100 | 48.059 | 1.00 | 39.18 | H |
| ATOM | 2552 | O | THR | 115 | 137.823 | 30.918 | 48.406 | 1.00 | 28.11 | H |
| ATOM | 2553 | N | VAL | 116 | 137.958 | 32.490 | 46.791 | 1.00 | 36.51 | H |
| ATOM | 2554 | CA | VAL | 116 | 137.840 | 31.537 | 45.708 | 1.00 | 40.64 | H |
| ATOM | 2555 | CB | VAL | 116 | 136.443 | 31.616 | 45.051 | 1.00 | 41.04 | H |
| ATOM | 2556 | CG1 | VAL | 116 | 136.337 | 30.599 | 43.931 | 1.00 | 35.25 | H |
| ATOM | 2557 | CG2 | VAL | 116 | 135.362 | 31.359 | 46.096 | 1.00 | 33.28 | H |
| ATOM | 2558 | C | VAL | 116 | 138.899 | 31.816 | 44.661 | 1.00 | 43.76 | H |
| ATOM | 2559 | O | VAL | 116 | 139.009 | 32.929 | 44.146 | 1.00 | 46.23 | H |
| ATOM | 2560 | N | THR | 117 | 139.683 | 30.791 | 44.354 | 1.00 | 44.39 | H |
| ATOM | 2561 | CA | THR | 117 | 140.740 | 30.919 | 43.370 | 1.00 | 40.89 | H |
| ATOM | 2562 | CB | THR | 117 | 142.095 | 30.552 | 43.969 | 1.00 | 38.40 | H |
| ATOM | 2563 | OG1 | THR | 117 | 142.320 | 31.340 | 45.145 | 1.00 | 36.59 | H |
| ATOM | 2564 | CG2 | THR | 117 | 143.205 | 30.810 | 42.966 | 1.00 | 32.70 | H |
| ATOM | 2565 | C | THR | 117 | 140.449 | 30.001 | 42.203 | 1.00 | 38.02 | H |
| ATOM | 2566 | O | THR | 117 | 139.802 | 28.971 | 42.357 | 1.00 | 37.58 | H |
| ATOM | 2567 | N | VAL | 118 | 140.928 | 30.386 | 41.031 | 1.00 | 45.45 | H |
| ATOM | 2568 | CA | VAL | 118 | 140.705 | 29.597 | 39.838 | 1.00 | 47.20 | H |
| ATOM | 2569 | CB | VAL | 118 | 140.199 | 30.481 | 38.694 | 1.00 | 54.07 | H |
| ATOM | 2570 | CG1 | VAL | 118 | 138.698 | 30.704 | 38.844 | 1.00 | 40.64 | H |
| ATOM | 2571 | CG2 | VAL | 118 | 140.942 | 31.807 | 38.700 | 1.00 | 46.30 | H |
| ATOM | 2572 | C | VAL | 118 | 141.973 | 28.890 | 39.400 | 1.00 | 42.28 | H |
| ATOM | 2573 | O | VAL | 118 | 141.946 | 27.706 | 39.060 | 1.00 | 42.04 | H |
| ATOM | 2574 | N | SER | 119 | 143.081 | 29.622 | 39.415 | 1.00 | 40.12 | H |
| ATOM | 2575 | CA | SER | 119 | 144.381 | 29.089 | 39.015 | 1.00 | 48.99 | H |
| ATOM | 2576 | CB | SER | 119 | 145.469 | 29.569 | 39.983 | 1.00 | 49.51 | H |
| ATOM | 2577 | OG | SER | 119 | 146.419 | 30.398 | 39.331 | 1.00 | 31.69 | H |
| ATOM | 2578 | C | SER | 119 | 144.418 | 27.563 | 38.929 | 1.00 | 49.87 | H |
| ATOM | 2579 | O | SER | 119 | 144.028 | 26.856 | 39.870 | 1.00 | 42.52 | H |
| ATOM | 2580 | N | SER | 120 | 144.887 | 27.067 | 37.787 | 1.00 | 55.96 | H |
| ATOM | 2581 | CA | SER | 120 | 144.996 | 25.633 | 37.540 | 1.00 | 53.80 | H |
| ATOM | 2582 | CB | SER | 120 | 144.774 | 25.334 | 36.050 | 1.00 | 57.59 | H |
| ATOM | 2583 | OG | SER | 120 | 145.785 | 25.919 | 35.239 | 1.00 | 55.34 | H |
| ATOM | 2584 | C | SER | 120 | 146.377 | 25.145 | 37.965 | 1.00 | 53.97 | H |
| ATOM | 2585 | O | SER | 120 | 146.879 | 24.149 | 37.447 | 1.00 | 49.63 | H |
| ATOM | 2586 | N | ALA | 121 | 146.974 | 25.858 | 38.919 | 1.00 | 62.49 | H |
| ATOM | 2587 | CA | ALA | 121 | 148.307 | 25.544 | 39.445 | 1.00 | 58.34 | H |
| ATOM | 2588 | CB | ALA | 121 | 148.830 | 26.714 | 40.278 | 1.00 | 52.59 | H |
| ATOM | 2589 | C | ALA | 121 | 148.333 | 24.268 | 40.284 | 1.00 | 54.04 | H |
| ATOM | 2590 | O | ALA | 121 | 147.318 | 23.584 | 40.432 | 1.00 | 56.38 | H |
| ATOM | 2591 | N | LYS | 122 | 149.498 | 23.951 | 40.841 | 1.00 | 48.35 | H |
| ATOM | 2592 | CA | LYS | 122 | 149.624 | 22.750 | 41.649 | 1.00 | 46.60 | H |
| ATOM | 2593 | CB | LYS | 122 | 150.912 | 21.998 | 41.318 | 1.00 | 51.72 | H |
| ATOM | 2594 | CG | LYS | 122 | 150.682 | 20.565 | 40.843 | 1.00 | 51.16 | H |

TABLE 4-continued

Co-ordinates of the CD28/5.11A1 crystal structure

| ATOM | 2595 | CD  | LYS | 122 | 150.117 | 19.675 | 41.948 | 1.00 | 40.43  | H |
|------|------|-----|-----|-----|---------|--------|--------|------|--------|---|
| ATOM | 2596 | CE  | LYS | 122 | 151.191 | 18.754 | 42.525 | 1.00 | 52.69  | H |
| ATOM | 2597 | NZ  | LYS | 122 | 150.980 | 17.320 | 42.166 | 1.00 | 52.23  | H |
| ATOM | 2598 | C   | LYS | 122 | 149.577 | 23.043 | 43.133 | 1.00 | 52.24  | H |
| ATOM | 2599 | O   | LYS | 122 | 150.258 | 23.933 | 43.644 | 1.00 | 51.54  | H |
| ATOM | 2600 | N   | THR | 123 | 148.758 | 22.255 | 43.811 | 1.00 | 58.75  | H |
| ATOM | 2601 | CA  | THR | 123 | 148.562 | 22.363 | 45.249 | 1.00 | 59.16  | H |
| ATOM | 2602 | CB  | THR | 123 | 147.422 | 21.459 | 45.722 | 1.00 | 70.62  | H |
| ATOM | 2603 | OG1 | THR | 123 | 146.234 | 21.774 | 44.989 | 1.00 | 100.00 | H |
| ATOM | 2604 | CG2 | THR | 123 | 147.174 | 21.644 | 47.216 | 1.00 | 71.56  | H |
| ATOM | 2605 | C   | THR | 123 | 149.851 | 21.904 | 45.913 | 1.00 | 59.76  | H |
| ATOM | 2606 | O   | THR | 123 | 150.327 | 20.797 | 45.654 | 1.00 | 51.50  | H |
| ATOM | 2607 | N   | THR | 124 | 150.430 | 22.671 | 46.957 | 1.00 | 60.58  | H |
| ATOM | 2608 | CA  | THR | 124 | 151.805 | 22.409 | 47.339 | 1.00 | 54.63  | H |
| ATOM | 2609 | CB  | THR | 124 | 152.776 | 23.187 | 46.433 | 1.00 | 44.65  | H |
| ATOM | 2610 | OG1 | THR | 124 | 152.458 | 22.930 | 45.055 | 1.00 | 43.48  | H |
| ATOM | 2611 | CG2 | THR | 124 | 154.207 | 22.779 | 46.719 | 1.00 | 35.75  | H |
| ATOM | 2612 | C   | THR | 124 | 152.034 | 22.844 | 48.776 | 1.00 | 61.90  | H |
| ATOM | 2613 | O   | THR | 124 | 151.832 | 24.005 | 49.113 | 1.00 | 66.47  | H |
| ATOM | 2614 | N   | PRO | 125 | 152.470 | 21.918 | 49.644 | 1.00 | 63.12  | H |
| ATOM | 2615 | CD  | PRO | 125 | 152.792 | 20.505 | 49.387 | 1.00 | 43.60  | H |
| ATOM | 2616 | CA  | PRO | 125 | 152.705 | 22.286 | 51.044 | 1.00 | 64.11  | H |
| ATOM | 2617 | CB  | PRO | 125 | 153.012 | 20.956 | 51.725 | 1.00 | 53.31  | H |
| ATOM | 2618 | CG  | PRO | 125 | 153.525 | 20.089 | 50.636 | 1.00 | 27.09  | H |
| ATOM | 2619 | C   | PRO | 125 | 153.858 | 23.274 | 51.141 | 1.00 | 60.12  | H |
| ATOM | 2620 | O   | PRO | 125 | 154.781 | 23.255 | 50.329 | 1.00 | 49.68  | H |
| ATOM | 2621 | N   | PRO | 126 | 153.811 | 24.153 | 52.140 | 1.00 | 55.19  | H |
| ATOM | 2622 | CD  | PRO | 126 | 152.761 | 24.258 | 53.169 | 1.00 | 61.07  | H |
| ATOM | 2623 | CA  | PRO | 126 | 154.855 | 25.156 | 52.333 | 1.00 | 47.53  | H |
| ATOM | 2624 | CB  | PRO | 126 | 154.213 | 26.141 | 53.296 | 1.00 | 49.84  | H |
| ATOM | 2625 | CG  | PRO | 126 | 153.315 | 25.289 | 54.118 | 1.00 | 73.92  | H |
| ATOM | 2626 | C   | PRO | 126 | 156.155 | 24.608 | 52.891 | 1.00 | 49.11  | H |
| ATOM | 2627 | O   | PRO | 126 | 156.148 | 23.695 | 53.716 | 1.00 | 53.71  | H |
| ATOM | 2628 | N   | SER | 127 | 157.266 | 25.174 | 52.429 | 1.00 | 38.85  | H |
| ATOM | 2629 | CA  | SER | 127 | 158.586 | 24.792 | 52.913 | 1.00 | 21.97  | H |
| ATOM | 2630 | CB  | SER | 127 | 159.628 | 24.904 | 51.798 | 1.00 | 39.50  | H |
| ATOM | 2631 | OG  | SER | 127 | 159.487 | 23.866 | 50.845 | 1.00 | 52.42  | H |
| ATOM | 2632 | C   | SER | 127 | 158.864 | 25.826 | 53.990 | 1.00 | 33.98  | H |
| ATOM | 2633 | O   | SER | 127 | 159.021 | 27.008 | 53.687 | 1.00 | 34.88  | H |
| ATOM | 2634 | N   | VAL | 128 | 158.903 | 25.393 | 55.243 | 1.00 | 39.20  | H |
| ATOM | 2635 | CA  | VAL | 128 | 159.135 | 26.308 | 56.353 | 1.00 | 46.26  | H |
| ATOM | 2636 | CB  | VAL | 128 | 158.247 | 25.929 | 57.562 | 1.00 | 49.37  | H |
| ATOM | 2637 | CG1 | VAL | 128 | 158.162 | 27.089 | 58.545 | 1.00 | 42.90  | H |
| ATOM | 2638 | CG2 | VAL | 128 | 156.862 | 25.538 | 57.078 | 1.00 | 51.53  | H |
| ATOM | 2639 | C   | VAL | 128 | 160.594 | 26.350 | 56.794 | 1.00 | 37.55  | H |
| ATOM | 2640 | O   | VAL | 128 | 161.183 | 25.329 | 57.153 | 1.00 | 49.56  | H |
| ATOM | 2641 | N   | TYR | 129 | 161.172 | 27.545 | 56.765 | 1.00 | 48.51  | H |
| ATOM | 2642 | CA  | TYR | 129 | 162.562 | 27.740 | 57.150 | 1.00 | 44.86  | H |
| ATOM | 2643 | CB  | TYR | 129 | 163.364 | 28.279 | 55.969 | 1.00 | 35.54  | H |
| ATOM | 2644 | CG  | TYR | 129 | 163.348 | 27.402 | 54.736 | 1.00 | 27.55  | H |
| ATOM | 2645 | CD1 | TYR | 129 | 163.718 | 26.059 | 54.800 | 1.00 | 42.44  | H |
| ATOM | 2646 | CE1 | TYR | 129 | 163.729 | 25.256 | 53.654 | 1.00 | 44.45  | H |
| ATOM | 2647 | CD2 | TYR | 129 | 162.986 | 27.928 | 53.497 | 1.00 | 28.77  | H |
| ATOM | 2648 | CE2 | TYR | 129 | 162.991 | 27.135 | 52.345 | 1.00 | 44.26  | H |
| ATOM | 2649 | CZ  | TYR | 129 | 163.363 | 25.806 | 52.430 | 1.00 | 46.95  | H |
| ATOM | 2650 | OH  | TYR | 129 | 163.366 | 25.036 | 51.291 | 1.00 | 71.81  | H |
| ATOM | 2651 | C   | TYR | 129 | 162.670 | 28.722 | 58.312 | 1.00 | 41.49  | H |
| ATOM | 2652 | O   | TYR | 129 | 162.195 | 29.856 | 58.225 | 1.00 | 48.76  | H |
| ATOM | 2653 | N   | PRO | 130 | 163.309 | 28.302 | 59.415 | 1.00 | 46.24  | H |
| ATOM | 2654 | CD  | PRO | 130 | 163.913 | 26.972 | 59.604 | 1.00 | 58.08  | H |
| ATOM | 2655 | CA  | PRO | 130 | 163.482 | 29.152 | 60.597 | 1.00 | 40.62  | H |
| ATOM | 2656 | CB  | PRO | 130 | 163.970 | 28.180 | 61.661 | 1.00 | 49.21  | H |
| ATOM | 2657 | CG  | PRO | 130 | 164.699 | 27.132 | 60.872 | 1.00 | 50.86  | H |
| ATOM | 2658 | C   | PRO | 130 | 164.486 | 30.276 | 60.359 | 1.00 | 42.13  | H |
| ATOM | 2659 | O   | PRO | 130 | 165.506 | 30.079 | 59.704 | 1.00 | 49.80  | H |
| ATOM | 2660 | N   | LEU | 131 | 164.195 | 31.455 | 60.895 | 1.00 | 40.92  | H |
| ATOM | 2661 | CA  | LEU | 131 | 165.081 | 32.598 | 60.732 | 1.00 | 35.23  | H |
| ATOM | 2662 | CB  | LEU | 131 | 164.319 | 33.772 | 60.120 | 1.00 | 34.49  | H |
| ATOM | 2663 | CG  | LEU | 131 | 163.916 | 33.644 | 58.652 | 1.00 | 34.92  | H |
| ATOM | 2664 | CD1 | LEU | 131 | 163.135 | 34.878 | 58.245 | 1.00 | 11.51  | H |
| ATOM | 2665 | CD2 | LEU | 131 | 165.144 | 33.483 | 57.781 | 1.00 | 26.67  | H |
| ATOM | 2666 | C   | LEU | 131 | 165.666 | 33.014 | 62.077 | 1.00 | 40.36  | H |
| ATOM | 2667 | O   | LEU | 131 | 164.956 | 33.557 | 62.927 | 1.00 | 46.95  | H |
| ATOM | 2668 | N   | ALA | 132 | 166.956 | 32.755 | 62.263 | 1.00 | 56.70  | H |
| ATOM | 2669 | CA  | ALA | 132 | 167.632 | 33.110 | 63.507 | 1.00 | 56.71  | H |
| ATOM | 2670 | CB  | ALA | 132 | 168.300 | 31.886 | 64.096 | 1.00 | 57.53  | H |
| ATOM | 2671 | C   | ALA | 132 | 168.662 | 34.210 | 63.268 | 1.00 | 55.87  | H |

TABLE 4-continued

Co-ordinates of the CD28/5.11A1 crystal structure

| ATOM | 2672 | O | ALA | 132 | 169.276 | 34.279 | 62.204 | 1.00 | 54.54 | H |
|---|---|---|---|---|---|---|---|---|---|---|
| ATOM | 2673 | N | PRO | 133 | 168.864 | 35.091 | 64.262 | 1.00 | 57.72 | H |
| ATOM | 2674 | CD | PRO | 133 | 168.161 | 35.065 | 65.557 | 1.00 | 47.07 | H |
| ATOM | 2675 | CA | PRO | 133 | 169.815 | 36.206 | 64.187 | 1.00 | 60.50 | H |
| ATOM | 2676 | CB | PRO | 133 | 169.496 | 37.030 | 65.431 | 1.00 | 59.11 | H |
| ATOM | 2677 | CG | PRO | 133 | 168.946 | 36.033 | 66.393 | 1.00 | 46.85 | H |
| ATOM | 2678 | C | PRO | 133 | 171.285 | 35.780 | 64.154 | 1.00 | 64.47 | H |
| ATOM | 2679 | O | PRO | 133 | 171.743 | 35.030 | 65.021 | 1.00 | 63.82 | H |
| ATOM | 2680 | N | GLY | 134 | 172.021 | 36.276 | 63.161 | 1.00 | 66.38 | H |
| ATOM | 2681 | CA | GLY | 134 | 173.429 | 35.937 | 63.030 | 1.00 | 54.50 | H |
| ATOM | 2682 | C | GLY | 134 | 174.356 | 36.531 | 64.074 | 1.00 | 60.13 | H |
| ATOM | 2683 | O | GLY | 134 | 175.515 | 36.851 | 63.795 | 1.00 | 70.75 | H |
| ATOM | 2684 | N | SER | 135 | 173.893 | 36.652 | 65.276 | 1.00 | 74.93 | H |
| ATOM | 2685 | CA | SER | 135 | 174.743 | 37.216 | 66.319 | 1.00 | 86.16 | H |
| ATOM | 2686 | CB | SER | 135 | 176.038 | 36.396 | 66.439 | 1.00 | 90.22 | H |
| ATOM | 2687 | OG | SER | 135 | 176.965 | 36.773 | 65.426 | 1.00 | 100.00 | H |
| ATOM | 2688 | C | SER | 135 | 175.096 | 38.660 | 65.950 | 1.00 | 88.57 | H |
| ATOM | 2689 | O | SER | 135 | 176.088 | 38.928 | 65.255 | 1.00 | 77.68 | H |
| ATOM | 2690 | N | ALA | 136 | 174.255 | 39.552 | 66.431 | 1.00 | 94.60 | H |
| ATOM | 2691 | CA | ALA | 136 | 174.413 | 40.992 | 66.206 | 1.00 | 96.15 | H |
| ATOM | 2692 | CB | ALA | 136 | 174.299 | 41.304 | 64.714 | 1.00 | 91.75 | H |
| ATOM | 2693 | C | ALA | 136 | 173.334 | 41.759 | 66.962 | 1.00 | 99.99 | H |
| ATOM | 2694 | O | ALA | 136 | 172.158 | 41.398 | 66.918 | 1.00 | 99.98 | H |
| ATOM | 2695 | N | ALA | 137 | 173.740 | 42.818 | 67.655 | 1.00 | 99.99 | H |
| ATOM | 2696 | CA | ALA | 137 | 172.802 | 43.637 | 68.417 | 1.00 | 100.00 | H |
| ATOM | 2697 | CB | ALA | 137 | 173.565 | 44.631 | 69.285 | 1.00 | 89.73 | H |
| ATOM | 2698 | C | ALA | 137 | 171.860 | 44.377 | 67.474 | 1.00 | 99.97 | H |
| ATOM | 2699 | O | ALA | 137 | 172.119 | 45.518 | 67.094 | 1.00 | 99.95 | H |
| ATOM | 2700 | N | GLN | 138 | 170.768 | 43.718 | 67.103 | 1.00 | 99.99 | H |
| ATOM | 2701 | CA | GLN | 138 | 169.788 | 44.308 | 66.198 | 1.00 | 99.99 | H |
| ATOM | 2702 | CB | GLN | 138 | 168.740 | 43.264 | 65.804 | 1.00 | 92.32 | H |
| ATOM | 2703 | CG | GLN | 138 | 167.946 | 42.702 | 66.972 | 1.00 | 80.27 | H |
| ATOM | 2704 | CD | GLN | 138 | 166.461 | 42.627 | 66.679 | 1.00 | 62.10 | H |
| ATOM | 2705 | OE1 | GLN | 138 | 166.051 | 42.463 | 65.530 | 1.00 | 72.23 | H |
| ATOM | 2706 | NE2 | GLN | 138 | 165.646 | 42.749 | 67.720 | 1.00 | 47.02 | H |
| ATOM | 2707 | C | GLN | 138 | 169.100 | 45.522 | 66.818 | 1.00 | 99.97 | H |
| ATOM | 2708 | O | GLN | 138 | 168.850 | 46.516 | 66.136 | 1.00 | 99.97 | H |
| ATOM | 2709 | N | THR | 139 | 168.797 | 45.438 | 68.116 | 1.00 | 99.99 | H |
| ATOM | 2710 | CA | THR | 139 | 168.138 | 46.530 | 68.810 | 1.00 | 100.00 | H |
| ATOM | 2711 | CB | THR | 139 | 166.629 | 46.520 | 68.570 | 1.00 | 100.00 | H |
| ATOM | 2712 | OG1 | THR | 139 | 166.068 | 45.306 | 69.085 | 1.00 | 99.99 | H |
| ATOM | 2713 | CG2 | THR | 139 | 166.326 | 46.637 | 67.084 | 1.00 | 99.99 | H |
| ATOM | 2714 | C | THR | 139 | 168.421 | 46.461 | 70.301 | 1.00 | 99.99 | H |
| ATOM | 2715 | O | THR | 139 | 167.865 | 45.622 | 71.014 | 1.00 | 99.98 | H |
| ATOM | 2716 | N | ASN | 140 | 169.282 | 47.359 | 70.792 | 1.00 | 99.98 | H |
| ATOM | 2717 | CA | ASN | 140 | 169.654 | 47.435 | 72.187 | 1.00 | 96.92 | H |
| ATOM | 2718 | CB | ASN | 140 | 168.714 | 48.381 | 72.927 | 1.00 | 94.82 | H |
| ATOM | 2719 | CG | ASN | 140 | 168.783 | 49.786 | 72.357 | 1.00 | 91.71 | H |
| ATOM | 2720 | OD1 | ASN | 140 | 169.866 | 50.280 | 72.032 | 1.00 | 88.37 | H |
| ATOM | 2721 | ND2 | ASN | 140 | 167.633 | 50.433 | 72.229 | 1.00 | 91.05 | H |
| ATOM | 2722 | C | ASN | 140 | 169.724 | 46.052 | 72.801 | 1.00 | 93.43 | H |
| ATOM | 2723 | O | ASN | 140 | 170.715 | 45.321 | 72.647 | 1.00 | 83.04 | H |
| ATOM | 2724 | N | SER | 141 | 168.684 | 45.691 | 73.529 | 1.00 | 91.74 | H |
| ATOM | 2725 | CA | SER | 141 | 168.629 | 44.391 | 74.200 | 1.00 | 78.99 | H |
| ATOM | 2726 | CB | SER | 141 | 168.101 | 44.544 | 75.629 | 1.00 | 69.11 | H |
| ATOM | 2727 | OG | SER | 141 | 166.899 | 45.297 | 75.639 | 1.00 | 60.50 | H |
| ATOM | 2728 | C | SER | 141 | 167.726 | 43.431 | 73.432 | 1.00 | 75.37 | H |
| ATOM | 2729 | O | SER | 141 | 168.173 | 42.413 | 72.896 | 1.00 | 88.08 | H |
| ATOM | 2730 | N | MET | 142 | 166.479 | 43.787 | 73.391 | 1.00 | 59.56 | H |
| ATOM | 2731 | CA | MET | 142 | 165.449 | 42.970 | 72.766 | 1.00 | 44.97 | H |
| ATOM | 2732 | CB | MET | 142 | 164.206 | 43.807 | 72.516 | 1.00 | 56.70 | H |
| ATOM | 2733 | CG | MET | 142 | 163.645 | 44.397 | 73.800 | 1.00 | 86.09 | H |
| ATOM | 2734 | SD | MET | 142 | 162.177 | 45.354 | 73.535 | 1.00 | 99.97 | H |
| ATOM | 2735 | CE | MET | 142 | 162.239 | 46.814 | 74.546 | 1.00 | 99.42 | H |
| ATOM | 2736 | C | MET | 142 | 165.871 | 42.372 | 71.432 | 1.00 | 32.94 | H |
| ATOM | 2737 | O | MET | 142 | 166.780 | 42.880 | 70.772 | 1.00 | 33.63 | H |
| ATOM | 2738 | N | VAL | 143 | 165.183 | 41.304 | 71.027 | 1.00 | 27.18 | H |
| ATOM | 2739 | CA | VAL | 143 | 165.501 | 40.615 | 69.779 | 1.00 | 24.76 | H |
| ATOM | 2740 | CB | VAL | 143 | 166.197 | 39.272 | 70.065 | 1.00 | 10.57 | H |
| ATOM | 2741 | CG1 | VAL | 143 | 165.186 | 38.268 | 70.594 | 1.00 | 34.15 | H |
| ATOM | 2742 | CG2 | VAL | 143 | 166.872 | 38.750 | 68.800 | 1.00 | 21.19 | H |
| ATOM | 2743 | C | VAL | 143 | 164.299 | 40.345 | 68.871 | 1.00 | 32.37 | H |
| ATOM | 2744 | O | VAL | 143 | 163.150 | 40.451 | 69.293 | 1.00 | 31.65 | H |
| ATOM | 2745 | N | THR | 144 | 164.588 | 39.981 | 67.623 | 1.00 | 32.76 | H |
| ATOM | 2746 | CA | THR | 144 | 163.561 | 39.686 | 66.630 | 1.00 | 32.18 | H |
| ATOM | 2747 | CB | THR | 144 | 163.459 | 40.810 | 65.580 | 1.00 | 23.79 | H |
| ATOM | 2748 | OG1 | THR | 144 | 162.934 | 41.991 | 66.196 | 1.00 | 53.98 | H |

TABLE 4-continued

Co-ordinates of the CD28/5.11A1 crystal structure

| ATOM | 2749 | CG2 | THR | 144 | 162.543 | 40.394 | 64.436 | 1.00 | 20.69 | H |
|---|---|---|---|---|---|---|---|---|---|---|
| ATOM | 2750 | C | THR | 144 | 163.855 | 38.384 | 65.891 | 1.00 | 39.99 | H |
| ATOM | 2751 | O | THR | 144 | 164.958 | 38.178 | 65.384 | 1.00 | 46.16 | H |
| ATOM | 2752 | N | LEU | 145 | 162.858 | 37.507 | 65.830 | 1.00 | 32.72 | H |
| ATOM | 2753 | CA | LEU | 145 | 163.004 | 36.237 | 65.138 | 1.00 | 13.00 | H |
| ATOM | 2754 | CB | LEU | 145 | 162.645 | 35.082 | 66.062 | 1.00 | 22.16 | H |
| ATOM | 2755 | CG | LEU | 145 | 163.748 | 34.615 | 67.003 | 1.00 | 24.64 | H |
| ATOM | 2756 | CD1 | LEU | 145 | 163.529 | 35.237 | 68.376 | 1.00 | 21.35 | H |
| ATOM | 2757 | CD2 | LEU | 145 | 163.736 | 33.095 | 67.084 | 1.00 | 18.63 | H |
| ATOM | 2758 | C | LEU | 145 | 162.064 | 36.220 | 63.948 | 1.00 | 24.06 | H |
| ATOM | 2759 | O | LEU | 145 | 161.188 | 37.073 | 63.831 | 1.00 | 32.59 | H |
| ATOM | 2760 | N | GLY | 146 | 162.244 | 35.240 | 63.072 | 1.00 | 32.97 | H |
| ATOM | 2761 | CA | GLY | 146 | 161.397 | 35.153 | 61.903 | 1.00 | 32.08 | H |
| ATOM | 2762 | C | GLY | 146 | 161.254 | 33.741 | 61.381 | 1.00 | 29.89 | H |
| ATOM | 2763 | O | GLY | 146 | 161.995 | 32.845 | 61.778 | 1.00 | 19.61 | H |
| ATOM | 2764 | N | CYS | 147 | 160.283 | 33.553 | 60.499 | 1.00 | 39.08 | H |
| ATOM | 2765 | CA | CYS | 147 | 160.023 | 32.258 | 59.885 | 1.00 | 38.87 | H |
| ATOM | 2766 | C | CYS | 147 | 159.696 | 32.518 | 58.425 | 1.00 | 30.42 | H |
| ATOM | 2767 | O | CYS | 147 | 158.934 | 33.431 | 58.109 | 1.00 | 37.75 | H |
| ATOM | 2768 | CB | CYS | 147 | 158.843 | 31.560 | 60.574 | 1.00 | 55.35 | H |
| ATOM | 2769 | SG | CYS | 147 | 159.313 | 30.021 | 61.435 | 1.00 | 81.70 | H |
| ATOM | 2770 | N | LEU | 148 | 160.288 | 31.730 | 57.536 | 1.00 | 28.82 | H |
| ATOM | 2771 | CA | LEU | 148 | 160.037 | 31.891 | 56.115 | 1.00 | 27.56 | H |
| ATOM | 2772 | CB | LEU | 148 | 161.363 | 31.967 | 55.352 | 1.00 | 34.75 | H |
| ATOM | 2773 | CG | LEU | 148 | 161.254 | 32.129 | 53.831 | 1.00 | 34.95 | H |
| ATOM | 2774 | CD1 | LEU | 148 | 160.549 | 33.425 | 53.488 | 1.00 | 18.93 | H |
| ATOM | 2775 | CD2 | LEU | 148 | 162.636 | 32.111 | 53.219 | 1.00 | 21.69 | H |
| ATOM | 2776 | C | LEU | 148 | 159.187 | 30.737 | 55.580 | 1.00 | 24.86 | H |
| ATOM | 2777 | O | LEU | 148 | 159.576 | 29.572 | 55.663 | 1.00 | 30.70 | H |
| ATOM | 2778 | N | VAL | 149 | 158.020 | 31.077 | 55.045 | 1.00 | 27.57 | H |
| ATOM | 2779 | CA | VAL | 149 | 157.091 | 30.096 | 54.487 | 1.00 | 25.23 | H |
| ATOM | 2780 | CB | VAL | 149 | 155.658 | 30.376 | 54.969 | 1.00 | 3.47 | H |
| ATOM | 2781 | CG1 | VAL | 149 | 154.800 | 29.127 | 54.827 | 1.00 | 25.66 | H |
| ATOM | 2782 | CG2 | VAL | 149 | 155.695 | 30.830 | 56.417 | 1.00 | 15.58 | H |
| ATOM | 2783 | C | VAL | 149 | 157.152 | 30.207 | 52.969 | 1.00 | 43.19 | H |
| ATOM | 2784 | O | VAL | 149 | 156.520 | 31.080 | 52.375 | 1.00 | 55.54 | H |
| ATOM | 2785 | N | LYS | 150 | 157.906 | 29.313 | 52.341 | 1.00 | 45.51 | H |
| ATOM | 2786 | CA | LYS | 150 | 158.078 | 29.377 | 50.897 | 1.00 | 36.67 | H |
| ATOM | 2787 | CB | LYS | 150 | 159.572 | 29.376 | 50.570 | 1.00 | 23.27 | H |
| ATOM | 2788 | CG | LYS | 150 | 159.950 | 30.226 | 49.366 | 1.00 | 37.80 | H |
| ATOM | 2789 | CD | LYS | 150 | 161.441 | 30.145 | 49.070 | 1.00 | 45.44 | H |
| ATOM | 2790 | CE | LYS | 150 | 161.689 | 29.729 | 47.631 | 1.00 | 47.90 | H |
| ATOM | 2791 | NZ | LYS | 150 | 163.035 | 30.147 | 47.149 | 1.00 | 74.67 | H |
| ATOM | 2792 | C | LYS | 150 | 157.393 | 28.322 | 50.047 | 1.00 | 47.62 | H |
| ATOM | 2793 | O | LYS | 150 | 157.086 | 27.225 | 50.503 | 1.00 | 61.91 | H |
| ATOM | 2794 | N | GLY | 151 | 157.172 | 28.686 | 48.789 | 1.00 | 52.19 | H |
| ATOM | 2795 | CA | GLY | 151 | 156.562 | 27.808 | 47.805 | 1.00 | 56.42 | H |
| ATOM | 2796 | C | GLY | 151 | 155.344 | 26.981 | 48.176 | 1.00 | 65.95 | H |
| ATOM | 2797 | O | GLY | 151 | 155.404 | 25.751 | 48.146 | 1.00 | 83.19 | H |
| ATOM | 2798 | N | TYR | 152 | 154.238 | 27.641 | 48.522 | 1.00 | 68.59 | H |
| ATOM | 2799 | CA | TYR | 152 | 153.018 | 26.919 | 48.866 | 1.00 | 57.51 | H |
| ATOM | 2800 | CB | TYR | 152 | 152.646 | 27.131 | 50.342 | 1.00 | 55.56 | H |
| ATOM | 2801 | CG | TYR | 152 | 152.211 | 28.529 | 50.695 | 1.00 | 49.75 | H |
| ATOM | 2802 | CD1 | TYR | 152 | 150.893 | 28.938 | 50.497 | 1.00 | 37.14 | H |
| ATOM | 2803 | CE1 | TYR | 152 | 150.474 | 30.222 | 50.847 | 1.00 | 37.53 | H |
| ATOM | 2804 | CD2 | TYR | 152 | 153.104 | 29.437 | 51.250 | 1.00 | 44.59 | H |
| ATOM | 2805 | CE2 | TYR | 152 | 152.696 | 30.726 | 51.605 | 1.00 | 49.92 | H |
| ATOM | 2806 | CZ | TYR | 152 | 151.379 | 31.107 | 51.400 | 1.00 | 51.57 | H |
| ATOM | 2807 | OH | TYR | 152 | 150.967 | 32.371 | 51.745 | 1.00 | 62.33 | H |
| ATOM | 2808 | C | TYR | 152 | 151.874 | 27.358 | 47.965 | 1.00 | 48.01 | H |
| ATOM | 2809 | O | TYR | 152 | 151.962 | 28.386 | 47.291 | 1.00 | 28.34 | H |
| ATOM | 2810 | N | PHE | 153 | 150.810 | 26.567 | 47.947 | 1.00 | 50.83 | H |
| ATOM | 2811 | CA | PHE | 153 | 149.646 | 26.857 | 47.125 | 1.00 | 59.21 | H |
| ATOM | 2812 | CB | PHE | 153 | 150.003 | 26.728 | 45.646 | 1.00 | 64.09 | H |
| ATOM | 2813 | CG | PHE | 153 | 148.926 | 27.214 | 44.725 | 1.00 | 66.51 | H |
| ATOM | 2814 | CD1 | PHE | 153 | 148.786 | 28.571 | 44.464 | 1.00 | 66.83 | H |
| ATOM | 2815 | CD2 | PHE | 153 | 148.036 | 26.323 | 44.147 | 1.00 | 60.06 | H |
| ATOM | 2816 | CE1 | PHE | 153 | 147.770 | 29.037 | 43.638 | 1.00 | 55.52 | H |
| ATOM | 2817 | CE2 | PHE | 153 | 147.013 | 26.775 | 43.316 | 1.00 | 50.07 | H |
| ATOM | 2818 | CZ | PHE | 153 | 146.880 | 28.138 | 43.061 | 1.00 | 49.86 | H |
| ATOM | 2819 | C | PHE | 153 | 148.499 | 25.907 | 47.449 | 1.00 | 52.00 | H |
| ATOM | 2820 | O | PHE | 153 | 148.709 | 24.702 | 47.619 | 1.00 | 57.40 | H |
| ATOM | 2821 | N | PRO | 154 | 147.265 | 26.436 | 47.538 | 1.00 | 46.46 | H |
| ATOM | 2822 | CD | PRO | 154 | 146.057 | 25.644 | 47.815 | 1.00 | 39.60 | H |
| ATOM | 2823 | CA | PRO | 154 | 146.931 | 27.851 | 47.353 | 1.00 | 44.22 | H |
| ATOM | 2824 | CB | PRO | 154 | 145.533 | 27.795 | 46.772 | 1.00 | 48.46 | H |
| ATOM | 2825 | CG | PRO | 154 | 144.923 | 26.614 | 47.482 | 1.00 | 49.48 | H |

TABLE 4-continued

Co-ordinates of the CD28/5.11A1 crystal structure

| ATOM | 2826 | C | PRO | 154 | 146.932 | 28.559 | 48.694 | 1.00 | 48.75 | H |
|---|---|---|---|---|---|---|---|---|---|---|
| ATOM | 2827 | O | PRO | 154 | 147.255 | 27.958 | 49.722 | 1.00 | 45.97 | H |
| ATOM | 2828 | N | GLU | 155 | 146.573 | 29.835 | 48.683 | 1.00 | 45.51 | H |
| ATOM | 2829 | CA | GLU | 155 | 146.508 | 30.585 | 49.927 | 1.00 | 46.54 | H |
| ATOM | 2830 | CB | GLU | 155 | 146.287 | 32.072 | 49.649 | 1.00 | 42.15 | H |
| ATOM | 2831 | CG | GLU | 155 | 147.565 | 32.888 | 49.519 | 1.00 | 52.55 | H |
| ATOM | 2832 | CD | GLU | 155 | 147.866 | 33.696 | 50.773 | 1.00 | 54.96 | H |
| ATOM | 2833 | OE1 | GLU | 155 | 148.005 | 33.096 | 51.862 | 1.00 | 38.84 | H |
| ATOM | 2834 | OE2 | GLU | 155 | 147.964 | 34.938 | 50.667 | 1.00 | 57.00 | H |
| ATOM | 2835 | C | GLU | 155 | 145.292 | 30.003 | 50.625 | 1.00 | 43.57 | H |
| ATOM | 2836 | O | GLU | 155 | 144.445 | 29.388 | 49.974 | 1.00 | 52.29 | H |
| ATOM | 2837 | N | PRO | 156 | 145.203 | 30.148 | 51.953 | 1.00 | 28.63 | H |
| ATOM | 2838 | CD | PRO | 156 | 143.990 | 29.751 | 52.682 | 1.00 | 21.85 | H |
| ATOM | 2839 | CA | PRO | 156 | 146.134 | 30.804 | 52.873 | 1.00 | 32.78 | H |
| ATOM | 2840 | CB | PRO | 156 | 145.212 | 31.685 | 53.699 | 1.00 | 41.77 | H |
| ATOM | 2841 | CG | PRO | 156 | 143.896 | 30.824 | 53.775 | 1.00 | 10.50 | H |
| ATOM | 2842 | C | PRO | 156 | 146.879 | 29.797 | 53.776 | 1.00 | 40.11 | H |
| ATOM | 2843 | O | PRO | 156 | 146.757 | 28.583 | 53.613 | 1.00 | 30.70 | H |
| ATOM | 2844 | N | VAL | 157 | 147.641 | 30.333 | 54.722 | 1.00 | 47.16 | H |
| ATOM | 2845 | CA | VAL | 157 | 148.383 | 29.540 | 55.693 | 1.00 | 58.27 | H |
| ATOM | 2846 | CB | VAL | 157 | 149.898 | 29.452 | 55.362 | 1.00 | 52.20 | H |
| ATOM | 2847 | CG1 | VAL | 157 | 150.106 | 28.797 | 54.011 | 1.00 | 56.74 | H |
| ATOM | 2848 | CG2 | VAL | 157 | 150.525 | 30.837 | 55.387 | 1.00 | 45.36 | H |
| ATOM | 2849 | C | VAL | 157 | 148.239 | 30.258 | 57.032 | 1.00 | 68.19 | H |
| ATOM | 2850 | O | VAL | 157 | 147.993 | 31.466 | 57.076 | 1.00 | 78.90 | H |
| ATOM | 2851 | N | THR | 158 | 148.395 | 29.520 | 58.122 | 1.00 | 68.08 | H |
| ATOM | 2852 | CA | THR | 158 | 148.282 | 30.116 | 59.442 | 1.00 | 63.24 | H |
| ATOM | 2853 | CB | THR | 158 | 147.209 | 29.396 | 60.279 | 1.00 | 61.67 | H |
| ATOM | 2854 | OG1 | THR | 158 | 145.962 | 29.426 | 59.573 | 1.00 | 52.99 | H |
| ATOM | 2855 | CG2 | THR | 158 | 147.034 | 30.079 | 61.632 | 1.00 | 56.86 | H |
| ATOM | 2856 | C | THR | 158 | 149.623 | 30.035 | 60.154 | 1.00 | 64.54 | H |
| ATOM | 2857 | O | THR | 158 | 150.187 | 28.954 | 60.312 | 1.00 | 65.02 | H |
| ATOM | 2858 | N | VAL | 159 | 150.131 | 31.190 | 60.571 | 1.00 | 48.72 | H |
| ATOM | 2859 | CA | VAL | 159 | 151.409 | 31.266 | 61.256 | 1.00 | 38.04 | H |
| ATOM | 2860 | CB | VAL | 159 | 152.384 | 32.209 | 60.517 | 1.00 | 35.68 | H |
| ATOM | 2861 | CG1 | VAL | 159 | 153.745 | 32.207 | 61.195 | 1.00 | 13.69 | H |
| ATOM | 2862 | CG2 | VAL | 159 | 152.520 | 31.765 | 59.072 | 1.00 | 35.33 | H |
| ATOM | 2863 | C | VAL | 159 | 151.239 | 31.746 | 62.690 | 1.00 | 32.37 | H |
| ATOM | 2864 | O | VAL | 159 | 150.940 | 32.917 | 62.951 | 1.00 | 46.22 | H |
| ATOM | 2865 | N | THR | 160 | 151.430 | 30.812 | 63.616 | 1.00 | 34.81 | H |
| ATOM | 2866 | CA | THR | 160 | 151.316 | 31.088 | 65.037 | 1.00 | 30.02 | H |
| ATOM | 2867 | CB | THR | 160 | 150.305 | 30.146 | 65.702 | 1.00 | 29.19 | H |
| ATOM | 2868 | OG1 | THR | 160 | 149.788 | 29.230 | 64.729 | 1.00 | 41.86 | H |
| ATOM | 2869 | CG2 | THR | 160 | 149.165 | 30.943 | 66.295 | 1.00 | 40.64 | H |
| ATOM | 2870 | C | THR | 160 | 152.676 | 30.872 | 65.681 | 1.00 | 28.21 | H |
| ATOM | 2871 | O | THR | 160 | 153.501 | 30.118 | 65.169 | 1.00 | 44.55 | H |
| ATOM | 2872 | N | TRP | 161 | 152.909 | 31.546 | 66.800 | 1.00 | 43.52 | H |
| ATOM | 2873 | CA | TRP | 161 | 154.171 | 31.404 | 67.506 | 1.00 | 54.28 | H |
| ATOM | 2874 | CB | TRP | 161 | 154.833 | 32.773 | 67.672 | 1.00 | 46.91 | H |
| ATOM | 2875 | CG | TRP | 161 | 155.369 | 33.327 | 66.379 | 1.00 | 31.10 | H |
| ATOM | 2876 | CD2 | TRP | 161 | 156.648 | 33.059 | 65.790 | 1.00 | 39.01 | H |
| ATOM | 2877 | CE2 | TRP | 161 | 156.710 | 33.782 | 64.579 | 1.00 | 43.01 | H |
| ATOM | 2878 | CE3 | TRP | 161 | 157.748 | 32.277 | 66.169 | 1.00 | 31.39 | H |
| ATOM | 2879 | CD1 | TRP | 161 | 154.727 | 34.179 | 65.525 | 1.00 | 30.94 | H |
| ATOM | 2880 | NE1 | TRP | 161 | 155.525 | 34.458 | 64.443 | 1.00 | 31.32 | H |
| ATOM | 2881 | CZ2 | TRP | 161 | 157.829 | 33.749 | 63.741 | 1.00 | 35.89 | H |
| ATOM | 2882 | CZ3 | TRP | 161 | 158.861 | 32.242 | 65.335 | 1.00 | 23.31 | H |
| ATOM | 2883 | CH2 | TRP | 161 | 158.893 | 32.975 | 64.134 | 1.00 | 38.71 | H |
| ATOM | 2884 | C | TRP | 161 | 153.920 | 30.746 | 68.862 | 1.00 | 57.21 | H |
| ATOM | 2885 | O | TRP | 161 | 153.157 | 31.255 | 69.691 | 1.00 | 61.27 | H |
| ATOM | 2886 | N | ASN | 162 | 154.569 | 29.602 | 69.071 | 1.00 | 56.37 | H |
| ATOM | 2887 | CA | ASN | 162 | 154.426 | 28.829 | 70.298 | 1.00 | 50.72 | H |
| ATOM | 2888 | CB | ASN | 162 | 154.818 | 29.676 | 71.515 | 1.00 | 39.98 | H |
| ATOM | 2889 | CG | ASN | 162 | 156.331 | 29.771 | 71.698 | 1.00 | 45.87 | H |
| ATOM | 2890 | OD1 | ASN | 162 | 157.103 | 29.298 | 70.854 | 1.00 | 61.54 | H |
| ATOM | 2891 | ND2 | ASN | 162 | 156.760 | 30.385 | 72.801 | 1.00 | 49.15 | H |
| ATOM | 2892 | C | ASN | 162 | 152.979 | 28.365 | 70.399 | 1.00 | 44.59 | H |
| ATOM | 2893 | O | ASN | 162 | 152.387 | 28.329 | 71.479 | 1.00 | 33.04 | H |
| ATOM | 2894 | N | SER | 163 | 152.419 | 28.021 | 69.242 | 1.00 | 55.71 | H |
| ATOM | 2895 | CA | SER | 163 | 151.048 | 27.541 | 69.133 | 1.00 | 65.28 | H |
| ATOM | 2896 | CB | SER | 163 | 150.858 | 26.313 | 70.021 | 1.00 | 69.26 | H |
| ATOM | 2897 | OG | SER | 163 | 151.917 | 25.391 | 69.823 | 1.00 | 87.88 | H |
| ATOM | 2898 | C | SER | 163 | 149.993 | 28.592 | 69.468 | 1.00 | 64.07 | H |
| ATOM | 2899 | O | SER | 163 | 148.799 | 28.363 | 69.267 | 1.00 | 71.86 | H |
| ATOM | 2900 | N | GLY | 164 | 150.430 | 29.744 | 69.970 | 1.00 | 56.72 | H |
| ATOM | 2901 | CA | GLY | 164 | 149.490 | 30.798 | 70.308 | 1.00 | 44.67 | H |
| ATOM | 2902 | C | GLY | 164 | 149.953 | 31.629 | 71.482 | 1.00 | 45.89 | H |

TABLE 4-continued

Co-ordinates of the CD28/5.11A1 crystal structure

| ATOM | 2903 | O   | GLY | 164 | 149.611 | 32.807 | 71.597 | 1.00 | 41.13 | H |
|------|------|-----|-----|-----|---------|--------|--------|------|-------|---|
| ATOM | 2904 | N   | SER | 165 | 150.739 | 31.011 | 72.355 | 1.00 | 56.45 | H |
| ATOM | 2905 | CA  | SER | 165 | 151.259 | 31.688 | 73.533 | 1.00 | 57.02 | H |
| ATOM | 2906 | CB  | SER | 165 | 152.169 | 30.745 | 74.316 | 1.00 | 62.37 | H |
| ATOM | 2907 | OG  | SER | 165 | 151.418 | 29.663 | 74.836 | 1.00 | 50.35 | H |
| ATOM | 2908 | C   | SER | 165 | 152.020 | 32.945 | 73.153 | 1.00 | 57.97 | H |
| ATOM | 2909 | O   | SER | 165 | 152.276 | 33.809 | 73.989 | 1.00 | 41.07 | H |
| ATOM | 2910 | N   | LEU | 166 | 152.385 | 33.049 | 71.883 | 1.00 | 64.03 | H |
| ATOM | 2911 | CA  | LEU | 166 | 153.102 | 34.227 | 71.421 | 1.00 | 56.74 | H |
| ATOM | 2912 | CB  | LEU | 166 | 154.493 | 33.841 | 70.923 | 1.00 | 37.44 | H |
| ATOM | 2913 | CG  | LEU | 166 | 155.626 | 34.088 | 71.922 | 1.00 | 41.79 | H |
| ATOM | 2914 | CD1 | LEU | 166 | 156.948 | 33.782 | 71.254 | 1.00 | 36.73 | H |
| ATOM | 2915 | CD2 | LEU | 166 | 155.598 | 35.532 | 72.416 | 1.00 | 58.45 | H |
| ATOM | 2916 | C   | LEU | 166 | 152.318 | 34.920 | 70.319 | 1.00 | 60.22 | H |
| ATOM | 2917 | O   | LEU | 166 | 152.399 | 34.547 | 69.147 | 1.00 | 63.00 | H |
| ATOM | 2918 | N   | SER | 167 | 151.547 | 35.928 | 70.708 | 1.00 | 65.96 | H |
| ATOM | 2919 | CA  | SER | 167 | 150.740 | 36.684 | 69.762 | 1.00 | 64.77 | H |
| ATOM | 2920 | CB  | SER | 167 | 149.255 | 36.347 | 69.946 | 1.00 | 66.65 | H |
| ATOM | 2921 | OG  | SER | 167 | 148.697 | 37.030 | 71.057 | 1.00 | 54.23 | H |
| ATOM | 2922 | C   | SER | 167 | 150.978 | 38.172 | 69.977 | 1.00 | 65.40 | H |
| ATOM | 2923 | O   | SER | 167 | 150.141 | 39.009 | 69.637 | 1.00 | 63.94 | H |
| ATOM | 2924 | N   | SER | 168 | 152.134 | 38.486 | 70.548 | 1.00 | 72.22 | H |
| ATOM | 2925 | CA  | SER | 168 | 152.515 | 39.868 | 70.814 | 1.00 | 66.97 | H |
| ATOM | 2926 | CB  | SER | 168 | 152.814 | 40.052 | 72.306 | 1.00 | 83.10 | H |
| ATOM | 2927 | OG  | SER | 168 | 153.476 | 41.282 | 72.551 | 1.00 | 92.96 | H |
| ATOM | 2928 | C   | SER | 168 | 153.754 | 40.212 | 69.997 | 1.00 | 58.05 | H |
| ATOM | 2929 | O   | SER | 168 | 154.694 | 39.422 | 69.922 | 1.00 | 58.07 | H |
| ATOM | 2930 | N   | GLY | 169 | 153.754 | 41.392 | 69.381 | 1.00 | 49.62 | H |
| ATOM | 2931 | CA  | GLY | 169 | 154.897 | 41.799 | 68.582 | 1.00 | 43.99 | H |
| ATOM | 2932 | C   | GLY | 169 | 155.088 | 40.916 | 67.366 | 1.00 | 44.05 | H |
| ATOM | 2933 | O   | GLY | 169 | 156.205 | 40.731 | 66.887 | 1.00 | 49.35 | H |
| ATOM | 2934 | N   | VAL | 170 | 153.991 | 40.366 | 66.862 | 1.00 | 45.75 | H |
| ATOM | 2935 | CA  | VAL | 170 | 154.058 | 39.506 | 65.697 | 1.00 | 34.35 | H |
| ATOM | 2936 | CB  | VAL | 170 | 153.135 | 38.291 | 65.854 | 1.00 | 29.09 | H |
| ATOM | 2937 | CG1 | VAL | 170 | 153.213 | 37.418 | 64.614 | 1.00 | 23.76 | H |
| ATOM | 2938 | CG2 | VAL | 170 | 153.539 | 37.492 | 67.079 | 1.00 | 30.40 | H |
| ATOM | 2939 | C   | VAL | 170 | 153.660 | 40.269 | 64.445 | 1.00 | 37.22 | H |
| ATOM | 2940 | O   | VAL | 170 | 152.732 | 41.074 | 64.460 | 1.00 | 35.69 | H |
| ATOM | 2941 | N   | HIS | 171 | 154.383 | 40.017 | 63.364 | 1.00 | 38.69 | H |
| ATOM | 2942 | CA  | HIS | 171 | 154.118 | 40.664 | 62.088 | 1.00 | 33.69 | H |
| ATOM | 2943 | CB  | HIS | 171 | 155.167 | 41.743 | 61.802 | 1.00 | 38.36 | H |
| ATOM | 2944 | CG  | HIS | 171 | 155.011 | 42.971 | 62.636 | 1.00 | 40.32 | H |
| ATOM | 2945 | CD2 | HIS | 171 | 155.806 | 44.055 | 62.783 | 1.00 | 49.35 | H |
| ATOM | 2946 | ND1 | HIS | 171 | 153.923 | 43.182 | 63.456 | 1.00 | 58.85 | H |
| ATOM | 2947 | CE1 | HIS | 171 | 154.053 | 44.343 | 64.068 | 1.00 | 58.33 | H |
| ATOM | 2948 | NE2 | HIS | 171 | 155.189 | 44.896 | 63.678 | 1.00 | 51.33 | H |
| ATOM | 2949 | C   | HIS | 171 | 154.172 | 39.623 | 60.985 | 1.00 | 37.90 | H |
| ATOM | 2950 | O   | HIS | 171 | 155.251 | 39.144 | 60.626 | 1.00 | 52.25 | H |
| ATOM | 2951 | N   | THR | 172 | 153.012 | 39.250 | 60.465 | 1.00 | 36.40 | H |
| ATOM | 2952 | CA  | THR | 172 | 152.974 | 38.289 | 59.379 | 1.00 | 37.99 | H |
| ATOM | 2953 | CB  | THR | 172 | 151.865 | 37.251 | 59.576 | 1.00 | 30.37 | H |
| ATOM | 2954 | OG1 | THR | 172 | 152.160 | 36.452 | 60.729 | 1.00 | 16.22 | H |
| ATOM | 2955 | CG2 | THR | 172 | 151.760 | 36.351 | 58.356 | 1.00 | 18.72 | H |
| ATOM | 2956 | C   | THR | 172 | 152.708 | 39.097 | 58.118 | 1.00 | 43.29 | H |
| ATOM | 2957 | O   | THR | 172 | 151.690 | 39.782 | 58.011 | 1.00 | 42.87 | H |
| ATOM | 2958 | N   | PHE | 173 | 153.635 | 39.031 | 57.172 | 1.00 | 42.03 | H |
| ATOM | 2959 | CA  | PHE | 173 | 153.500 | 39.783 | 55.935 | 1.00 | 41.59 | H |
| ATOM | 2960 | CB  | PHE | 173 | 154.889 | 40.102 | 55.372 | 1.00 | 69.43 | H |
| ATOM | 2961 | CG  | PHE | 173 | 155.707 | 40.945 | 56.285 | 1.00 | 69.16 | H |
| ATOM | 2962 | CD1 | PHE | 173 | 155.577 | 42.326 | 56.264 | 1.00 | 69.14 | H |
| ATOM | 2963 | CD2 | PHE | 173 | 156.555 | 40.360 | 57.216 | 1.00 | 71.48 | H |
| ATOM | 2964 | CE1 | PHE | 173 | 156.277 | 43.117 | 57.165 | 1.00 | 47.16 | H |
| ATOM | 2965 | CE2 | PHE | 173 | 157.260 | 41.140 | 58.122 | 1.00 | 46.77 | H |
| ATOM | 2966 | CZ  | PHE | 173 | 157.120 | 42.523 | 58.097 | 1.00 | 50.06 | H |
| ATOM | 2967 | C   | PHE | 173 | 152.651 | 39.103 | 54.870 | 1.00 | 51.94 | H |
| ATOM | 2968 | O   | PHE | 173 | 152.670 | 37.881 | 54.715 | 1.00 | 45.37 | H |
| ATOM | 2969 | N   | PRO | 174 | 151.873 | 39.901 | 54.128 | 1.00 | 47.56 | H |
| ATOM | 2970 | CD  | PRO | 174 | 151.760 | 41.360 | 54.268 | 1.00 | 40.08 | H |
| ATOM | 2971 | CA  | PRO | 174 | 151.010 | 39.369 | 53.070 | 1.00 | 39.95 | H |
| ATOM | 2972 | CB  | PRO | 174 | 150.417 | 40.618 | 52.419 | 1.00 | 38.02 | H |
| ATOM | 2973 | CG  | PRO | 174 | 151.234 | 41.778 | 52.945 | 1.00 | 41.70 | H |
| ATOM | 2974 | C   | PRO | 174 | 151.793 | 38.515 | 52.080 | 1.00 | 34.30 | H |
| ATOM | 2975 | O   | PRO | 174 | 152.926 | 38.844 | 51.719 | 1.00 | 38.61 | H |
| ATOM | 2976 | N   | ALA | 175 | 151.191 | 37.407 | 51.655 | 1.00 | 33.98 | H |
| ATOM | 2977 | CA  | ALA | 175 | 151.834 | 36.505 | 50.711 | 1.00 | 28.24 | H |
| ATOM | 2978 | CB  | ALA | 175 | 150.947 | 35.303 | 50.455 | 1.00 | 24.04 | H |
| ATOM | 2979 | C   | ALA | 175 | 152.106 | 37.226 | 49.411 | 1.00 | 43.10 | H |

TABLE 4-continued

Co-ordinates of the CD28/5.11A1 crystal structure

| ATOM | 2980 | O   | ALA | 175 | 151.420 | 38.182 | 49.064 | 1.00 | 41.83 | H |
|------|------|-----|-----|-----|---------|--------|--------|------|-------|---|
| ATOM | 2981 | N   | VAL | 176 | 153.119 | 36.758 | 48.691 | 1.00 | 47.34 | H |
| ATOM | 2982 | CA  | VAL | 176 | 153.479 | 37.340 | 47.409 | 1.00 | 46.04 | H |
| ATOM | 2983 | CB  | VAL | 176 | 154.660 | 38.335 | 47.546 | 1.00 | 48.76 | H |
| ATOM | 2984 | CG1 | VAL | 176 | 155.822 | 37.686 | 48.280 | 1.00 | 50.38 | H |
| ATOM | 2985 | CG2 | VAL | 176 | 155.100 | 38.809 | 46.167 | 1.00 | 64.07 | H |
| ATOM | 2986 | C   | VAL | 176 | 153.858 | 36.205 | 46.462 | 1.00 | 36.12 | H |
| ATOM | 2987 | O   | VAL | 176 | 154.544 | 35.263 | 46.857 | 1.00 | 30.73 | H |
| ATOM | 2988 | N   | LEU | 177 | 153.392 | 36.298 | 45.220 | 1.00 | 48.02 | H |
| ATOM | 2989 | CA  | LEU | 177 | 153.647 | 35.282 | 44.205 | 1.00 | 60.32 | H |
| ATOM | 2990 | CB  | LEU | 177 | 152.686 | 35.467 | 43.036 | 1.00 | 39.51 | H |
| ATOM | 2991 | CG  | LEU | 177 | 152.048 | 34.165 | 42.557 | 1.00 | 27.99 | H |
| ATOM | 2992 | CD1 | LEU | 177 | 151.014 | 33.698 | 43.572 | 1.00 | 30.57 | H |
| ATOM | 2993 | CD2 | LEU | 177 | 151.410 | 34.378 | 41.197 | 1.00 | 38.71 | H |
| ATOM | 2994 | C   | LEU | 177 | 155.074 | 35.257 | 43.679 | 1.00 | 73.61 | H |
| ATOM | 2995 | O   | LEU | 177 | 155.621 | 36.275 | 43.254 | 1.00 | 78.42 | H |
| ATOM | 2996 | N   | GLN | 178 | 155.669 | 34.074 | 43.694 | 1.00 | 79.08 | H |
| ATOM | 2997 | CA  | GLN | 178 | 157.031 | 33.895 | 43.227 | 1.00 | 95.82 | H |
| ATOM | 2998 | CB  | GLN | 178 | 157.981 | 33.932 | 44.432 | 1.00 | 99.99 | H |
| ATOM | 2999 | CG  | GLN | 178 | 159.244 | 33.098 | 44.308 | 1.00 | 99.99 | H |
| ATOM | 3000 | CD  | GLN | 178 | 160.357 | 33.583 | 45.224 | 1.00 | 99.99 | H |
| ATOM | 3001 | OE1 | GLN | 178 | 160.327 | 33.367 | 46.439 | 1.00 | 98.52 | H |
| ATOM | 3002 | NE2 | GLN | 178 | 161.350 | 34.244 | 44.637 | 1.00 | 99.99 | H |
| ATOM | 3003 | C   | GLN | 178 | 157.123 | 32.564 | 42.483 | 1.00 | 99.99 | H |
| ATOM | 3004 | O   | GLN | 178 | 157.289 | 31.504 | 43.092 | 1.00 | 99.97 | H |
| ATOM | 3005 | N   | SER | 179 | 156.984 | 32.637 | 41.159 | 1.00 | 96.75 | H |
| ATOM | 3006 | CA  | SER | 179 | 157.047 | 31.465 | 40.289 | 1.00 | 87.63 | H |
| ATOM | 3007 | CB  | SER | 179 | 158.307 | 30.641 | 40.589 | 1.00 | 93.06 | H |
| ATOM | 3008 | OG  | SER | 179 | 159.098 | 30.472 | 39.425 | 1.00 | 67.71 | H |
| ATOM | 3009 | C   | SER | 179 | 155.815 | 30.580 | 40.430 | 1.00 | 81.94 | H |
| ATOM | 3010 | O   | SER | 179 | 155.927 | 29.351 | 40.461 | 1.00 | 85.05 | H |
| ATOM | 3011 | N   | ASP | 180 | 154.649 | 31.217 | 40.517 | 1.00 | 61.79 | H |
| ATOM | 3012 | CA  | ASP | 180 | 153.367 | 30.518 | 40.643 | 1.00 | 53.42 | H |
| ATOM | 3013 | CB  | ASP | 180 | 153.284 | 29.372 | 39.633 | 1.00 | 63.39 | H |
| ATOM | 3014 | CG  | ASP | 180 | 152.902 | 29.846 | 38.251 | 1.00 | 90.41 | H |
| ATOM | 3015 | OD1 | ASP | 180 | 151.736 | 30.262 | 38.066 | 1.00 | 95.28 | H |
| ATOM | 3016 | OD2 | ASP | 180 | 153.771 | 29.804 | 37.350 | 1.00 | 91.35 | H |
| ATOM | 3017 | C   | ASP | 180 | 153.036 | 29.975 | 42.030 | 1.00 | 48.83 | H |
| ATOM | 3018 | O   | ASP | 180 | 151.965 | 29.414 | 42.234 | 1.00 | 32.55 | H |
| ATOM | 3019 | N   | LEU | 181 | 153.955 | 30.120 | 42.976 | 1.00 | 49.73 | H |
| ATOM | 3020 | CA  | LEU | 181 | 153.716 | 29.646 | 44.332 | 1.00 | 42.63 | H |
| ATOM | 3021 | CB  | LEU | 181 | 154.751 | 28.594 | 44.730 | 1.00 | 51.61 | H |
| ATOM | 3022 | CG  | LEU | 181 | 154.817 | 27.335 | 43.865 | 1.00 | 45.19 | H |
| ATOM | 3023 | CD1 | LEU | 181 | 155.788 | 26.358 | 44.503 | 1.00 | 36.88 | H |
| ATOM | 3024 | CD2 | LEU | 181 | 153.429 | 26.712 | 43.723 | 1.00 | 49.90 | H |
| ATOM | 3025 | C   | LEU | 181 | 153.811 | 30.840 | 45.265 | 1.00 | 36.09 | H |
| ATOM | 3026 | O   | LEU | 181 | 154.401 | 31.859 | 44.914 | 1.00 | 47.48 | H |
| ATOM | 3027 | N   | TYR | 182 | 153.235 | 30.711 | 46.454 | 1.00 | 34.48 | H |
| ATOM | 3028 | CA  | TYR | 182 | 153.254 | 31.803 | 47.410 | 1.00 | 34.99 | H |
| ATOM | 3029 | CB  | TYR | 182 | 151.965 | 31.824 | 48.221 | 1.00 | 43.15 | H |
| ATOM | 3030 | CG  | TYR | 182 | 150.768 | 32.266 | 47.431 | 1.00 | 26.23 | H |
| ATOM | 3031 | CD1 | TYR | 182 | 150.514 | 33.621 | 47.219 | 1.00 | 24.46 | H |
| ATOM | 3032 | CE1 | TYR | 182 | 149.437 | 34.034 | 46.455 | 1.00 | 26.76 | H |
| ATOM | 3033 | CD2 | TYR | 182 | 149.908 | 31.332 | 46.864 | 1.00 | 28.50 | H |
| ATOM | 3034 | CE2 | TYR | 182 | 148.827 | 31.733 | 46.097 | 1.00 | 40.52 | H |
| ATOM | 3035 | CZ  | TYR | 182 | 148.596 | 33.085 | 45.893 | 1.00 | 31.63 | H |
| ATOM | 3036 | OH  | TYR | 182 | 147.538 | 33.480 | 45.108 | 1.00 | 52.38 | H |
| ATOM | 3037 | C   | TYR | 182 | 154.410 | 31.694 | 48.361 | 1.00 | 34.67 | H |
| ATOM | 3038 | O   | TYR | 182 | 154.902 | 30.604 | 48.642 | 1.00 | 30.57 | H |
| ATOM | 3039 | N   | THR | 183 | 154.842 | 32.844 | 48.860 | 1.00 | 46.64 | H |
| ATOM | 3040 | CA  | THR | 183 | 155.915 | 32.914 | 49.838 | 1.00 | 32.69 | H |
| ATOM | 3041 | CB  | THR | 183 | 157.250 | 33.348 | 49.232 | 1.00 | 32.26 | H |
| ATOM | 3042 | OG1 | THR | 183 | 157.678 | 32.396 | 48.250 | 1.00 | 39.58 | H |
| ATOM | 3043 | CG2 | THR | 183 | 158.288 | 33.442 | 50.318 | 1.00 | 33.99 | H |
| ATOM | 3044 | C   | THR | 183 | 155.483 | 33.981 | 50.823 | 1.00 | 28.00 | H |
| ATOM | 3045 | O   | THR | 183 | 154.927 | 35.009 | 50.440 | 1.00 | 38.20 | H |
| ATOM | 3046 | N   | LEU | 184 | 155.737 | 33.743 | 52.097 | 1.00 | 27.54 | H |
| ATOM | 3047 | CA  | LEU | 184 | 155.353 | 34.696 | 53.114 | 1.00 | 30.19 | H |
| ATOM | 3048 | CB  | LEU | 184 | 153.926 | 34.380 | 53.559 | 1.00 | 30.95 | H |
| ATOM | 3049 | CG  | LEU | 184 | 153.483 | 34.617 | 54.996 | 1.00 | 46.42 | H |
| ATOM | 3050 | CD1 | LEU | 184 | 151.969 | 34.814 | 55.016 | 1.00 | 25.32 | H |
| ATOM | 3051 | CD2 | LEU | 184 | 153.891 | 33.439 | 55.867 | 1.00 | 45.00 | H |
| ATOM | 3052 | C   | LEU | 184 | 156.337 | 34.598 | 54.271 | 1.00 | 30.88 | H |
| ATOM | 3053 | O   | LEU | 184 | 157.075 | 33.623 | 54.383 | 1.00 | 17.03 | H |
| ATOM | 3054 | N   | SER | 185 | 156.370 | 35.613 | 55.122 | 1.00 | 29.51 | H |
| ATOM | 3055 | CA  | SER | 185 | 157.278 | 35.599 | 56.252 | 1.00 | 24.01 | H |
| ATOM | 3056 | CB  | SER | 185 | 158.573 | 36.350 | 55.914 | 1.00 | 21.45 | H |

TABLE 4-continued

Co-ordinates of the CD28/5.11A1 crystal structure

| ATOM | 3057 | OG | SER | 185 | 158.354 | 37.749 | 55.844 | 1.00 | 46.01 | H |
|---|---|---|---|---|---|---|---|---|---|---|
| ATOM | 3058 | C | SER | 185 | 156.610 | 36.235 | 57.449 | 1.00 | 28.20 | H |
| ATOM | 3059 | O | SER | 185 | 155.828 | 37.173 | 57.312 | 1.00 | 26.88 | H |
| ATOM | 3060 | N | SER | 186 | 156.917 | 35.710 | 58.625 | 1.00 | 38.58 | H |
| ATOM | 3061 | CA | SER | 186 | 156.354 | 36.229 | 59.853 | 1.00 | 34.31 | H |
| ATOM | 3062 | CB | SER | 186 | 155.389 | 35.210 | 60.463 | 1.00 | 37.09 | H |
| ATOM | 3063 | OG | SER | 186 | 154.862 | 35.685 | 61.689 | 1.00 | 44.43 | H |
| ATOM | 3064 | C | SER | 186 | 157.487 | 36.510 | 60.822 | 1.00 | 25.01 | H |
| ATOM | 3065 | O | SER | 186 | 158.356 | 35.663 | 61.036 | 1.00 | 38.29 | H |
| ATOM | 3066 | N | SER | 187 | 157.491 | 37.703 | 61.395 | 1.00 | 15.70 | H |
| ATOM | 3067 | CA | SER | 187 | 158.524 | 38.066 | 62.348 | 1.00 | 25.23 | H |
| ATOM | 3068 | CB | SER | 187 | 159.100 | 39.440 | 62.008 | 1.00 | 18.98 | H |
| ATOM | 3069 | OG | SER | 187 | 158.187 | 40.466 | 62.346 | 1.00 | 36.58 | H |
| ATOM | 3070 | C | SER | 187 | 157.905 | 38.092 | 63.739 | 1.00 | 27.63 | H |
| ATOM | 3071 | O | SER | 187 | 156.692 | 38.240 | 63.882 | 1.00 | 26.02 | H |
| ATOM | 3072 | N | VAL | 188 | 158.739 | 37.926 | 64.762 | 1.00 | 31.12 | H |
| ATOM | 3073 | CA | VAL | 188 | 158.266 | 37.950 | 66.141 | 1.00 | 31.94 | H |
| ATOM | 3074 | CB | VAL | 188 | 157.996 | 36.524 | 66.681 | 1.00 | 32.97 | H |
| ATOM | 3075 | CG1 | VAL | 188 | 159.298 | 35.776 | 66.878 | 1.00 | 21.32 | H |
| ATOM | 3076 | CG2 | VAL | 188 | 157.221 | 36.606 | 67.987 | 1.00 | 48.09 | H |
| ATOM | 3077 | C | VAL | 188 | 159.284 | 38.646 | 67.030 | 1.00 | 29.00 | H |
| ATOM | 3078 | O | VAL | 188 | 160.469 | 38.322 | 67.016 | 1.00 | 18.81 | H |
| ATOM | 3079 | N | THR | 189 | 158.811 | 39.618 | 67.799 | 1.00 | 43.09 | H |
| ATOM | 3080 | CA | THR | 189 | 159.664 | 40.385 | 68.691 | 1.00 | 52.62 | H |
| ATOM | 3081 | CB | THR | 189 | 159.381 | 41.890 | 68.535 | 1.00 | 55.64 | H |
| ATOM | 3082 | OG1 | THR | 189 | 159.915 | 42.346 | 67.288 | 1.00 | 72.06 | H |
| ATOM | 3083 | CG2 | THR | 189 | 160.006 | 42.678 | 69.676 | 1.00 | 47.82 | H |
| ATOM | 3084 | C | THR | 189 | 159.450 | 39.981 | 70.147 | 1.00 | 47.05 | H |
| ATOM | 3085 | O | THR | 189 | 158.313 | 39.914 | 70.622 | 1.00 | 51.99 | H |
| ATOM | 3086 | N | VAL | 190 | 160.547 | 39.715 | 70.846 | 1.00 | 33.42 | H |
| ATOM | 3087 | CA | VAL | 190 | 160.489 | 39.327 | 72.251 | 1.00 | 49.20 | H |
| ATOM | 3088 | CB | VAL | 190 | 160.501 | 37.795 | 72.408 | 1.00 | 46.79 | H |
| ATOM | 3089 | CG1 | VAL | 190 | 159.222 | 37.205 | 71.839 | 1.00 | 24.58 | H |
| ATOM | 3090 | CG2 | VAL | 190 | 161.717 | 37.217 | 71.715 | 1.00 | 27.47 | H |
| ATOM | 3091 | C | VAL | 190 | 161.670 | 39.893 | 73.037 | 1.00 | 57.65 | H |
| ATOM | 3092 | O | VAL | 190 | 162.797 | 39.935 | 72.538 | 1.00 | 35.32 | H |
| ATOM | 3093 | N | PRO | 191 | 161.419 | 40.347 | 74.277 | 1.00 | 74.09 | H |
| ATOM | 3094 | CD | PRO | 191 | 160.096 | 40.363 | 74.931 | 1.00 | 85.05 | H |
| ATOM | 3095 | CA | PRO | 191 | 162.461 | 40.912 | 75.142 | 1.00 | 73.28 | H |
| ATOM | 3096 | CB | PRO | 191 | 161.769 | 41.033 | 76.496 | 1.00 | 85.43 | H |
| ATOM | 3097 | CG | PRO | 191 | 160.328 | 41.206 | 76.155 | 1.00 | 90.65 | H |
| ATOM | 3098 | C | PRO | 191 | 163.708 | 40.031 | 75.207 | 1.00 | 69.24 | H |
| ATOM | 3099 | O | PRO | 191 | 163.618 | 38.814 | 75.392 | 1.00 | 45.94 | H |
| ATOM | 3100 | N | SER | 192 | 164.871 | 40.663 | 75.063 | 1.00 | 75.06 | H |
| ATOM | 3101 | CA | SER | 192 | 166.146 | 39.952 | 75.082 | 1.00 | 71.45 | H |
| ATOM | 3102 | CB | SER | 192 | 167.311 | 40.955 | 75.103 | 1.00 | 59.57 | H |
| ATOM | 3103 | OG | SER | 192 | 167.154 | 41.923 | 76.129 | 1.00 | 83.36 | H |
| ATOM | 3104 | C | SER | 192 | 166.291 | 38.977 | 76.248 | 1.00 | 74.48 | H |
| ATOM | 3105 | O | SER | 192 | 167.095 | 38.051 | 76.184 | 1.00 | 78.55 | H |
| ATOM | 3106 | N | SER | 193 | 165.498 | 39.169 | 77.297 | 1.00 | 78.60 | H |
| ATOM | 3107 | CA | SER | 193 | 165.574 | 38.315 | 78.476 | 1.00 | 75.62 | H |
| ATOM | 3108 | CB | SER | 193 | 164.901 | 39.019 | 79.661 | 1.00 | 88.02 | H |
| ATOM | 3109 | OG | SER | 193 | 163.490 | 39.027 | 79.525 | 1.00 | 99.66 | H |
| ATOM | 3110 | C | SER | 193 | 165.013 | 36.898 | 78.345 | 1.00 | 67.52 | H |
| ATOM | 3111 | O | SER | 193 | 165.430 | 35.998 | 79.073 | 1.00 | 55.75 | H |
| ATOM | 3112 | N | THR | 194 | 164.083 | 36.684 | 77.418 | 1.00 | 72.49 | H |
| ATOM | 3113 | CA | THR | 194 | 163.464 | 35.365 | 77.259 | 1.00 | 71.00 | H |
| ATOM | 3114 | CB | THR | 194 | 161.967 | 35.507 | 76.936 | 1.00 | 85.22 | H |
| ATOM | 3115 | OG1 | THR | 194 | 161.795 | 36.425 | 75.846 | 1.00 | 87.88 | H |
| ATOM | 3116 | CG2 | THR | 194 | 161.213 | 36.023 | 78.154 | 1.00 | 86.98 | H |
| ATOM | 3117 | C | THR | 194 | 164.082 | 34.432 | 76.219 | 1.00 | 51.89 | H |
| ATOM | 3118 | O | THR | 194 | 163.726 | 33.253 | 76.150 | 1.00 | 40.90 | H |
| ATOM | 3119 | N | TRP | 195 | 164.996 | 34.957 | 75.408 | 1.00 | 50.33 | H |
| ATOM | 3120 | CA | TRP | 195 | 165.654 | 34.154 | 74.381 | 1.00 | 48.60 | H |
| ATOM | 3121 | CB | TRP | 195 | 165.109 | 34.515 | 72.990 | 1.00 | 43.12 | H |
| ATOM | 3122 | CG | TRP | 195 | 165.338 | 33.444 | 71.945 | 1.00 | 50.92 | H |
| ATOM | 3123 | CD2 | TRP | 195 | 166.332 | 33.451 | 70.907 | 1.00 | 56.48 | H |
| ATOM | 3124 | CE2 | TRP | 195 | 166.199 | 32.235 | 70.192 | 1.00 | 47.66 | H |
| ATOM | 3125 | CE3 | TRP | 195 | 167.320 | 34.365 | 70.513 | 1.00 | 53.35 | H |
| ATOM | 3126 | CD1 | TRP | 195 | 164.664 | 32.259 | 71.817 | 1.00 | 57.45 | H |
| ATOM | 3127 | NE1 | TRP | 195 | 165.175 | 31.528 | 70.766 | 1.00 | 58.35 | H |
| ATOM | 3128 | CZ2 | TRP | 195 | 167.019 | 31.911 | 69.104 | 1.00 | 45.39 | H |
| ATOM | 3129 | CZ3 | TRP | 195 | 168.136 | 34.040 | 69.430 | 1.00 | 48.84 | H |
| ATOM | 3130 | CH2 | TRP | 195 | 167.979 | 32.821 | 68.741 | 1.00 | 37.86 | H |
| ATOM | 3131 | C | TRP | 195 | 167.164 | 34.383 | 74.420 | 1.00 | 55.91 | H |
| ATOM | 3132 | O | TRP | 195 | 167.620 | 35.492 | 74.702 | 1.00 | 67.87 | H |
| ATOM | 3133 | N | PRO | 196 | 167.960 | 33.334 | 74.143 | 1.00 | 55.52 | H |

TABLE 4-continued

Co-ordinates of the CD28/5.11A1 crystal structure

| ATOM | 3134 | CD  | PRO | 196 | 169.426 | 33.449 | 74.122 | 1.00 | 48.86 | H |
|------|------|-----|-----|-----|---------|--------|--------|------|-------|---|
| ATOM | 3135 | CA  | PRO | 196 | 167.526 | 31.972 | 73.804 | 1.00 | 46.54 | H |
| ATOM | 3136 | CB  | PRO | 196 | 168.764 | 31.339 | 73.154 | 1.00 | 39.17 | H |
| ATOM | 3137 | CG  | PRO | 196 | 169.812 | 32.444 | 73.087 | 1.00 | 48.88 | H |
| ATOM | 3138 | C   | PRO | 196 | 167.047 | 31.179 | 75.016 | 1.00 | 48.13 | H |
| ATOM | 3139 | O   | PRO | 196 | 166.920 | 29.951 | 74.958 | 1.00 | 51.32 | H |
| ATOM | 3140 | N   | SER | 197 | 166.789 | 31.891 | 76.109 | 1.00 | 63.32 | H |
| ATOM | 3141 | CA  | SER | 197 | 166.315 | 31.282 | 77.343 | 1.00 | 62.46 | H |
| ATOM | 3142 | CB  | SER | 197 | 165.718 | 32.353 | 78.255 | 1.00 | 69.33 | H |
| ATOM | 3143 | OG  | SER | 197 | 166.324 | 32.329 | 79.533 | 1.00 | 75.74 | H |
| ATOM | 3144 | C   | SER | 197 | 165.261 | 30.225 | 77.029 | 1.00 | 55.85 | H |
| ATOM | 3145 | O   | SER | 197 | 165.557 | 29.029 | 76.979 | 1.00 | 63.63 | H |
| ATOM | 3146 | N   | GLU | 198 | 164.032 | 30.680 | 76.809 | 1.00 | 50.23 | H |
| ATOM | 3147 | CA  | GLU | 198 | 162.925 | 29.787 | 76.494 | 1.00 | 57.31 | H |
| ATOM | 3148 | CB  | GLU | 198 | 161.605 | 30.416 | 76.945 | 1.00 | 72.95 | H |
| ATOM | 3149 | CG  | GLU | 198 | 161.645 | 30.972 | 78.360 | 1.00 | 75.15 | H |
| ATOM | 3150 | CD  | GLU | 198 | 160.646 | 32.093 | 78.584 | 1.00 | 85.11 | H |
| ATOM | 3151 | OE1 | GLU | 198 | 159.817 | 32.341 | 77.680 | 1.00 | 99.04 | H |
| ATOM | 3152 | OE2 | GLU | 198 | 160.689 | 32.725 | 79.664 | 1.00 | 77.93 | H |
| ATOM | 3153 | C   | GLU | 198 | 162.889 | 29.516 | 74.995 | 1.00 | 56.54 | H |
| ATOM | 3154 | O   | GLU | 198 | 163.247 | 30.384 | 74.201 | 1.00 | 63.21 | H |
| ATOM | 3155 | N   | THR | 199 | 162.462 | 28.314 | 74.614 | 1.00 | 54.93 | H |
| ATOM | 3156 | CA  | THR | 199 | 162.392 | 27.937 | 73.203 | 1.00 | 53.51 | H |
| ATOM | 3157 | CB  | THR | 199 | 162.304 | 26.400 | 73.031 | 1.00 | 61.18 | H |
| ATOM | 3158 | OG1 | THR | 199 | 161.128 | 25.903 | 73.681 | 1.00 | 51.25 | H |
| ATOM | 3159 | CG2 | THR | 199 | 163.536 | 25.727 | 73.623 | 1.00 | 78.07 | H |
| ATOM | 3160 | C   | THR | 199 | 161.205 | 28.583 | 72.485 | 1.00 | 59.63 | H |
| ATOM | 3161 | O   | THR | 199 | 160.120 | 28.730 | 73.054 | 1.00 | 59.98 | H |
| ATOM | 3162 | N   | VAL | 200 | 161.429 | 28.966 | 71.228 | 1.00 | 57.25 | H |
| ATOM | 3163 | CA  | VAL | 200 | 160.407 | 29.603 | 70.405 | 1.00 | 51.96 | H |
| ATOM | 3164 | CB  | VAL | 200 | 160.815 | 31.039 | 70.035 | 1.00 | 33.42 | H |
| ATOM | 3165 | CG1 | VAL | 200 | 159.951 | 31.540 | 68.899 | 1.00 | 17.75 | H |
| ATOM | 3166 | CG2 | VAL | 200 | 160.680 | 31.944 | 71.239 | 1.00 | 31.97 | H |
| ATOM | 3167 | C   | VAL | 200 | 160.195 | 28.832 | 69.112 | 1.00 | 51.65 | H |
| ATOM | 3168 | O   | VAL | 200 | 161.136 | 28.613 | 68.353 | 1.00 | 62.16 | H |
| ATOM | 3169 | N   | THR | 201 | 158.955 | 28.427 | 68.862 | 1.00 | 39.44 | H |
| ATOM | 3170 | CA  | THR | 201 | 158.631 | 27.684 | 67.648 | 1.00 | 32.31 | H |
| ATOM | 3171 | CB  | THR | 201 | 158.116 | 26.267 | 67.969 | 1.00 | 41.49 | H |
| ATOM | 3172 | OG1 | THR | 201 | 159.042 | 25.602 | 68.831 | 1.00 | 51.63 | H |
| ATOM | 3173 | CG2 | THR | 201 | 157.949 | 25.458 | 66.688 | 1.00 | 39.87 | H |
| ATOM | 3174 | C   | THR | 201 | 157.545 | 28.399 | 66.860 | 1.00 | 26.58 | H |
| ATOM | 3175 | O   | THR | 201 | 156.682 | 29.055 | 67.438 | 1.00 | 25.18 | H |
| ATOM | 3176 | N   | CYS | 202 | 157.593 | 28.279 | 65.538 | 1.00 | 22.39 | H |
| ATOM | 3177 | CA  | CYS | 202 | 156.582 | 28.902 | 64.699 | 1.00 | 25.43 | H |
| ATOM | 3178 | C   | CYS | 202 | 155.765 | 27.777 | 64.064 | 1.00 | 25.96 | H |
| ATOM | 3179 | O   | CYS | 202 | 156.324 | 26.826 | 63.522 | 1.00 | 34.22 | H |
| ATOM | 3180 | CB  | CYS | 202 | 157.243 | 29.820 | 63.649 | 1.00 | 49.34 | H |
| ATOM | 3181 | SG  | CYS | 202 | 157.564 | 29.150 | 61.983 | 1.00 | 74.97 | H |
| ATOM | 3182 | N   | ASN | 203 | 154.441 | 27.871 | 64.172 | 1.00 | 24.52 | H |
| ATOM | 3183 | CA  | ASN | 203 | 153.554 | 26.842 | 63.628 | 1.00 | 29.46 | H |
| ATOM | 3184 | CB  | ASN | 203 | 152.539 | 26.387 | 64.686 | 1.00 | 36.69 | H |
| ATOM | 3185 | CG  | ASN | 203 | 152.926 | 26.807 | 66.099 | 1.00 | 44.66 | H |
| ATOM | 3186 | OD1 | ASN | 203 | 152.586 | 27.904 | 66.552 | 1.00 | 28.02 | H |
| ATOM | 3187 | ND2 | ASN | 203 | 153.629 | 25.926 | 66.805 | 1.00 | 33.32 | H |
| ATOM | 3188 | C   | ASN | 203 | 152.800 | 27.293 | 62.389 | 1.00 | 18.74 | H |
| ATOM | 3189 | O   | ASN | 203 | 151.964 | 28.196 | 62.447 | 1.00 | 38.03 | H |
| ATOM | 3190 | N   | VAL | 204 | 153.099 | 26.646 | 61.270 | 1.00 | 23.45 | H |
| ATOM | 3191 | CA  | VAL | 204 | 152.451 | 26.957 | 60.006 | 1.00 | 38.87 | H |
| ATOM | 3192 | CB  | VAL | 204 | 153.473 | 27.049 | 58.853 | 1.00 | 39.50 | H |
| ATOM | 3193 | CG1 | VAL | 204 | 152.795 | 27.575 | 57.599 | 1.00 | 52.52 | H |
| ATOM | 3194 | CG2 | VAL | 204 | 154.624 | 27.944 | 59.254 | 1.00 | 29.99 | H |
| ATOM | 3195 | C   | VAL | 204 | 151.461 | 25.854 | 59.676 | 1.00 | 41.89 | H |
| ATOM | 3196 | O   | VAL | 204 | 151.733 | 24.682 | 59.919 | 1.00 | 46.77 | H |
| ATOM | 3197 | N   | ALA | 205 | 150.312 | 26.236 | 59.126 | 1.00 | 41.52 | H |
| ATOM | 3198 | CA  | ALA | 205 | 149.285 | 25.273 | 58.751 | 1.00 | 32.14 | H |
| ATOM | 3199 | CB  | ALA | 205 | 148.156 | 25.281 | 59.777 | 1.00 | 44.74 | H |
| ATOM | 3200 | C   | ALA | 205 | 148.749 | 25.614 | 57.365 | 1.00 | 28.16 | H |
| ATOM | 3201 | O   | ALA | 205 | 148.349 | 26.750 | 57.104 | 1.00 | 23.06 | H |
| ATOM | 3202 | N   | HIS | 206 | 148.756 | 24.629 | 56.474 | 1.00 | 38.89 | H |
| ATOM | 3203 | CA  | HIS | 206 | 148.267 | 24.825 | 55.121 | 1.00 | 31.01 | H |
| ATOM | 3204 | CB  | HIS | 206 | 149.357 | 24.497 | 54.112 | 1.00 | 34.08 | H |
| ATOM | 3205 | CG  | HIS | 206 | 149.025 | 24.909 | 52.715 | 1.00 | 25.51 | H |
| ATOM | 3206 | CD2 | HIS | 206 | 148.521 | 26.065 | 52.227 | 1.00 | 33.37 | H |
| ATOM | 3207 | ND1 | HIS | 206 | 149.193 | 24.073 | 51.635 | 1.00 | 28.36 | H |
| ATOM | 3208 | CE1 | HIS | 206 | 148.807 | 24.698 | 50.535 | 1.00 | 30.36 | H |
| ATOM | 3209 | NE2 | HIS | 206 | 148.393 | 25.907 | 50.868 | 1.00 | 29.53 | H |
| ATOM | 3210 | C   | HIS | 206 | 147.061 | 23.930 | 54.876 | 1.00 | 38.48 | H |

TABLE 4-continued

Co-ordinates of the CD28/5.11A1 crystal structure

| ATOM | 3211 | O | HIS | 206 | 147.198 | 22.819 | 54.371 | 1.00 | 42.18 | H |
|---|---|---|---|---|---|---|---|---|---|---|
| ATOM | 3212 | N | PRO | 207 | 145.856 | 24.417 | 55.228 | 1.00 | 46.11 | H |
| ATOM | 3213 | CD | PRO | 207 | 145.636 | 25.758 | 55.802 | 1.00 | 59.24 | H |
| ATOM | 3214 | CA | PRO | 207 | 144.597 | 23.684 | 55.065 | 1.00 | 49.09 | H |
| ATOM | 3215 | CB | PRO | 207 | 143.538 | 24.780 | 55.138 | 1.00 | 55.68 | H |
| ATOM | 3216 | CG | PRO | 207 | 144.146 | 25.814 | 56.018 | 1.00 | 65.42 | H |
| ATOM | 3217 | C | PRO | 207 | 144.504 | 22.890 | 53.769 | 1.00 | 60.16 | H |
| ATOM | 3218 | O | PRO | 207 | 144.293 | 21.680 | 53.787 | 1.00 | 51.48 | H |
| ATOM | 3219 | N | ALA | 208 | 144.664 | 23.577 | 52.646 | 1.00 | 56.11 | H |
| ATOM | 3220 | CA | ALA | 208 | 144.584 | 22.933 | 51.342 | 1.00 | 41.51 | H |
| ATOM | 3221 | CB | ALA | 208 | 145.043 | 23.899 | 50.261 | 1.00 | 34.52 | H |
| ATOM | 3222 | C | ALA | 208 | 145.397 | 21.638 | 51.269 | 1.00 | 43.41 | H |
| ATOM | 3223 | O | ALA | 208 | 144.983 | 20.676 | 50.615 | 1.00 | 51.37 | H |
| ATOM | 3224 | N | SER | 209 | 146.550 | 21.615 | 51.933 | 1.00 | 47.62 | H |
| ATOM | 3225 | CA | SER | 209 | 147.396 | 20.424 | 51.923 | 1.00 | 48.72 | H |
| ATOM | 3226 | CB | SER | 209 | 148.852 | 20.811 | 51.634 | 1.00 | 44.67 | H |
| ATOM | 3227 | OG | SER | 209 | 149.387 | 21.642 | 52.650 | 1.00 | 55.80 | H |
| ATOM | 3228 | C | SER | 209 | 147.304 | 19.643 | 53.236 | 1.00 | 53.29 | H |
| ATOM | 3229 | O | SER | 209 | 147.973 | 18.624 | 53.411 | 1.00 | 52.35 | H |
| ATOM | 3230 | N | SER | 210 | 146.462 | 20.119 | 54.148 | 1.00 | 71.17 | H |
| ATOM | 3231 | CA | SER | 210 | 146.269 | 19.475 | 55.444 | 1.00 | 82.90 | H |
| ATOM | 3232 | CB | SER | 210 | 145.509 | 18.158 | 55.277 | 1.00 | 90.95 | H |
| ATOM | 3233 | OG | SER | 210 | 144.137 | 18.333 | 55.578 | 1.00 | 100.00 | H |
| ATOM | 3234 | C | SER | 210 | 147.579 | 19.213 | 56.169 | 1.00 | 79.59 | H |
| ATOM | 3235 | O | SER | 210 | 147.702 | 18.234 | 56.908 | 1.00 | 80.94 | H |
| ATOM | 3236 | N | THR | 211 | 148.555 | 20.088 | 55.950 | 1.00 | 73.59 | H |
| ATOM | 3237 | CA | THR | 211 | 149.854 | 19.964 | 56.594 | 1.00 | 75.14 | H |
| ATOM | 3238 | CB | THR | 211 | 151.027 | 20.111 | 55.599 | 1.00 | 76.28 | H |
| ATOM | 3239 | OG1 | THR | 211 | 150.990 | 21.414 | 55.008 | 1.00 | 73.09 | H |
| ATOM | 3240 | CG2 | THR | 211 | 150.950 | 19.062 | 54.510 | 1.00 | 89.67 | H |
| ATOM | 3241 | C | THR | 211 | 150.024 | 21.051 | 57.643 | 1.00 | 74.45 | H |
| ATOM | 3242 | O | THR | 211 | 149.536 | 22.172 | 57.491 | 1.00 | 76.65 | H |
| ATOM | 3243 | N | LYS | 212 | 150.711 | 20.699 | 58.722 | 1.00 | 69.16 | H |
| ATOM | 3244 | CA | LYS | 212 | 150.988 | 21.645 | 59.783 | 1.00 | 61.67 | H |
| ATOM | 3245 | CB | LYS | 212 | 150.041 | 21.450 | 60.967 | 1.00 | 73.38 | H |
| ATOM | 3246 | CG | LYS | 212 | 150.718 | 21.612 | 62.317 | 1.00 | 89.85 | H |
| ATOM | 3247 | CD | LYS | 212 | 150.006 | 22.614 | 63.192 | 1.00 | 99.99 | H |
| ATOM | 3248 | CE | LYS | 212 | 150.452 | 22.449 | 64.637 | 1.00 | 97.52 | H |
| ATOM | 3249 | NZ | LYS | 212 | 150.308 | 23.707 | 65.419 | 1.00 | 95.76 | H |
| ATOM | 3250 | C | LYS | 212 | 152.413 | 21.344 | 60.198 | 1.00 | 51.18 | H |
| ATOM | 3251 | O | LYS | 212 | 152.730 | 20.222 | 60.594 | 1.00 | 46.57 | H |
| ATOM | 3252 | N | VAL | 213 | 153.275 | 22.349 | 60.081 | 1.00 | 47.52 | H |
| ATOM | 3253 | CA | VAL | 213 | 154.672 | 22.201 | 60.434 | 1.00 | 33.06 | H |
| ATOM | 3254 | CB | VAL | 213 | 155.593 | 22.651 | 59.282 | 1.00 | 35.68 | H |
| ATOM | 3255 | CG1 | VAL | 213 | 157.002 | 22.136 | 59.511 | 1.00 | 51.97 | H |
| ATOM | 3256 | CG2 | VAL | 213 | 155.047 | 22.154 | 57.948 | 1.00 | 53.21 | H |
| ATOM | 3257 | C | VAL | 213 | 155.011 | 23.028 | 61.661 | 1.00 | 30.06 | H |
| ATOM | 3258 | O | VAL | 213 | 154.324 | 23.996 | 61.991 | 1.00 | 34.34 | H |
| ATOM | 3259 | N | ASP | 214 | 156.071 | 22.625 | 62.343 | 1.00 | 35.26 | H |
| ATOM | 3260 | CA | ASP | 214 | 156.541 | 23.325 | 63.523 | 1.00 | 39.19 | H |
| ATOM | 3261 | CB | ASP | 214 | 156.228 | 22.526 | 64.791 | 1.00 | 58.41 | H |
| ATOM | 3262 | CG | ASP | 214 | 154.791 | 22.709 | 65.259 | 1.00 | 63.54 | H |
| ATOM | 3263 | OD1 | ASP | 214 | 154.397 | 23.857 | 65.553 | 1.00 | 65.10 | H |
| ATOM | 3264 | OD2 | ASP | 214 | 154.059 | 21.699 | 65.336 | 1.00 | 80.45 | H |
| ATOM | 3265 | C | ASP | 214 | 158.046 | 23.454 | 63.342 | 1.00 | 37.64 | H |
| ATOM | 3266 | O | ASP | 214 | 158.725 | 22.489 | 62.983 | 1.00 | 41.00 | H |
| ATOM | 3267 | N | LYS | 215 | 158.564 | 24.652 | 63.564 | 1.00 | 34.85 | H |
| ATOM | 3268 | CA | LYS | 215 | 159.985 | 24.877 | 63.410 | 1.00 | 35.83 | H |
| ATOM | 3269 | CB | LYS | 215 | 160.261 | 25.637 | 62.112 | 1.00 | 37.75 | H |
| ATOM | 3270 | CG | LYS | 215 | 161.248 | 24.948 | 61.191 | 1.00 | 59.89 | H |
| ATOM | 3271 | CD | LYS | 215 | 160.536 | 23.992 | 60.251 | 1.00 | 59.31 | H |
| ATOM | 3272 | CE | LYS | 215 | 161.386 | 22.766 | 59.964 | 1.00 | 53.98 | H |
| ATOM | 3273 | NZ | LYS | 215 | 160.573 | 21.613 | 59.475 | 1.00 | 65.45 | H |
| ATOM | 3274 | C | LYS | 215 | 160.515 | 25.659 | 64.588 | 1.00 | 38.73 | H |
| ATOM | 3275 | O | LYS | 215 | 160.030 | 26.745 | 64.904 | 1.00 | 53.68 | H |
| ATOM | 3276 | N | LYS | 216 | 161.511 | 25.084 | 65.244 | 1.00 | 48.31 | H |
| ATOM | 3277 | CA | LYS | 216 | 162.141 | 25.714 | 66.389 | 1.00 | 47.35 | H |
| ATOM | 3278 | CB | LYS | 216 | 162.649 | 24.641 | 67.357 | 1.00 | 48.55 | H |
| ATOM | 3279 | CG | LYS | 216 | 162.043 | 23.256 | 67.119 | 1.00 | 74.84 | H |
| ATOM | 3280 | CD | LYS | 216 | 162.861 | 22.156 | 67.793 | 1.00 | 85.40 | H |
| ATOM | 3281 | CE | LYS | 216 | 162.592 | 22.085 | 69.296 | 1.00 | 94.97 | H |
| ATOM | 3282 | NZ | LYS | 216 | 162.133 | 20.733 | 69.738 | 1.00 | 92.19 | H |
| ATOM | 3283 | C | LYS | 216 | 163.305 | 26.543 | 65.860 | 1.00 | 46.24 | H |
| ATOM | 3284 | O | LYS | 216 | 163.898 | 26.203 | 64.838 | 1.00 | 34.41 | H |
| ATOM | 3285 | N | ILE | 217 | 163.622 | 27.637 | 66.541 | 1.00 | 41.02 | H |
| ATOM | 3286 | CA | ILE | 217 | 164.719 | 28.497 | 66.116 | 1.00 | 44.97 | H |
| ATOM | 3287 | CB | ILE | 217 | 164.273 | 29.978 | 66.046 | 1.00 | 41.86 | H |

TABLE 4-continued

Co-ordinates of the CD28/5.11A1 crystal structure

| ATOM | 3288 | CG2 | ILE | 217 | 165.094 | 30.716 | 64.991 | 1.00 | 44.48 | H |
|---|---|---|---|---|---|---|---|---|---|---|
| ATOM | 3289 | CG1 | ILE | 217 | 162.768 | 30.063 | 65.749 | 1.00 | 33.66 | H |
| ATOM | 3290 | CD1 | ILE | 217 | 162.407 | 30.038 | 64.270 | 1.00 | 17.95 | H |
| ATOM | 3291 | C | ILE | 217 | 165.890 | 28.363 | 67.094 | 1.00 | 47.47 | H |
| ATOM | 3292 | O | ILE | 217 | 165.690 | 28.400 | 68.310 | 1.00 | 43.27 | H |
| ATOM | 3293 | N | VAL | 218 | 167.103 | 28.219 | 66.559 | 1.00 | 50.40 | H |
| ATOM | 3294 | CA | VAL | 218 | 168.301 | 28.054 | 67.394 | 1.00 | 50.95 | H |
| ATOM | 3295 | CB | VAL | 218 | 169.003 | 26.705 | 67.084 | 1.00 | 57.08 | H |
| ATOM | 3296 | CG1 | VAL | 218 | 167.974 | 25.686 | 66.599 | 1.00 | 55.44 | H |
| ATOM | 3297 | CG2 | VAL | 218 | 170.105 | 26.903 | 66.037 | 1.00 | 73.39 | H |
| ATOM | 3298 | C | VAL | 218 | 169.344 | 29.175 | 67.289 | 1.00 | 41.93 | H |
| ATOM | 3299 | O | VAL | 218 | 170.001 | 29.458 | 68.317 | 1.00 | 46.19 | H |
| ATOM | 3300 | OT | VAL | 218 | 170.011 | 29.390 | 69.119 | 1.00 | 52.14 | H |
| ATOM | 3301 | CB | LYS | 2 | 95.854 | 32.588 | 47.685 | 1.00 | 42.79 | C |
| ATOM | 3302 | CG | LYS | 2 | 95.825 | 31.435 | 46.699 | 1.00 | 53.80 | C |
| ATOM | 3303 | CD | LYS | 2 | 94.407 | 30.925 | 46.486 | 1.00 | 62.43 | C |
| ATOM | 3304 | CE | LYS | 2 | 94.373 | 29.740 | 45.531 | 1.00 | 62.95 | C |
| ATOM | 3305 | NZ | LYS | 2 | 94.065 | 28.460 | 46.232 | 1.00 | 60.28 | C |
| ATOM | 3306 | C | LYS | 2 | 94.693 | 33.099 | 49.840 | 1.00 | 46.91 | C |
| ATOM | 3307 | O | LYS | 2 | 93.606 | 32.673 | 50.239 | 1.00 | 58.66 | C |
| ATOM | 3308 | N | LYS | 2 | 95.259 | 30.740 | 49.234 | 1.00 | 34.71 | C |
| ATOM | 3309 | CA | LYS | 2 | 95.690 | 32.169 | 49.150 | 1.00 | 47.34 | C |
| ATOM | 3310 | N | ILE | 3 | 95.072 | 34.368 | 49.975 | 1.00 | 39.77 | C |
| ATOM | 3311 | CA | ILE | 3 | 94.226 | 35.372 | 50.621 | 1.00 | 41.61 | C |
| ATOM | 3312 | CB | ILE | 3 | 95.062 | 36.456 | 51.331 | 1.00 | 43.12 | C |
| ATOM | 3313 | CG2 | ILE | 3 | 94.142 | 37.421 | 52.074 | 1.00 | 41.52 | C |
| ATOM | 3314 | CG1 | ILE | 3 | 96.056 | 35.818 | 52.301 | 1.00 | 48.11 | C |
| ATOM | 3315 | CD1 | ILE | 3 | 97.282 | 36.672 | 52.556 | 1.00 | 29.73 | C |
| ATOM | 3316 | C | ILE | 3 | 93.346 | 36.101 | 49.623 | 1.00 | 38.09 | C |
| ATOM | 3317 | O | ILE | 3 | 93.645 | 36.147 | 48.437 | 1.00 | 41.06 | C |
| ATOM | 3318 | N | LEU | 4 | 92.266 | 36.686 | 50.124 | 1.00 | 41.63 | C |
| ATOM | 3319 | CA | LEU | 4 | 91.349 | 37.439 | 49.287 | 1.00 | 47.21 | C |
| ATOM | 3320 | CB | LEU | 4 | 89.906 | 37.026 | 49.581 | 1.00 | 47.90 | C |
| ATOM | 3321 | CG | LEU | 4 | 89.389 | 35.782 | 48.852 | 1.00 | 49.25 | C |
| ATOM | 3322 | CD1 | LEU | 4 | 89.552 | 35.970 | 47.351 | 1.00 | 37.24 | C |
| ATOM | 3323 | CD2 | LEU | 4 | 90.138 | 34.543 | 49.324 | 1.00 | 54.80 | C |
| ATOM | 3324 | C | LEU | 4 | 91.536 | 38.927 | 49.569 | 1.00 | 48.08 | C |
| ATOM | 3325 | O | LEU | 4 | 91.868 | 39.322 | 50.695 | 1.00 | 31.46 | C |
| ATOM | 3326 | N | VAL | 5 | 91.326 | 39.743 | 48.538 | 1.00 | 43.17 | C |
| ATOM | 3327 | CA | VAL | 5 | 91.469 | 41.190 | 48.660 | 1.00 | 33.62 | C |
| ATOM | 3328 | CB | VAL | 5 | 92.806 | 41.673 | 48.047 | 1.00 | 32.71 | C |
| ATOM | 3329 | CG1 | VAL | 5 | 93.315 | 42.880 | 48.803 | 1.00 | 22.52 | C |
| ATOM | 3330 | CG2 | VAL | 5 | 93.836 | 40.559 | 48.081 | 1.00 | 29.21 | C |
| ATOM | 3331 | C | VAL | 5 | 90.325 | 41.911 | 47.945 | 1.00 | 36.98 | C |
| ATOM | 3332 | O | VAL | 5 | 90.028 | 41.628 | 46.788 | 1.00 | 50.54 | C |
| ATOM | 3333 | N | LYS | 6 | 89.689 | 42.844 | 48.640 | 1.00 | 39.70 | C |
| ATOM | 3334 | CA | LYS | 6 | 88.593 | 43.622 | 48.068 | 1.00 | 41.54 | C |
| ATOM | 3335 | CB | LYS | 6 | 87.299 | 43.378 | 48.857 | 1.00 | 38.28 | C |
| ATOM | 3336 | CG | LYS | 6 | 86.443 | 42.233 | 48.341 | 1.00 | 48.43 | C |
| ATOM | 3337 | CD | LYS | 6 | 85.343 | 41.841 | 49.339 | 1.00 | 58.62 | C |
| ATOM | 3338 | CE | LYS | 6 | 85.905 | 41.158 | 50.593 | 1.00 | 47.34 | C |
| ATOM | 3339 | NZ | LYS | 6 | 86.645 | 39.893 | 50.281 | 1.00 | 51.47 | C |
| ATOM | 3340 | C | LYS | 6 | 88.957 | 45.108 | 48.147 | 1.00 | 32.95 | C |
| ATOM | 3341 | O | LYS | 6 | 89.265 | 45.614 | 49.222 | 1.00 | 43.88 | C |
| ATOM | 3342 | N | GLN | 7 | 88.926 | 45.805 | 47.021 | 1.00 | 30.15 | C |
| ATOM | 3343 | CA | GLN | 7 | 89.258 | 47.224 | 47.022 | 1.00 | 39.07 | C |
| ATOM | 3344 | CB | GLN | 7 | 90.631 | 47.449 | 46.395 | 1.00 | 44.76 | C |
| ATOM | 3345 | CG | GLN | 7 | 91.355 | 46.178 | 46.002 | 1.00 | 48.85 | C |
| ATOM | 3346 | CD | GLN | 7 | 92.745 | 46.462 | 45.467 | 1.00 | 53.95 | C |
| ATOM | 3347 | OE1 | GLN | 7 | 93.575 | 45.560 | 45.334 | 1.00 | 50.12 | C |
| ATOM | 3348 | NE2 | GLN | 7 | 93.007 | 47.730 | 45.155 | 1.00 | 35.66 | C |
| ATOM | 3349 | C | GLN | 7 | 88.230 | 48.035 | 46.262 | 1.00 | 36.89 | C |
| ATOM | 3350 | O | GLN | 7 | 87.567 | 47.514 | 45.370 | 1.00 | 42.41 | C |
| ATOM | 3351 | N | SER | 8 | 88.095 | 49.307 | 46.623 | 1.00 | 34.89 | C |
| ATOM | 3352 | CA | SER | 8 | 87.148 | 50.178 | 45.940 | 1.00 | 33.64 | C |
| ATOM | 3353 | CB | SER | 8 | 87.247 | 51.613 | 46.475 | 1.00 | 39.10 | C |
| ATOM | 3354 | OG | SER | 8 | 86.259 | 51.882 | 47.465 | 1.00 | 33.65 | C |
| ATOM | 3355 | C | SER | 8 | 87.564 | 50.141 | 44.481 | 1.00 | 36.57 | C |
| ATOM | 3356 | O | SER | 8 | 88.751 | 50.012 | 44.180 | 1.00 | 34.54 | C |
| ATOM | 3357 | N | PRO | 9 | 86.596 | 50.239 | 43.553 | 1.00 | 45.61 | C |
| ATOM | 3358 | CD | PRO | 9 | 85.146 | 50.390 | 43.755 | 1.00 | 42.54 | C |
| ATOM | 3359 | CA | PRO | 9 | 86.946 | 50.207 | 42.128 | 1.00 | 42.76 | C |
| ATOM | 3360 | CB | PRO | 9 | 85.594 | 50.325 | 41.411 | 1.00 | 35.11 | C |
| ATOM | 3361 | CG | PRO | 9 | 84.577 | 49.955 | 42.428 | 1.00 | 29.77 | C |
| ATOM | 3362 | C | PRO | 9 | 87.879 | 51.370 | 41.813 | 1.00 | 45.27 | C |
| ATOM | 3363 | O | PRO | 9 | 88.929 | 51.194 | 41.190 | 1.00 | 49.59 | C |
| ATOM | 3364 | N | MET | 10 | 87.486 | 52.561 | 42.254 | 1.00 | 34.14 | C |

TABLE 4-continued

Co-ordinates of the CD28/5.11A1 crystal structure

| ATOM | 3365 | CA | MET | 10 | 88.292 | 53.749 | 42.041 | 1.00 | 36.35 | C |
|---|---|---|---|---|---|---|---|---|---|---|
| ATOM | 3366 | CB | MET | 10 | 87.975 | 54.374 | 40.674 | 1.00 | 51.67 | C |
| ATOM | 3367 | CG | MET | 10 | 87.958 | 55.908 | 40.628 | 1.00 | 45.29 | C |
| ATOM | 3368 | SD | MET | 10 | 86.852 | 56.596 | 39.357 | 1.00 | 41.23 | C |
| ATOM | 3369 | CE | MET | 10 | 88.067 | 57.323 | 38.239 | 1.00 | 36.20 | C |
| ATOM | 3370 | C | MET | 10 | 88.031 | 54.730 | 43.172 | 1.00 | 31.46 | C |
| ATOM | 3371 | O | MET | 10 | 87.032 | 54.629 | 43.882 | 1.00 | 22.69 | C |
| ATOM | 3372 | N | LEU | 11 | 88.962 | 55.661 | 43.344 | 1.00 | 34.82 | C |
| ATOM | 3373 | CA | LEU | 11 | 88.890 | 56.669 | 44.385 | 1.00 | 23.35 | C |
| ATOM | 3374 | CB | LEU | 11 | 89.826 | 56.264 | 45.530 | 1.00 | 20.95 | C |
| ATOM | 3375 | CG | LEU | 11 | 89.592 | 54.804 | 45.946 | 1.00 | 18.02 | C |
| ATOM | 3376 | CD1 | LEU | 11 | 90.765 | 54.235 | 46.696 | 1.00 | 5.04 | C |
| ATOM | 3377 | CD2 | LEU | 11 | 88.339 | 54.745 | 46.785 | 1.00 | 31.87 | C |
| ATOM | 3378 | C | LEU | 11 | 89.306 | 58.008 | 43.789 | 1.00 | 22.25 | C |
| ATOM | 3379 | O | LEU | 11 | 90.294 | 58.093 | 43.061 | 1.00 | 23.22 | C |
| ATOM | 3380 | N | VAL | 12 | 88.540 | 59.051 | 44.075 | 1.00 | 23.39 | C |
| ATOM | 3381 | CA | VAL | 12 | 88.871 | 60.365 | 43.551 | 1.00 | 25.58 | C |
| ATOM | 3382 | CB | VAL | 12 | 87.610 | 61.166 | 43.174 | 1.00 | 37.83 | C |
| ATOM | 3383 | CG1 | VAL | 12 | 88.008 | 62.509 | 42.585 | 1.00 | 20.17 | C |
| ATOM | 3384 | CG2 | VAL | 12 | 86.771 | 60.387 | 42.173 | 1.00 | 25.83 | C |
| ATOM | 3385 | C | VAL | 12 | 89.655 | 61.133 | 44.603 | 1.00 | 30.45 | C |
| ATOM | 3386 | O | VAL | 12 | 89.106 | 61.605 | 45.597 | 1.00 | 47.50 | C |
| ATOM | 3387 | N | ALA | 13 | 90.955 | 61.246 | 44.379 | 1.00 | 37.89 | C |
| ATOM | 3388 | CA | ALA | 13 | 91.820 | 61.943 | 45.307 | 1.00 | 26.16 | C |
| ATOM | 3389 | CB | ALA | 13 | 93.203 | 62.091 | 44.706 | 1.00 | 30.65 | C |
| ATOM | 3390 | C | ALA | 13 | 91.241 | 63.309 | 45.615 | 1.00 | 33.79 | C |
| ATOM | 3391 | O | ALA | 13 | 90.816 | 64.028 | 44.711 | 1.00 | 39.57 | C |
| ATOM | 3392 | N | TYR | 14 | 91.206 | 63.657 | 46.895 | 1.00 | 39.35 | C |
| ATOM | 3393 | CA | TYR | 14 | 90.711 | 64.959 | 47.306 | 1.00 | 37.04 | C |
| ATOM | 3394 | CB | TYR | 14 | 89.660 | 64.835 | 48.410 | 1.00 | 33.79 | C |
| ATOM | 3395 | CG | TYR | 14 | 89.555 | 66.110 | 49.213 | 1.00 | 48.57 | C |
| ATOM | 3396 | CD1 | TYR | 14 | 90.182 | 66.233 | 50.458 | 1.00 | 50.52 | C |
| ATOM | 3397 | CE1 | TYR | 14 | 90.178 | 67.444 | 51.148 | 1.00 | 54.90 | C |
| ATOM | 3398 | CD2 | TYR | 14 | 88.913 | 67.231 | 48.685 | 1.00 | 44.13 | C |
| ATOM | 3399 | CE2 | TYR | 14 | 88.904 | 68.441 | 49.364 | 1.00 | 49.92 | C |
| ATOM | 3400 | CZ | TYR | 14 | 89.538 | 68.545 | 50.590 | 1.00 | 58.83 | C |
| ATOM | 3401 | OH | TYR | 14 | 89.536 | 69.761 | 51.240 | 1.00 | 69.05 | C |
| ATOM | 3402 | C | TYR | 14 | 91.884 | 65.765 | 47.846 | 1.00 | 39.91 | C |
| ATOM | 3403 | O | TYR | 14 | 92.626 | 65.283 | 48.703 | 1.00 | 36.85 | C |
| ATOM | 3404 | N | ASP | 15 | 92.041 | 66.992 | 47.359 | 1.00 | 34.60 | C |
| ATOM | 3405 | CA | ASP | 15 | 93.131 | 67.838 | 47.820 | 1.00 | 35.97 | C |
| ATOM | 3406 | CB | ASP | 15 | 92.958 | 68.141 | 49.307 | 1.00 | 54.21 | C |
| ATOM | 3407 | CG | ASP | 15 | 92.605 | 69.588 | 49.573 | 1.00 | 74.11 | C |
| ATOM | 3408 | OD1 | ASP | 15 | 92.300 | 70.322 | 48.604 | 1.00 | 77.84 | C |
| ATOM | 3409 | OD2 | ASP | 15 | 92.634 | 69.985 | 50.758 | 1.00 | 75.11 | C |
| ATOM | 3410 | C | ASP | 15 | 94.448 | 67.112 | 47.603 | 1.00 | 33.47 | C |
| ATOM | 3411 | O | ASP | 15 | 95.389 | 67.265 | 48.380 | 1.00 | 34.49 | C |
| ATOM | 3412 | N | ASN | 16 | 94.499 | 66.309 | 46.543 | 1.00 | 44.74 | C |
| ATOM | 3413 | CA | ASN | 16 | 95.683 | 65.534 | 46.196 | 1.00 | 48.87 | C |
| ATOM | 3414 | CB | ASN | 16 | 96.898 | 66.457 | 46.053 | 1.00 | 62.07 | C |
| ATOM | 3415 | CG | ASN | 16 | 96.840 | 67.292 | 44.793 | 1.00 | 64.94 | C |
| ATOM | 3416 | OD1 | ASN | 16 | 96.213 | 68.355 | 44.760 | 1.00 | 66.06 | C |
| ATOM | 3417 | ND2 | ASN | 16 | 97.497 | 66.816 | 43.742 | 1.00 | 73.29 | C |
| ATOM | 3418 | C | ASN | 16 | 95.983 | 64.449 | 47.225 | 1.00 | 48.29 | C |
| ATOM | 3419 | O | ASN | 16 | 97.148 | 64.096 | 47.451 | 1.00 | 38.81 | C |
| ATOM | 3420 | N | ALA | 17 | 94.923 | 63.923 | 47.835 | 1.00 | 34.08 | C |
| ATOM | 3421 | CA | ALA | 17 | 95.055 | 62.867 | 48.840 | 1.00 | 29.57 | C |
| ATOM | 3422 | CB | ALA | 17 | 94.996 | 63.459 | 50.237 | 1.00 | 33.14 | C |
| ATOM | 3423 | C | ALA | 17 | 93.955 | 61.832 | 48.667 | 1.00 | 29.96 | C |
| ATOM | 3424 | O | ALA | 17 | 92.931 | 62.107 | 48.049 | 1.00 | 32.16 | C |
| ATOM | 3425 | N | VAL | 18 | 94.169 | 60.642 | 49.213 | 1.00 | 28.09 | C |
| ATOM | 3426 | CA | VAL | 18 | 93.188 | 59.568 | 49.111 | 1.00 | 30.54 | C |
| ATOM | 3427 | CB | VAL | 18 | 93.339 | 58.824 | 47.767 | 1.00 | 15.07 | C |
| ATOM | 3428 | CG1 | VAL | 18 | 94.517 | 57.889 | 47.829 | 1.00 | 23.83 | C |
| ATOM | 3429 | CG2 | VAL | 18 | 92.086 | 58.054 | 47.448 | 1.00 | 16.29 | C |
| ATOM | 3430 | C | VAL | 18 | 93.356 | 58.575 | 50.266 | 1.00 | 33.43 | C |
| ATOM | 3431 | O | VAL | 18 | 94.314 | 58.660 | 51.029 | 1.00 | 28.92 | C |
| ATOM | 3432 | N | ASN | 19 | 92.419 | 57.643 | 50.398 | 1.00 | 30.17 | C |
| ATOM | 3433 | CA | ASN | 19 | 92.496 | 56.642 | 51.456 | 1.00 | 28.35 | C |
| ATOM | 3434 | CB | ASN | 19 | 91.468 | 56.959 | 52.545 | 1.00 | 37.98 | C |
| ATOM | 3435 | CG | ASN | 19 | 92.105 | 57.540 | 53.794 | 1.00 | 36.06 | C |
| ATOM | 3436 | OD1 | ASN | 19 | 92.991 | 56.923 | 54.385 | 1.00 | 36.77 | C |
| ATOM | 3437 | ND2 | ASN | 19 | 91.659 | 58.732 | 54.205 | 1.00 | 27.02 | C |
| ATOM | 3438 | C | ASN | 19 | 92.241 | 55.260 | 50.867 | 1.00 | 28.23 | C |
| ATOM | 3439 | O | ASN | 19 | 91.113 | 54.941 | 50.502 | 1.00 | 25.92 | C |
| ATOM | 3440 | N | LEU | 20 | 93.291 | 54.446 | 50.781 | 1.00 | 37.11 | C |
| ATOM | 3441 | CA | LEU | 20 | 93.192 | 53.097 | 50.204 | 1.00 | 39.33 | C |

TABLE 4-continued

Co-ordinates of the CD28/5.11A1 crystal structure

| ATOM | 3442 | CB | LEU | 20 | 94.382 | 52.830 | 49.284 | 1.00 | 52.73 | C |
|---|---|---|---|---|---|---|---|---|---|---|
| ATOM | 3443 | CG | LEU | 20 | 94.409 | 53.492 | 47.913 | 1.00 | 59.34 | C |
| ATOM | 3444 | CD1 | LEU | 20 | 95.375 | 54.657 | 47.953 | 1.00 | 54.35 | C |
| ATOM | 3445 | CD2 | LEU | 20 | 94.826 | 52.478 | 46.855 | 1.00 | 58.17 | C |
| ATOM | 3446 | C | LEU | 20 | 93.122 | 51.946 | 51.202 | 1.00 | 24.88 | C |
| ATOM | 3447 | O | LEU | 20 | 94.141 | 51.349 | 51.532 | 1.00 | 27.29 | C |
| ATOM | 3448 | N | SER | 21 | 91.926 | 51.619 | 51.670 | 1.00 | 24.25 | C |
| ATOM | 3449 | CA | SER | 21 | 91.795 | 50.515 | 52.601 | 1.00 | 32.93 | C |
| ATOM | 3450 | CB | SER | 21 | 90.474 | 50.603 | 53.357 | 1.00 | 22.84 | C |
| ATOM | 3451 | OG | SER | 21 | 90.626 | 50.123 | 54.682 | 1.00 | 42.82 | C |
| ATOM | 3452 | C | SER | 21 | 91.834 | 49.250 | 51.760 | 1.00 | 36.87 | C |
| ATOM | 3453 | O | SER | 21 | 91.633 | 49.308 | 50.551 | 1.00 | 50.83 | C |
| ATOM | 3454 | N | CYS | 22 | 92.098 | 48.109 | 52.384 | 1.00 | 41.84 | C |
| ATOM | 3455 | CA | CYS | 22 | 92.142 | 46.858 | 51.636 | 1.00 | 34.97 | C |
| ATOM | 3456 | C | CYS | 22 | 91.519 | 45.728 | 52.420 | 1.00 | 29.54 | C |
| ATOM | 3457 | O | CYS | 22 | 92.086 | 45.250 | 53.400 | 1.00 | 31.51 | C |
| ATOM | 3458 | CB | CYS | 22 | 93.578 | 46.504 | 51.294 | 1.00 | 44.42 | C |
| ATOM | 3459 | SG | CYS | 22 | 94.382 | 47.674 | 50.162 | 1.00 | 54.15 | C |
| ATOM | 3460 | N | LYS | 23 | 90.339 | 45.312 | 51.983 | 1.00 | 9.94 | C |
| ATOM | 3461 | CA | LYS | 23 | 89.630 | 44.234 | 52.639 | 1.00 | 27.48 | C |
| ATOM | 3462 | CB | LYS | 23 | 88.196 | 44.149 | 52.099 | 1.00 | 45.60 | C |
| ATOM | 3463 | CG | LYS | 23 | 87.083 | 44.123 | 53.160 | 1.00 | 46.91 | C |
| ATOM | 3464 | CD | LYS | 23 | 85.742 | 44.572 | 52.558 | 1.00 | 49.03 | C |
| ATOM | 3465 | CE | LYS | 23 | 84.537 | 43.911 | 53.219 | 1.00 | 44.60 | C |
| ATOM | 3466 | NZ | LYS | 23 | 83.321 | 43.966 | 52.347 | 1.00 | 31.56 | C |
| ATOM | 3467 | C | LYS | 23 | 90.373 | 42.933 | 52.354 | 1.00 | 28.04 | C |
| ATOM | 3468 | O | LYS | 23 | 90.727 | 42.651 | 51.209 | 1.00 | 27.74 | C |
| ATOM | 3469 | N | TYR | 24 | 90.616 | 42.154 | 53.404 | 1.00 | 48.19 | C |
| ATOM | 3470 | CA | TYR | 24 | 91.305 | 40.869 | 53.279 | 1.00 | 51.31 | C |
| ATOM | 3471 | CB | TYR | 24 | 92.585 | 40.864 | 54.121 | 1.00 | 33.41 | C |
| ATOM | 3472 | CG | TYR | 24 | 93.582 | 41.914 | 53.708 | 1.00 | 28.69 | C |
| ATOM | 3473 | CD1 | TYR | 24 | 94.190 | 41.867 | 52.454 | 1.00 | 41.70 | C |
| ATOM | 3474 | CE1 | TYR | 24 | 95.089 | 42.846 | 52.049 | 1.00 | 20.51 | C |
| ATOM | 3475 | CD2 | TYR | 24 | 93.901 | 42.971 | 54.554 | 1.00 | 29.67 | C |
| ATOM | 3476 | CE2 | TYR | 24 | 94.803 | 43.960 | 54.159 | 1.00 | 21.03 | C |
| ATOM | 3477 | CZ | TYR | 24 | 95.389 | 43.889 | 52.905 | 1.00 | 18.10 | C |
| ATOM | 3478 | OH | TYR | 24 | 96.263 | 44.862 | 52.495 | 1.00 | 37.76 | C |
| ATOM | 3479 | C | TYR | 24 | 90.403 | 39.736 | 53.749 | 1.00 | 47.73 | C |
| ATOM | 3480 | O | TYR | 24 | 89.264 | 39.957 | 54.151 | 1.00 | 49.24 | C |
| ATOM | 3481 | N | SER | 25 | 90.920 | 38.518 | 53.690 | 1.00 | 57.38 | C |
| ATOM | 3482 | CA | SER | 25 | 90.175 | 37.353 | 54.146 | 1.00 | 60.28 | C |
| ATOM | 3483 | CB | SER | 25 | 89.888 | 36.407 | 52.975 | 1.00 | 59.25 | C |
| ATOM | 3484 | OG | SER | 25 | 91.068 | 36.142 | 52.238 | 1.00 | 69.79 | C |
| ATOM | 3485 | C | SER | 25 | 91.076 | 36.668 | 55.164 | 1.00 | 54.52 | C |
| ATOM | 3486 | O | SER | 25 | 91.290 | 35.455 | 55.108 | 1.00 | 60.55 | C |
| ATOM | 3487 | N | TYR | 26 | 91.606 | 37.458 | 56.096 | 1.00 | 43.18 | C |
| ATOM | 3488 | CA | TYR | 26 | 92.516 | 36.933 | 57.101 | 1.00 | 31.88 | C |
| ATOM | 3489 | CB | TYR | 26 | 93.949 | 36.995 | 56.566 | 1.00 | 26.62 | C |
| ATOM | 3490 | CG | TYR | 26 | 94.845 | 35.878 | 57.060 | 1.00 | 37.63 | C |
| ATOM | 3491 | CD1 | TYR | 26 | 95.606 | 36.026 | 58.220 | 1.00 | 43.69 | C |
| ATOM | 3492 | CE1 | TYR | 26 | 96.443 | 35.003 | 58.673 | 1.00 | 50.14 | C |
| ATOM | 3493 | CD2 | TYR | 26 | 94.941 | 34.677 | 56.363 | 1.00 | 43.23 | C |
| ATOM | 3494 | CE2 | TYR | 26 | 95.776 | 33.646 | 56.809 | 1.00 | 62.28 | C |
| ATOM | 3495 | CZ | TYR | 26 | 96.524 | 33.816 | 57.964 | 1.00 | 56.86 | C |
| ATOM | 3496 | OH | TYR | 26 | 97.352 | 32.801 | 58.404 | 1.00 | 54.48 | C |
| ATOM | 3497 | C | TYR | 26 | 92.455 | 37.637 | 58.451 | 1.00 | 30.34 | C |
| ATOM | 3498 | O | TYR | 26 | 92.275 | 38.851 | 58.518 | 1.00 | 12.16 | C |
| ATOM | 3499 | N | ASN | 27 | 92.626 | 36.832 | 59.504 | 1.00 | 35.16 | C |
| ATOM | 3500 | CA | ASN | 27 | 92.639 | 37.230 | 60.920 | 1.00 | 43.53 | C |
| ATOM | 3501 | CB | ASN | 27 | 94.092 | 37.461 | 61.380 | 1.00 | 44.74 | C |
| ATOM | 3502 | CG | ASN | 27 | 94.595 | 38.869 | 61.095 | 1.00 | 54.71 | C |
| ATOM | 3503 | OD1 | ASN | 27 | 93.890 | 39.691 | 60.503 | 1.00 | 49.86 | C |
| ATOM | 3504 | ND2 | ASN | 27 | 95.833 | 39.153 | 61.521 | 1.00 | 38.35 | C |
| ATOM | 3505 | C | ASN | 27 | 91.760 | 38.379 | 61.413 | 1.00 | 52.07 | C |
| ATOM | 3506 | O | ASN | 27 | 91.255 | 39.159 | 60.582 | 1.00 | 64.58 | C |
| ATOM | 3507 | OT | ASN | 27 | 91.583 | 38.478 | 62.651 | 1.00 | 38.64 | C |
| ATOM | 3508 | CB | SER | 30 | 98.029 | 39.101 | 66.273 | 1.00 | 38.67 | C |
| ATOM | 3509 | OG | SER | 30 | 99.164 | 39.940 | 66.371 | 1.00 | 28.74 | C |
| ATOM | 3510 | C | SER | 30 | 99.198 | 37.741 | 64.527 | 1.00 | 48.62 | C |
| ATOM | 3511 | O | SER | 30 | 99.534 | 36.748 | 65.163 | 1.00 | 42.19 | C |
| ATOM | 3512 | N | SER | 30 | 96.758 | 37.537 | 64.847 | 1.00 | 40.61 | C |
| ATOM | 3513 | CA | SER | 30 | 97.910 | 38.480 | 64.881 | 1.00 | 46.89 | C |
| ATOM | 3514 | N | ARG | 31 | 99.906 | 38.226 | 63.505 | 1.00 | 52.76 | C |
| ATOM | 3515 | CA | ARG | 31 | 101.156 | 37.606 | 63.056 | 1.00 | 48.62 | C |
| ATOM | 3516 | CB | ARG | 31 | 100.864 | 36.509 | 62.014 | 1.00 | 48.21 | C |
| ATOM | 3517 | CG | ARG | 31 | 99.390 | 36.316 | 61.654 | 1.00 | 45.83 | C |
| ATOM | 3518 | CD | ARG | 31 | 99.123 | 34.913 | 61.098 | 1.00 | 45.48 | C |

TABLE 4-continued

Co-ordinates of the CD28/5.11A1 crystal structure

| ATOM | 3519 | NE | ARG | 31 | 98.202 | 34.159 | 61.946 | 1.00 | 56.80 | C |
|---|---|---|---|---|---|---|---|---|---|---|
| ATOM | 3520 | CZ | ARG | 31 | 97.819 | 32.904 | 61.723 | 1.00 | 60.88 | C |
| ATOM | 3521 | NH1 | ARG | 31 | 98.273 | 32.238 | 60.666 | 1.00 | 53.06 | C |
| ATOM | 3522 | NH2 | ARG | 31 | 96.980 | 32.312 | 62.565 | 1.00 | 65.41 | C |
| ATOM | 3523 | C | ARG | 31 | 102.140 | 38.620 | 62.457 | 1.00 | 42.34 | C |
| ATOM | 3524 | O | ARG | 31 | 102.024 | 39.821 | 62.696 | 1.00 | 37.05 | C |
| ATOM | 3525 | N | GLU | 32 | 103.109 | 38.119 | 61.688 | 1.00 | 33.63 | C |
| ATOM | 3526 | CA | GLU | 32 | 104.114 | 38.959 | 61.035 | 1.00 | 28.55 | C |
| ATOM | 3527 | CB | GLU | 32 | 105.510 | 38.366 | 61.211 | 1.00 | 35.76 | C |
| ATOM | 3528 | CG | GLU | 32 | 106.639 | 39.289 | 60.762 | 1.00 | 44.46 | C |
| ATOM | 3529 | CD | GLU | 32 | 107.993 | 38.584 | 60.704 | 1.00 | 47.94 | C |
| ATOM | 3530 | OE1 | GLU | 32 | 108.183 | 37.588 | 61.436 | 1.00 | 50.54 | C |
| ATOM | 3531 | OE2 | GLU | 32 | 108.870 | 39.024 | 59.931 | 1.00 | 43.16 | C |
| ATOM | 3532 | C | GLU | 32 | 103.777 | 39.047 | 59.550 | 1.00 | 32.96 | C |
| ATOM | 3533 | O | GLU | 32 | 103.876 | 38.061 | 58.815 | 1.00 | 19.87 | C |
| ATOM | 3534 | N | PHE | 33 | 103.394 | 40.244 | 59.122 | 1.00 | 41.41 | C |
| ATOM | 3535 | CA | PHE | 33 | 102.989 | 40.488 | 57.747 | 1.00 | 35.05 | C |
| ATOM | 3536 | CB | PHE | 33 | 101.494 | 40.691 | 57.715 | 1.00 | 26.59 | C |
| ATOM | 3537 | CG | PHE | 33 | 101.065 | 41.944 | 58.408 | 1.00 | 24.17 | C |
| ATOM | 3538 | CD1 | PHE | 33 | 101.369 | 43.192 | 57.861 | 1.00 | 23.40 | C |
| ATOM | 3539 | CD2 | PHE | 33 | 100.374 | 41.889 | 59.611 | 1.00 | 15.64 | C |
| ATOM | 3540 | CE1 | PHE | 33 | 100.989 | 44.367 | 58.496 | 1.00 | 28.02 | C |
| ATOM | 3541 | CE2 | PHE | 33 | 99.984 | 43.063 | 60.260 | 1.00 | 24.23 | C |
| ATOM | 3542 | CZ | PHE | 33 | 100.292 | 44.304 | 59.703 | 1.00 | 31.35 | C |
| ATOM | 3543 | C | PHE | 33 | 103.640 | 41.716 | 57.121 | 1.00 | 34.54 | C |
| ATOM | 3544 | O | PHE | 33 | 104.134 | 42.613 | 57.813 | 1.00 | 21.74 | C |
| ATOM | 3545 | N | ARG | 34 | 103.564 | 41.771 | 55.797 | 1.00 | 28.28 | C |
| ATOM | 3546 | CA | ARG | 34 | 104.145 | 42.864 | 55.045 | 1.00 | 21.13 | C |
| ATOM | 3547 | CB | ARG | 34 | 105.469 | 42.413 | 54.437 | 1.00 | 12.61 | C |
| ATOM | 3548 | CG | ARG | 34 | 106.189 | 43.483 | 53.643 | 1.00 | 19.39 | C |
| ATOM | 3549 | CD | ARG | 34 | 106.709 | 42.916 | 52.339 | 1.00 | 18.93 | C |
| ATOM | 3550 | NE | ARG | 34 | 108.026 | 43.440 | 51.995 | 1.00 | 36.83 | C |
| ATOM | 3551 | CZ | ARG | 34 | 108.251 | 44.344 | 51.045 | 1.00 | 40.83 | C |
| ATOM | 3552 | NH1 | ARG | 34 | 107.239 | 44.825 | 50.340 | 1.00 | 45.97 | C |
| ATOM | 3553 | NH2 | ARG | 34 | 109.490 | 44.752 | 50.785 | 1.00 | 38.52 | C |
| ATOM | 3554 | C | ARG | 34 | 103.202 | 43.309 | 53.940 | 1.00 | 32.95 | C |
| ATOM | 3555 | O | ARG | 34 | 103.239 | 42.779 | 52.831 | 1.00 | 41.93 | C |
| ATOM | 3556 | N | ALA | 35 | 102.362 | 44.294 | 54.239 | 1.00 | 34.63 | C |
| ATOM | 3557 | CA | ALA | 35 | 101.416 | 44.798 | 53.251 | 1.00 | 26.09 | C |
| ATOM | 3558 | CB | ALA | 35 | 100.381 | 45.657 | 53.921 | 1.00 | 26.37 | C |
| ATOM | 3559 | C | ALA | 35 | 102.134 | 45.599 | 52.173 | 1.00 | 28.19 | C |
| ATOM | 3560 | O | ALA | 35 | 103.201 | 46.163 | 52.414 | 1.00 | 19.20 | C |
| ATOM | 3561 | N | SER | 36 | 101.545 | 45.641 | 50.980 | 1.00 | 36.87 | C |
| ATOM | 3562 | CA | SER | 36 | 102.136 | 46.374 | 49.863 | 1.00 | 39.36 | C |
| ATOM | 3563 | CB | SER | 36 | 103.172 | 45.488 | 49.160 | 1.00 | 51.82 | C |
| ATOM | 3564 | OG | SER | 36 | 103.705 | 44.516 | 50.050 | 1.00 | 62.97 | C |
| ATOM | 3565 | C | SER | 36 | 101.099 | 46.886 | 48.847 | 1.00 | 32.13 | C |
| ATOM | 3566 | O | SER | 36 | 100.092 | 46.238 | 48.575 | 1.00 | 28.44 | C |
| ATOM | 3567 | N | LEU | 37 | 101.364 | 48.069 | 48.304 | 1.00 | 34.51 | C |
| ATOM | 3568 | CA | LEU | 37 | 100.496 | 48.705 | 47.320 | 1.00 | 31.61 | C |
| ATOM | 3569 | CB | LEU | 37 | 99.897 | 49.987 | 47.895 | 1.00 | 36.64 | C |
| ATOM | 3570 | CG | LEU | 37 | 98.943 | 50.801 | 47.023 | 1.00 | 21.97 | C |
| ATOM | 3571 | CD1 | LEU | 37 | 97.533 | 50.720 | 47.578 | 1.00 | 21.64 | C |
| ATOM | 3572 | CD2 | LEU | 37 | 99.412 | 52.231 | 46.991 | 1.00 | 26.43 | C |
| ATOM | 3573 | C | LEU | 37 | 101.393 | 49.042 | 46.148 | 1.00 | 28.60 | C |
| ATOM | 3574 | O | LEU | 37 | 102.341 | 49.811 | 46.295 | 1.00 | 35.19 | C |
| ATOM | 3575 | N | HIS | 38 | 101.112 | 48.454 | 44.993 | 1.00 | 22.34 | C |
| ATOM | 3576 | CA | HIS | 38 | 101.935 | 48.694 | 43.816 | 1.00 | 21.00 | C |
| ATOM | 3577 | CB | HIS | 38 | 102.418 | 47.370 | 43.232 | 1.00 | 29.80 | C |
| ATOM | 3578 | CG | HIS | 38 | 103.038 | 46.464 | 44.248 | 1.00 | 41.65 | C |
| ATOM | 3579 | CD2 | HIS | 38 | 104.324 | 46.102 | 44.458 | 1.00 | 36.66 | C |
| ATOM | 3580 | ND1 | HIS | 38 | 102.296 | 45.819 | 45.218 | 1.00 | 51.35 | C |
| ATOM | 3581 | CE1 | HIS | 38 | 103.102 | 45.102 | 45.978 | 1.00 | 45.79 | C |
| ATOM | 3582 | NE2 | HIS | 38 | 104.337 | 45.256 | 45.539 | 1.00 | 50.11 | C |
| ATOM | 3583 | C | HIS | 38 | 101.138 | 49.458 | 42.794 | 1.00 | 20.21 | C |
| ATOM | 3584 | O | HIS | 38 | 99.935 | 49.263 | 42.679 | 1.00 | 24.62 | C |
| ATOM | 3585 | N | LYS | 39 | 101.807 | 50.334 | 42.055 | 1.00 | 17.62 | C |
| ATOM | 3586 | CA | LYS | 39 | 101.135 | 51.154 | 41.065 | 1.00 | 28.42 | C |
| ATOM | 3587 | CB | LYS | 39 | 101.458 | 52.627 | 41.334 | 1.00 | 33.83 | C |
| ATOM | 3588 | CG | LYS | 39 | 100.938 | 53.579 | 40.281 | 1.00 | 47.76 | C |
| ATOM | 3589 | CD | LYS | 39 | 102.046 | 54.496 | 39.767 | 1.00 | 56.33 | C |
| ATOM | 3590 | CE | LYS | 39 | 101.922 | 54.727 | 38.264 | 1.00 | 52.05 | C |
| ATOM | 3591 | NZ | LYS | 39 | 101.573 | 56.133 | 37.920 | 1.00 | 39.26 | C |
| ATOM | 3592 | C | LYS | 39 | 101.527 | 50.784 | 39.644 | 1.00 | 37.38 | C |
| ATOM | 3593 | O | LYS | 39 | 102.715 | 50.697 | 39.323 | 1.00 | 38.26 | C |
| ATOM | 3594 | N | GLY | 40 | 100.528 | 50.559 | 38.793 | 1.00 | 33.72 | C |
| ATOM | 3595 | CA | GLY | 40 | 100.819 | 50.230 | 37.412 | 1.00 | 30.90 | C |

TABLE 4-continued

Co-ordinates of the CD28/5.11A1 crystal structure

| ATOM | 3596 | C   | GLY | 40 | 100.183 | 48.957 | 36.913 | 1.00 | 33.65 | C |
|------|------|-----|-----|----|---------|--------|--------|------|-------|---|
| ATOM | 3597 | O   | GLY | 40 | 100.025 | 47.997 | 37.665 | 1.00 | 26.93 | C |
| ATOM | 3598 | N   | LEU | 41 | 99.819  | 48.962 | 35.634 | 1.00 | 48.13 | C |
| ATOM | 3599 | CA  | LEU | 41 | 99.196  | 47.809 | 34.988 | 1.00 | 43.35 | C |
| ATOM | 3600 | CB  | LEU | 41 | 98.598  | 48.211 | 33.633 | 1.00 | 41.37 | C |
| ATOM | 3601 | CG  | LEU | 41 | 97.256  | 47.613 | 33.178 | 1.00 | 50.66 | C |
| ATOM | 3602 | CD1 | LEU | 41 | 96.622  | 46.783 | 34.283 | 1.00 | 41.32 | C |
| ATOM | 3603 | CD2 | LEU | 41 | 96.324  | 48.742 | 32.756 | 1.00 | 36.16 | C |
| ATOM | 3604 | C   | LEU | 41 | 100.270 | 46.758 | 34.791 | 1.00 | 44.95 | C |
| ATOM | 3605 | O   | LEU | 41 | 99.976  | 45.585 | 34.577 | 1.00 | 48.29 | C |
| ATOM | 3606 | N   | ASP | 42 | 101.522 | 47.197 | 34.841 | 1.00 | 51.52 | C |
| ATOM | 3607 | CA  | ASP | 42 | 102.648 | 46.285 | 34.713 | 1.00 | 53.82 | C |
| ATOM | 3608 | CB  | ASP | 42 | 103.666 | 46.804 | 33.690 | 1.00 | 44.60 | C |
| ATOM | 3609 | CG  | ASP | 42 | 104.352 | 48.090 | 34.125 | 1.00 | 49.55 | C |
| ATOM | 3610 | OD1 | ASP | 42 | 103.874 | 48.765 | 35.063 | 1.00 | 40.26 | C |
| ATOM | 3611 | OD2 | ASP | 42 | 105.385 | 48.427 | 33.510 | 1.00 | 48.33 | C |
| ATOM | 3612 | C   | ASP | 42 | 103.249 | 46.241 | 36.106 | 1.00 | 57.65 | C |
| ATOM | 3613 | O   | ASP | 42 | 104.394 | 45.836 | 36.298 | 1.00 | 57.61 | C |
| ATOM | 3614 | N   | SER | 43 | 102.433 | 46.679 | 37.065 | 1.00 | 57.54 | C |
| ATOM | 3615 | CA  | SER | 43 | 102.767 | 46.741 | 38.486 | 1.00 | 56.75 | C |
| ATOM | 3616 | CB  | SER | 43 | 102.299 | 45.467 | 39.177 | 1.00 | 40.78 | C |
| ATOM | 3617 | OG  | SER | 43 | 100.896 | 45.502 | 39.359 | 1.00 | 32.86 | C |
| ATOM | 3618 | C   | SER | 43 | 104.234 | 46.995 | 38.803 | 1.00 | 59.27 | C |
| ATOM | 3619 | O   | SER | 43 | 104.795 | 46.413 | 39.732 | 1.00 | 57.66 | C |
| ATOM | 3620 | N   | ALA | 44 | 104.847 | 47.884 | 38.033 | 1.00 | 54.64 | C |
| ATOM | 3621 | CA  | ALA | 44 | 106.244 | 48.215 | 38.224 | 1.00 | 41.67 | C |
| ATOM | 3622 | CB  | ALA | 44 | 106.654 | 49.295 | 37.239 | 1.00 | 41.38 | C |
| ATOM | 3623 | C   | ALA | 44 | 106.514 | 48.679 | 39.646 | 1.00 | 42.01 | C |
| ATOM | 3624 | O   | ALA | 44 | 107.073 | 47.935 | 40.449 | 1.00 | 48.39 | C |
| ATOM | 3625 | N   | VAL | 45 | 106.083 | 49.904 | 39.943 | 1.00 | 40.52 | C |
| ATOM | 3626 | CA  | VAL | 45 | 106.290 | 50.563 | 41.239 | 1.00 | 34.97 | C |
| ATOM | 3627 | CB  | VAL | 45 | 106.036 | 52.073 | 41.094 | 1.00 | 27.80 | C |
| ATOM | 3628 | CG1 | VAL | 45 | 106.126 | 52.753 | 42.441 | 1.00 | 32.20 | C |
| ATOM | 3629 | CG2 | VAL | 45 | 107.036 | 52.674 | 40.126 | 1.00 | 35.71 | C |
| ATOM | 3630 | C   | VAL | 45 | 105.526 | 50.100 | 42.489 | 1.00 | 35.47 | C |
| ATOM | 3631 | O   | VAL | 45 | 104.307 | 49.956 | 42.462 | 1.00 | 45.80 | C |
| ATOM | 3632 | N   | GLU | 46 | 106.259 | 49.893 | 43.585 | 1.00 | 39.87 | C |
| ATOM | 3633 | CA  | GLU | 46 | 105.666 | 49.503 | 44.868 | 1.00 | 41.71 | C |
| ATOM | 3634 | CB  | GLU | 46 | 106.546 | 48.488 | 45.615 | 1.00 | 50.85 | C |
| ATOM | 3635 | CG  | GLU | 46 | 106.163 | 48.251 | 47.094 | 1.00 | 34.64 | C |
| ATOM | 3636 | CD  | GLU | 46 | 106.638 | 46.895 | 47.637 | 1.00 | 57.55 | C |
| ATOM | 3637 | OE1 | GLU | 46 | 107.869 | 46.712 | 47.809 | 1.00 | 47.66 | C |
| ATOM | 3638 | OE2 | GLU | 46 | 105.783 | 46.014 | 47.893 | 1.00 | 29.27 | C |
| ATOM | 3639 | C   | GLU | 46 | 105.575 | 50.791 | 45.680 | 1.00 | 37.48 | C |
| ATOM | 3640 | O   | GLU | 46 | 106.530 | 51.189 | 46.338 | 1.00 | 43.67 | C |
| ATOM | 3641 | N   | VAL | 47 | 104.418 | 51.433 | 45.614 | 1.00 | 25.13 | C |
| ATOM | 3642 | CA  | VAL | 47 | 104.173 | 52.692 | 46.297 | 1.00 | 15.83 | C |
| ATOM | 3643 | CB  | VAL | 47 | 102.736 | 53.146 | 46.037 | 1.00 | 19.37 | C |
| ATOM | 3644 | CG1 | VAL | 47 | 102.428 | 54.405 | 46.826 | 1.00 | 28.90 | C |
| ATOM | 3645 | CG2 | VAL | 47 | 102.543 | 53.374 | 44.547 | 1.00 | 26.86 | C |
| ATOM | 3646 | C   | VAL | 47 | 104.437 | 52.717 | 47.800 | 1.00 | 29.17 | C |
| ATOM | 3647 | O   | VAL | 47 | 105.070 | 53.641 | 48.310 | 1.00 | 31.30 | C |
| ATOM | 3648 | N   | CYS | 48 | 103.952 | 51.709 | 48.512 | 1.00 | 40.43 | C |
| ATOM | 3649 | CA  | CYS | 48 | 104.142 | 51.665 | 49.955 | 1.00 | 37.33 | C |
| ATOM | 3650 | C   | CYS | 48 | 104.145 | 50.246 | 50.495 | 1.00 | 27.79 | C |
| ATOM | 3651 | O   | CYS | 48 | 103.618 | 49.331 | 49.864 | 1.00 | 20.24 | C |
| ATOM | 3652 | CB  | CYS | 48 | 103.035 | 52.459 | 50.644 | 1.00 | 57.93 | C |
| ATOM | 3653 | SG  | CYS | 48 | 103.314 | 52.822 | 52.407 | 1.00 | 69.94 | C |
| ATOM | 3654 | N   | VAL | 49 | 104.747 | 50.070 | 51.664 | 1.00 | 18.58 | C |
| ATOM | 3655 | CA  | VAL | 49 | 104.802 | 48.764 | 52.290 | 1.00 | 20.44 | C |
| ATOM | 3656 | CB  | VAL | 49 | 106.139 | 48.030 | 51.966 | 1.00 | 27.56 | C |
| ATOM | 3657 | CG1 | VAL | 49 | 107.042 | 48.931 | 51.131 | 1.00 | 18.34 | C |
| ATOM | 3658 | CG2 | VAL | 49 | 106.851 | 47.592 | 53.249 | 1.00 | 17.63 | C |
| ATOM | 3659 | C   | VAL | 49 | 104.654 | 48.926 | 53.794 | 1.00 | 33.14 | C |
| ATOM | 3660 | O   | VAL | 49 | 105.537 | 49.471 | 54.455 | 1.00 | 29.92 | C |
| ATOM | 3661 | N   | VAL | 50 | 103.523 | 48.467 | 54.324 | 1.00 | 41.12 | C |
| ATOM | 3662 | CA  | VAL | 50 | 103.255 | 48.539 | 55.759 | 1.00 | 44.37 | C |
| ATOM | 3663 | CB  | VAL | 50 | 101.796 | 48.932 | 56.031 | 1.00 | 48.04 | C |
| ATOM | 3664 | CG1 | VAL | 50 | 101.486 | 48.786 | 57.511 | 1.00 | 45.70 | C |
| ATOM | 3665 | CG2 | VAL | 50 | 101.562 | 50.367 | 55.576 | 1.00 | 35.76 | C |
| ATOM | 3666 | C   | VAL | 50 | 103.553 | 47.176 | 56.385 | 1.00 | 38.20 | C |
| ATOM | 3667 | O   | VAL | 50 | 102.899 | 46.176 | 56.085 | 1.00 | 36.51 | C |
| ATOM | 3668 | N   | TYR | 51 | 104.543 | 47.146 | 57.264 | 1.00 | 25.60 | C |
| ATOM | 3669 | CA  | TYR | 51 | 104.957 | 45.898 | 57.879 | 1.00 | 34.11 | C |
| ATOM | 3670 | CB  | TYR | 51 | 106.479 | 45.779 | 57.799 | 1.00 | 34.41 | C |
| ATOM | 3671 | CG  | TYR | 51 | 107.060 | 44.744 | 58.724 | 1.00 | 31.19 | C |
| ATOM | 3672 | CD1 | TYR | 51 | 107.617 | 45.109 | 59.944 | 1.00 | 38.77 | C |

TABLE 4-continued

Co-ordinates of the CD28/5.11A1 crystal structure

| ATOM | 3673 | CE1 | TYR | 51 | 108.122 | 44.153 | 60.822 | 1.00 | 44.07 | C |
|------|------|-----|-----|----|---------|--------|--------|------|-------|---|
| ATOM | 3674 | CD2 | TYR | 51 | 107.025 | 43.396 | 58.395 | 1.00 | 33.29 | C |
| ATOM | 3675 | CE2 | TYR | 51 | 107.525 | 42.432 | 59.265 | 1.00 | 41.62 | C |
| ATOM | 3676 | CZ  | TYR | 51 | 108.068 | 42.818 | 60.477 | 1.00 | 39.08 | C |
| ATOM | 3677 | OH  | TYR | 51 | 108.511 | 41.867 | 61.364 | 1.00 | 47.15 | C |
| ATOM | 3678 | C   | TYR | 51 | 104.507 | 45.729 | 59.315 | 1.00 | 33.68 | C |
| ATOM | 3679 | O   | TYR | 51 | 104.696 | 46.613 | 60.145 | 1.00 | 23.59 | C |
| ATOM | 3680 | N   | GLY | 52 | 103.927 | 44.571 | 59.603 | 1.00 | 29.01 | C |
| ATOM | 3681 | CA  | GLY | 52 | 103.459 | 44.300 | 60.947 | 1.00 | 30.05 | C |
| ATOM | 3682 | C   | GLY | 52 | 104.067 | 43.041 | 61.527 | 1.00 | 39.73 | C |
| ATOM | 3683 | O   | GLY | 52 | 104.393 | 42.096 | 60.806 | 1.00 | 40.35 | C |
| ATOM | 3684 | N   | ASN | 53 | 104.224 | 43.032 | 62.843 | 1.00 | 46.66 | C |
| ATOM | 3685 | CA  | ASN | 53 | 104.798 | 41.888 | 63.537 | 1.00 | 57.56 | C |
| ATOM | 3686 | CB  | ASN | 53 | 106.308 | 42.073 | 63.721 | 1.00 | 32.73 | C |
| ATOM | 3687 | CG  | ASN | 53 | 106.971 | 40.851 | 64.322 | 1.00 | 30.74 | C |
| ATOM | 3688 | OD1 | ASN | 53 | 106.474 | 39.728 | 64.185 | 1.00 | 25.99 | C |
| ATOM | 3689 | ND2 | ASN | 53 | 108.099 | 41.059 | 64.995 | 1.00 | 35.70 | C |
| ATOM | 3690 | C   | ASN | 53 | 104.141 | 41.729 | 64.897 | 1.00 | 63.15 | C |
| ATOM | 3691 | O   | ASN | 53 | 104.709 | 42.114 | 65.918 | 1.00 | 67.81 | C |
| ATOM | 3692 | N   | TYR | 54 | 102.941 | 41.159 | 64.906 | 1.00 | 66.70 | C |
| ATOM | 3693 | CA  | TYR | 54 | 102.213 | 40.953 | 66.149 | 1.00 | 70.87 | C |
| ATOM | 3694 | CB  | TYR | 54 | 103.004 | 40.008 | 67.072 | 1.00 | 60.20 | C |
| ATOM | 3695 | CG  | TYR | 54 | 103.185 | 38.604 | 66.521 | 1.00 | 54.18 | C |
| ATOM | 3696 | CD1 | TYR | 54 | 104.380 | 38.215 | 65.923 | 1.00 | 49.72 | C |
| ATOM | 3697 | CE1 | TYR | 54 | 104.538 | 36.931 | 65.393 | 1.00 | 51.50 | C |
| ATOM | 3698 | CD2 | TYR | 54 | 102.149 | 37.672 | 66.579 | 1.00 | 63.25 | C |
| ATOM | 3699 | CE2 | TYR | 54 | 102.297 | 36.386 | 66.052 | 1.00 | 53.22 | C |
| ATOM | 3700 | CZ  | TYR | 54 | 103.489 | 36.025 | 65.461 | 1.00 | 51.26 | C |
| ATOM | 3701 | OH  | TYR | 54 | 103.625 | 34.761 | 64.931 | 1.00 | 41.36 | C |
| ATOM | 3702 | C   | TYR | 54 | 102.018 | 42.313 | 66.811 | 1.00 | 75.80 | C |
| ATOM | 3703 | O   | TYR | 54 | 101.118 | 43.072 | 66.443 | 1.00 | 70.77 | C |
| ATOM | 3704 | N   | SER | 55 | 102.870 | 42.617 | 67.784 | 1.00 | 83.17 | C |
| ATOM | 3705 | CA  | SER | 55 | 102.805 | 43.892 | 68.483 | 1.00 | 89.21 | C |
| ATOM | 3706 | CB  | SER | 55 | 103.373 | 43.750 | 69.896 | 1.00 | 89.77 | C |
| ATOM | 3707 | OG  | SER | 55 | 102.332 | 43.662 | 70.853 | 1.00 | 90.69 | C |
| ATOM | 3708 | C   | SER | 55 | 103.617 | 44.916 | 67.695 | 1.00 | 90.09 | C |
| ATOM | 3709 | O   | SER | 55 | 103.181 | 45.378 | 66.639 | 1.00 | 92.24 | C |
| ATOM | 3710 | N   | GLN | 56 | 104.796 | 45.251 | 68.218 | 1.00 | 90.35 | C |
| ATOM | 3711 | CA  | GLN | 56 | 105.715 | 46.207 | 67.600 | 1.00 | 93.42 | C |
| ATOM | 3712 | CB  | GLN | 56 | 106.882 | 45.448 | 66.957 | 1.00 | 91.24 | C |
| ATOM | 3713 | CG  | GLN | 56 | 107.492 | 44.372 | 67.861 | 1.00 | 94.20 | C |
| ATOM | 3714 | CD  | GLN | 56 | 108.069 | 43.192 | 67.088 | 1.00 | 99.99 | C |
| ATOM | 3715 | OE1 | GLN | 56 | 108.128 | 42.066 | 67.595 | 1.00 | 87.06 | C |
| ATOM | 3716 | NE2 | GLN | 56 | 108.500 | 43.446 | 65.854 | 1.00 | 99.99 | C |
| ATOM | 3717 | C   | GLN | 56 | 105.040 | 47.121 | 66.572 | 1.00 | 96.11 | C |
| ATOM | 3718 | O   | GLN | 56 | 104.866 | 46.744 | 65.413 | 1.00 | 99.98 | C |
| ATOM | 3719 | N   | GLN | 57 | 104.670 | 48.323 | 67.013 | 1.00 | 90.45 | C |
| ATOM | 3720 | CA  | GLN | 57 | 103.995 | 49.318 | 66.177 | 1.00 | 83.45 | C |
| ATOM | 3721 | CB  | GLN | 57 | 104.417 | 50.732 | 66.589 | 1.00 | 85.60 | C |
| ATOM | 3722 | CG  | GLN | 57 | 104.367 | 50.991 | 68.084 | 1.00 | 89.34 | C |
| ATOM | 3723 | CD  | GLN | 57 | 105.744 | 50.966 | 68.718 | 1.00 | 87.16 | C |
| ATOM | 3724 | OE1 | GLN | 57 | 106.497 | 51.937 | 68.635 | 1.00 | 76.99 | C |
| ATOM | 3725 | NE2 | GLN | 57 | 106.080 | 49.849 | 69.355 | 1.00 | 90.12 | C |
| ATOM | 3726 | C   | GLN | 57 | 104.185 | 49.175 | 64.669 | 1.00 | 80.35 | C |
| ATOM | 3727 | O   | GLN | 57 | 105.278 | 48.877 | 64.182 | 1.00 | 77.96 | C |
| ATOM | 3728 | N   | LEU | 58 | 103.095 | 49.401 | 63.943 | 1.00 | 76.47 | C |
| ATOM | 3729 | CA  | LEU | 58 | 103.077 | 49.331 | 62.487 | 1.00 | 61.35 | C |
| ATOM | 3730 | CB  | LEU | 58 | 101.723 | 49.838 | 61.972 | 1.00 | 52.59 | C |
| ATOM | 3731 | CG  | LEU | 58 | 100.956 | 49.130 | 60.845 | 1.00 | 50.02 | C |
| ATOM | 3732 | CD1 | LEU | 58 | 100.916 | 47.634 | 61.070 | 1.00 | 55.58 | C |
| ATOM | 3733 | CD2 | LEU | 58 | 99.535  | 49.671 | 60.794 | 1.00 | 39.64 | C |
| ATOM | 3734 | C   | LEU | 58 | 104.209 | 50.181 | 61.906 | 1.00 | 54.39 | C |
| ATOM | 3735 | O   | LEU | 58 | 104.387 | 51.345 | 62.284 | 1.00 | 51.09 | C |
| ATOM | 3736 | N   | GLN | 59 | 104.976 | 49.589 | 60.997 | 1.00 | 51.81 | C |
| ATOM | 3737 | CA  | GLN | 59 | 106.080 | 50.290 | 60.346 | 1.00 | 46.97 | C |
| ATOM | 3738 | CB  | GLN | 59 | 107.394 | 49.516 | 60.524 | 1.00 | 35.66 | C |
| ATOM | 3739 | CG  | GLN | 59 | 108.469 | 50.260 | 61.308 | 1.00 | 32.42 | C |
| ATOM | 3740 | CD  | GLN | 59 | 109.327 | 49.340 | 62.171 | 1.00 | 53.43 | C |
| ATOM | 3741 | OE1 | GLN | 59 | 110.198 | 49.799 | 62.912 | 1.00 | 50.95 | C |
| ATOM | 3742 | NE2 | GLN | 59 | 109.082 | 48.037 | 62.079 | 1.00 | 46.72 | C |
| ATOM | 3743 | C   | GLN | 59 | 105.748 | 50.417 | 58.859 | 1.00 | 43.43 | C |
| ATOM | 3744 | O   | GLN | 59 | 105.697 | 49.422 | 58.138 | 1.00 | 42.60 | C |
| ATOM | 3745 | N   | VAL | 60 | 105.505 | 51.645 | 58.412 | 1.00 | 40.75 | C |
| ATOM | 3746 | CA  | VAL | 60 | 105.172 | 51.907 | 57.018 | 1.00 | 39.80 | C |
| ATOM | 3747 | CB  | VAL | 60 | 103.828 | 52.659 | 56.896 | 1.00 | 26.19 | C |
| ATOM | 3748 | CG1 | VAL | 60 | 103.878 | 53.955 | 57.678 | 1.00 | 21.41 | C |
| ATOM | 3749 | CG2 | VAL | 60 | 103.528 | 52.946 | 55.448 | 1.00 | 27.26 | C |

TABLE 4-continued

Co-ordinates of the CD28/5.11A1 crystal structure

| ATOM | 3750 | C   | VAL | 60 | 106.267 | 52.745 | 56.371 | 1.00 | 41.05 | C |
|------|------|-----|-----|----|---------|--------|--------|------|-------|---|
| ATOM | 3751 | O   | VAL | 60 | 106.733 | 53.727 | 56.950 | 1.00 | 51.96 | C |
| ATOM | 3752 | N   | TYR | 61 | 106.692 | 52.349 | 55.177 | 1.00 | 37.63 | C |
| ATOM | 3753 | CA  | TYR | 61 | 107.731 | 53.086 | 54.477 | 1.00 | 25.83 | C |
| ATOM | 3754 | CB  | TYR | 61 | 109.118 | 52.575 | 54.861 | 1.00 | 12.00 | C |
| ATOM | 3755 | CG  | TYR | 61 | 109.496 | 51.237 | 54.274 | 1.00 | 18.91 | C |
| ATOM | 3756 | CD1 | TYR | 61 | 109.216 | 50.053 | 54.953 | 1.00 | 42.23 | C |
| ATOM | 3757 | CE1 | TYR | 61 | 109.599 | 48.819 | 54.439 | 1.00 | 33.05 | C |
| ATOM | 3758 | CD2 | TYR | 61 | 110.173 | 51.150 | 53.057 | 1.00 | 38.49 | C |
| ATOM | 3759 | CE2 | TYR | 61 | 110.562 | 49.918 | 52.533 | 1.00 | 23.48 | C |
| ATOM | 3760 | CZ  | TYR | 61 | 110.269 | 48.758 | 53.231 | 1.00 | 29.34 | C |
| ATOM | 3761 | OH  | TYR | 61 | 110.627 | 47.535 | 52.714 | 1.00 | 30.14 | C |
| ATOM | 3762 | C   | TYR | 61 | 107.540 | 52.981 | 52.986 | 1.00 | 35.71 | C |
| ATOM | 3763 | O   | TYR | 61 | 106.694 | 52.214 | 52.513 | 1.00 | 35.76 | C |
| ATOM | 3764 | N   | SER | 62 | 108.322 | 53.775 | 52.258 | 1.00 | 39.08 | C |
| ATOM | 3765 | CA  | SER | 62 | 108.268 | 53.813 | 50.805 | 1.00 | 39.42 | C |
| ATOM | 3766 | CB  | SER | 62 | 107.247 | 54.857 | 50.345 | 1.00 | 32.31 | C |
| ATOM | 3767 | OG  | SER | 62 | 107.120 | 54.853 | 48.932 | 1.00 | 23.48 | C |
| ATOM | 3768 | C   | SER | 62 | 109.643 | 54.137 | 50.220 | 1.00 | 45.43 | C |
| ATOM | 3769 | O   | SER | 62 | 110.287 | 55.116 | 50.601 | 1.00 | 42.20 | C |
| ATOM | 3770 | N   | LYS | 63 | 110.094 | 53.302 | 49.294 | 1.00 | 50.45 | C |
| ATOM | 3771 | CA  | LYS | 63 | 111.388 | 53.499 | 48.655 | 1.00 | 44.30 | C |
| ATOM | 3772 | CB  | LYS | 63 | 112.040 | 52.136 | 48.373 | 1.00 | 41.16 | C |
| ATOM | 3773 | CG  | LYS | 63 | 113.045 | 51.676 | 49.431 | 1.00 | 41.13 | C |
| ATOM | 3774 | CD  | LYS | 63 | 112.720 | 50.288 | 49.969 | 1.00 | 36.52 | C |
| ATOM | 3775 | CE  | LYS | 63 | 113.769 | 49.809 | 50.972 | 1.00 | 27.51 | C |
| ATOM | 3776 | NZ  | LYS | 63 | 114.917 | 49.099 | 50.322 | 1.00 | 14.01 | C |
| ATOM | 3777 | C   | LYS | 63 | 111.173 | 54.243 | 47.343 | 1.00 | 40.39 | C |
| ATOM | 3778 | O   | LYS | 63 | 112.079 | 54.322 | 46.515 | 1.00 | 43.49 | C |
| ATOM | 3779 | N   | THR | 64 | 109.977 | 54.802 | 47.166 | 1.00 | 38.77 | C |
| ATOM | 3780 | CA  | THR | 64 | 109.635 | 55.496 | 45.926 | 1.00 | 33.97 | C |
| ATOM | 3781 | CB  | THR | 64 | 108.407 | 54.837 | 45.264 | 1.00 | 45.65 | C |
| ATOM | 3782 | OG1 | THR | 64 | 107.445 | 54.502 | 46.272 | 1.00 | 61.07 | C |
| ATOM | 3783 | CG2 | THR | 64 | 108.811 | 53.576 | 44.520 | 1.00 | 45.91 | C |
| ATOM | 3784 | C   | THR | 64 | 109.360 | 56.988 | 46.033 | 1.00 | 33.47 | C |
| ATOM | 3785 | O   | THR | 64 | 109.122 | 57.651 | 45.023 | 1.00 | 25.44 | C |
| ATOM | 3786 | N   | GLY | 65 | 109.375 | 57.525 | 47.244 | 1.00 | 35.21 | C |
| ATOM | 3787 | CA  | GLY | 65 | 109.119 | 58.946 | 47.383 | 1.00 | 35.72 | C |
| ATOM | 3788 | C   | GLY | 65 | 107.644 | 59.286 | 47.468 | 1.00 | 35.69 | C |
| ATOM | 3789 | O   | GLY | 65 | 107.198 | 60.317 | 46.970 | 1.00 | 41.32 | C |
| ATOM | 3790 | N   | PHE | 66 | 106.881 | 58.405 | 48.100 | 1.00 | 31.14 | C |
| ATOM | 3791 | CA  | PHE | 66 | 105.454 | 58.616 | 48.280 | 1.00 | 22.44 | C |
| ATOM | 3792 | CB  | PHE | 66 | 104.680 | 57.350 | 47.914 | 1.00 | 15.68 | C |
| ATOM | 3793 | CG  | PHE | 66 | 104.307 | 57.256 | 46.463 | 1.00 | 27.36 | C |
| ATOM | 3794 | CD1 | PHE | 66 | 105.243 | 56.859 | 45.514 | 1.00 | 38.42 | C |
| ATOM | 3795 | CD2 | PHE | 66 | 103.009 | 57.536 | 46.042 | 1.00 | 42.24 | C |
| ATOM | 3796 | CE1 | PHE | 66 | 104.889 | 56.738 | 44.159 | 1.00 | 42.03 | C |
| ATOM | 3797 | CE2 | PHE | 66 | 102.648 | 57.419 | 44.694 | 1.00 | 38.62 | C |
| ATOM | 3798 | CZ  | PHE | 66 | 103.590 | 57.018 | 43.750 | 1.00 | 28.00 | C |
| ATOM | 3799 | C   | PHE | 66 | 105.238 | 58.921 | 49.758 | 1.00 | 29.60 | C |
| ATOM | 3800 | O   | PHE | 66 | 105.701 | 58.176 | 50.622 | 1.00 | 28.41 | C |
| ATOM | 3801 | N   | ASN | 67 | 104.569 | 60.028 | 50.053 | 1.00 | 29.26 | C |
| ATOM | 3802 | CA  | ASN | 67 | 104.289 | 60.375 | 51.436 | 1.00 | 28.71 | C |
| ATOM | 3803 | CB  | ASN | 67 | 103.776 | 61.814 | 51.516 | 1.00 | 44.50 | C |
| ATOM | 3804 | CG  | ASN | 67 | 103.832 | 62.385 | 52.923 | 1.00 | 56.37 | C |
| ATOM | 3805 | OD1 | ASN | 67 | 103.890 | 63.603 | 53.110 | 1.00 | 55.38 | C |
| ATOM | 3806 | ND2 | ASN | 67 | 103.816 | 61.507 | 53.922 | 1.00 | 49.90 | C |
| ATOM | 3807 | C   | ASN | 67 | 103.208 | 59.390 | 51.891 | 1.00 | 30.16 | C |
| ATOM | 3808 | O   | ASN | 67 | 102.018 | 59.698 | 51.893 | 1.00 | 22.60 | C |
| ATOM | 3809 | N   | CYS | 68 | 103.627 | 58.190 | 52.276 | 1.00 | 45.93 | C |
| ATOM | 3810 | CA  | CYS | 68 | 102.678 | 57.165 | 52.691 | 1.00 | 37.84 | C |
| ATOM | 3811 | C   | CYS | 68 | 102.480 | 56.998 | 54.198 | 1.00 | 40.89 | C |
| ATOM | 3812 | O   | CYS | 68 | 103.414 | 57.122 | 54.986 | 1.00 | 26.35 | C |
| ATOM | 3813 | CB  | CYS | 68 | 103.087 | 55.824 | 52.089 | 1.00 | 23.40 | C |
| ATOM | 3814 | SG  | CYS | 68 | 102.108 | 54.426 | 52.713 | 1.00 | 53.33 | C |
| ATOM | 3815 | N   | ASP | 69 | 101.243 | 56.700 | 54.579 | 1.00 | 44.34 | C |
| ATOM | 3816 | CA  | ASP | 69 | 100.880 | 56.482 | 55.974 | 1.00 | 40.80 | C |
| ATOM | 3817 | CB  | ASP | 69 | 100.101 | 57.683 | 56.515 | 1.00 | 56.37 | C |
| ATOM | 3818 | CG  | ASP | 69 | 100.821 | 59.001 | 56.287 | 1.00 | 59.33 | C |
| ATOM | 3819 | OD1 | ASP | 69 | 100.303 | 59.840 | 55.520 | 1.00 | 66.37 | C |
| ATOM | 3820 | OD2 | ASP | 69 | 101.902 | 59.200 | 56.877 | 1.00 | 68.80 | C |
| ATOM | 3821 | C   | ASP | 69 | 100.001 | 55.240 | 56.013 | 1.00 | 32.24 | C |
| ATOM | 3822 | O   | ASP | 69 | 99.172  | 55.051 | 55.128 | 1.00 | 33.63 | C |
| ATOM | 3823 | N   | GLY | 70 | 100.175 | 54.395 | 57.026 | 1.00 | 34.87 | C |
| ATOM | 3824 | CA  | GLY | 70 | 99.369  | 53.184 | 57.107 | 1.00 | 28.23 | C |
| ATOM | 3825 | C   | GLY | 70 | 98.691  | 52.933 | 58.444 | 1.00 | 28.75 | C |
| ATOM | 3826 | O   | GLY | 70 | 99.260  | 53.198 | 59.501 | 1.00 | 34.76 | C |

TABLE 4-continued

Co-ordinates of the CD28/5.11A1 crystal structure

| ATOM | 3827 | N | LYS | 71 | 97.468 | 52.416 | 58.394 | 1.00 | 40.41 | C |
|---|---|---|---|---|---|---|---|---|---|---|
| ATOM | 3828 | CA | LYS | 71 | 96.697 | 52.123 | 59.599 | 1.00 | 49.78 | C |
| ATOM | 3829 | CB | LYS | 71 | 95.522 | 53.095 | 59.714 | 1.00 | 57.09 | C |
| ATOM | 3830 | CG | LYS | 71 | 95.747 | 54.285 | 60.629 | 1.00 | 56.31 | C |
| ATOM | 3831 | CD | LYS | 71 | 94.477 | 55.139 | 60.720 | 1.00 | 55.32 | C |
| ATOM | 3832 | CE | LYS | 71 | 94.459 | 56.004 | 61.984 | 1.00 | 59.27 | C |
| ATOM | 3833 | NZ | LYS | 71 | 93.094 | 56.536 | 62.310 | 1.00 | 33.49 | C |
| ATOM | 3834 | C | LYS | 71 | 96.160 | 50.690 | 59.553 | 1.00 | 51.01 | C |
| ATOM | 3835 | O | LYS | 71 | 95.553 | 50.274 | 58.568 | 1.00 | 42.24 | C |
| ATOM | 3836 | N | LEU | 72 | 96.373 | 49.940 | 60.628 | 1.00 | 51.79 | C |
| ATOM | 3837 | CA | LEU | 72 | 95.907 | 48.564 | 60.684 | 1.00 | 61.74 | C |
| ATOM | 3838 | CB | LEU | 72 | 96.773 | 47.760 | 61.650 | 1.00 | 62.34 | C |
| ATOM | 3839 | CG | LEU | 72 | 97.284 | 46.425 | 61.103 | 1.00 | 66.36 | C |
| ATOM | 3840 | CD1 | LEU | 72 | 98.165 | 45.754 | 62.147 | 1.00 | 68.74 | C |
| ATOM | 3841 | CD2 | LEU | 72 | 96.107 | 45.527 | 60.736 | 1.00 | 53.65 | C |
| ATOM | 3842 | C | LEU | 72 | 94.436 | 48.447 | 61.090 | 1.00 | 73.73 | C |
| ATOM | 3843 | O | LEU | 72 | 93.860 | 49.374 | 61.663 | 1.00 | 88.59 | C |
| ATOM | 3844 | N | GLY | 73 | 93.835 | 47.298 | 60.789 | 1.00 | 67.09 | C |
| ATOM | 3845 | CA | GLY | 73 | 92.443 | 47.075 | 61.126 | 1.00 | 50.60 | C |
| ATOM | 3846 | C | GLY | 73 | 91.964 | 45.670 | 60.808 | 1.00 | 56.73 | C |
| ATOM | 3847 | O | GLY | 73 | 91.356 | 45.434 | 59.760 | 1.00 | 64.99 | C |
| ATOM | 3848 | N | ASN | 74 | 92.246 | 44.735 | 61.713 | 1.00 | 46.04 | C |
| ATOM | 3849 | CA | ASN | 74 | 91.828 | 43.342 | 61.566 | 1.00 | 54.16 | C |
| ATOM | 3850 | CB | ASN | 74 | 90.316 | 43.231 | 61.790 | 1.00 | 79.65 | C |
| ATOM | 3851 | CG | ASN | 74 | 89.953 | 42.174 | 62.814 | 1.00 | 90.87 | C |
| ATOM | 3852 | OD1 | ASN | 74 | 88.992 | 42.334 | 63.574 | 1.00 | 90.68 | C |
| ATOM | 3853 | ND2 | ASN | 74 | 90.715 | 41.086 | 62.838 | 1.00 | 89.35 | C |
| ATOM | 3854 | C | ASN | 74 | 92.180 | 42.738 | 60.215 | 1.00 | 54.40 | C |
| ATOM | 3855 | O | ASN | 74 | 93.332 | 42.413 | 59.951 | 1.00 | 62.07 | C |
| ATOM | 3856 | N | GLU | 75 | 91.171 | 42.577 | 59.364 | 1.00 | 55.88 | C |
| ATOM | 3857 | CA | GLU | 75 | 91.364 | 42.010 | 58.035 | 1.00 | 47.09 | C |
| ATOM | 3858 | CB | GLU | 75 | 90.269 | 40.988 | 57.722 | 1.00 | 56.56 | C |
| ATOM | 3859 | CG | GLU | 75 | 88.966 | 41.211 | 58.471 | 1.00 | 48.68 | C |
| ATOM | 3860 | CD | GLU | 75 | 88.614 | 40.047 | 59.379 | 1.00 | 58.55 | C |
| ATOM | 3861 | OE1 | GLU | 75 | 88.407 | 38.928 | 58.859 | 1.00 | 55.16 | C |
| ATOM | 3862 | OE2 | GLU | 75 | 88.547 | 40.250 | 60.612 | 1.00 | 54.08 | C |
| ATOM | 3863 | C | GLU | 75 | 91.323 | 43.127 | 57.013 | 1.00 | 44.01 | C |
| ATOM | 3864 | O | GLU | 75 | 90.606 | 43.055 | 56.017 | 1.00 | 27.15 | C |
| ATOM | 3865 | N | SER | 76 | 92.107 | 44.162 | 57.268 | 1.00 | 36.46 | C |
| ATOM | 3866 | CA | SER | 76 | 92.143 | 45.296 | 56.376 | 1.00 | 31.85 | C |
| ATOM | 3867 | CB | SER | 76 | 90.835 | 46.072 | 56.492 | 1.00 | 24.92 | C |
| ATOM | 3868 | OG | SER | 76 | 90.835 | 46.835 | 57.681 | 1.00 | 16.45 | C |
| ATOM | 3869 | C | SER | 76 | 93.292 | 46.208 | 56.733 | 1.00 | 32.47 | C |
| ATOM | 3870 | O | SER | 76 | 93.689 | 46.294 | 57.892 | 1.00 | 34.00 | C |
| ATOM | 3871 | N | VAL | 77 | 93.826 | 46.884 | 55.723 | 1.00 | 38.60 | C |
| ATOM | 3872 | CA | VAL | 77 | 94.906 | 47.848 | 55.908 | 1.00 | 32.38 | C |
| ATOM | 3873 | CB | VAL | 77 | 96.272 | 47.308 | 55.386 | 1.00 | 45.71 | C |
| ATOM | 3874 | CG1 | VAL | 77 | 96.747 | 48.122 | 54.190 | 1.00 | 37.47 | C |
| ATOM | 3875 | CG2 | VAL | 77 | 97.327 | 47.372 | 56.484 | 1.00 | 19.29 | C |
| ATOM | 3876 | C | VAL | 77 | 94.509 | 49.083 | 55.101 | 1.00 | 33.67 | C |
| ATOM | 3877 | O | VAL | 77 | 93.934 | 48.972 | 54.013 | 1.00 | 38.06 | C |
| ATOM | 3878 | N | THR | 78 | 94.811 | 50.260 | 55.630 | 1.00 | 40.03 | C |
| ATOM | 3879 | CA | THR | 78 | 94.475 | 51.493 | 54.929 | 1.00 | 38.24 | C |
| ATOM | 3880 | CB | THR | 78 | 93.548 | 52.377 | 55.787 | 1.00 | 35.10 | C |
| ATOM | 3881 | OG1 | THR | 78 | 92.594 | 51.551 | 56.472 | 1.00 | 36.53 | C |
| ATOM | 3882 | CG2 | THR | 78 | 92.804 | 53.363 | 54.916 | 1.00 | 36.45 | C |
| ATOM | 3883 | C | THR | 78 | 95.745 | 52.269 | 54.580 | 1.00 | 35.91 | C |
| ATOM | 3884 | O | THR | 78 | 96.574 | 52.540 | 55.451 | 1.00 | 31.92 | C |
| ATOM | 3885 | N | PHE | 79 | 95.896 | 52.610 | 53.301 | 1.00 | 39.13 | C |
| ATOM | 3886 | CA | PHE | 79 | 97.059 | 53.358 | 52.824 | 1.00 | 29.89 | C |
| ATOM | 3887 | CB | PHE | 79 | 97.532 | 52.801 | 51.487 | 1.00 | 35.47 | C |
| ATOM | 3888 | CG | PHE | 79 | 97.996 | 51.380 | 51.553 | 1.00 | 41.67 | C |
| ATOM | 3889 | CD1 | PHE | 79 | 97.174 | 50.342 | 51.123 | 1.00 | 46.33 | C |
| ATOM | 3890 | CD2 | PHE | 79 | 99.271 | 51.077 | 52.019 | 1.00 | 35.39 | C |
| ATOM | 3891 | CE1 | PHE | 79 | 97.621 | 49.026 | 51.155 | 1.00 | 34.72 | C |
| ATOM | 3892 | CE2 | PHE | 79 | 99.724 | 49.765 | 52.054 | 1.00 | 17.78 | C |
| ATOM | 3893 | CZ | PHE | 79 | 98.895 | 48.736 | 51.619 | 1.00 | 26.82 | C |
| ATOM | 3894 | C | PHE | 79 | 96.687 | 54.816 | 52.645 | 1.00 | 20.01 | C |
| ATOM | 3895 | O | PHE | 79 | 95.843 | 55.143 | 51.817 | 1.00 | 39.07 | C |
| ATOM | 3896 | N | TYR | 80 | 97.328 | 55.690 | 53.414 | 1.00 | 37.92 | C |
| ATOM | 3897 | CA | TYR | 80 | 97.048 | 57.123 | 53.361 | 1.00 | 39.66 | C |
| ATOM | 3898 | CB | TYR | 80 | 97.043 | 57.706 | 54.775 | 1.00 | 41.42 | C |
| ATOM | 3899 | CG | TYR | 80 | 96.541 | 59.125 | 54.849 | 1.00 | 29.87 | C |
| ATOM | 3900 | CD1 | TYR | 80 | 95.857 | 59.702 | 53.782 | 1.00 | 31.82 | C |
| ATOM | 3901 | CE1 | TYR | 80 | 95.404 | 61.008 | 53.842 | 1.00 | 38.26 | C |
| ATOM | 3902 | CD2 | TYR | 80 | 96.756 | 59.895 | 55.984 | 1.00 | 35.48 | C |
| ATOM | 3903 | CE2 | TYR | 80 | 96.307 | 61.207 | 56.060 | 1.00 | 38.78 | C |

TABLE 4-continued

Co-ordinates of the CD28/5.11A1 crystal structure

| ATOM | 3904 | CZ  | TYR | 80 | 95.632  | 61.758 | 54.984 | 1.00 | 46.52 | C |
|------|------|-----|-----|----|---------|--------|--------|------|-------|---|
| ATOM | 3905 | OH  | TYR | 80 | 95.195  | 63.066 | 55.046 | 1.00 | 43.37 | C |
| ATOM | 3906 | C   | TYR | 80 | 98.034  | 57.901 | 52.508 | 1.00 | 36.43 | C |
| ATOM | 3907 | O   | TYR | 80 | 98.960  | 58.529 | 53.028 | 1.00 | 41.51 | C |
| ATOM | 3908 | N   | LEU | 81 | 97.817  | 57.873 | 51.199 | 1.00 | 37.66 | C |
| ATOM | 3909 | CA  | LEU | 81 | 98.694  | 58.576 | 50.268 | 1.00 | 43.35 | C |
| ATOM | 3910 | CB  | LEU | 81 | 98.538  | 57.997 | 48.861 | 1.00 | 40.97 | C |
| ATOM | 3911 | CG  | LEU | 81 | 98.392  | 56.485 | 48.721 | 1.00 | 35.20 | C |
| ATOM | 3912 | CD1 | LEU | 81 | 98.068  | 56.154 | 47.268 | 1.00 | 41.59 | C |
| ATOM | 3913 | CD2 | LEU | 81 | 99.670  | 55.798 | 49.141 | 1.00 | 34.03 | C |
| ATOM | 3914 | C   | LEU | 81 | 98.457  | 60.092 | 50.216 | 1.00 | 39.41 | C |
| ATOM | 3915 | O   | LEU | 81 | 97.410  | 60.552 | 49.759 | 1.00 | 30.90 | C |
| ATOM | 3916 | N   | GLN | 82 | 99.450  | 60.853 | 50.678 | 1.00 | 45.56 | C |
| ATOM | 3917 | CA  | GLN | 82 | 99.397  | 62.315 | 50.681 | 1.00 | 47.39 | C |
| ATOM | 3918 | CB  | GLN | 82 | 99.884  | 62.868 | 52.023 | 1.00 | 48.95 | C |
| ATOM | 3919 | CG  | GLN | 82 | 99.479  | 62.062 | 53.246 | 1.00 | 42.53 | C |
| ATOM | 3920 | CD  | GLN | 82 | 99.397  | 62.921 | 54.491 | 1.00 | 35.76 | C |
| ATOM | 3921 | OE1 | GLN | 82 | 99.826  | 62.514 | 55.575 | 1.00 | 35.27 | C |
| ATOM | 3922 | NE2 | GLN | 82 | 98.857  | 64.127 | 54.339 | 1.00 | 29.92 | C |
| ATOM | 3923 | C   | GLN | 82 | 100.280 | 62.884 | 49.571 | 1.00 | 42.88 | C |
| ATOM | 3924 | O   | GLN | 82 | 101.148 | 62.194 | 49.035 | 1.00 | 41.58 | C |
| ATOM | 3925 | N   | ASN | 83 | 100.060 | 64.148 | 49.237 | 1.00 | 45.46 | C |
| ATOM | 3926 | CA  | ASN | 83 | 100.843 | 64.806 | 48.197 | 1.00 | 43.88 | C |
| ATOM | 3927 | CB  | ASN | 83 | 102.229 | 65.139 | 48.748 | 1.00 | 38.56 | C |
| ATOM | 3928 | CG  | ASN | 83 | 102.170 | 66.242 | 49.779 | 1.00 | 47.82 | C |
| ATOM | 3929 | OD1 | ASN | 83 | 101.274 | 67.083 | 49.735 | 1.00 | 46.58 | C |
| ATOM | 3930 | ND2 | ASN | 83 | 103.118 | 66.249 | 50.715 | 1.00 | 33.98 | C |
| ATOM | 3931 | C   | ASN | 83 | 100.951 | 63.966 | 46.933 | 1.00 | 37.91 | C |
| ATOM | 3932 | O   | ASN | 83 | 102.045 | 63.718 | 46.424 | 1.00 | 45.24 | C |
| ATOM | 3933 | N   | LEU | 84 | 99.803  | 63.535 | 46.430 | 1.00 | 28.03 | C |
| ATOM | 3934 | CA  | LEU | 84 | 99.760  | 62.723 | 45.230 | 1.00 | 19.39 | C |
| ATOM | 3935 | CB  | LEU | 84 | 98.540  | 61.802 | 45.263 | 1.00 | 26.73 | C |
| ATOM | 3936 | CG  | LEU | 84 | 98.774  | 60.341 | 45.664 | 1.00 | 34.93 | C |
| ATOM | 3937 | CD1 | LEU | 84 | 97.483  | 59.552 | 45.502 | 1.00 | 37.57 | C |
| ATOM | 3938 | CD2 | LEU | 84 | 99.877  | 59.729 | 44.812 | 1.00 | 36.66 | C |
| ATOM | 3939 | C   | LEU | 84 | 99.675  | 63.650 | 44.037 | 1.00 | 20.07 | C |
| ATOM | 3940 | O   | LEU | 84 | 98.914  | 64.609 | 44.049 | 1.00 | 31.39 | C |
| ATOM | 3941 | N   | TYR | 85 | 100.460 | 63.365 | 43.006 | 1.00 | 33.90 | C |
| ATOM | 3942 | CA  | TYR | 85 | 100.464 | 64.187 | 41.806 | 1.00 | 40.42 | C |
| ATOM | 3943 | CB  | TYR | 85 | 101.840 | 64.117 | 41.123 | 1.00 | 59.23 | C |
| ATOM | 3944 | CG  | TYR | 85 | 102.989 | 64.613 | 41.980 | 1.00 | 61.79 | C |
| ATOM | 3945 | CD1 | TYR | 85 | 103.155 | 65.973 | 42.242 | 1.00 | 63.76 | C |
| ATOM | 3946 | CE1 | TYR | 85 | 104.193 | 66.430 | 43.053 | 1.00 | 67.56 | C |
| ATOM | 3947 | CD2 | TYR | 85 | 103.897 | 63.717 | 42.549 | 1.00 | 64.22 | C |
| ATOM | 3948 | CE2 | TYR | 85 | 104.938 | 64.162 | 43.360 | 1.00 | 65.83 | C |
| ATOM | 3949 | CZ  | TYR | 85 | 105.079 | 65.519 | 43.610 | 1.00 | 70.24 | C |
| ATOM | 3950 | OH  | TYR | 85 | 106.093 | 65.965 | 44.428 | 1.00 | 73.68 | C |
| ATOM | 3951 | C   | TYR | 85 | 99.378  | 63.724 | 40.841 | 1.00 | 33.25 | C |
| ATOM | 3952 | O   | TYR | 85 | 98.880  | 62.606 | 40.943 | 1.00 | 33.16 | C |
| ATOM | 3953 | N   | VAL | 86 | 99.018  | 64.598 | 39.907 | 1.00 | 32.80 | C |
| ATOM | 3954 | CA  | VAL | 86 | 97.994  | 64.297 | 38.914 | 1.00 | 31.92 | C |
| ATOM | 3955 | CB  | VAL | 86 | 97.503  | 65.600 | 38.241 | 1.00 | 29.33 | C |
| ATOM | 3956 | CG1 | VAL | 86 | 98.476  | 66.730 | 38.548 | 1.00 | 32.20 | C |
| ATOM | 3957 | CG2 | VAL | 86 | 97.361  | 65.409 | 36.743 | 1.00 | 34.84 | C |
| ATOM | 3958 | C   | VAL | 86 | 98.504  | 63.312 | 37.854 | 1.00 | 30.06 | C |
| ATOM | 3959 | O   | VAL | 86 | 97.721  | 62.621 | 37.204 | 1.00 | 28.12 | C |
| ATOM | 3960 | N   | ASN | 87 | 99.819  | 63.246 | 37.685 | 1.00 | 37.39 | C |
| ATOM | 3961 | CA  | ASN | 87 | 100.411 | 62.330 | 36.716 | 1.00 | 31.78 | C |
| ATOM | 3962 | CB  | ASN | 87 | 101.803 | 62.811 | 36.348 | 1.00 | 30.37 | C |
| ATOM | 3963 | CG  | ASN | 87 | 102.721 | 62.866 | 37.542 | 1.00 | 15.74 | C |
| ATOM | 3964 | OD1 | ASN | 87 | 102.334 | 62.461 | 38.631 | 1.00 | 26.61 | C |
| ATOM | 3965 | ND2 | ASN | 87 | 103.939 | 63.370 | 37.350 | 1.00 | 44.07 | C |
| ATOM | 3966 | C   | ASN | 87 | 100.504 | 60.955 | 37.374 | 1.00 | 31.73 | C |
| ATOM | 3967 | O   | ASN | 87 | 100.964 | 59.981 | 36.773 | 1.00 | 29.36 | C |
| ATOM | 3968 | N   | GLN | 88 | 100.063 | 60.897 | 38.627 | 1.00 | 33.61 | C |
| ATOM | 3969 | CA  | GLN | 88 | 100.082 | 59.665 | 39.402 | 1.00 | 24.73 | C |
| ATOM | 3970 | CB  | GLN | 88 | 100.430 | 59.983 | 40.871 | 1.00 | 26.06 | C |
| ATOM | 3971 | CG  | GLN | 88 | 101.721 | 59.314 | 41.400 | 1.00 | 44.43 | C |
| ATOM | 3972 | CD  | GLN | 88 | 102.692 | 60.285 | 42.081 | 1.00 | 36.54 | C |
| ATOM | 3973 | OE1 | GLN | 88 | 102.504 | 60.675 | 43.235 | 1.00 | 26.99 | C |
| ATOM | 3974 | NE2 | GLN | 88 | 103.743 | 60.668 | 41.363 | 1.00 | 38.97 | C |
| ATOM | 3975 | C   | GLN | 88 | 98.747  | 58.896 | 39.322 | 1.00 | 26.16 | C |
| ATOM | 3976 | O   | GLN | 88 | 98.635  | 57.805 | 39.872 | 1.00 | 22.71 | C |
| ATOM | 3977 | N   | THR | 89 | 97.735  | 59.448 | 38.645 | 1.00 | 29.74 | C |
| ATOM | 3978 | CA  | THR | 89 | 96.450  | 58.742 | 38.548 | 1.00 | 35.51 | C |
| ATOM | 3979 | CB  | THR | 89 | 95.381  | 59.548 | 37.786 | 1.00 | 23.56 | C |
| ATOM | 3980 | OG1 | THR | 89 | 95.586  | 59.391 | 36.381 | 1.00 | 37.82 | C |

TABLE 4-continued

Co-ordinates of the CD28/5.11A1 crystal structure

| ATOM | 3981 | CG2 | THR | 89 | 95.456 | 61.008 | 38.140 | 1.00 | 8.56 | C |
|---|---|---|---|---|---|---|---|---|---|---|
| ATOM | 3982 | C | THR | 89 | 96.686 | 57.434 | 37.808 | 1.00 | 30.57 | C |
| ATOM | 3983 | O | THR | 89 | 97.222 | 57.427 | 36.701 | 1.00 | 19.99 | C |
| ATOM | 3984 | N | ASP | 90 | 96.274 | 56.326 | 38.411 | 1.00 | 26.02 | C |
| ATOM | 3985 | CA | ASP | 90 | 96.520 | 55.032 | 37.799 | 1.00 | 29.88 | C |
| ATOM | 3986 | CB | ASP | 90 | 98.023 | 54.758 | 37.848 | 1.00 | 17.27 | C |
| ATOM | 3987 | CG | ASP | 90 | 98.492 | 53.857 | 36.738 | 1.00 | 29.31 | C |
| ATOM | 3988 | OD1 | ASP | 90 | 99.661 | 54.010 | 36.312 | 1.00 | 28.02 | C |
| ATOM | 3989 | OD2 | ASP | 90 | 97.695 | 53.002 | 36.299 | 1.00 | 35.12 | C |
| ATOM | 3990 | C | ASP | 90 | 95.774 | 53.918 | 38.519 | 1.00 | 32.73 | C |
| ATOM | 3991 | O | ASP | 90 | 94.869 | 54.181 | 39.307 | 1.00 | 28.33 | C |
| ATOM | 3992 | N | ILE | 91 | 96.155 | 52.674 | 38.234 | 1.00 | 33.15 | C |
| ATOM | 3993 | CA | ILE | 91 | 95.549 | 51.524 | 38.891 | 1.00 | 29.34 | C |
| ATOM | 3994 | CB | ILE | 91 | 95.320 | 50.330 | 37.960 | 1.00 | 19.19 | C |
| ATOM | 3995 | CG2 | ILE | 91 | 93.891 | 49.803 | 38.124 | 1.00 | 7.46 | C |
| ATOM | 3996 | CG1 | ILE | 91 | 95.613 | 50.734 | 36.525 | 1.00 | 24.90 | C |
| ATOM | 3997 | CD1 | ILE | 91 | 96.736 | 49.967 | 35.904 | 1.00 | 37.36 | C |
| ATOM | 3998 | C | ILE | 91 | 96.539 | 51.070 | 39.929 | 1.00 | 33.79 | C |
| ATOM | 3999 | O | ILE | 91 | 97.707 | 50.844 | 39.615 | 1.00 | 35.59 | C |
| ATOM | 4000 | N | TYR | 92 | 96.064 | 50.948 | 41.162 | 1.00 | 39.40 | C |
| ATOM | 4001 | CA | TYR | 92 | 96.891 | 50.521 | 42.274 | 1.00 | 25.36 | C |
| ATOM | 4002 | CB | TYR | 92 | 96.817 | 51.555 | 43.398 | 1.00 | 24.66 | C |
| ATOM | 4003 | CG | TYR | 92 | 97.472 | 52.872 | 43.039 | 1.00 | 27.16 | C |
| ATOM | 4004 | CD1 | TYR | 92 | 98.646 | 53.282 | 43.669 | 1.00 | 32.14 | C |
| ATOM | 4005 | CE1 | TYR | 92 | 99.265 | 54.474 | 43.327 | 1.00 | 24.99 | C |
| ATOM | 4006 | CD2 | TYR | 92 | 96.933 | 53.697 | 42.051 | 1.00 | 24.44 | C |
| ATOM | 4007 | CE2 | TYR | 92 | 97.547 | 54.896 | 41.703 | 1.00 | 24.44 | C |
| ATOM | 4008 | CZ | TYR | 92 | 98.712 | 55.275 | 42.344 | 1.00 | 18.97 | C |
| ATOM | 4009 | OH | TYR | 92 | 99.332 | 56.454 | 42.010 | 1.00 | 18.71 | C |
| ATOM | 4010 | C | TYR | 92 | 96.381 | 49.179 | 42.761 | 1.00 | 25.56 | C |
| ATOM | 4011 | O | TYR | 92 | 95.173 | 48.942 | 42.791 | 1.00 | 36.33 | C |
| ATOM | 4012 | N | PHE | 93 | 97.303 | 48.298 | 43.127 | 1.00 | 28.40 | C |
| ATOM | 4013 | CA | PHE | 93 | 96.931 | 46.984 | 43.621 | 1.00 | 29.94 | C |
| ATOM | 4014 | CB | PHE | 93 | 97.448 | 45.893 | 42.689 | 1.00 | 17.97 | C |
| ATOM | 4015 | CG | PHE | 93 | 97.105 | 46.113 | 41.258 | 1.00 | 24.43 | C |
| ATOM | 4016 | CD1 | PHE | 93 | 97.978 | 46.793 | 40.422 | 1.00 | 27.44 | C |
| ATOM | 4017 | CD2 | PHE | 93 | 95.921 | 45.617 | 40.733 | 1.00 | 30.96 | C |
| ATOM | 4018 | CE1 | PHE | 93 | 97.673 | 46.973 | 39.076 | 1.00 | 46.97 | C |
| ATOM | 4019 | CE2 | PHE | 93 | 95.610 | 45.792 | 39.391 | 1.00 | 31.89 | C |
| ATOM | 4020 | CZ | PHE | 93 | 96.483 | 46.467 | 38.562 | 1.00 | 33.13 | C |
| ATOM | 4021 | C | PHE | 93 | 97.470 | 46.739 | 45.020 | 1.00 | 35.26 | C |
| ATOM | 4022 | O | PHE | 93 | 98.635 | 47.022 | 45.325 | 1.00 | 34.73 | C |
| ATOM | 4023 | N | CYS | 94 | 96.601 | 46.209 | 45.870 | 1.00 | 48.06 | C |
| ATOM | 4024 | CA | CYS | 94 | 96.969 | 45.907 | 47.235 | 1.00 | 36.83 | C |
| ATOM | 4025 | C | CYS | 94 | 97.635 | 44.546 | 47.284 | 1.00 | 31.31 | C |
| ATOM | 4026 | O | CYS | 94 | 97.397 | 43.692 | 46.431 | 1.00 | 33.02 | C |
| ATOM | 4027 | CB | CYS | 94 | 95.738 | 45.921 | 48.121 | 1.00 | 39.16 | C |
| ATOM | 4028 | SG | CYS | 94 | 96.102 | 46.711 | 49.706 | 1.00 | 59.22 | C |
| ATOM | 4029 | N | LYS | 95 | 98.475 | 44.349 | 48.288 | 1.00 | 35.15 | C |
| ATOM | 4030 | CA | LYS | 95 | 99.194 | 43.093 | 48.430 | 1.00 | 32.02 | C |
| ATOM | 4031 | CB | LYS | 95 | 100.593 | 43.227 | 47.824 | 1.00 | 20.95 | C |
| ATOM | 4032 | CG | LYS | 95 | 101.265 | 41.913 | 47.532 | 1.00 | 16.51 | C |
| ATOM | 4033 | CD | LYS | 95 | 102.720 | 42.111 | 47.179 | 1.00 | 20.20 | C |
| ATOM | 4034 | CE | LYS | 95 | 103.419 | 40.772 | 46.979 | 1.00 | 39.20 | C |
| ATOM | 4035 | NZ | LYS | 95 | 104.812 | 40.931 | 46.471 | 1.00 | 47.09 | C |
| ATOM | 4036 | C | LYS | 95 | 99.301 | 42.731 | 49.896 | 1.00 | 29.30 | C |
| ATOM | 4037 | O | LYS | 95 | 99.224 | 43.602 | 50.759 | 1.00 | 32.79 | C |
| ATOM | 4038 | N | ILE | 96 | 99.480 | 41.444 | 50.172 | 1.00 | 24.46 | C |
| ATOM | 4039 | CA | ILE | 96 | 99.619 | 40.978 | 51.542 | 1.00 | 19.72 | C |
| ATOM | 4040 | CB | ILE | 96 | 98.258 | 40.925 | 52.251 | 1.00 | 14.76 | C |
| ATOM | 4041 | CG2 | ILE | 96 | 97.299 | 40.052 | 51.477 | 1.00 | 17.83 | C |
| ATOM | 4042 | CG1 | ILE | 96 | 98.434 | 40.405 | 53.673 | 1.00 | 17.25 | C |
| ATOM | 4043 | CD1 | ILE | 96 | 99.184 | 41.352 | 54.570 | 1.00 | 5.02 | C |
| ATOM | 4044 | C | ILE | 96 | 100.276 | 39.599 | 51.602 | 1.00 | 26.57 | C |
| ATOM | 4045 | O | ILE | 96 | 99.852 | 38.662 | 50.916 | 1.00 | 34.37 | C |
| ATOM | 4046 | N | GLU | 97 | 101.321 | 39.491 | 52.419 | 1.00 | 20.47 | C |
| ATOM | 4047 | CA | GLU | 97 | 102.052 | 38.243 | 52.592 | 1.00 | 27.23 | C |
| ATOM | 4048 | CB | GLU | 97 | 103.367 | 38.279 | 51.793 | 1.00 | 32.57 | C |
| ATOM | 4049 | CG | GLU | 97 | 104.186 | 39.550 | 51.949 | 1.00 | 38.60 | C |
| ATOM | 4050 | CD | GLU | 97 | 104.535 | 40.193 | 50.618 | 1.00 | 46.08 | C |
| ATOM | 4051 | OE1 | GLU | 97 | 105.239 | 39.548 | 49.815 | 1.00 | 37.73 | C |
| ATOM | 4052 | OE2 | GLU | 97 | 104.108 | 41.348 | 50.379 | 1.00 | 54.19 | C |
| ATOM | 4053 | C | GLU | 97 | 102.343 | 37.951 | 54.071 | 1.00 | 30.22 | C |
| ATOM | 4054 | O | GLU | 97 | 102.705 | 38.841 | 54.844 | 1.00 | 27.30 | C |
| ATOM | 4055 | N | VAL | 98 | 102.158 | 36.694 | 54.455 | 1.00 | 24.37 | C |
| ATOM | 4056 | CA | VAL | 98 | 102.395 | 36.256 | 55.817 | 1.00 | 17.97 | C |
| ATOM | 4057 | CB | VAL | 98 | 101.361 | 35.183 | 56.224 | 1.00 | 33.66 | C |

TABLE 4-continued

Co-ordinates of the CD28/5.11A1 crystal structure

| ATOM | 4058 | CG1 | VAL | 98  | 102.002 | 34.115 | 57.113 | 1.00 | 46.61 | C |
| ---- | ---- | --- | --- | --- | ------- | ------ | ------ | ---- | ----- | - |
| ATOM | 4059 | CG2 | VAL | 98  | 100.200 | 35.844 | 56.931 | 1.00 | 31.46 | C |
| ATOM | 4060 | C   | VAL | 98  | 103.787 | 35.664 | 55.808 | 1.00 | 24.36 | C |
| ATOM | 4061 | O   | VAL | 98  | 104.147 | 34.979 | 54.858 | 1.00 | 17.44 | C |
| ATOM | 4062 | N   | MET | 99  | 104.569 | 35.936 | 56.851 | 1.00 | 41.56 | C |
| ATOM | 4063 | CA  | MET | 99  | 105.932 | 35.414 | 56.940 | 1.00 | 37.25 | C |
| ATOM | 4064 | CB  | MET | 99  | 106.951 | 36.540 | 56.753 | 1.00 | 26.44 | C |
| ATOM | 4065 | CG  | MET | 99  | 106.449 | 37.906 | 57.176 | 1.00 | 37.71 | C |
| ATOM | 4066 | SD  | MET | 99  | 106.981 | 39.212 | 56.039 | 1.00 | 49.54 | C |
| ATOM | 4067 | CE  | MET | 99  | 105.587 | 39.271 | 54.899 | 1.00 | 38.22 | C |
| ATOM | 4068 | C   | MET | 99  | 106.182 | 34.728 | 58.273 | 1.00 | 37.57 | C |
| ATOM | 4069 | O   | MET | 99  | 107.286 | 34.241 | 58.526 | 1.00 | 31.40 | C |
| ATOM | 4070 | N   | TYR | 100 | 105.154 | 34.712 | 59.119 | 1.00 | 45.50 | C |
| ATOM | 4071 | CA  | TYR | 100 | 105.210 | 34.084 | 60.439 | 1.00 | 45.47 | C |
| ATOM | 4072 | CB  | TYR | 100 | 106.441 | 34.532 | 61.218 | 1.00 | 49.87 | C |
| ATOM | 4073 | CG  | TYR | 100 | 106.979 | 33.489 | 62.176 | 1.00 | 54.53 | C |
| ATOM | 4074 | CD1 | TYR | 100 | 107.908 | 32.545 | 61.745 | 1.00 | 66.10 | C |
| ATOM | 4075 | CE1 | TYR | 100 | 108.466 | 31.625 | 62.622 | 1.00 | 67.96 | C |
| ATOM | 4076 | CD2 | TYR | 100 | 106.611 | 33.483 | 63.523 | 1.00 | 50.84 | C |
| ATOM | 4077 | CE2 | TYR | 100 | 107.166 | 32.559 | 64.415 | 1.00 | 57.94 | C |
| ATOM | 4078 | CZ  | TYR | 100 | 108.098 | 31.636 | 63.951 | 1.00 | 57.97 | C |
| ATOM | 4079 | OH  | TYR | 100 | 108.687 | 30.728 | 64.801 | 1.00 | 53.54 | C |
| ATOM | 4080 | C   | TYR | 100 | 103.978 | 34.429 | 61.259 | 1.00 | 49.53 | C |
| ATOM | 4081 | O   | TYR | 100 | 103.561 | 35.587 | 61.307 | 1.00 | 42.87 | C |
| ATOM | 4082 | N   | PRO | 101 | 103.380 | 33.422 | 61.920 | 1.00 | 53.02 | C |
| ATOM | 4083 | CD  | PRO | 101 | 102.180 | 33.528 | 62.771 | 1.00 | 52.41 | C |
| ATOM | 4084 | CA  | PRO | 101 | 103.902 | 32.054 | 61.844 | 1.00 | 46.66 | C |
| ATOM | 4085 | CB  | PRO | 101 | 103.126 | 31.300 | 62.927 | 1.00 | 42.16 | C |
| ATOM | 4086 | CG  | PRO | 101 | 101.906 | 32.115 | 63.189 | 1.00 | 38.19 | C |
| ATOM | 4087 | C   | PRO | 101 | 103.711 | 31.468 | 60.441 | 1.00 | 57.32 | C |
| ATOM | 4088 | O   | PRO | 101 | 102.901 | 31.960 | 59.648 | 1.00 | 47.74 | C |
| ATOM | 4089 | N   | PRO | 102 | 104.455 | 30.400 | 60.122 | 1.00 | 58.81 | C |
| ATOM | 4090 | CD  | PRO | 102 | 105.410 | 29.707 | 61.000 | 1.00 | 43.99 | C |
| ATOM | 4091 | CA  | PRO | 102 | 104.368 | 29.758 | 58.807 | 1.00 | 54.29 | C |
| ATOM | 4092 | CB  | PRO | 102 | 105.585 | 28.824 | 58.766 | 1.00 | 46.96 | C |
| ATOM | 4093 | CG  | PRO | 102 | 106.354 | 29.090 | 60.030 | 1.00 | 46.28 | C |
| ATOM | 4094 | C   | PRO | 102 | 103.072 | 28.997 | 58.565 | 1.00 | 50.83 | C |
| ATOM | 4095 | O   | PRO | 102 | 102.265 | 28.812 | 59.475 | 1.00 | 51.79 | C |
| ATOM | 4096 | N   | PRO | 103 | 102.858 | 28.550 | 57.321 | 1.00 | 43.58 | C |
| ATOM | 4097 | CD  | PRO | 103 | 101.692 | 27.757 | 56.901 | 1.00 | 38.84 | C |
| ATOM | 4098 | CA  | PRO | 103 | 103.784 | 28.756 | 56.209 | 1.00 | 34.80 | C |
| ATOM | 4099 | CB  | PRO | 103 | 103.457 | 27.611 | 55.247 | 1.00 | 35.84 | C |
| ATOM | 4100 | CG  | PRO | 103 | 102.280 | 26.863 | 55.860 | 1.00 | 31.11 | C |
| ATOM | 4101 | C   | PRO | 103 | 103.581 | 30.127 | 55.566 | 1.00 | 39.20 | C |
| ATOM | 4102 | O   | PRO | 103 | 102.790 | 30.939 | 56.055 | 1.00 | 35.30 | C |
| ATOM | 4103 | N   | TYR | 104 | 104.311 | 30.382 | 54.481 | 1.00 | 40.51 | C |
| ATOM | 4104 | CA  | TYR | 104 | 104.199 | 31.644 | 53.760 | 1.00 | 40.50 | C |
| ATOM | 4105 | CB  | TYR | 104 | 105.226 | 31.719 | 52.630 | 1.00 | 34.12 | C |
| ATOM | 4106 | CG  | TYR | 104 | 105.224 | 33.036 | 51.888 | 1.00 | 35.99 | C |
| ATOM | 4107 | CD1 | TYR | 104 | 104.659 | 33.143 | 50.615 | 1.00 | 49.18 | C |
| ATOM | 4108 | CE1 | TYR | 104 | 104.652 | 34.363 | 49.926 | 1.00 | 50.34 | C |
| ATOM | 4109 | CD2 | TYR | 104 | 105.784 | 34.179 | 52.458 | 1.00 | 34.98 | C |
| ATOM | 4110 | CE2 | TYR | 104 | 105.782 | 35.403 | 51.779 | 1.00 | 35.62 | C |
| ATOM | 4111 | CZ  | TYR | 104 | 105.215 | 35.485 | 50.518 | 1.00 | 39.99 | C |
| ATOM | 4112 | OH  | TYR | 104 | 105.205 | 36.685 | 49.853 | 1.00 | 32.85 | C |
| ATOM | 4113 | C   | TYR | 104 | 102.804 | 31.725 | 53.168 | 1.00 | 44.36 | C |
| ATOM | 4114 | O   | TYR | 104 | 102.311 | 30.749 | 52.603 | 1.00 | 46.76 | C |
| ATOM | 4115 | N   | LEU | 105 | 102.171 | 32.885 | 53.304 | 1.00 | 47.99 | C |
| ATOM | 4116 | CA  | LEU | 105 | 100.827 | 33.096 | 52.778 | 1.00 | 43.06 | C |
| ATOM | 4117 | CB  | LEU | 105 | 99.859  | 33.347 | 53.929 | 1.00 | 44.75 | C |
| ATOM | 4118 | CG  | LEU | 105 | 98.748  | 32.310 | 54.097 | 1.00 | 55.87 | C |
| ATOM | 4119 | CD1 | LEU | 105 | 98.181  | 31.958 | 52.725 | 1.00 | 60.46 | C |
| ATOM | 4120 | CD2 | LEU | 105 | 99.289  | 31.062 | 54.797 | 1.00 | 56.52 | C |
| ATOM | 4121 | C   | LEU | 105 | 100.819 | 34.283 | 51.813 | 1.00 | 45.31 | C |
| ATOM | 4122 | O   | LEU | 105 | 101.438 | 35.308 | 52.085 | 1.00 | 44.10 | C |
| ATOM | 4123 | N   | ASP | 106 | 100.107 | 34.144 | 50.696 | 1.00 | 53.21 | C |
| ATOM | 4124 | CA  | ASP | 106 | 100.046 | 35.199 | 49.681 | 1.00 | 56.65 | C |
| ATOM | 4125 | CB  | ASP | 106 | 100.961 | 34.827 | 48.512 | 1.00 | 73.34 | C |
| ATOM | 4126 | CG  | ASP | 106 | 101.724 | 36.011 | 47.979 | 1.00 | 81.75 | C |
| ATOM | 4127 | OD1 | ASP | 106 | 101.437 | 37.143 | 48.432 | 1.00 | 85.62 | C |
| ATOM | 4128 | OD2 | ASP | 106 | 102.603 | 35.802 | 47.109 | 1.00 | 80.61 | C |
| ATOM | 4129 | C   | ASP | 106 | 98.639  | 35.462 | 49.145 | 1.00 | 52.61 | C |
| ATOM | 4130 | O   | ASP | 106 | 97.772  | 34.592 | 49.199 | 1.00 | 62.59 | C |
| ATOM | 4131 | N   | ASN | 107 | 98.422  | 36.658 | 48.609 | 1.00 | 42.29 | C |
| ATOM | 4132 | CA  | ASN | 107 | 97.110  | 37.028 | 48.072 | 1.00 | 50.80 | C |
| ATOM | 4133 | CB  | ASN | 107 | 96.826  | 38.492 | 48.359 | 1.00 | 42.50 | C |
| ATOM | 4134 | CG  | ASN | 107 | 97.855  | 39.393 | 47.736 | 1.00 | 41.45 | C |

TABLE 4-continued

Co-ordinates of the CD28/5.11A1 crystal structure

| ATOM | 4135 | OD1 | ASN | 107 | 97.691 | 39.852 | 46.607 | 1.00 | 44.69 | C |
|---|---|---|---|---|---|---|---|---|---|---|
| ATOM | 4136 | ND2 | ASN | 107 | 98.940 | 39.637 | 48.461 | 1.00 | 38.52 | C |
| ATOM | 4137 | C | ASN | 107 | 96.997 | 36.815 | 46.564 | 1.00 | 55.83 | C |
| ATOM | 4138 | O | ASN | 107 | 97.990 | 36.865 | 45.840 | 1.00 | 54.74 | C |
| ATOM | 4139 | N | GLU | 108 | 95.771 | 36.601 | 46.098 | 1.00 | 61.82 | C |
| ATOM | 4140 | CA | GLU | 108 | 95.513 | 36.393 | 44.678 | 1.00 | 62.32 | C |
| ATOM | 4141 | CB | GLU | 108 | 94.305 | 35.474 | 44.485 | 1.00 | 65.84 | C |
| ATOM | 4142 | CG | GLU | 108 | 93.817 | 34.809 | 45.757 | 1.00 | 72.69 | C |
| ATOM | 4143 | CD | GLU | 108 | 92.445 | 35.295 | 46.180 | 1.00 | 73.87 | C |
| ATOM | 4144 | OE1 | GLU | 108 | 91.534 | 34.453 | 46.327 | 1.00 | 58.56 | C |
| ATOM | 4145 | OE2 | GLU | 108 | 92.285 | 36.522 | 46.366 | 1.00 | 79.05 | C |
| ATOM | 4146 | C | GLU | 108 | 95.244 | 37.722 | 43.991 | 1.00 | 64.40 | C |
| ATOM | 4147 | O | GLU | 108 | 94.094 | 38.171 | 43.936 | 1.00 | 61.70 | C |
| ATOM | 4148 | N | LYS | 109 | 96.306 | 38.339 | 43.467 | 1.00 | 64.63 | C |
| ATOM | 4149 | CA | LYS | 109 | 96.215 | 39.629 | 42.782 | 1.00 | 60.84 | C |
| ATOM | 4150 | CB | LYS | 109 | 96.054 | 39.420 | 41.274 | 1.00 | 43.96 | C |
| ATOM | 4151 | CG | LYS | 109 | 97.094 | 38.496 | 40.666 | 1.00 | 66.29 | C |
| ATOM | 4152 | CD | LYS | 109 | 98.399 | 39.235 | 40.373 | 1.00 | 84.02 | C |
| ATOM | 4153 | CE | LYS | 109 | 99.309 | 38.435 | 39.432 | 1.00 | 77.45 | C |
| ATOM | 4154 | NZ | LYS | 109 | 100.234 | 39.299 | 38.636 | 1.00 | 53.39 | C |
| ATOM | 4155 | C | LYS | 109 | 95.040 | 40.435 | 43.331 | 1.00 | 59.47 | C |
| ATOM | 4156 | O | LYS | 109 | 94.893 | 40.571 | 44.545 | 1.00 | 73.09 | C |
| ATOM | 4157 | N | SER | 110 | 94.201 | 40.950 | 42.440 | 1.00 | 49.53 | C |
| ATOM | 4158 | CA | SER | 110 | 93.038 | 41.734 | 42.841 | 1.00 | 50.60 | C |
| ATOM | 4159 | CB | SER | 110 | 93.404 | 42.706 | 43.969 | 1.00 | 48.38 | C |
| ATOM | 4160 | OG | SER | 110 | 93.807 | 43.962 | 43.448 | 1.00 | 55.94 | C |
| ATOM | 4161 | C | SER | 110 | 92.455 | 42.520 | 41.670 | 1.00 | 49.16 | C |
| ATOM | 4162 | O | SER | 110 | 93.098 | 42.693 | 40.634 | 1.00 | 36.85 | C |
| ATOM | 4163 | N | ASN | 111 | 91.228 | 43.000 | 41.841 | 1.00 | 50.24 | C |
| ATOM | 4164 | CA | ASN | 111 | 90.580 | 43.770 | 40.795 | 1.00 | 48.26 | C |
| ATOM | 4165 | CB | ASN | 111 | 89.073 | 43.868 | 41.068 | 1.00 | 50.05 | C |
| ATOM | 4166 | CG | ASN | 111 | 88.273 | 42.770 | 40.364 | 1.00 | 52.55 | C |
| ATOM | 4167 | OD1 | ASN | 111 | 87.101 | 42.539 | 40.671 | 1.00 | 30.90 | C |
| ATOM | 4168 | ND2 | ASN | 111 | 88.912 | 42.089 | 39.413 | 1.00 | 60.36 | C |
| ATOM | 4169 | C | ASN | 111 | 91.212 | 45.162 | 40.708 | 1.00 | 42.47 | C |
| ATOM | 4170 | O | ASN | 111 | 90.982 | 45.896 | 39.748 | 1.00 | 48.01 | C |
| ATOM | 4171 | N | GLY | 112 | 92.007 | 45.517 | 41.717 | 1.00 | 44.01 | C |
| ATOM | 4172 | CA | GLY | 112 | 92.682 | 46.808 | 41.729 | 1.00 | 36.00 | C |
| ATOM | 4173 | C | GLY | 112 | 91.830 | 48.015 | 42.081 | 1.00 | 36.58 | C |
| ATOM | 4174 | O | GLY | 112 | 90.630 | 47.892 | 42.343 | 1.00 | 33.31 | C |
| ATOM | 4175 | N | THR | 113 | 92.455 | 49.189 | 42.094 | 1.00 | 28.16 | C |
| ATOM | 4176 | CA | THR | 113 | 91.738 | 50.416 | 42.403 | 1.00 | 29.29 | C |
| ATOM | 4177 | CB | THR | 113 | 91.671 | 50.667 | 43.929 | 1.00 | 25.84 | C |
| ATOM | 4178 | OG1 | THR | 113 | 90.959 | 51.884 | 44.186 | 1.00 | 13.15 | C |
| ATOM | 4179 | CG2 | THR | 113 | 93.061 | 50.762 | 44.514 | 1.00 | 35.81 | C |
| ATOM | 4180 | C | THR | 113 | 92.344 | 51.636 | 41.722 | 1.00 | 29.94 | C |
| ATOM | 4181 | O | THR | 113 | 93.375 | 52.157 | 42.133 | 1.00 | 21.21 | C |
| ATOM | 4182 | N | ILE | 114 | 91.679 | 52.074 | 40.662 | 1.00 | 31.79 | C |
| ATOM | 4183 | CA | ILE | 114 | 92.093 | 53.243 | 39.905 | 1.00 | 24.64 | C |
| ATOM | 4184 | CB | ILE | 114 | 91.132 | 53.521 | 38.721 | 1.00 | 29.78 | C |
| ATOM | 4185 | CG2 | ILE | 114 | 91.159 | 55.001 | 38.361 | 1.00 | 29.89 | C |
| ATOM | 4186 | CG1 | ILE | 114 | 91.510 | 52.661 | 37.519 | 1.00 | 45.18 | C |
| ATOM | 4187 | CD1 | ILE | 114 | 91.376 | 53.376 | 36.182 | 1.00 | 48.49 | C |
| ATOM | 4188 | C | ILE | 114 | 92.019 | 54.450 | 40.821 | 1.00 | 21.71 | C |
| ATOM | 4189 | O | ILE | 114 | 91.050 | 54.632 | 41.546 | 1.00 | 23.04 | C |
| ATOM | 4190 | N | ILE | 115 | 93.028 | 55.296 | 40.770 | 1.00 | 22.63 | C |
| ATOM | 4191 | CA | ILE | 115 | 93.003 | 56.483 | 41.593 | 1.00 | 25.37 | C |
| ATOM | 4192 | CB | ILE | 115 | 94.147 | 56.461 | 42.585 | 1.00 | 19.98 | C |
| ATOM | 4193 | CG2 | ILE | 115 | 94.249 | 57.798 | 43.307 | 1.00 | 15.47 | C |
| ATOM | 4194 | CG1 | ILE | 115 | 93.925 | 55.312 | 43.558 | 1.00 | 5.93 | C |
| ATOM | 4195 | CD1 | ILE | 115 | 95.089 | 55.086 | 44.508 | 1.00 | 25.93 | C |
| ATOM | 4196 | C | ILE | 115 | 93.104 | 57.712 | 40.701 | 1.00 | 36.88 | C |
| ATOM | 4197 | O | ILE | 115 | 94.147 | 57.984 | 40.112 | 1.00 | 39.31 | C |
| ATOM | 4198 | N | HIS | 116 | 92.003 | 58.445 | 40.604 | 1.00 | 36.64 | C |
| ATOM | 4199 | CA | HIS | 116 | 91.951 | 59.641 | 39.779 | 1.00 | 42.31 | C |
| ATOM | 4200 | CB | HIS | 116 | 90.530 | 59.854 | 39.250 | 1.00 | 55.50 | C |
| ATOM | 4201 | CG | HIS | 116 | 90.397 | 61.008 | 38.303 | 1.00 | 53.01 | C |
| ATOM | 4202 | CD2 | HIS | 116 | 89.311 | 61.534 | 37.690 | 1.00 | 53.38 | C |
| ATOM | 4203 | ND1 | HIS | 116 | 91.473 | 61.764 | 37.884 | 1.00 | 49.21 | C |
| ATOM | 4204 | CE1 | HIS | 116 | 91.054 | 62.700 | 37.058 | 1.00 | 52.55 | C |
| ATOM | 4205 | NE2 | HIS | 116 | 89.744 | 62.584 | 36.920 | 1.00 | 46.03 | C |
| ATOM | 4206 | C | HIS | 116 | 92.380 | 60.847 | 40.592 | 1.00 | 38.13 | C |
| ATOM | 4207 | O | HIS | 116 | 91.655 | 61.278 | 41.486 | 1.00 | 35.69 | C |
| ATOM | 4208 | N | VAL | 117 | 93.554 | 61.387 | 40.274 | 1.00 | 35.30 | C |
| ATOM | 4209 | CA | VAL | 117 | 94.078 | 62.550 | 40.980 | 1.00 | 36.81 | C |
| ATOM | 4210 | CB | VAL | 117 | 95.606 | 62.463 | 41.146 | 1.00 | 24.40 | C |
| ATOM | 4211 | CG1 | VAL | 117 | 96.075 | 63.529 | 42.109 | 1.00 | 30.24 | C |

TABLE 4-continued

Co-ordinates of the CD28/5.11A1 crystal structure

| ATOM | 4212 | CG2 | VAL | 117 | 96.004 | 61.087 | 41.647 | 1.00 | 21.51 | C |
|------|------|-----|-----|-----|--------|--------|--------|------|-------|---|
| ATOM | 4213 | C   | VAL | 117 | 93.747 | 63.857 | 40.271 | 1.00 | 44.32 | C |
| ATOM | 4214 | O   | VAL | 117 | 93.901 | 63.973 | 39.054 | 1.00 | 48.83 | C |
| ATOM | 4215 | N   | LYS | 118 | 93.304 | 64.837 | 41.055 | 1.00 | 61.70 | C |
| ATOM | 4216 | CA  | LYS | 118 | 92.926 | 66.160 | 40.555 | 1.00 | 65.79 | C |
| ATOM | 4217 | CB  | LYS | 118 | 94.076 | 66.809 | 39.779 | 1.00 | 48.95 | C |
| ATOM | 4218 | CG  | LYS | 118 | 94.137 | 68.329 | 39.934 | 1.00 | 51.90 | C |
| ATOM | 4219 | CD  | LYS | 118 | 93.956 | 69.065 | 38.603 | 1.00 | 54.76 | C |
| ATOM | 4220 | CE  | LYS | 118 | 94.163 | 70.575 | 38.754 | 1.00 | 49.49 | C |
| ATOM | 4221 | NZ  | LYS | 118 | 95.564 | 71.003 | 38.435 | 1.00 | 45.55 | C |
| ATOM | 4222 | C   | LYS | 118 | 91.693 | 66.107 | 39.664 | 1.00 | 78.13 | C |
| ATOM | 4223 | O   | LYS | 118 | 91.566 | 67.006 | 38.807 | 1.00 | 88.53 | C |
| ATOM | 4224 | OT  | LYS | 118 | 90.872 | 65.178 | 39.832 | 1.00 | 83.59 | C |
| END  |      |     |     |     |        |        |        |      |       |   |

TABLE 5

DNA sequence of human CD28 cDNA (SEQ ID NO: 15)

```
agactctcag gccttggcag gtgcgtcttt cagttcccct cacacttcgg gttcctcggg    60
gaggagggc tggaaccta gcccatcgtc aggacaaaga tgctcaggct gctcttggct   120
ctcaacttat tcccttcaat tcaagtaaca ggaaacaaga ttttggtgaa gcagtcgccc   180
atgcttgtag cgtacgacaa tgcggtcaac cttagctgca agtattccta caatctcttc   240
tcaagggagt tccgggcatc ccttcacaaa ggactggata gtgctgtgga agtctgtgtt   300
gtatatggga attactccca gcagcttcag gtttactcaa aaacgggggtt caactgtgat   360
gggaaattgg gcaatgaatc agtgacattc tacctccaga atttgtatgt taaccaaaca   420
gatatttact tctgcaaaat tgaagttatg tatcctcctc cttacctaga caatgagaag   480
agcaatggaa ccattatcca tgtgaaaggg aaacaccttt gtccaagtcc cctatttccc   540
ggaccttcta agccctttg ggtgctggtg gtggttggtg gagtcctggc ttgctatagc   600
ttgctagtaa cagtggcctt tattatttc tgggtcgagga gtaagaggag caggctcctg   660
cacagtgact acatgaacat gactccccgc cgccccgggc ccacccgcaa gcattaccag   720
ccctatgccc caccacgcga cttcgcagcc tatcgctcct gacacggacg cctatccaga   780
agccagccgg ctggcagccc ccatctgctc aatatcactg ctctggatag gaaatgaccg   840
ccatctccag ccgccacct cagccccctgt tgggccacca atgccaattt ttctcgagtg   900
actagaccaa atatcaagat catttgaga ctctgaaatg aagtaaaga gatttcctgt   960
gacaggccaa gtcttacagt gccatggccc acattccaac ttaccatgta cttagtgact  1020
tgactgagaa gttagggtag aaaacaaaaa gggagtggat tctgggagcc tcttcccttt  1080
ctcactcacc tgcacatctc agtcaagcaa agtgtggtat ccacagacat tttagttgca  1140
gaagaaaggc taggaaatca ttcctttggg ttaaatgggt gtttaatctt ttggttagtg  1200
ggttaaacgg ggtaagtag agtaggggga gggataggaa gacatatta aaaaccatta  1260
aaacactgtc tcccactcat gaaatgagcc acgtagttcc tatttaatgc tgttttcctt  1320
tagtttagaa atacatagac attgtctttt atgaattctg atcatattta gtcatttga  1380
ccaaatgagg gatttggtca aatgagggat tccctcaaag caatatcagg taaaccaagt  1440
tgctttcctc actccctgtc atgagacttc agtgttaatg ttcacaatat actttcgaaa  1500
gaataaaata gttc                                                     1514
```

Amino acid sequence of human CD28 (SEQ ID NO: 1)

(SEQ ID NO:1)

MLRLLLALNL FPSIQVTGNK ILVKQSPMLV AYDNAVNLSC KYSYNLFSRE FRASLHKGLD

TABLE 5-continued

SAVEVCVVYG NYSQQLQVYS KTGFNCDGKL GNESVTFYLQ NLYVNQTDIY FCKIEVMYPP

PYLDNEKSNG TIIHV<u>KGKHL CPSPLFPGPS KP</u>FWVLVVVG GVLACYSLLV TVAFIIFWVR

SKRSRLLHSD YMNMTPRRPG PTRKHYQPYA PPRDFAAYRS

The extracellular domain is shown in bold
The stalk region is underlined

TABLE 6

CD28TFc sequence (SEQ ID NO:2)
(thrombin site separating the two halves of the chimera
is shown in bold)

```
         CCCCATCCGCTCAAGCAGGCCACCATGGATTGGCTGCGGAACTTGCTATTCCTGATGGCG
      1  ---------+---------+---------+---------+---------+---------+   60
         GGGGTAGGCGAGTTCGTCCGGTGGTACCTAACCGACGCCTTGAACGATAAGGACTACCGC
a                                  M  D  W  L  R  N  L  L  F  L  M  A

GCCGCTCAAAGTATCAACGCGAACAAGATCTTGGTGAAGCAGTCGCCCATGCTTGTAGCG
     61  ---------+---------+---------+---------+---------+---------+  120
         CGGCGAGTTTCATAGTTGCGCTTGTTCTAGAACCACTTCGTCAGCGGGTACGAACATCGC
a         A  A  Q  S  I  N  A  N  K  I  L  V  K  Q  S  P  M  L  V  A

TACGACAATGCGGTCAACCTTAGCTGCAAGTATTCCTACAATCTCTTCTCAAGGGAGTTC
    121  ---------+---------+---------+---------+---------+---------+  180
         ATGCTGTTACGCCAGTTGGAATCGACGTTCATAAGGATGTTAGAGAAGAGTTCCCTCAAG
a         Y  D  N  A  V  N  L  S  C  K  Y  S  Y  N  L  F  S  R  E  F

CGGGCATCCCTTCACAAAGGACTGGATAGTGCTGTGGAAGTCTGTGTTGTATATGGGAAT
    181  ---------+---------+---------+---------+---------+---------+  240
         GCCCGTAGGGAAGTGTTTCCTGACCTATCACGACACCTTCAGACACAACATATACCCTTA
a         R  A  S  L  H  K  G  L  D  S  A  V  E  V  C  V  V  Y  G  N

TACTCCCAGCAGCTTCAGGTTTACTCAAAAACGGGGTTCAACTGTGATGGGAAATTGGGC
    241  ---------+---------+---------+---------+---------+---------+  300
         ATGAGGGTCGTCGAAGTCCAAATGAGTTTTTGCCCCAAGTTGACACTACCCTTTAACCCG
a         Y  S  Q  Q  L  Q  V  Y  S  K  T  G  F  N  C  D  G  K  L  G

AATGAATCAGTGACATTCTACCTCCAGAATTTGTATGTTAACCAAACAGATATTTACTTC
    301  ---------+---------+---------+---------+---------+---------+  360
         TTACTTAGTCACTGTAAGATGGAGGTCTTAAACATACAATTGGTTTGTCTATAAATGAAG
a         N  E  S  V  T  F  Y  L  Q  N  L  Y  V  N  Q  T  D  I  Y  F

TGCAAAATTGAAGTTATGTATCCTCCTCCTTACCTAGACAATGAGAAGAGCAATGGTACC
    361  ---------+---------+---------+---------+---------+---------+  420
         ACGTTTTAACTTCAATACATAGGAGGAGGAATGGATCTGTTACTCTTCTCGTTACCATGG
a         C  K  I  E  V  M  Y  P  P  P  Y  L  D  N  E  K  S  N  G  T

ATTATCCATGTGAAAGGGAAACACCTTTGTCCAAGTCCGCTATTTCCCGGACCTTCTAAG
    421  ---------+---------+---------+---------+---------+---------+  480
         TAATAGGTACACTTTCCCTTTGTGGAAACAGGTTCAGGCGATAAAGGGCCTGGAAGATTC
a         I  I  H  V  K  G  K  H  L  C  P  S  P  L  F  P  G  P  S  K

CCCCTGGTACCCAGGGGTAGTGGTAGTAAGCCTAGCATAAGTACAGTCCCAGAAGTATCA
    481  ---------+---------+---------+---------+---------+---------+  540
         GGGGACCATGGGTCCCCATCACCATCATTCGGATCGTATTCATGTCAGGGTCTTCATAGT
a         P  L  V  P  R  G  S  G  S  K  P  S  I  S  T  V  P  E  V  S

TCTGTCTTCATCTTCCCCCCAAAGCCCAAGGATGTGCTCACCATTACTCTGACTCCTAAG
    541  ---------+---------+---------+---------+---------+---------+  600
         AGACAGAAGTAGAAGGGGGTTTCGGGTTCCTACACGAGTGGTAATGAGACTGAGGATTC
a         S  V  F  I  F  P  P  K  P  K  D  V  L  T  I  T  L  T  P  K

GTCACGTGTGTTGTGGTAGACATCAGCAAGGATGATCCCGAGGTCCAGTTCAGCTGGTTT
    601  ---------+---------+---------+---------+---------+---------+  660
         CAGTGCACACAACACCATCTGTAGTCGTTCCTACTAGGGCTCCAGGTCAAGTCGACCAAA
a         V  T  C  V  V  V  D  I  S  K  D  D  P  E  V  Q  F  S  W  F

GTAGATGATGTGGAGGTGCACACAGCTCAGACGCAACCCCGGGAGGAGCAGTTCAACAGC
    661  ---------+---------+---------+---------+---------+---------+  720
         CATCTACTACACCTCCACGTGTGTCGAGTCTGCGTTGGGGCCCTCCTCGTCAAGTTGTCG
a         V  D  D  V  E  V  H  T  A  Q  T  Q  P  R  E  E  Q  F  N  S

ACTTTCCGCTCAGTCAGTGAACTTCCCATCATGCACCAGGACTGGCTCAATGGCAAGGAG
```

TABLE 6-continued

CD28TFc sequence (SEQ ID NO:2)
(thrombin site separating the two halves of the chimera
is shown in bold)

```
      TGAAAGGCGAGTCAGTCACTTGAAGGGTAGTACGTGGTCCTGACCGAGTTACCGTTCCTC
  721 ---------+---------+---------+---------+---------+---------+  780
      ACTTTCCGCTCAGTCAGTGAACTTCCCATCATGCACCAGGACTGGCTCAATGGCAAGGAG
a      T  F  R  S  V  S  E  L  P  I  M  H  Q  D  W  L  N  G  K  E

TTCAAATGCAGGGTCAACAGTGCAGCTTTCCCTGCCCCCATCGAGAAAACCATCTCCAAA
  781 ---------+---------+---------+---------+---------+---------+  840
      AAGTTTACGTCCCAGTTGTCACGTCGAAAGGGACGGGGGTAGCTCTTTTGGTAGAGGTTT
a      F  K  C  R  V  N  S  A  A  F  P  A  P  I  E  K  T  I  S  K

ACCAAAGGCAGACCGAAGGCTCCACAGGTGTACACCATTCCACCTCCCAAGGAGCAGATG
  841 ---------+---------+---------+---------+---------+---------+  900
      TGGTTTCCGTCTGGCTTCCGAGGTGTCCACATGTGGTAAGGTGGAGGGTTCCTCGTCTAC
a      T  K  G  R  P  K  A  P  Q  V  Y  T  I  P  P  P  K  E  Q  M

GCCAAGGATAAAGTCAGTCTGACCTGCATGATAACAGACTTCTTCCCTGAAGACATTACT
  901 ---------+---------+---------+---------+---------+---------+  960
      CGGTTCCTATTTCAGTCAGACTGGACGTACTATTGTCTGAAGAAGGGACTTCTGTAATGA
a      A  K  D  K  V  S  L  T  C  M  I  T  D  F  F  P  E  D  I  T

GTGGAGTGGCAGTGGAATGGGCAGCCAGCGGAGAACTACAAGAACACTCAGCCCATCATG
  961 ---------+---------+---------+---------+---------+---------+ 1020
      CACCTCACCGTCACCTTACCCGTCGGTCGCCTCTTGATGTTCTTGTGAGTCGGGTAGTAC
a      V  E  W  Q  W  N  G  Q  P  A  E  N  Y  K  N  T  Q  P  I  M

GACACAGATGGCTCTTACTTCGTCTACAGCAAGCTCAATGTGCAGAAGAGCAACTGGGAG
 1021 ---------+---------+---------+---------+---------+---------+ 1080
      CTGTGTCTACCGAGAATGAAGCAGATGTCGTTCGAGTTACACGTCTTCTCGTTGACCCTC
a      D  T  D  G  S  Y  F  V  Y  S  K  L  N  V  Q  K  S  N  W  E

GCAGGAAATACTTTCACCTGCTCTGTGTTACATGAGGGCCTGCACAACCACCATACTGAG
 1081 ---------+---------+---------+---------+---------+---------+ 1140
      CGTCCTTTATGAAAGTGGACGAGACACAATGTACTCCCGGACGTGTTGGTGGTATGACTC
a      A  G  N  T  F  T  C  S  V  L  H  E  G  L  H  N  H  H  T  E

AAGAGCCTCTCCCACTCTCCTGGTAAATAA
 1141 ---------+---------+---------+                                1170
      TTCTCGGAGAGGGTGAGAGGACCATTTATT
a      K  S  L  S  H  S  P  G  K  *
```

---

The invention claimed is:

1. An antibody that binds to the extracellular portion of the human PD-1 receptor at a membrane proximal region and said antibody binds to an epitope comprising SEQ ID NO: 44, SEQ ID NO: 46, SEQ ID NO: 48, SEQ ID NO: 50, SEQ ID NO: 52, SEQ ID NO: 54, SEQ ID NO: 56 or SEQ ID NO: 61, wherein:
 a) said antibody does not only bind to a peptide consisting of LAAFPEDRSQPGQDCR (SEQ ID NO: 61), the human PD-1 equivalent of the C'-D loop of human CD28; and
 b) said antibody induces superagonistic signaling of the PD-1 receptor by binding to a membrane proximal region of the human PD-1 receptor that is within 75 Å of a cell surface or wherein said antibody binds to a membrane proximal region of human PD-1 expressed on the surface of a cell and holds the cell surface within 200 Å of a substrate to which said antibody is immobilized.

2. The antibody according to claim 1, wherein said antibody binds to an epitope comprising SEQ ID NO: 44.

3. The antibody according to claim 1, wherein said antibody binds to an epitope comprising SEQ ID NO: 46.

4. The antibody according to claim 1, wherein said antibody binds to an epitope comprising SEQ ID NO: 48.

5. The antibody according to claim 1, wherein said antibody binds to an epitope comprising SEQ ID NO: 50.

6. The antibody according to claim 1, wherein said antibody binds to an epitope comprising SEQ ID NO: 52.

7. The antibody according to claim 1, wherein said antibody binds to an epitope comprising SEQ ID NO: 54.

8. The antibody according to claim 1, wherein said antibody binds to an epitope comprising SEQ ID NO: 56.

9. The antibody according to claim 1, wherein said antibody binds to an epitope comprising SEQ ID NO: 61.

10. The antibody according to claim 1, wherein said antibody is a monoclonal antibody.

11. The antibody according to claim 10, wherein said antibody is a humanized antibody.

12. The antibody according to claim 10, wherein said antibody is a complementarity determining region (CDR)-grafted antibody.

13. The antibody according to claim 10, wherein said antibody is a chimeric antibody.

14. The antibody according to claim 1, wherein said antibody induces superagonistic signaling of the PD-1 receptor by binding to a membrane proximal region of the human PD-1 receptor that is within 60 Å of a cell surface.

15. The antibody according to claim 1, wherein said antibody induces superagonistic signaling of the PD-1 receptor by binding to a membrane proximal region of the human PD-1 receptor that is within 50 Å of a cell surface.

16. The antibody according to claim 1, wherein said antibody induces superagonistic signaling of the PD-1 receptor by binding to a membrane proximal region of the human PD-1 receptor that is within 40 Å of a cell surface.

17. The antibody according to claim 1, wherein said antibody binds to a membrane proximal region of human PD-1 expressed on the surface of a cell and holds the cell surface within 180 Å of a substrate to which said antibody is immobilized.

18. The antibody according to claim 1, wherein said antibody hinds to a membrane proximal region of human PD-1 expressed on the surface of a cell and holds the cell surface within 150 Å of a substrate to which said antibody is immobilized.

19. The antibody according to claim 1, wherein said antibody binds to a membrane proximal region of human PD-1 expressed on the surface of a cell and holds the cell surface within 120 Å of a substrate to which said antibody is immobilized.

* * * * *

UNITED STATES PATENT AND TRADEMARK OFFICE
CERTIFICATE OF CORRECTION

PATENT NO.        : 7,851,598 B2
APPLICATION NO.   : 10/585491
DATED             : December 14, 2010
INVENTOR(S)       : Simon Davis It is certified that error appears in the above-identified patent and that said Letters Patent is hereby corrected as shown below:

Column 8,
Line 33, "(Yxx/Ix$_{7-12}$YxxL/I)" should read --(YxxL/Ix$_{7-12}$YxxL/I)--.

Column 13,
Line 13, "(http://www.ncbi.nhn.nih.gov/)" should read
 --(http://www.ncbi.nlm.nih.gov/)--.

Column 18,

Line 11, "cysteine ● HCl" should read --cysteine●HCl--.

Line 14, "cysteine-HCl" should read --cysteine●HCl--.

Column 22,
Table 1, Column "Protein", "hpd-1" should read --hPD-1--.

Column 45,
Table 4, Row "ATOM 890", "41.625" should read --41.525--.

Column 49,
Table 4, Row "ATOM 1016", "46.58" should read --46.88--.

Column 133,
Table 5, Line 11, "tattatttc tgggtcgagga" should read --tattattttc tgggtgagga--.

Signed and Sealed this
Eighth Day of March, 2011

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,851,598 B2 |
| APPLICATION NO. | : 10/585491 |
| DATED | : December 14, 2010 |
| INVENTOR(S) | : Simon Davis |

It is certified that error appears in the above-identified patent and that said Letters Patent is hereby corrected as shown below:

Column 8,
Line 33, "(Yxx/Ix$_{7-12}$YxxL/I)" should read --(YxxL/Ix$_{7-12}$YxxL/I)--.

Column 13,
Line 13, "(http://www.ncbi.nhn.nih.gov/)" should read
  --(http://www.ncbi.nlm.nih.gov/)--.

Column 18,

Line 11, "cysteine ● HCl" should read --cysteine●HCl--.

Line 14, "cysteine-HCl" should read --cysteine●HCl--.

Column 22,
Table 1, Column "Protein", "hpd-1" should read --hPD-1--.

Column 45,
Table 4, Row "ATOM 890", "41.625" should read --41.525--.

Column 49,
Table 4, Row "ATOM 1016", "46.58" should read --46.88--.

Column 133,
Table 5, Line 11, "tattatttc tgggtcgagga" should read --tattattttc tgggtgagga--.

This certificate supersedes the Certificate of Correction issued March 8, 2011.

Signed and Sealed this
Nineteenth Day of April, 2011

David J. Kappos
*Director of the United States Patent and Trademark Office*

SEQUENCE LISTING

<160> NUMBER OF SEQ ID NOS: 61

<210> SEQ ID NO 1
<211> LENGTH: 220
<212> TYPE: PRT
<213> ORGANISM: Homo sapiens
<220> FEATURE:
<221> NAME/KEY: MISC_FEATURE
<222> LOCATION: (1)..(220)
<223> OTHER INFORMATION: HUMAN CD28

<400> SEQUENCE: 1

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

```
Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 2
<211> LENGTH: 381
<212> TYPE: PRT
<213> ORGANISM: Artificial sequence
<220> FEATURE:
<223> OTHER INFORMATION: CD28/Fc fusion protein

<400> SEQUENCE: 2

Met Asp Trp Leu Arg Asn Leu Leu Phe Leu Met Ala Ala Ala Gln Ser
1               5                   10                  15

Ile Asn Ala Asn Lys Ile Leu Val Lys Gln Ser Pro Met Leu Val Ala
            20                  25                  30

Tyr Asp Asn Ala Val Asn Leu Ser Cys Lys Tyr Ser Tyr Asn Leu Phe
        35                  40                  45

Ser Arg Glu Phe Arg Ala Ser Leu His Lys Gly Leu Asp Ser Ala Val
    50                  55                  60

Glu Val Cys Val Val Tyr Gly Asn Tyr Ser Gln Gln Leu Gln Val Tyr
65                  70                  75                  80

Ser Lys Thr Gly Phe Asn Cys Asp Gly Lys Leu Gly Asn Glu Ser Val
                85                  90                  95

Thr Phe Tyr Leu Gln Asn Leu Tyr Val Asn Gln Thr Asp Ile Tyr Phe
            100                 105                 110

Cys Lys Ile Glu Val Met Tyr Pro Pro Tyr Leu Asp Asn Glu Lys
        115                 120                 125

Ser Asn Gly Thr Ile Ile His Val Lys Gly Lys His Leu Cys Pro Ser
    130                 135                 140

Pro Leu Phe Pro Gly Pro Ser Lys Pro Leu Val Pro Arg Gly Ser Gly
145                 150                 155                 160

Ser Lys Pro Ser Ile Ser Thr Val Pro Glu Val Ser Ser Val Phe Ile
                165                 170                 175

Phe Pro Pro Lys Pro Lys Asp Val Leu Thr Ile Thr Leu Thr Pro Lys
            180                 185                 190

Val Thr Cys Val Val Val Asp Ile Ser Lys Asp Pro Glu Val Gln
        195                 200                 205

Phe Ser Trp Phe Val Asp Asp Val Glu Val His Thr Ala Gln Thr Gln
    210                 215                 220
```

-continued

```
Pro Arg Glu Glu Gln Phe Asn Ser Thr Phe Arg Ser Val Ser Glu Leu
225                 230                 235                 240

Pro Ile Met His Gln Asp Trp Leu Asn Gly Lys Glu Phe Lys Cys Arg
                245                 250                 255

Val Asn Ser Ala Ala Phe Pro Ala Pro Ile Glu Lys Thr Ile Ser Lys
            260                 265                 270

Thr Lys Gly Arg Pro Lys Ala Pro Gln Val Tyr Thr Ile Pro Pro Pro
        275                 280                 285

Lys Glu Gln Met Ala Lys Asp Lys Val Ser Leu Thr Cys Met Ile Thr
    290                 295                 300

Asp Phe Phe Pro Glu Asp Ile Thr Val Glu Trp Gln Trp Asn Gly Gln
305                 310                 315                 320

Pro Ala Glu Asn Tyr Lys Asn Thr Gln Pro Ile Met Asp Thr Asp Gly
                325                 330                 335

Ser Tyr Phe Val Tyr Ser Lys Leu Asn Val Gln Lys Ser Asn Trp Glu
            340                 345                 350

Ala Gly Asn Thr Phe Thr Cys Ser Val Leu His Glu Gly Leu His Asn
        355                 360                 365

His His Thr Glu Lys Ser Leu Ser His Ser Pro Gly Lys
    370                 375                 380

<210> SEQ ID NO 3
<211> LENGTH: 15
<212> TYPE: PRT
<213> ORGANISM: Artificial sequence
<220> FEATURE:
<223> OTHER INFORMATION: activating ITAM motif
<220> FEATURE:
<221> NAME/KEY: MISC_FEATURE
<222> LOCATION: (2)..(3)
<223> OTHER INFORMATION: Xaa IS ANY AMINO ACID
<220> FEATURE:
<221> NAME/KEY: MISC_FEATURE
<222> LOCATION: (4)..(4)
<223> OTHER INFORMATION: Xaa IS LEUCINE/ISOLEUCINE
<220> FEATURE:
<221> NAME/KEY: MISC_FEATURE
<222> LOCATION: (5)..(11)
<223> OTHER INFORMATION: Xaa IS ANY AMINO ACID
<220> FEATURE:
<221> NAME/KEY: MISC_FEATURE
<222> LOCATION: (13)..(14)
<223> OTHER INFORMATION: Xaa IS ANY AMINO ACID
<220> FEATURE:
<221> NAME/KEY: MISC_FEATURE
<222> LOCATION: (15)..(15)
<223> OTHER INFORMATION: Xaa IS LEUCINE/ISOLEUCINE

<400> SEQUENCE: 3

Tyr Xaa Xaa Xaa Xaa Xaa Xaa Xaa Xaa Xaa Tyr Xaa Xaa Xaa
1               5                   10                  15

<210> SEQ ID NO 4
<211> LENGTH: 16
<212> TYPE: PRT
<213> ORGANISM: Artificial sequence
<220> FEATURE:
<223> OTHER INFORMATION: activating ITAM motif
<220> FEATURE:
<221> NAME/KEY: MISC_FEATURE
<222> LOCATION: (2)..(3)
<223> OTHER INFORMATION: Xaa IS ANY AMINO ACID
<220> FEATURE:
<221> NAME/KEY: MISC_FEATURE
<222> LOCATION: (4)..(4)
<223> OTHER INFORMATION: Xaa IS LEUCINE/ISOLEUCINE
<220> FEATURE:
```

```
-continued

<221> NAME/KEY: MISC_FEATURE
<222> LOCATION: (5)..(12)
<223> OTHER INFORMATION: Xaa IS ANY AMINO ACID
<220> FEATURE:
<221> NAME/KEY: MISC_FEATURE
<222> LOCATION: (14)..(15)
<223> OTHER INFORMATION: Xaa IS ANY AMINO ACID
<220> FEATURE:
<221> NAME/KEY: MISC_FEATURE
<222> LOCATION: (16)..(16)
<223> OTHER INFORMATION: Xaa IS LEUCINE/ISOLEUCINE

<400> SEQUENCE: 4

Tyr Xaa Xaa Xaa Xaa Xaa Xaa Xaa Xaa Xaa Xaa Xaa Tyr Xaa Xaa Xaa
1               5                   10                  15

<210> SEQ ID NO 5
<211> LENGTH: 17
<212> TYPE: PRT
<213> ORGANISM: Artificial sequence
<220> FEATURE:
<223> OTHER INFORMATION: activating ITAM motif
<220> FEATURE:
<221> NAME/KEY: MISC_FEATURE
<222> LOCATION: (2)..(3)
<223> OTHER INFORMATION: Xaa IS ANY AMINO ACID
<220> FEATURE:
<221> NAME/KEY: MISC_FEATURE
<222> LOCATION: (4)..(4)
<223> OTHER INFORMATION: Xaa IS LEUCINE/ISOLEUCINE
<220> FEATURE:
<221> NAME/KEY: MISC_FEATURE
<222> LOCATION: (5)..(13)
<223> OTHER INFORMATION: Xaa IS ANY AMINO ACID
<220> FEATURE:
<221> NAME/KEY: MISC_FEATURE
<222> LOCATION: (15)..(16)
<223> OTHER INFORMATION: Xaa IS ANY AMINO ACID
<220> FEATURE:
<221> NAME/KEY: MISC_FEATURE
<222> LOCATION: (17)..(17)
<223> OTHER INFORMATION: Xaa IS LEUCINE/ISOLEUCINE

<400> SEQUENCE: 5

Tyr Xaa Xaa Xaa Xaa Xaa Xaa Xaa Xaa Xaa Xaa Xaa Xaa Tyr Xaa Xaa
1               5                   10                  15

Xaa

<210> SEQ ID NO 6
<211> LENGTH: 18
<212> TYPE: PRT
<213> ORGANISM: Artificial sequence
<220> FEATURE:
<223> OTHER INFORMATION: activating ITAM motif
<220> FEATURE:
<221> NAME/KEY: MISC_FEATURE
<222> LOCATION: (2)..(3)
<223> OTHER INFORMATION: Xaa IS ANY AMINO ACID
<220> FEATURE:
<221> NAME/KEY: MISC_FEATURE
<222> LOCATION: (4)..(4)
<223> OTHER INFORMATION: Xaa IS LEUCINE/ISOLEUCINE
<220> FEATURE:
<221> NAME/KEY: MISC_FEATURE
<222> LOCATION: (5)..(14)
<223> OTHER INFORMATION: Xaa IS ANY AMINO ACID
<220> FEATURE:
<221> NAME/KEY: MISC_FEATURE
<222> LOCATION: (16)..(17)
<223> OTHER INFORMATION: Xaa IS ANY AMINO ACID
<220> FEATURE:
<221> NAME/KEY: MISC_FEATURE
<222> LOCATION: (18)..(18)
<223> OTHER INFORMATION: Xaa IS LEUCINE/ISOLEUCINE
```

```
<400> SEQUENCE: 6

Tyr Xaa Xaa Xaa Xaa Xaa Xaa Xaa Xaa Xaa Xaa Xaa Xaa Xaa Tyr Xaa
1               5                   10                  15

Xaa Xaa

<210> SEQ ID NO 7
<211> LENGTH: 19
<212> TYPE: PRT
<213> ORGANISM: Artificial sequence
<220> FEATURE:
<223> OTHER INFORMATION: activating ITAM motif
<220> FEATURE:
<221> NAME/KEY: MISC_FEATURE
<222> LOCATION: (2)..(3)
<223> OTHER INFORMATION: Xaa IS ANY AMINO ACID
<220> FEATURE:
<221> NAME/KEY: MISC_FEATURE
<222> LOCATION: (4)..(4)
<223> OTHER INFORMATION: Xaa IS LEUCINE/ISOLEUCINE
<220> FEATURE:
<221> NAME/KEY: MISC_FEATURE
<222> LOCATION: (5)..(15)
<223> OTHER INFORMATION: Xaa IS ANY AMINO ACID
<220> FEATURE:
<221> NAME/KEY: MISC_FEATURE
<222> LOCATION: (17)..(18)
<223> OTHER INFORMATION: Xaa IS ANY AMINO ACID
<220> FEATURE:
<221> NAME/KEY: MISC_FEATURE
<222> LOCATION: (19)..(19)
<223> OTHER INFORMATION: Xaa IS LEUCINE/ISOLEUCINE

<400> SEQUENCE: 7

Tyr Xaa Xaa Xaa Xaa Xaa Xaa Xaa Xaa Xaa Xaa Xaa Xaa Xaa Xaa Tyr
1               5                   10                  15

Xaa Xaa Xaa

<210> SEQ ID NO 8
<211> LENGTH: 20
<212> TYPE: PRT
<213> ORGANISM: Artificial sequence
<220> FEATURE:
<223> OTHER INFORMATION: activating ITAM motif
<220> FEATURE:
<221> NAME/KEY: MISC_FEATURE
<222> LOCATION: (2)..(3)
<223> OTHER INFORMATION: Xaa IS ANY AMINO ACID
<220> FEATURE:
<221> NAME/KEY: MISC_FEATURE
<222> LOCATION: (4)..(4)
<223> OTHER INFORMATION: Xaa IS LEUCINE/ISOLEUCINE
<220> FEATURE:
<221> NAME/KEY: MISC_FEATURE
<222> LOCATION: (5)..(16)
<223> OTHER INFORMATION: Xaa IS ANY AMINO ACID
<220> FEATURE:
<221> NAME/KEY: MISC_FEATURE
<222> LOCATION: (18)..(19)
<223> OTHER INFORMATION: Xaa IS ANY AMINO ACID
<220> FEATURE:
<221> NAME/KEY: MISC_FEATURE
<222> LOCATION: (20)..(20)
<223> OTHER INFORMATION: Xaa IS LEUCINE/ISOLEUCINE

<400> SEQUENCE: 8

Tyr Xaa Xaa Xaa Xaa Xaa Xaa Xaa Xaa Xaa Xaa Xaa Xaa Xaa Xaa Xaa
1               5                   10                  15

Tyr Xaa Xaa Xaa
            20
```

```
<210> SEQ ID NO 9
<211> LENGTH: 6
<212> TYPE: PRT
<213> ORGANISM: Artificial sequence
<220> FEATURE:
<223> OTHER INFORMATION: inhibitory ITIM motif
<220> FEATURE:
<221> NAME/KEY: MISC_FEATURE
<222> LOCATION: (1)..(1)
<223> OTHER INFORMATION: Xaa IS ISOLEUCINE/VALINE/LEUCINE/SERINE
<220> FEATURE:
<221> NAME/KEY: MISC_FEATURE
<222> LOCATION: (2)..(2)
<223> OTHER INFORMATION: Xaa IS ANY AMINO ACID
<220> FEATURE:
<221> NAME/KEY: MISC_FEATURE
<222> LOCATION: (4)..(5)
<223> OTHER INFORMATION: Xaa IS ANY AMINO ACID
<220> FEATURE:
<221> NAME/KEY: MISC_FEATURE
<222> LOCATION: (6)..(6)
<223> OTHER INFORMATION: Xaa IS LEUCINE/VALINE

<400> SEQUENCE: 9

Xaa Xaa Tyr Xaa Xaa Xaa
1               5

<210> SEQ ID NO 10
<211> LENGTH: 6
<212> TYPE: PRT
<213> ORGANISM: Artificial sequence
<220> FEATURE:
<223> OTHER INFORMATION: "switch" signalling motif
<220> FEATURE:
<221> NAME/KEY: MISC_FEATURE
<222> LOCATION: (2)..(2)
<223> OTHER INFORMATION: Xaa IS ANY AMINO ACID
<220> FEATURE:
<221> NAME/KEY: MISC_FEATURE
<222> LOCATION: (4)..(5)
<223> OTHER INFORMATION: Xaa IS ANY AMINO ACID
<220> FEATURE:
<221> NAME/KEY: MISC_FEATURE
<222> LOCATION: (6)..(6)
<223> OTHER INFORMATION: Xaa IS VALINE/ISOLEUCINE

<400> SEQUENCE: 10

Thr Xaa Tyr Xaa Xaa Xaa
1               5

<210> SEQ ID NO 11
<211> LENGTH: 57
<212> TYPE: DNA
<213> ORGANISM: Artificial sequence
<220> FEATURE:
<223> OTHER INFORMATION: OLIGONUCLEOTIDE PRIMER

<400> SEQUENCE: 11
tagtagtcta gacccatcc gctcaagcag gccaccatgg attggctgcg gaacttg      57

<210> SEQ ID NO 12
<211> LENGTH: 31
<212> TYPE: DNA
<213> ORGANISM: Artificial sequence
<220> FEATURE:
<223> OTHER INFORMATION: OLIGONUCLEOTIDE PRIMER

<400> SEQUENCE: 12
ctaccactac ccctgggtac caggggctta g                                  31
```

```
<210> SEQ ID NO 13
<211> LENGTH: 31
<212> TYPE: DNA
<213> ORGANISM: Artificial sequence
<220> FEATURE:
<223> OTHER INFORMATION: OLIGONUCLEOTIDE PRIMER

<400> SEQUENCE: 13
ctaagcccct ggtacccagg ggtagtggta g                                 31

<210> SEQ ID NO 14
<211> LENGTH: 34
<212> TYPE: DNA
<213> ORGANISM: Artificial sequence
<220> FEATURE:
<223> OTHER INFORMATION: OLIGONUCLEOTIDE PRIMER

<400> SEQUENCE: 14
ctactatcta gattatttac caggagagtg ggag                              34

<210> SEQ ID NO 15
<211> LENGTH: 1514
<212> TYPE: DNA
<213> ORGANISM: Homo sapiens
<220> FEATURE:
<221> NAME/KEY: misc_feature
<222> LOCATION: (1)..(1514)
<223> OTHER INFORMATION: HUMAN CD28 cDNA

<400> SEQUENCE: 15
agactctcag gccttggcag gtgcgtcttt cagttcccct cacacttcgg gttcctcggg    60
gaggaggggc tggaaccta gcccatcgtc aggacaaaga tgctcaggct gctcttggct   120
ctcaacttat tcccttcaat tcaagtaaca ggaaacaaga ttttggtgaa gcagtcgccc   180
atgcttgtag cgtacgacaa tgcggtcaac cttagctgca agtattccta caatctcttc   240
tcaagggagt tccgggcatc ccttcacaaa ggactggata tgctgtgga agtctgtgtt    300 gtatatggga attactccca gcagcttcag gtttactcaa aaacgggggtt caactgtgat   360 gggaaattgg gcaatgaatc agtgacattc tacctccaga atttgtatgt taaccaaaca   420
gatatttact tctgcaaaat tgaagttatg tatcctcctc cttacctaga caatgagaag   480
agcaatggaa ccattatcca tgtgaaaggg aaacactttt gtccaagtcc cctatttccc   540
ggaccttcta gcccttttg ggtgctggtg gtggttggtg gagtcctggc ttgctatagc    600
ttgctagtaa cagtggcctt tattattttc tgggtgagga gtaagaggag caggctcctg   660
cacagtgact acatgaacat gactccccgc cgccccgggc ccacccgcaa gcattaccag   720
ccctatgccc caccacgcga cttcgcagcc tatcgctcct gacacggacg cctatccaga   780
agccagccgg ctggcagccc ccatctgctc aatatcactg ctctggatag gaaatgaccg    840
ccatctccag ccggccacct cagccctgt gggccacca atgccaattt ttctcgagtg    900
actagaccaa atatcaagat cattttgaga ctctgaaatg aagtaaaaga gatttcctgt    960
gacaggccaa gtcttacagt gccatggccc acattccaac ttaccatgta cttagtgact  1020
tgactgagaa gttagggtag aaaacaaaa gggagtggat tctgggagcc tcttcccttt   1080
ctcactcacc tgcacatctc agtcaagcaa agtgtggtat ccacagacat tttagttgca  1140
gaagaaaggc taggaaatca ttccttttgg ttaaatgggt gtttaatctt ttggttagtg  1200
ggttaaacgg ggtaagttag agtagggga gggataggaa gacatattta aaaaccatta  1260
aaacactgtc tcccactcat gaaatgagcc acgtagttcc tatttaatgc tgttttcctt  1320
```

-continued

| | |
|---|---|
| tagtttagaa atacatagac attgtctttt atgaattctg atcatattta gtcattttga | 1380 |
| ccaaatgagg gatttggtca aatgagggat tccctcaaag caatatcagg taaaccaagt | 1440 |
| tgctttcctc actccctgtc atgagacttc agtgttaatg ttcacaatat actttcgaaa | 1500 |
| gaataaaata gttc | 1514 |

<210> SEQ ID NO 16
<211> LENGTH: 1170
<212> TYPE: DNA
<213> ORGANISM: Artificial sequence
<220> FEATURE:
<223> OTHER INFORMATION: CD28TFc SEQUENCE

<400> SEQUENCE: 16

| | |
|---|---|
| ccccatccgc tcaagcaggc caccatggat tggctgcgga acttgctatt cctgatggcg | 60 |
| gccgctcaaa gtatcaacgc gaacaagatc ttggtgaagc agtcgcccat gcttgtagcg | 120 |
| tacgacaatg cggtcaacct agctgcaag tattcctaca atctcttctc aagggagttc | 180 |
| cgggcatccc ttcacaaagg actggatagt gctgtggaag tctgtgttgt atatgggaat | 240 |
| tactcccagc agcttcaggt ttactcaaaa acgggggtca actgtgatgg gaaattgggc | 300 |
| aatgaatcag tgacattcta cctccagaat ttgtatgtta ccaaacaga tatttacttc | 360 |
| tgcaaaattg aagttatgta tcctcctcct tacctagaca atgagaagag caatggtacc | 420 |
| attatccatg tgaaagggaa acacctttgt ccaagtccgc tatttcccgg accttctaag | 480 |
| cccctggtac ccaggggtag tggtagtaag cctagcataa gtacagtccc agaagtatca | 540 |
| tctgtcttca tcttccccc aaagcccaag gatgtgctca ccattactct gactcctaag | 600 |
| gtcacgtgtg ttgtggtaga catcagcaag gatgatcccg aggtccagtt cagctggttt | 660 |
| gtagatgatg tggaggtgca cacagctcag acgcaacccc gggaggagca gttcaacagc | 720 |
| actttccgct cagtcagtga acttcccatc atgcaccagg actggctcaa tggcaaggag | 780 |
| ttcaaatgca gggtcaacag tgcagctttc cctgccccca tcgagaaaac catctccaaa | 840 |
| accaaaggca gaccgaaggc tccacaggtg tacaccattc cacctcccaa ggagcagatg | 900 |
| gccaaggata aagtcagtct gacctgcatg ataacagact tcttccctga agacattact | 960 |
| gtggagtggc agtggaatgg gcagccagcg gagaactaca agaacactca gcccatcatg | 1020 |
| gacacagatg gctcttactt cgtctacagc aagctcaatg tgcagaagag caactgggag | 1080 |
| gcaggaaata ctttcacctg ctctgtgtta catgagggcc tgcacaacca ccatactgag | 1140 |
| aagagcctct cccactctcc tggtaaataa | 1170 |

<210> SEQ ID NO 17
<211> LENGTH: 115
<212> TYPE: PRT
<213> ORGANISM: Homo sapiens
<220> FEATURE:
<221> NAME/KEY: MISC_FEATURE
<222> LOCATION: (1)..(115)
<223> OTHER INFORMATION: HUMAN CTLA-4

<400> SEQUENCE: 17

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Leu Asp Asp
    50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
                100                 105                 110

Ile Tyr Val
        115

<210> SEQ ID NO 18
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: HUMAN ICOS

<400> SEQUENCE: 18

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
                20                  25                  30

Met Gln Leu Leu Lys Gly Gly Gln Ile Leu Cys Asp Leu Thr Lys Thr
                35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile
                100                 105                 110

<210> SEQ ID NO 19
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: HUMAN PD-1

<400> SEQUENCE: 19

Pro Pro Thr Phe Phe Pro Ala Leu Leu Val Val Thr Glu Gly Asp Asn
1               5                   10                  15

Ala Thr Phe Thr Cys Ser Phe Ser Asn Thr Ser Glu Ser Phe Val Leu
                20                  25                  30

Asn Trp Tyr Arg Met Ser Pro Ser Asn Gln Thr Asp Lys Leu Ala Ala
                35                  40                  45

Phe Pro Glu Asp Arg Ser Gln Pro Gly Gln Asp Cys Arg Phe Arg Val
    50                  55                  60

Thr Gln Leu Pro Asn Gly Arg Asp Phe His Met Ser Val Val Arg Ala
65                  70                  75                  80

Arg Arg Asn Asp Ser Gly Thr Tyr Leu Cys Gly Ala Ile Ser Leu Ala
                85                  90                  95

Pro Lys Ala Gln Ile Lys Glu Ser Leu Arg Ala Glu Leu Arg

```
                        100                 105                 110
```

<210> SEQ ID NO 20
<211> LENGTH: 106
<212> TYPE: PRT
<213> ORGANISM: Homo sapiens
<220> FEATURE:
<221> NAME/KEY: MISC_FEATURE
<222> LOCATION: (1)..(106)
<223> OTHER INFORMATION: HUMAN IgL-KAPPA

<400> SEQUENCE: 20

```
Gln Met Thr Gln Ser Pro Ser Ser Leu Ser Ala Ser Val Gly Asp Arg
1               5                   10                  15

Val Thr Phe Thr Cys Arg Ser Ser Gln Thr Ile Gly Thr Tyr Leu Asn
            20                  25                  30

Trp Tyr Gln Gln Lys Pro Gly Gln Ala Pro Lys Leu Leu Ile Phe Ala
        35                  40                  45

Ala Ser Ser Leu Leu Asn Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser His Ser Ala Pro Pro Tyr Thr
                85                  90                  95

Phe Gly Gln Gly Thr Arg Leu Glu Met Lys
            100                 105
```

<210> SEQ ID NO 21
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: HUMAN TCR ALPHA

<400> SEQUENCE: 21

```
Gln Val Glu Gln Ser Pro Pro Asp Leu Ile Leu Gln Glu Gly Ala Asn
1               5                   10                  15

Ser Thr Leu Arg Cys Asn Phe Ser Asp Ser Val Asn Asn Leu Gln Trp
            20                  25                  30

Phe His Gln Asn Pro Trp Gly Gln Leu Ile Asn Leu Phe Tyr Ile Pro
        35                  40                  45

Ser Gly Thr Lys Gln Asn Gly Arg Leu Ser Ala Thr Thr Val Ala Thr
    50                  55                  60

Glu Arg Tyr Ser Leu Leu Tyr Ile Ser Ser Ser Gln Thr Thr Asp Ser
65                  70                  75                  80

Gly Val Tyr Phe Cys Ala Ala Leu Asp Leu Trp Gly Gly Ala Asp Gly
                85                  90                  95

Leu Thr Phe Gly Lys Gly Thr His Leu Ile Ile Gln
            100                 105
```

<210> SEQ ID NO 22
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: HUMAN BTLA

<400> SEQUENCE: 22

-continued

```
Gln Leu Tyr Ile Lys Arg Gln Ser Glu His Ser Ile Leu Ala Gly Asp
1               5                   10                  15

Pro Phe Glu Leu Glu Cys Pro Val Lys Tyr Cys Ala Asn Arg Pro His
            20                  25                  30

Val Thr Trp Cys Lys Leu Asn Gly Thr Thr Cys Val Lys Leu Glu Asp
        35                  40                  45

Arg Gln Thr Ser Trp Lys Glu Lys Asn Ile Ser Phe Phe Ile Leu
    50                  55                  60

His Phe Glu Pro Met Leu Pro Asn Asp Asn Gly Ser Tyr Arg Cys Ser
65                  70                  75                  80

Ala Asn Phe Gln Ser Asn Leu Ile Glu Ser His Ser Thr Thr Leu Tyr
                85                  90                  95

Val Thr

<210> SEQ ID NO 23
<211> LENGTH: 5
<212> TYPE: PRT
<213> ORGANISM: Artificial Sequence
<220> FEATURE:
<223> OTHER INFORMATION: hCD28 epitope

<400> SEQUENCE: 23

Ser Pro Met Leu Val
1               5

<210> SEQ ID NO 24
<211> LENGTH: 5
<212> TYPE: PRT
<213> ORGANISM: Artificial Sequence
<220> FEATURE:
<223> OTHER INFORMATION: hCTLA-4 epitope

<400> SEQUENCE: 24

Pro Ala Val Val Leu
1               5

<210> SEQ ID NO 25
<211> LENGTH: 5
<212> TYPE: PRT
<213> ORGANISM: Artificial sequence
<220> FEATURE:
<223> OTHER INFORMATION: hICOS epitope

<400> SEQUENCE: 25

Tyr Glu Met Phe Ile
1               5

<210> SEQ ID NO 26
<211> LENGTH: 5
<212> TYPE: PRT
<213> ORGANISM: Artificial Sequence
<220> FEATURE:
<223> OTHER INFORMATION: hCD28 epitope

<400> SEQUENCE: 26

Ala Val Asn Leu Ser
1               5

<210> SEQ ID NO 27
<211> LENGTH: 6
<212> TYPE: PRT
<213> ORGANISM: Artificial sequence
<220> FEATURE:
```

-continued

<223> OTHER INFORMATION: hCTLA-4 epitope

<400> SEQUENCE: 27

Gly Ile Ala Ser Phe Val
1               5

<210> SEQ ID NO 28
<211> LENGTH: 5
<212> TYPE: PRT
<213> ORGANISM: Artificial sequence
<220> FEATURE:
<223> OTHER INFORMATION: hICOS epitope

<400> SEQUENCE: 28

Gly Val Gln Ile Leu
1               5

<210> SEQ ID NO 29
<211> LENGTH: 14
<212> TYPE: PRT
<213> ORGANISM: Artificial sequence
<220> FEATURE:
<223> OTHER INFORMATION: hCD28 epitope

<400> SEQUENCE: 29

Ser Leu His Lys Gly Leu Asp Ser Ala Val Glu Val Cys Val
1               5                   10

<210> SEQ ID NO 30
<211> LENGTH: 15
<212> TYPE: PRT
<213> ORGANISM: Artificial sequence
<220> FEATURE:
<223> OTHER INFORMATION: hCTLA-4 epitope

<400> SEQUENCE: 30

Thr Val Leu Arg Gln Ala Asp Ser Gln Val Thr Glu Val Cys Ala
1               5                   10                  15

<210> SEQ ID NO 31
<211> LENGTH: 11
<212> TYPE: PRT
<213> ORGANISM: Artificial sequence
<220> FEATURE:
<223> OTHER INFORMATION: hICOS epitope

<400> SEQUENCE: 31

Gln Leu Leu Lys Gly Gly Gln Ile Leu Cys Asp
1               5                   10

<210> SEQ ID NO 32
<211> LENGTH: 11
<212> TYPE: PRT
<213> ORGANISM: Artificial sequence
<220> FEATURE:
<223> OTHER INFORMATION: hCD28 epitope

<400> SEQUENCE: 32

Val Tyr Ser Lys Thr Gly Phe Asn Cys Asp Gly
1               5                   10

<210> SEQ ID NO 33
<211> LENGTH: 9
<212> TYPE: PRT
<213> ORGANISM: Artificial sequence
<220> FEATURE:
<223> OTHER INFORMATION: hCTLA-4 epitope

```
<400> SEQUENCE: 33

Phe Leu Asp Asp Ser Ile Cys Thr Gly
1               5

<210> SEQ ID NO 34
<211> LENGTH: 11
<212> TYPE: PRT
<213> ORGANISM: Artificial sequence
<220> FEATURE:
<223> OTHER INFORMATION: hICOS epitope

<400> SEQUENCE: 34

Val Ser Ile Lys Ser Leu Lys Phe Cys His Ser
1               5                   10

<210> SEQ ID NO 35
<211> LENGTH: 5
<212> TYPE: PRT
<213> ORGANISM: Artificial sequence
<220> FEATURE:
<223> OTHER INFORMATION: hCD28 epitope

<400> SEQUENCE: 35

Phe Tyr Leu Gln Asn
1               5

<210> SEQ ID NO 36
<211> LENGTH: 5
<212> TYPE: PRT
<213> ORGANISM: Artificial sequence
<220> FEATURE:
<223> OTHER INFORMATION: hCTLA-4 epitope

<400> SEQUENCE: 36

Leu Thr Ile Gln Gly
1               5

<210> SEQ ID NO 37
<211> LENGTH: 5
<212> TYPE: PRT
<213> ORGANISM: Artificial sequence
<220> FEATURE:
<223> OTHER INFORMATION: hICOS epitope

<400> SEQUENCE: 37

Phe Phe Leu Tyr Asn
1               5

<210> SEQ ID NO 38
<211> LENGTH: 6
<212> TYPE: PRT
<213> ORGANISM: Artificial sequence
<220> FEATURE:
<223> OTHER INFORMATION: hCD28 epitope

<400> SEQUENCE: 38

Thr Asp Ile Tyr Phe Cys
1               5

<210> SEQ ID NO 39
<211> LENGTH: 6
<212> TYPE: PRT
<213> ORGANISM: Artificial sequence
<220> FEATURE:
<223> OTHER INFORMATION: hCTLA-4 epitope
```

```
<400> SEQUENCE: 39

Thr Gly Leu Tyr Ile Cys
1               5

<210> SEQ ID NO 40
<211> LENGTH: 6
<212> TYPE: PRT
<213> ORGANISM: Artificial sequence
<220> FEATURE:
<223> OTHER INFORMATION: hICOS epitope

<400> SEQUENCE: 40

Ala Asn Tyr Tyr Phe Cys
1               5

<210> SEQ ID NO 41
<211> LENGTH: 7
<212> TYPE: PRT
<213> ORGANISM: Artificial sequence
<220> FEATURE:
<223> OTHER INFORMATION: hCD28 epitope

<400> SEQUENCE: 41

Asn Gly Thr Ile Ile His Val
1               5

<210> SEQ ID NO 42
<211> LENGTH: 7
<212> TYPE: PRT
<213> ORGANISM: Artificial sequence
<220> FEATURE:
<223> OTHER INFORMATION: hCTLA-4 epitope

<400> SEQUENCE: 42

Asn Gly Thr Gln Ile Tyr Val
1               5

<210> SEQ ID NO 43
<211> LENGTH: 7
<212> TYPE: PRT
<213> ORGANISM: Artificial sequence
<220> FEATURE:
<223> OTHER INFORMATION: hICOS epitope

<400> SEQUENCE: 43

Thr Gly Gly Tyr Leu His Ile
1               5

<210> SEQ ID NO 44
<211> LENGTH: 6
<212> TYPE: PRT
<213> ORGANISM: Artificial sequence
<220> FEATURE:
<223> OTHER INFORMATION: hPD-1 epitope

<400> SEQUENCE: 44

Pro Ala Leu Leu Val Val
1               5

<210> SEQ ID NO 45
<211> LENGTH: 6
<212> TYPE: PRT
<213> ORGANISM: Artificial sequence
<220> FEATURE:
<223> OTHER INFORMATION: hBTLA epitope

<400> SEQUENCE: 45
```

```
Gln Ser Glu His Ser Ile
1               5

<210> SEQ ID NO 46
<211> LENGTH: 5
<212> TYPE: PRT
<213> ORGANISM: Artificial sequence
<220> FEATURE:
<223> OTHER INFORMATION: hPD-1 epitope

<400> SEQUENCE: 46

Asp Asn Ala Thr Phe
1               5

<210> SEQ ID NO 47
<211> LENGTH: 5
<212> TYPE: PRT
<213> ORGANISM: Artificial sequence
<220> FEATURE:
<223> OTHER INFORMATION: hBTLA epitope

<400> SEQUENCE: 47

Asp Pro Phe Glu Leu
1               5

<210> SEQ ID NO 48
<211> LENGTH: 10
<212> TYPE: PRT
<213> ORGANISM: Artificial sequence
<220> FEATURE:
<223> OTHER INFORMATION: hPD-1 epitope

<400> SEQUENCE: 48

Arg Met Ser Pro Ser Asn Gln Thr Asp Lys
1               5                   10

<210> SEQ ID NO 49
<211> LENGTH: 4
<212> TYPE: PRT
<213> ORGANISM: Artificial sequence
<220> FEATURE:
<223> OTHER INFORMATION: hBTLA epitope

<400> SEQUENCE: 49

Lys Leu Asn Gly
1

<210> SEQ ID NO 50
<211> LENGTH: 9
<212> TYPE: PRT
<213> ORGANISM: Artificial sequence
<220> FEATURE:
<223> OTHER INFORMATION: hPD-1 epitope

<400> SEQUENCE: 50

Gln Pro Gly Gln Asp Cys Arg Phe Arg
1               5

<210> SEQ ID NO 51
<211> LENGTH: 5
<212> TYPE: PRT
<213> ORGANISM: Artificial sequence
<220> FEATURE:
<223> OTHER INFORMATION: hBTLA epitope

<400> SEQUENCE: 51
```

```
Gln Thr Ser Trp Lys
1               5

<210> SEQ ID NO 52
<211> LENGTH: 5
<212> TYPE: PRT
<213> ORGANISM: Artificial sequence
<220> FEATURE:
<223> OTHER INFORMATION: hPD-1 epitope

<400> SEQUENCE: 52

Met Ser Val Val Arg
1               5

<210> SEQ ID NO 53
<211> LENGTH: 5
<212> TYPE: PRT
<213> ORGANISM: Artificial sequence
<220> FEATURE:
<223> OTHER INFORMATION: hBTLA epitope

<400> SEQUENCE: 53

Leu His Phe Glu Pro
1               5

<210> SEQ ID NO 54
<211> LENGTH: 6
<212> TYPE: PRT
<213> ORGANISM: Artificial sequence
<220> FEATURE:
<223> OTHER INFORMATION: hPD-1 epitope

<400> SEQUENCE: 54

Asn Asp Ser Gly Thr Tyr
1               5

<210> SEQ ID NO 55
<211> LENGTH: 6
<212> TYPE: PRT
<213> ORGANISM: Artificial sequence
<220> FEATURE:
<223> OTHER INFORMATION: hBTLA epitope

<400> SEQUENCE: 55

Asn Asp Asn Gly Ser Tyr
1               5

<210> SEQ ID NO 56
<211> LENGTH: 6
<212> TYPE: PRT
<213> ORGANISM: Artificial sequence
<220> FEATURE:
<223> OTHER INFORMATION: hPD-1 epitope

<400> SEQUENCE: 56

Leu Arg Ala Glu Leu Arg
1               5

<210> SEQ ID NO 57
<211> LENGTH: 6
<212> TYPE: PRT
<213> ORGANISM: Artificial sequence
<220> FEATURE:
<223> OTHER INFORMATION: hBTLA epitope

<400> SEQUENCE: 57

Thr Thr Leu Tyr Val Thr
```

-continued

```
<210> SEQ ID NO 58
<211> LENGTH: 15
<212> TYPE: PRT
<213> ORGANISM: Artificial sequence
<220> FEATURE:
<223> OTHER INFORMATION: hCD28 epitope

<400> SEQUENCE: 58

Gly Asn Tyr Ser Gln Gln Leu Gln Val Tyr Ser Lys Thr Gly Phe
1               5                   10                  15

<210> SEQ ID NO 59
<211> LENGTH: 13
<212> TYPE: PRT
<213> ORGANISM: Artificial sequence
<220> FEATURE:
<223> OTHER INFORMATION: hCTLA-4 epitope

<400> SEQUENCE: 59

Tyr Met Met Gly Asn Glu Leu Thr Phe Leu Asp Asp Ser
1               5                   10

<210> SEQ ID NO 60
<211> LENGTH: 15
<212> TYPE: PRT
<213> ORGANISM: Artificial sequence
<220> FEATURE:
<223> OTHER INFORMATION: hICOS epitope

<400> SEQUENCE: 60

Lys Thr Lys Gly Ser Gly Asn Thr Val Ser Ile Lys Ser Leu Lys
1               5                   10                  15

<210> SEQ ID NO 61
<211> LENGTH: 16
<212> TYPE: PRT
<213> ORGANISM: Artificial sequence
<220> FEATURE:
<223> OTHER INFORMATION: hPD-1 epitope

<400> SEQUENCE: 61

Leu Ala Ala Phe Pro Glu Asp Arg Ser Gln Pro Gly Gln Asp Cys Arg
1               5                   10                  15
```